(12) United States Patent
Blum et al.

(10) Patent No.: US 11,638,772 B2
(45) Date of Patent: May 2, 2023

(54) SYSTEM FOR CAPTURING AND CLEANING EXHALED AIR

(71) Applicant: Air-Clenz Systems, LLC, Atlanta, GA (US)

(72) Inventors: Ronald Blum, Atlanta, GA (US); Anita Broach, Christiansburg, VA (US); Jack Loeb, Fisher Island, FL (US); Stuart Sheldon, Atlanta, GA (US)

(73) Assignee: Air-Clenz Systems, LLC, Atlanta, GA (US)

( * ) Notice: Subject to any disclaimer, the term of this patent is extended or adjusted under 35 U.S.C. 154(b) by 0 days.

(21) Appl. No.: 17/741,732

(22) Filed: May 11, 2022

(65) Prior Publication Data
US 2022/0273839 A1    Sep. 1, 2022

Related U.S. Application Data

(63) Continuation-in-part of application No. 17/300,936, filed on Dec. 15, 2021, which is a continuation of application No. 17/404,570, filed on Aug. 17, 2021, which is a continuation of application No. 17/353,341, filed on Jun. 21, 2021, which is a continuation of application No. 17/331,239, filed on May 26, 2021, now Pat. No. 11,324,850, application No. 17/741,732 is a continuation-in-part of application No. 17/722,981, filed on Apr. 18, 2022, now Pat. No. 11,471,553.

(60) Provisional application No. 63/323,911, filed on Mar. 25, 2022, provisional application No. 63/318,700, filed on Mar. 10, 2022, provisional application No. 63/315,253, filed on Mar. 1, 2022, provisional
(Continued)

(51) Int. Cl.
*A61L 9/20* (2006.01)
*A61L 9/22* (2006.01)

(52) U.S. Cl.
CPC .................. *A61L 9/20* (2013.01); *A61L 9/22* (2013.01); *A61L 2209/111* (2013.01); *A61L 2209/134* (2013.01); *A61L 2209/14* (2013.01); *A61L 2209/15* (2013.01)

(58) Field of Classification Search
CPC ..... A61L 9/16; A61L 9/18; A61L 9/20; A61L 9/205; A61L 9/22; A61L 2209/111; A61L 2209/134; A61L 2209/14; A61L 2209/15
See application file for complete search history.

(56) References Cited

U.S. PATENT DOCUMENTS

| 2011/0025933 A1 | 2/2011 | Schindler et al. |
| 2021/0104145 A1 | 4/2021 | Wakita |
| 2022/0054699 A1* | 2/2022 | Nakama ................. B64D 13/00 |

FOREIGN PATENT DOCUMENTS

| CN | 203757865 U | 8/2014 |
| CN | 205899457 U | 1/2017 |

(Continued)

OTHER PUBLICATIONS

Machine translation of JP-2004113561-A (Year: 2004).*
(Continued)

*Primary Examiner* — Timothy C Cleveland
(74) *Attorney, Agent, or Firm* — Woods Rogers Vandeventer Black PLC; Nathan A. Evans

(57) ABSTRACT

An exhaled air capture and air cleaning system comprising an exhaled air collector and an air purification chamber providing the ability to capture, transport, and clean exhaled air.

26 Claims, 91 Drawing Sheets

Related U.S. Application Data application No. 63/311,339, filed on Feb. 17, 2022, provisional application No. 63/310,087, filed on Feb. 14, 2022, provisional application No. 63/309,572, filed on Feb. 13, 2022, provisional application No. 63/307,971, filed on Feb. 8, 2022, provisional application No. 63/306,314, filed on Feb. 3, 2022, provisional application No. 63/304,036, filed on Jan. 28, 2022, provisional application No. 63/301,112, filed on Jan. 20, 2022, provisional application No. 63/299,559, filed on Jan. 14, 2022, provisional application No. 63/296,600, filed on Jan. 5, 2022, provisional application No. 63/283,524, filed on Nov. 28, 2021, provisional application No. 63/272,907, filed on Oct. 28, 2021, provisional application No. 63/271,933, filed on Oct. 26, 2021, provisional application No. 63/251,855, filed on Oct. 4, 2021, provisional application No. 63/240,795, filed on Sep. 3, 2021, provisional application No. 63/222,638, filed on Jul. 16, 2021, provisional application No. 63/216,644, filed on Jun. 30, 2021, provisional application No. 63/196,565, filed on Jun. 3, 2021, provisional application No. 63/195,608, filed on Jun. 1, 2021, provisional application No. 63/182,964, filed on May 2, 2021, provisional application No. 63/173,443, filed on Apr. 11, 2021, provisional application No. 63/158,983, filed on Mar. 10, 2021, provisional application No. 63/156,598, filed on Mar. 4, 2021, provisional application No. 63/149,581, filed on Feb. 15, 2021, provisional application No. 63/125,701, filed on Dec. 15, 2020, provisional application No. 63/063,727, filed on Aug. 10, 2020, provisional application No. 63/060,009, filed on Aug. 1, 2020, provisional application No. 63/051,309, filed on Jul. 13, 2020, provisional application No. 63/050,253, filed on Jul. 10, 2020, provisional application No. 63/048,877, filed on Jul. 7, 2020, provisional application No. 63/046,430, filed on Jun. 30, 2020, provisional application No. 63/031,321, filed on May 28, 2020, provisional application No. 63/029,956, filed on May 26, 2020.

(56) References Cited

FOREIGN PATENT DOCUMENTS

| | | | |
|---|---|---|---|
| CN | 207529266 U | | 6/2018 |
| EP | 1878977 A2 | | 1/2003 |
| JP | 2004113561 A | * | 4/2004 |
| KR | 101494856 B1 | | 2/2015 |
| WO | WO-2020137465 A1 | * | 7/2020 ............ A61L 9/205 |

OTHER PUBLICATIONS

Picchi, Aimee. "United Airlines fights COVID-19 with antimicrobial coating on seats, trays and bins." «https://www.cbsnews.com/news/united-airlines-covid-antimicrobial-coating/» Sep. 16, 2020. Accessed on Jul. 11, 2022. (Year: 2020).*

Application No. PCT/US2022/028717, International Search Report and Written Opinion dated Aug. 3, 2022.

* cited by examiner

EXHALED AIR COLLECTOR AND AIR PURIFICATION CHAMBER INTEGRATED WITH MONITOR

SHOWS A MONITOR THAT COMPRISES AN EXHALED AIR COLLECTOR AND AIR SUCTION INTAKES. THE MONITOR ALSO COMPRISES A PORT ON ITS BACK FOR ATTACHING TO AN AIR SUCTION CONDUIT THAT CONNECTS TO A DISTANCE SEPARATED EXHALED AIR PURIFICATION CHAMBER

AIR-SUCTION INTAKES

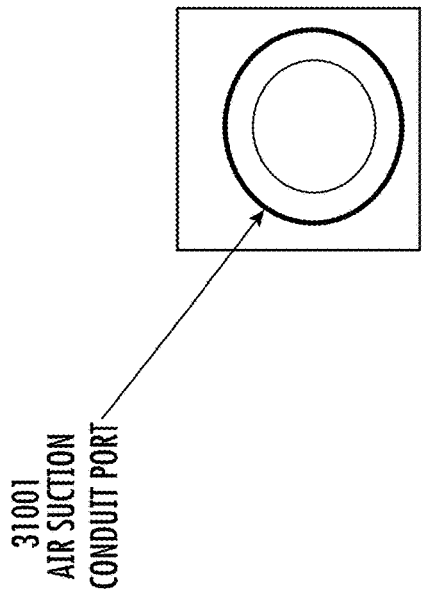
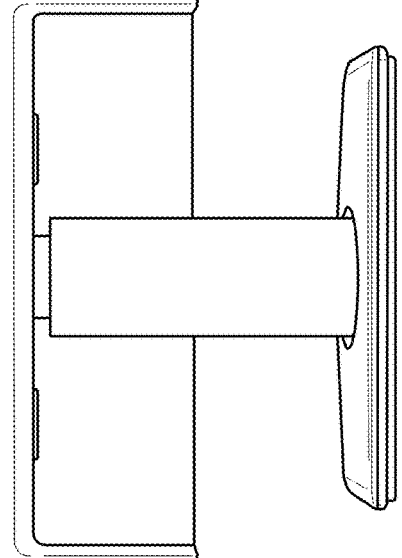
FIG. 31

ADJUSTABLE SIZE ATTACHABLE EXHALED AIR COLLECTOR

PORTABLE EXHALED AIR COLLECTOR EMBODIMENT FOR LAPTOP OR TABLET

DESKTOP COMPUTER SCREEN WITH "DETACHED" EXHALED AIR SUCTION INTAKE AND AIR PURIFICATION CHAMBER

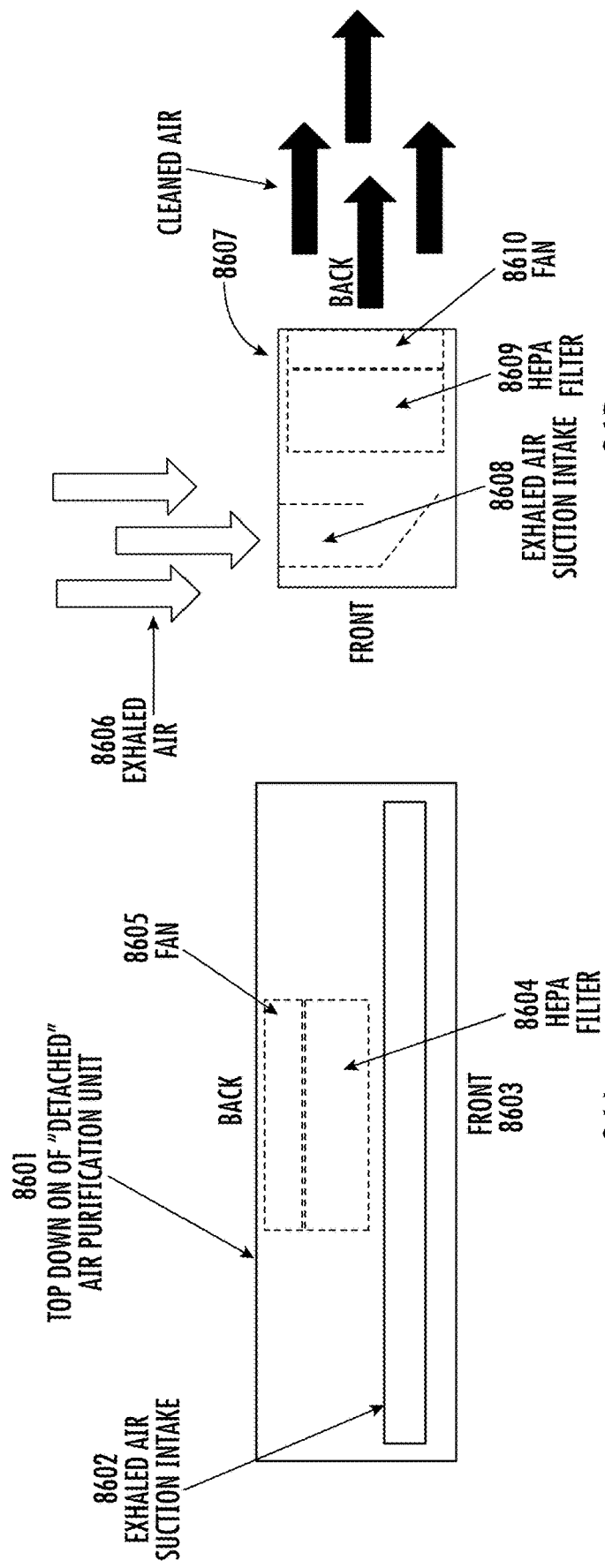

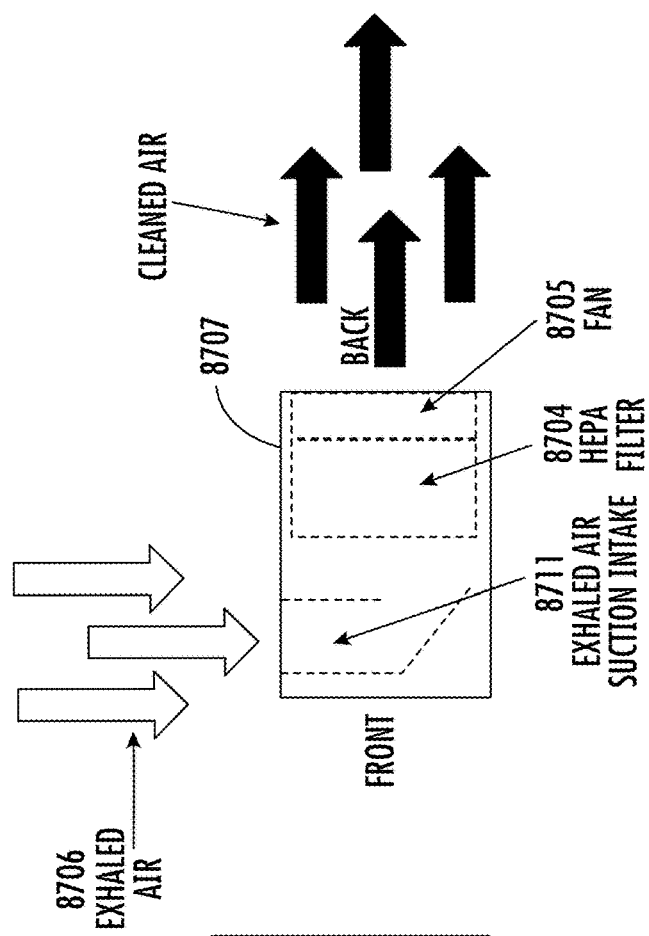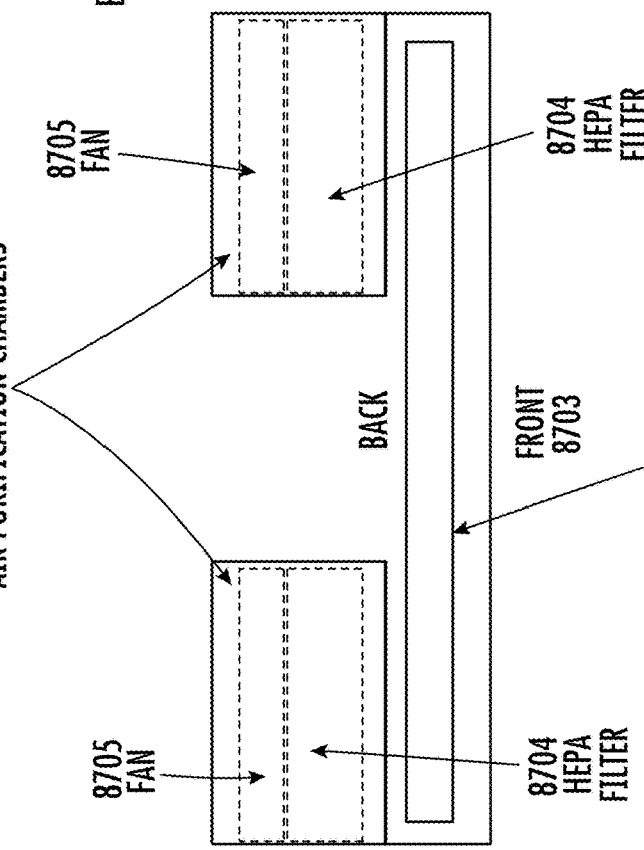

ated Air Purification for Desks and/or Tables, filed Jun. 3, 2021.

SYSTEM FOR CAPTURING AND CLEANING EXHALED AIR

CROSS-REFERENCE TO RELATED APPLICATIONS

The present application is a continuation of and relies on the disclosures of and claims priority to and the benefit of the filing date of U.S. application Ser. No. 17/722,981, filed Apr. 18, 2022, which relies on the disclosures of and claims priority to and the benefit of the filing date of U.S. application Ser. No. 17/331,239, filed May 26, 2021, which relies on the disclosures of and claims priority to and the benefit of the filing dates of the following U.S. Provisional Patent Applications:
U.S. Appl. No. 63/029,956, Microbe Protection Systems, filed May 26, 2020;
U.S. Appl. No. 63/031,321, Microbe Protection Modules, filed May 28, 2020;
U.S. Appl. No. 63/046,430, Air Suction Sterilization Elevator Car, filed Jun. 30, 2020;
U.S. Appl. No. 63/048,877, Vehicle Microbe Protection System, filed Jul. 7, 2020;
U.S. Appl. No. 63/050,253, Advanced Air Suction Sterilization Elevator Car, filed Jul. 10, 2020;
U.S. Appl. No. 63/051,309, Advanced Vehicle Microbe Protection System, filed Jul. 13, 2020;
U.S. Appl. No. 63/060,009, Advanced Air Suction Air Sterilization Protection System, filed Aug. 1, 2020;
U.S. Appl. No. 63/063,727, Advanced Microbe Trap and Face Mask, filed Aug. 10, 2020;
U.S. Appl. No. 63/125,701, Advanced Air Purification System for Multi-Person Environment, filed Dec. 15, 2020;
U.S. Appl. No. 63/149,581, Multi-person Venue Air Purification System, filed Feb. 15, 2021;
U.S. Appl. No. 63/156,598, Air Handling Purification System, filed Mar. 4, 2021;
U.S. Appl. No. 63/158,983, Air Handling Purification System, filed Mar. 10, 2021;
U.S. Appl. No. 63/173,443, Recessed Personal Air Purifier for Backside of Seat Back, filed Apr. 11, 2021; and
U.S. Appl. No. 63/182,964, Personal Air Purification Unit and System, filed May 2, 2021.
The present application is a continuation of and relies on the disclosures of and claims priority to and the benefit of the filing date of U.S. application Ser. No. 17/353,341, filed Jun. 21, 2021, which further relies on the disclosures and claims priority to and the benefit of the filing dates of:
U.S. Appl. No. 63/195,608, Exhaled Air Collector and Air Purification for Desks and/or Tables, filed Jun. 1, 2021; and
U.S. Appl. No. 63/196,565, Enhanced Exhaled Air Collector and Air Purification for Desks and/or Tables, filed Jun. 3, 2021.
The present application is a continuation of and relies on the disclosures of and claims priority to and the benefit of the filing date of U.S. application Ser. No. 17/404,570, filed Aug. 17, 2021, which further relies on the disclosures and claims priority to and the benefit of the filing dates of:
U.S. Appl. No. 63/216,644, Exhaled Air Guide for Exhaled Air Collector, filed Jun. 30, 2021; and
U.S. Appl. No. 63/222,638, Additional Exhaled Air Purification Units, filed Jul. 16, 2021.
The present application is a continuation of and relies on the disclosures of and claims priority to and the benefit of the filing date of U.S. application Ser. No. 17/300,936, filed Dec. 15, 2021, which further relies on the disclosures and claims priority to and the benefit of the filing dates of:
U.S. Appl. No. 63/240,795, Exhaled Air Trap, filed Sep. 3, 2021.
U.S. Appl. No. 63/251,855, Computer Screen Comprising Exhaled Air Collector and Connected Air Purification Chamber, filed Oct. 4, 2021.
U.S. Appl. No. 63/271,933, Air Cleaning Computer Monitor, filed Oct. 26, 2021.
U.S. Appl. No. 63/272,907, Air Cleaning Computer Monitor, filed Oct. 28, 2021.
U.S. Appl. No. 63/283,524, Enhanced Air Cleaning Computer Monitor, filed Nov. 28, 2021.
The present application also relies on the disclosures of and claims priority to and the benefit of the filing dates of the U.S. Provisional Applications Nos.:
U.S. Appl. No. 63/296,600, filed Jan. 5, 2022.
U.S. Appl. No. 63/299,559, filed Jan. 14, 2022.
U.S. Appl. No. 63/301,112, filed Jan. 20, 2022.
U.S. Appl. No. 63/304,036, filed Jan. 28, 2022.
U.S. Appl. No. 63/306,314, filed Feb. 3, 2022.
U.S. Appl. No. 63/307,971, filed Feb. 8, 2022.
U.S. Appl. No. 63/309,572, filed Feb. 13, 2022.
U.S. Appl. No. 63/310,087, filed Feb. 14, 2022.
U.S. Appl. No. 63/311,339, filed Feb. 17, 2022.
U.S. Appl. No. 63/315,253, filed Mar. 1, 2022.
U.S. Appl. No. 63/318,700, filed Mar. 10, 2022.
U.S. Appl. No. 63/323,911, filed Mar. 25, 2022.
The disclosures of all the above applications are hereby incorporated by reference herein in their entireties.

BACKGROUND OF THE INVENTION

Field of the Invention

The present invention is directed to an exhaled air capture and air cleaning system and/or device providing the ability to capture, isolate, transport, and/or destroy airborne pathogens and contaminants and/or pollutants, and signifies an improvement over currently available HVAC systems, HVAC purification systems, and/or HVAC air handling systems. By way of example only, airborne pathogens can float for over 15 minutes within a building, traveling meaningful distances before they are captured by the HVAC return. This is especially true for offices, auditoriums, theaters, and schools. It is estimated that 70% of the day spent at school is spent sitting at a desk or table. As with offices, workplaces, auditoriums, theaters, and school classrooms, many times the closest HVAC air return is far across the room from where the individual is seated. Thus, the exhaled air of multiple individuals must travel in the air across multiple rows of seats, desks, and/or tables before it is captured within the HVAC air return thus potentially infecting others on its way. There is the need for a system or device that can capture and clean exhaled air prior to it dispersing within the room's indoor air. In addition, it has been shown that increased ventilation resulting in reduced pollution, pathogens and lower CO2 in the air can improve job and/or academic performance, productivity, and attendance. It is also known that individuals read comfortably at a distance within the near and intermediate viewing distance range with the appropriate optical prescription, if required. Thus, most computer monitor screens are located within the range of 16-36 inches from one's face, with many within the range of 18 to 22 inches.

Description of the Related Art

Aerosol spray which transports viruses, including coronavirus ("COVID"), occurs from a human exhaled breath, talking, shouting, coughing, and sneezing. Under normal circumstances it is known that exhaled air forms a cone shape as it comes from the mouth and nose of an individual. Generally, at its origination at the nose and mouth it is approximately 55 mm in diameter. From there it usually (but not always) expands outward at 22 degrees-33 degrees and has a center trajectory of about 10 degrees downward. The louder the noise the human makes with his or her voice, lungs, throat, or mouth generally the faster the velocity of the exhaled air and the farther the viral or bacterial aerosol is moved in the air. Recent studies show that an aerosol comprising viral float can remain airborne for up to 15 minutes or more in a closed confined environment. Research studies have shown that singing, yelling, coughing, and sneezing can spread COVID aerosol up to 3+ meters. By way of example only, exhaled air in the form of a cough can obtain a velocity reaching up to ~20-50 miles per hour. Exhaled air in the form of a sneeze can obtain a velocity reaching up to ~100 miles per hour. Exhaled air in the form of a spoken word (talk) can obtain a velocity of ~8-10 miles per hour. And exhaled air in the form of an exhaled air breath can obtain a velocity of ~4-6 miles per hour. Furthermore, research has shown that with a sneeze upwards of 100,000 respiratory particles can be emitted, for a cough upward to 1,000+ particles, and when talking approximately 100 particles.

Respiratory infection can be spread from human to human by way of airborne pathogens, by way of example only, COVID 19, COVID variants, coronavirus, measles, mumps, SARS, smallpox, common colds, influenza, and tuberculosis. Closed confined multi-seated indoor environments are extremely vulnerable to coronaviral spread. In addition, it has now been shown that poor levels of ventilation cause increased CO2 which can reduce (by way of example only), the productivity and performance of workers within a workplace and students within a classroom. There is a need for capturing, isolating, and cleaning the exhaled air of individuals more rapidly and more effectively than what is typically possible with currently available systems (e.g., HVAC systems).

SUMMARY OF THE INVENTION

An objective of the invention disclosed herein can be that of an air capture and air cleaning device that captures and cleans exhaled air prior to it spreading widely within an indoor room environment. In certain cases, the invention can capture and clean 50% or more of the exhaled air of an individual. In certain cases, the invention can capture and clean 75% or more of the exhaled air in the form of an exhaled air breath, talk, cough, sneeze of an individual. In still other cases, the invention can capture and clean 75% or more of the exhaled air in the form of an exhaled air breath, talk, cough, or sneeze, of an individual. In other cases, the invention can capture and clean 90% or more of the exhaled air in the form of an exhaled air breath, talk, cough, or sneeze, of an individual. In other cases, the invention can capture and clean 99% or more of the exhaled air in the form of an exhaled air breath, talk, cough, or sneeze, of an individual. In still other cases the invention can capture 90% or more of exhaled air in the form of an exhaled air breath, talk (expressed word), cough, or sneeze, and can clean the captured air to a 99.9% level or greater free of particles having a size of 1 micron or greater. In still other cases the invention can capture 90% or more of exhaled air in the form of an exhaled air breath, talk (expressed word), cough, or sneeze and can clean the captured air to a 99.9% level or greater free of particles having a size of 0.3 micron or greater. In cases small particles less than 1 micron in size clump together such that the invention cleans an accumulation of particles that can be made of a plurality of smaller particles, etc.

While the invention disclosed herein targets exhaled air, in embodiments exhaled air and some indoor room air are captured and cleaned. When a plurality of exhaled air collectors and associated exhaled air purification chambers are used within a room, the additive result can increase clean air turns per hour within the room. In cases the exhaled air collectors and associated exhaled air purification chambers are utilized along with the room or venue's indoor air ventilation system, by way of example only, an HVAC system. The combination of both the plurality of exhaled air collectors and attached or connected air purification chambers along with the venue's indoor HVAC system can increase the room or venue's indoor clean air turns per hour. This is accomplished while at the same time capturing the exhaled air of the multiple users of each exhaled air collector.

In embodiments, the plurality of exhaled air collectors and associated exhaled air purification chambers can be attached to or releasably attached to, by way of example only, monitors, display screens, laptops, tablets, or TVs. In other embodiments the exhaled air collectors and the associated exhaled air purification chambers are separated and distance removed from, by way of example only, monitors, display screens, laptops, tablets, or TVs, but are positioned so that air suction intakes that open or connect to the associated air purification chambers are located beneath a bottom edge of the monitors, display screens, laptops, tablets, or TVs.

In embodiments, the monitor, display screen, laptop, tablet, or TV is located within 36 inches of the viewer/user exhaling air of such monitor, display screen, laptop, tablet, or TV. A TV that comprises or is attached to a larger exhaled air collector can be located within 15 feet of a viewer exhaling air. Such an enabled TV will capture a larger amount of mixed room air along with exhaled air compared to a TV located closer to the face of an individual or individuals exhaling air. The farther away from the individual or individuals whose exhaled air is being collected and cleaned (along with room air) the larger the format of the exhaled air blocking surface and the more suction CFM (cubic feet per minute) and CADR (clean air delivery rate) from the air purification chamber is required of the system or device.

As used herein, a monitor can be the housing and electronic display screen utilized with or for, by way of example only, a monitor, a desktop computer monitor, a laptop, a tablet, a TV, or a display monitor associated with retail, gambling, exercise workout equipment, travel, information display, gaming, gambling, advertising, consumer display, business, education, entertainment, or for any other uses where an electronic display screen might be used. As used herein, an air suction intake can mean an exhaled air suction intake. As used herein an air purification chamber can mean an exhaled air purification chamber. As used herein an exhaled air purification unit can comprise an exhaled air collector and an exhaled air purification chamber. As used herein an exhaled air purification unit can comprise an exhaled air collector comprising a distance separated air suction intake and air purification chamber.

The air suction intake and air purification chamber can be releasably attached to one or more of the bottom side or bottom edge, bottom front side, bottom back side of a monitor, or one or both sides of a monitor. The air suction intake and air purification chamber can be attached to one or more of the bottom side or bottom edge, bottom front side, bottom back side of a monitor, or one or both sides of a monitor. The air suction intake and air purification chamber can be located beneath, and distance separated from the bottom side or a bottom edge of a monitor. A portion of the distance separated air suction intake can be located beneath and forward that of the bottom of the monitor or the electronic display screen. A portion of the distance separated air suction intake can be located beneath and forward that of the bottom front of the monitor or the electronic display.

As used herein an air purification chamber can mean an exhaled air purification chamber. An exhaled air purification chamber can mean an air purification chamber. An air purification chamber can be capable of cleaning both exhaled air and room air or a mixture of exhaled air and room air.

As used herein, a conventional air purifier can mean a traditional air purifier. In certain embodiments a conventional air purifier can be releasably attached to the bottom of a monitor. In certain embodiments a conventional air purifier can be attached to the bottom of a monitor.

An exhaled air collector can comprise an open front. An exhaled air collector can comprise one or more exhaled air suction intakes. An exhaled air collector can comprise or partially or fully surround an exhaled air blocking surface. An exhaled air collector can comprise an attached or distance separated exhaled air catch basin. An exhaled air collector can comprise both an exhaled air catch basin, and one or more exhaled air suction intakes.

In embodiments an exhaled air collector can be devoid of an exhaled air catch basin.

In embodiments the one or more exhaled air suction intake(s) are adjacent to the exhaled air blocking surface. In embodiments the one or more exhaled air suction intake(s) can be distance removed from the exhaled air blocking surface. An exhaled air blocking surface can be that of the outer front surface of an electronic display screen that blocks, deflects, and/or redirects exhaled air. An exhaled air blocking surface can be that of a surface that is within 45 degrees of being perpendicular to the floor, tabletop or desktop that blocks, deflects, and/or redirects exhaled air. An exhaled air blocking surface can be recessed in relation to that of one wall height of the exhaled air collector. An exhaled air blocking surface can be planar in relation to that of one wall height of the exhaled air collector. An exhaled air blocking surface can be forward in relation to that of one wall height of the exhaled air collector.

In embodiments, the exhaled air blocking surface of the exhaled air collector can block, direct, or deflect 90%+ of an individual's exhaled air breath, talk (expressed word), cough, or sneeze when the individual is looking within 20 degrees (or less) of having his or her head perpendicular to an electronic display screen. In embodiments, the exhaled air blocking surface of the exhaled air collector can block, direct, or deflect 95%+ of an individual's exhaled air breath, talk (expressed word), cough, or sneeze when the individual is looking within 20 degrees (or less) of having his or her head perpendicular to an electronic display screen.

In embodiments, the exhaled air blocking surface of the exhaled air collector can capture 90%+ of an individual's exhaled air breath, talk (expressed word), cough, or sneeze when the individual is looking within 20 degrees (or less) of having his or her head perpendicular to an electronic display screen. In embodiments, the exhaled air blocking surface of the exhaled air collector can capture 95%+ of an individual's exhaled air breath, talk (expressed word), cough, or sneeze when the individual is looking within 20 degrees (or less) of having his or her head perpendicular to an electronic display screen.

An embodiment of the invention is an air capturing, air cleaning computer screen (or monitor), wherein the computer screen (or monitor) in addition to displaying images comprises an exhaled air collector, and wherein the exhaled air collector collects exhaled air mixed with room air and deflects or otherwise redirects the mixed exhaled air towards an exhaled air suction intake. In embodiments an exhaled air suction intake can be located at or beneath the bottom of the computer screen. In other embodiments an air suction intake is at the bottom of the computer screen (or monitor), at the top of the computer screen (monitor), at the right side of the computer screen (or monitor), at the left side of the computer screen (or monitor), at the bottom of the computer screen (or monitor), or any combination thereof. In embodiments, the exhaled air suction intake, including an air suction intake of the exhaled air collector, air purification chamber, or traditional air purifier, is located directly underneath and within 45 degrees of being perpendicular to a bottom front of the monitor/electronic display screen or the exhaled air blocking surface.

In embodiments the exhaled air collector and exhaled air purification chamber are built into (integrated) within the monitor. In embodiments the exhaled air collector and exhaled air purification chamber are attached to the monitor. In embodiments the exhaled air collector and exhaled air purification chamber are releasably attached to the monitor. In still other embodiments the exhaled air collector is attached to the monitor and the exhaled air purification chamber is distance separated from the monitor but connected to the exhaled air collector or monitor by way of a conduit. In other embodiments the exhaled air collector is attached or integrated into the monitor and the exhaled air purification chamber is distance separated and not connected to the monitor or exhaled air collector. In embodiments the exhaled air collector is connected to a monitor and an air purification chamber is attached or integrated to the monitor stand. In still other embodiments a conventional air purifier is positioned below and distant separated from the bottom of a monitor in such a way as to capture deflected exhaled air. In still other embodiments a conventional air purifier is positioned below and distant separated from the bottom of a monitor in such a way as to capture deflected exhaled air. In other embodiments a conventional air purifier is attached to the bottom of a monitor or the front lower portion of a monitor, or the back lower portion of a monitor. And in still other embodiments a conventional air purifier is attached to or integrated into the monitor stand.

FIG. 7 shows a front view 7001 and side view 7002 of an embodiment of the current invention. In 7001, a front view of the exhaled air collector 7006 is shown which can be attached to or integrated with a monitor, laptop computer, or tablet computer, by way of example. In this embodiment, the electronic display screen acts as an exhaled air blocking surface 7003. The embodiment uses a recessed exhaled air blocking surface with an outer lipped wall 7004 having one or more air suction intakes 7005 on one side, two sides, three sides, or four sides of the electronic display screen. The side view 7002 shows a section of an exhaled air collector 7006 comprising an exhaled air blocking surface (e.g., in this case the electronic display screen) 7003, and one or more air suction intakes 7005, wherein an outer lipped wall 7004 is used (e.g., sometimes may be around 1 micron or greater in, for example, depth). The lipped wall can extend out from being planar with the front surface of the electronic display screen by 1 micron or greater, making the air blocking surface/electronic display screen "recessed."

FIG. 8 shows a front view 8001 and side view 8002 of an embodiment of the current invention. In 8001, a front view of the exhaled air collector 8006 is shown which can be attached to or integrated with a monitor, laptop computer, or tablet computer, by way of example. In this embodiment, the electronic display screen acts as an exhaled air blocking surface 8003. In this embodiment, unlike that shown in FIG. 7, the exhaled air blocking surface is not recessed, but while still having one or more air suction intakes 8005 on one side, two sides, three sides, or four sides of the electronic display screen. The side view 8002 shows a section of an exhaled air collector 8006 comprising an exhaled air blocking surface (e.g., in this case the electronic display screen) 8003, and one or more air suction intakes 8005. Again, unlike FIG. 7, this electronic display screen is not recessed into the exhaled air collector (e.g., the electronic display screen is planar or substantially planar with or flush or substantially flush with the outer wall 8004). As shown in 8002, for example, the exhaled air collector outer wall 8004 is planar with a front surface of the electronic display screen within or by 1 micron.

FIG. 9 shows a front view 9001 and side view 9002 of an embodiment of the current invention. In 9001, a front view of the exhaled air collector 9006 is shown which can be attached to or integrated with a monitor, laptop computer, or tablet computer, by way of example. In this embodiment, the electronic display screen acts as an exhaled air blocking surface 9003. In this embodiment, unlike that shown in FIGS. 7 and 8, the exhaled air blocking surface is not recessed, but while still having one or more air suction intakes 9005 on one side, two sides, three sides, or four sides of the electronic display screen. The side view 9002 shows a section of an exhaled air collector 9006 comprising an exhaled air blocking surface (e.g., in this case the electronic display screen) 9003, and one or more air suction intakes 9005. Again, unlike FIGS. 7 and 8, this electronic display screen is not recessed into the exhaled air collector, or even planar/flush, but rather the electronic display screen extends out in front of the outer wall 8004 and air suction intake(s) 9005. As shown in 9002, for example, the exhaled air collector outer wall 9004 is closer to the back of the exhaled air collector than the front surface of the electronic display screen, meaning the front surface of the electronic display screen extends outwards to a user as compared to the front of the outer wall of the exhaled air collector. In other words 9002 shows a front surface of the electronic display screen being "forward of" the exhaled air collector walls.

FIG. 13 shows similar side view perspectives of an exhaled air blocking surface, but relative to a front surface of the one or more air suction intakes. Embodiment #1 13001 shows an example where a start of an air suction intake 13002 is behind or slightly behind a front of an exhaled air blocking surface/electronic display screen 13003. Exhaled air 13004 is suctioned by an air suction intake 13005, passed to an air purification chamber 13006 and cleaned air is exhausted 13007. Embodiment #2 13008 shows an example where a start of an air suction intake 13002 is planar with (or flush with) a front of an exhaled air blocking surface/electronic display screen 13003. Exhaled air 13004 is suctioned by an air suction intake 13005, passed to an air purification chamber 13006 and cleaned air is exhausted 13007. Embodiment #3 13009 shows an example where a start of an air suction intake 13002 is in front of a front of an exhaled air blocking surface/electronic display screen 13003. Exhaled air 13004 is suctioned by an air suction intake 13005, in this case having an outer lip 13005, passed to an air purification chamber 13006 and cleaned air is exhausted 13007. Embodiment #4 13010 shows an example where a start of an air suction intake 13002 is behind a front of an exhaled air blocking surface/electronic display screen 13003. Exhaled air 13004 is suctioned by an air suction intake 13005, passed to an air purification chamber 13006 and cleaned air is exhausted 13007. In embodiments, cleaned air from a conventional air purifier or exhaled air purification chamber is directed backwards and away from a back of an associated monitor, computer, or electronic display screen, and therefore away from a user of the monitor, computer, or electronic display screen.

The exhaled air suction intake can be covered, by way of example only, by one of: a screen, a mesh, a grid, and a filter. The exhaled air suction intake can be located within an exhaled air catch basin. The exhaled air suction intake can be located within the bottom of the exhaled air catch basin. The exhaled air suction intake can be in the back of the exhaled air catch basin. The exhaled air suction intake can be in one or both sides of the exhaled air catch basin. An exhaled air catch basin can be located at or below the bottom of the computer screen. The exhaled air suction intake can be located partially or fully around the periphery of the computer screen or monitor. A computer screen can be an electronic display screen. The exhaled air suction intake can be connected directly or indirectly to an exhaled air purification chamber. The indirect connection can be by way of an air suction conduit. The direct connection can be having the air purification chamber directly next to or adjacent to the air suction intake.

In embodiments the exhaled air collector can be attachable to the computer screen. When attachable to the computer screen or monitor the exhaled air collector can be an exhaled air collector assembly. In other embodiments the exhaled air collector can be designed into the computer screen or monitor. And in still other embodiments the exhaled air collector can be integrated into the computer screen or monitor. In preferred embodiments, the purpose of the exhaled air collector is to capture exhaled air in a form of a cough, sneeze, talk, whistle, and/or air breath, by blocking and deflecting the cone of exhaled air along with ambient room air towards an air suction intake whereby it is moved through a conduit or opening to a connected exhaled air purification chamber. The outer front surface of the electronic display screen provides for an exhaled air blocking surface, in aspects. The exhaled air travels at various speeds along the Z axis from an individual's mouth and nose. The speed of travel along the Z axis depends upon whether the exhaled air is in the form of a breath, talk, song, whistle, cough, or sneeze. The exhaled air blocking surface serves to stop the forward velocity along the Z axis and/or deflect the exhaled air towards and exhaled air suction intake.

A computer screen or monitor can be one of a desktop computer screen, a laptop computer screen, a tablet computer screen, a cellphone screen, and a mobile phone screen. The computer screen can display digital images, words, or numbers generated by the wired or wireless connected computer while at the same time capturing exhaled air of the user of the computer. An electronic display screen can be that of any electronic display including a monitor, television screen, or electronic communication screen. A monitor can be a computer monitor (such as by way of example only, a desktop monitor), gaming display monitor, television monitor, gambling display monitor (see FIG. 33 (showing display screen with exhaled air collector and connected air purification chamber 33001, as well as an exercise monitor with integrated air capture and air cleaning 33002)), advertising display monitor, exercise display monitor (see FIG. 32 (showing display screen with exhaled air collector and connected air purification chamber 32001, as well as an exercise monitor with integrated air capture and air cleaning 32002)), consumer display monitor, retail display monitor, business display monitor, or education display monitor.

In embodiments a user can be sitting within 36 inches of a monitor. In embodiments the user is sitting within 20 inches of the monitor. In other cases, the user is standing at a desk top computer or tabletop computer and is within 30 inches of the electronic display screen or monitor. In embodiments, the exhaled air collector comprises an exhaled air suction intake.

The exhaled air suction intake can be located within the bottom ⅓ of the exhaled air collector. In other cases, the exhaled air suction intake can be located around the perimeter of the computer screen or computer monitor (which can be that of a desktop, laptop, tablet, etc). In still other cases, four exhaled air suction intakes are located such that one is on the front top, one the front bottom and one on each of front of both sides adjacent to the screen or to the monitor housing. The multiple exhaled air suction intakes can be separated from each other. The multiple exhaled air suction intakes can be connected to each other. In still other cases four exhaled air suction intakes are located such that one is on the front bottom, one is on the top, and one on each of the two sides or the screen or monitor housing. In still other cases three exhaled air suction intakes are located such that one is on the front bottom and one on each of front of both sides adjacent to the screen or to the monitor housing. One or more exhaled air suction intakes can be located within the frame that surrounds the monitor. One or more exhaled air suction intakes can be located within the monitor cover that covers part or all the sides and back of the electronic display screen. In embodiments one exhaled air suction intake can be located beneath the computer screen or monitor. In other embodiments multiple exhaled air suction intakes can be located beneath but attached to the computer screen or monitor. In other embodiments multiple exhaled air suction intakes can be located beneath but distance separated from the computer screen or monitor.

In embodiments, the exhaled air suction intake, when located beneath the electronic display screen or bottom of the monitor, can be oriented so that the front to back opening (width of the opening) of the air suction intake is located within 45 degrees of being horizontal to the floor, tabletop, or desk. In embodiments, a portion of this width of the opening is in an alignment that would be directly beneath the bottom of the monitor or the bottom of the electronic display screen.

In other embodiments, the exhaled air suction intake, when located beneath the electronic display screen or the bottom of the monitor, can be oriented so that the vertical height of the exhaled air suction intake (width of the opening) is located within 45 degrees of being parallel with the front of the electronic display screen. In embodiments, a portion of this width of the opening is in an alignment that would be directly beneath the bottom of the monitor or the bottom of the electronic display screen.

The front opening of one or more exhaled air suction intake(s) (also referred to as an air suction intake(s) herein) can be planar with the outer front surface of the electronic display screen, slightly behind the outer front surface of the electronic display screen, behind the outer front surface of the electronic display screen, or in front of the outer front surface of the electronic display screen. The electronic display screen can act as an exhaled air blocking surface which deflects the blocked exhaled air towards an air suction intake. Such an exhaled air blocking surface can be important when capturing the cone of exhaled air for a normal exhaled air breath but even more important for capturing exhaled air from talking, whistling, singing and most important when capturing most of a cough or a sneeze.

The outer surface of such a monitor can comprise a hydrophobic coating. The outer surface of such a monitor can comprise a super hydrophobic coating. The outer surface of such a monitor can comprise a microbicidal agent.

In embodiments, the exhaled air collector can further comprise one or more fans that are located at or above the top of the computer screen and attached to the exhaled air collector or monitor.

The fan or fans can blow air downward thus helping to move exhaled air downward towards an exhaled air suction intake. In other cases, the exhaled air collector is devoid of a fan that is located towards the top of the exhaled air collector or monitor.

The exhaled air purification chamber can comprise one or more fans. The one or more fans can exhaust the cleaned air from the exhaled air purification chamber.

An exhaled air suction intake can provide air suction (air flow) volume, and velocity ranging between a total of 10 CFM and 750 CFM while either attached, connected, or integrated into the electronic display screen. In embodiments the exhaled air collector comprises a fan or fans that generates air suction air flow towards and into an air suction intake. In other embodiments the exhaled air collector can be used as a vessel that blocks and captures exhaled air and to which the air flow passes through, and whereby the air suction air flow is generated by a fan or fans either located in a conduit or a connected exhaled air purification chamber. In aspects, the air flow CFM required amount is dependent upon the size of the electronic display screen or monitor and the shape of the exhaled air collector. Depending upon the design or shape of the exhaled air collector, a larger electronic display screen or monitor may require a greater CFM, such as to adequately capture exhaled air of a user. This can also be the case when considering the required CADR for a connected or attached air purification chamber.

In embodiments, when the exhaled air collector having an exhaled air suction intake and comprising an outer lipped wall being higher than that of the front outer surface of the electronic display screen, the CFM and resulting CADR can be less. Such an outer lipped wall can be on one or more walls of the exhaled air collector. Such a design can result in the electronic display being recessed with respect to one or more of the outer walls of the exhaled air collector. As described herein, the electronic display screen when recessed can be called a recessed exhaled air blocking surface. Such an outer lipped wall can be 1 micron or more higher than the electronic display screen. Such an outer lipped wall can be 1 mm or more higher than the electronic display screen. Such an outer lipped wall can be 1 inch or more higher than the electronic display screen.

An embodiment can be that of an exhaled air collector capable of 90% or greater capture of exhaled air in the form of an individual talking, coughing, or sneezing within 30 inches from the exhaled air collector. In aspects, the exhaled air collector comprises an exhaled air blocking surface and an exhaled air suction intake having an outer lipped wall (causing the exhaled air blocking surface to be recessed), and wherein the air suction of the exhaled air suction intake is 20 CFM or more, and wherein the exhaled air suction intake circumvents 3 or 4 outer peripheral sides of a flat exhaled air blocking surface. Such a surface, by way of example only can be the outer front surface of a flat or curved electronic display screen. When using a horizontally curved electronic display screen such an air suction intake can be located on any one or a combination of peripheral sides of the electronic display screen. In embodiments such one or more air suction intake(s) is located beneath or at the lower bottom front of the electronic display screen or monitor. This design permits a connected or attached air purification chamber to exhaust 99%+ cleaned air with an airflow CADR of 10 or greater. For this embodiment (whether flat or curved) it has been discovered that the reason such a very low CFM and CADR works is that the velocity of the respiratory particles from a talk, cough, or sneeze propel respiratory particles forward in such a way that they strike the exhaled blocking surface largely ceasing their Z-axis forward velocity. The exhaled air blocking surface stops the forward motion along the Z-axis then deflects or directs these moving particles, which are further influenced by gravity and drag/friction of the outer surface of the electronic display screen, across the outer surface of the electronic display screen (e.g., a recessed exhaled air blocking surface) until they either enter the exhaled air suction intake or strike the inside wall of the outer lip of the exhaled air suction intake, where the air suction CFM takes over and sucks the particles into the intake. When an outer lipped wall is not present and with a lower air suction CFM, the particles in aspects can slide off the front surface of the electronic display screen (now a non-recessed exhaled air blocking surface), overshoot the exhaled air suction intake and move into the air flow of the room. Thus, in embodiments, the required CFM must increase and so must the corresponding CADR to achieve a 90% or better exhaled air capture rate of the particles approaching the exhaled air collector or monitor. Therefore, in aspects, by having a recessed exhaled air blocking surface, surrounded partially or fully by an air suction intake having an outer lip (thus causing a recessed exhaled air blocking surface) it is possible to reduce the CFM and CADR of the system. This can make the air handling device quieter, thinner, lighter, less expensive, and requires less energy.

As shown in FIGS. 1 and 2, a traditional monitor with no exhaled air capture and cleaning capabilities allows for nearly undeterred spread of respiratory particles upon a cough or sneeze. In FIG. 2, a computer model is shown where the current invention is implemented with a monitor but with 0 CADR. However, FIG. 3 shows the current invention, including the exhaled air collector 3001, and air suction intake with outer lip 3002, and wherein the outer surface of the electronic display screen of the exhaled air collector acts as an exhaled air blocking surface 3003. With a CADR of only one CADR, around 33 particles fall out resulting in a 90%+ capture/collection rate. Thus, as shown in FIG. 3, multiple coughs, according to computer modeling, are being collected and cleaned by an exhaled air collector, exhaled air blocking surface (e.g., outer, front surface of an electronic display screen), one or more air suction intakes, and an air purification chamber, using 6 CADR. FIG. 4 shows the current invention, including the exhaled air collector 4001, and air suction intake with outer lip 4002, and wherein the outer surface of the electronic display screen of the exhaled air collector acts as an exhaled air blocking surface 4003. With a CADR of 10 CADR, around zero particles fall out resulting in an around 100% capture/collection rate. Thus, as shown in FIG. 3, multiple coughs, according to computer modeling, are being collected and cleaned by an exhaled air collector, exhaled air blocking surface (e.g., outer, front surface of an electronic display screen), one or more air suction intakes, and an air purification chamber, using 60 CADR. Similarly, FIG. 5 shows exhaled air and room air captured and cleaned according to a computer model, showing respiratory particles spread by a cough after around 0.7 seconds from the cough. On the left is a traditional monitor 5001 without the invention showing undeterred, widespread potential infection spread. On the right is the monitor with the current invention 5002, wherein the system is using 25 CADR, the system accomplishes around 100% capture and around 99.97% clean rate. FIG. 6 shows exhaled air and room air captured and cleaned according to a computer model, showing respiratory particles spread by a cough after around 4.7 seconds from the cough. On the left is a traditional monitor 6001 without the invention showing undeterred, widespread potential infection spread, just like in FIG. 5. On the right is the monitor with the current invention 6002, wherein the system is using 25 CADR, the system accomplishes around 100% capture and around 99.97% clean rate.

The air suction air flow pulls exhaled air of the user of the computer screen or monitor along with some room air into the exhaled air collector, then into an exhaled air suction intake and then towards an air purification chamber where the exhaled air is cleaned by one or more of, by way of example only, a HEPA filter, a carbon filter, an activated carbon filter, a UV light, a UVC light, Ionization, heat, radiation, a microbicidal chemical, microbicidal energy, a microbicidal agent, and/or an anti-microbial agent. Upon being cleaned by the exhaled air purification chamber, the air (in most, but not all cases) is released back into the room where the computer screen or monitor is located. If a HEPA filter is utilized or another type of filter, the filter can comprise a microbicidal agent capable of destroying a pathogen or the filter can be subjected to, by way of example only, UV light prior to being replaced in the exhaled air purification chamber with a new filter.

An activated carbon filter can be utilized to reduce and possibly eliminate odors.

A CO2 reducer can be located, by way of example only, within an exhaled air catch basin beneath the monitor or computer screen. Thus prior to exhaled air and room air entering an air suction intake it would be pulled through, over, under, and/or around, the CO2 reducer.

Prior to exhaled air, along with room air, being moved into an air suction intake or the air purification chamber, in certain embodiments a CO2 reducer is utilized to reduce CO2 in the air. Such a CO2 reducer can be, by way of example only, one or more of a living plant, a CO2 absorber (such as by way of example only, nitrogen passing through a stack of electrochemical plates), electrochemical process, or an MIT process that includes a special type of plastic that can selectively pull-out $CO_2$ from a mix of gas—in air or exhaust—when charged with electricity.

In embodiments an exhaled air catch basin is located below the bottom of the electronic display screen or monitor. In embodiments an exhaled air catch basin is distance separated beneath the bottom of the electronic display screen or monitor. In embodiments an exhaled air catch basin is attached to the bottom of the electronic display screen or monitor. In embodiments an exhaled air catch basin is attached to the bottom front or back surface of the electronic display screen or monitor. The exhaled air catch basin can comprise one or more air suction intake(s). In other embodiments the exhaled air collector is devoid of an exhaled air catch basin.

The following are by way of example only, house plants that clean air of C02: Snake Plant, Succulents and Cacti, Prayer Plant, Dumb Cane, ZZ Plant, Pothos, Anthurium, rubber plant, and jade plant.

In embodiments involving either an exhaled air purification unit, exhaled air purification chamber, exhaled air suction intake, conventional air purifier, or a CO2 reducer (by way of example only, using a living plant), the CO2 reducer can, in aspects, be placed in front of the air suction intake such that air being pulled towards the air suction intake flows through the leaves of the plants (by way of example) and into the air suction intake, which then moves the room air and/or exhaled air into an air purification chamber for cleaning and/or purifying the air. Following this, the cleaned and/or purified air can then be released back into the room. The CO2 reducer can be supported or housed by a compartment or a housing that is attached, connected, or integrated with the exhaled air purification unit or the conventional air purifier. In embodiments, the CO2 reducer can be located (by way of example only) within an exhaled air catch basin. In other embodiments it can be located or supported by a flower or plant box member that permits watering of the plant or plants which are attached, connected or integrated with the exhaled air purification unit or conventional air purifier. Such an exhaled air purification unit or conventional air purifier can also include an air humidifier to ensure the appropriate level of humidity of the cleaned and/or purified air that is being released back into the room. Additionally, the exhaled air purification unit or conventional air purifier can also comprise, by way of example only, various fluids, chemicals, substances, and/or materials that emit certain pleasant odors, mixed along with the cleaned and/or purified air that is exhausted back into the room.

From the air suction intake, in aspects, the exhaled air travels towards and into an exhaled air purification chamber where the exhaled air and some room air is cleaned and/or purified. In cases the air cleaned is 99+% free of the presence 0.3 micron and larger particles. In other cases, the air cleaned is 99+% free of the presence of 0.5 micron and larger particles. In still other cases, the air cleaned is 99+% free of the presence of 1 micron and larger particles.

In embodiments, the exhaled air collector acts to capture as much exhaled air as possible in the form of a cough, sneeze, or exhaled air breath. In cases when the user of the desktop monitor, laptop, other monitor type, or other device comprising an electronic display screen, is within 36 inches of the front of the monitor and looking at the monitor or computer screen, the monitor or laptop's exhaled air collector captures 90%+ of the cough, sneeze, or exhaled air breath of the user.

In some cases when the user of the desktop monitor, laptop, other monitor type, or other device comprising an electronic display screen, is within 36 inches of the front of the monitor and looking at the monitor or computer screen, the monitor or laptop's exhaled air collector captures 50%+ of the cough, sneeze, or exhaled air breath of the user. Thus, in embodiments, the exhaled air collector is shaped to have an open front, top and/or bottom, and two sides. The exhaled air collector further comprises an exhaled air blocking surface and one or more air suction intakes each located within the exhaled air collector, in embodiments. The exhaled air collector collects exhaled air in the form of an exhaled air breath, cough, sneeze, whistle, talking, or singing due first to the velocity and trajectory of the exhaled air (e.g., cough or sneeze) and second due to the suction forces coming from the exhaled air suction intake(s). The exhaled air collector stops, deflects, and catches the exhaled air prior to it moving into one or more air suction intakes.

In embodiments, the total required CFM (cubic feet per minute) of air suction and total CADR (clean air delivery rate) for an air capture and air cleaning system depends on the size of the display screen being used as the exhaled air blocking surface, the design of the exhaled air collector, and the distance of the individual exhaling from the exhaled air collector. The "total" CFM or "total" CADR is the total of all air suction CFM of a fan or fans pulling air through one or more exhaled air suction intakes. The "total" CADR is the total of all exiting air flow from one or more air purification chambers.

When an exhaled air blocking surface is "recessed" such that it is partially or fully surrounded by an exhaled air suction intake comprising an outer wall that is of a height dimension that is 1 micron or greater in height compared to the outer front surface of the electronic display screen (thus the reason it is sometimes referred to herein as a lipped outer wall), the total CFM and total CADR of such an air handling system embodiment can in many cases be between 20 CFM or more, with a CADR of 13 CADR or more. Such an exhaled air collector design can achieve an exhaled air capture rate for a breath, talk, or cough, of 90% or greater with an exhaled air cleaning level of 99%+. The noise level in decibels ("dB") of the fan(s) can be as low as 40 dB or less. The noise level dB of the fan(s) can be as low as 30 dB or less.

For air handling systems where the outer front exhaled air blocking surface is "planar" with the outer wall of an exhaled air suction intake, or where the outer front exhaled air blocking surface is in front of ("forward to") that of the exhaled air suction intake's outer wall(s), in most cases, but not all, the required total CFM air intake to achieve a 90%+ air capture rate for an exhaled breath or cough, with a 99%+ air cleaned level can in many cases be 25 CFM or more, with the total CADR of the exiting air flow out of an exhaled air purification chamber ranging between 16 CADR or more. The noise level dB of the fan(s) can be as low as 60 dB or less.

The precise CFM and CADR required to achieve a 90%+ exhaled air capture rate with a 99%+ cleaning depends upon, for example, 1) the size of the exhaled air blocking surface or the outer dimensions of the exhaled air collector, 2) the design of the exhaled air collector, 3) the distance from the individual whose exhaled air is being captured and cleaned, and 4) the type of exhaled air being captured and cleaned (meaning by way of example only, exhaled air breath, talk, cough, or sneeze). In embodiments, for a monitor the required CFM can range between 25 CFM and 150 CFM with a required CADR ranging between 16 CADR and 100 CADR. In embodiments for a laptop the required CFM can range between 40 CFM and 100 CFM with the required CADR ranging between 25 CADR and 70 CADR. In embodiments for a tablet the required CFM can range between 20 CFM and 75 CFM with the required CADR ranging between 13 CADR and 50 CADR. In embodiments for a TV the required CFM can range between 50 CFM and 250 CFM with the required CADR ranging between 33 CADR and 170 CADR.

In embodiments, the exhaled air collector can comprise an exhaled air blocking surface that is the front surface of the computer screen or monitor. The exhaled air blocking surface can be recessed. The exhaled air blocking surface can be planar at the same plane of the exhaled air collector's outer wall height. The exhaled air blocking surface can be forward to that of the exhaled air collector's outer wall height. The exhaled air blocking surface can be partially or fully surrounded by the exhaled air collector.

The exhaled air blocking surface can be located within the perimeter of the exhaled air collector. In embodiments, the recessed exhaled air blocking surface can be that of the display screen, monitor, computer screen, or other solid surface.

An exhaled air collector can comprise an open front. An exhaled air collector can comprise an exhaled air blocking surface. An exhaled air collector can comprise an exhaled air suction intake. An exhaled air collector can comprise an open front, exhaled air blocking surface, and an adjacent exhaled air suction intake. An exhaled air collector can comprise an open front, exhaled air blocking surface, and a remote distant separated exhaled air suction intake. An exhaled air collector can comprise an open front, exhaled air blocking surface, an exhaled air catch basin, and an exhaled air suction intake.

One or more exhaled air suction intake(s) can be located outside of the exhaled air blocking surface. One or more exhaled air suction intake(s) can be located below the exhaled air blocking surface. An exhaled air suction intake can open to a conduit connecting an exhaled air purification chamber. An exhaled air suction intake can open to an exhaled air purification chamber. An exhaled air suction intake can connect to an exhaled air purification chamber.

An exhaled air purification chamber can be directly connected to an exhaled air collector. An exhaled air purification chamber can be indirectly connected to an exhaled air collector by way of a conduit. An exhaled air purification chamber can be distant separated from an exhaled air collector but connected to an air suction intake.

In other embodiments the air intake side of the exhaled air purification chamber can fill a portion, or all, of one or more of the top, the side, the bottom, and/or the back of the exhaled air collector. The way the exhaled air collector, the exhaled air purification chamber, and/or that of the exhaled air purification unit are designed can depend upon the venue to which it is being utilized. An exhaled air intake can mean the same as an air suction intake. The form of an exhaled air suction intake can be of any shape, by way of example only, rectangular, square, round, oval, polygonal, hexagonal, and so forth. In some embodiments a plurality of small apertures form air suction intakes. In some embodiments there are multiple air suction intakes. In other embodiments there is only one exhaled air suction intake.

As used herein an indoor room can be that of an indoor venue. As used herein an indoor room can be that of an indoor room within a building of any kind or vehicle of any kind (including aircraft). As used herein a desk and table can have the same meaning. As used herein a desktop and tabletop can have the same meaning. As used herein a desk and table can be that of a chair, a seat, or a bench that comprises a desk-like attachment. As used herein a desk and table can be that of chair, seat or bench that comprises a writing ledge attachment. As used herein a desk and table can be that of chair, seat, or bench that comprises an attached or integrated horizontal work surface. While in embodiments an individual is sitting or standing in front of an air purification unit resting on a desk or a table, the invention disclosure herein covers that of an individual standing in front of a standing desk or table that further supports a computer, by way of example only, a tablet, a laptop, a desktop, or a TV.

Exhaled air can be that of, by way of example only, an exhaled air breath, cough, sneeze, scream, talk, or whistle.

As used herein an airborne particulate can be that of, but is not limited to, a microbe, virus, bacteria, fungus, pathogen, pollutant, or contaminant.

As used herein the word capture can mean collect and the word collect can mean capture.

As used herein a pathogen can include bacteria, fungi, protozoa, worms, viruses, microbe, and even infectious proteins called prions. As used herein, "seat," "chair," "bench," and "sitting apparatus," have the same meaning and can be used interchangeably. As used herein the word "clean" or variations thereof can have the same meaning as purify. Clean air can mean the same as cleaned air. Cleaned air can be that of filtered air. Cleaned air can be that of purified air. Cleaned air can be that of sterilized air. The words purify and/or clean can imply that of partially cleaned, partially purified, or fully cleaned and fully purified. As used herein an exhaled air purifier can mean the same thing as an exhaled air purification chamber. As used herein an exhaled air purification chamber can mean the same thing as an exhaled air cleaning chamber. As used herein an air purification chamber can mean the same thing as an exhaled air purification chamber. When using the word integrated it is meant to be part of or designed in or built in, in examples. When using the words retrofit it is meant to be added on or attached post sale or post fabrication. Retrofit can mean attaching or connecting to an existing product, such as an existing table, desk, chair, electronic display screen, or computer.

Such exhaled air cleaning/purification can occur by way of one or more of filtration, chemical microbicidal purification, light microbicidal purification (such as, by way of example only, UVC light), radiation microbicidal purification, mechanical microbicidal purification, thermal microbicidal purification, acoustic microbicidal purification, microbicidal agents, or microbicidal materials. Filtration can be by way of any filtration device or member such as, by way of example only, a HEPA filter.

A filter can employ a microbicidal or anti-microbial agent. In embodiments, when exhaled air is collected and cleaned or purified, air from the room and/or venue is also mixed with the collected exhaled air. Room air can mean the same as ambient room air. In embodiments, an exhaled air purification unit comprises both an exhaled air collector and an exhaled air purification chamber. In embodiments, a traditional or conventional air purifier comprises one or more air suction intakes and an air purification chamber. In embodiments, a traditional or conventional air purifier is devoid of an open front exhaled air collector. In embodiments, a traditional or conventional air purifier is devoid of an exhaled air collector and an exhaled air blocking surface. In embodiments, when attaching a traditional or conventional air purifier to one or more of a monitor, a monitor stand, a laptop, a computer, or a tablet, where the combination provides for an exhaled air blocking surface (e.g., the electronic display screen) the combination of the exhaled air blocking surface plus that of the conventional or traditional air purifier becomes that of an air purification unit.

An exhaled air purification system can comprise a plurality of exhaled air purification units. Thus, when using the terms exhaled air collector, exhaled air purification chamber, or exhaled air purification unit, it is understood that the exhaled air collector, exhaled air purification chamber, and exhaled air purification unit can be handling and processing both exhaled air and that of the indoor venue's room air.

As used herein in certain embodiments, an exhaled air purification unit can comprise an exhaled air collector that partially or fully surrounds an exhaled air blocking surface and an integrated or attached exhaled air purification chamber. In certain embodiments an exhaled air purification unit comprises an exhaled air collector that partially or fully surrounds an exhaled air blocking surface and a separated and distant removed exhaled air purification chamber.

A separated and distance removed exhaled air purification chamber can comprise an exhaled air suction intake located in front, on top of, or adjacent to the where exhaled air is pulled into a chamber or space comprising a filter and/or microbicidal purification system/mechanism. The exhaled air suction intake can be covered by a screen, grate or other such member that comprises a plurality of small apertures.

In embodiments an exhaled air purification system can comprise an exhaled collector that partially or fully surrounds an exhaled air blocking surface and an attached or distance separated conventional air purifier. The conventional air purifier comprising an air suction intake and an air purification chamber.

An electronic display screen, computer screen, computer display screen, video display screen, or monitor screen can all have the same meaning. A monitor can be that of a display screen. A computer screen can be an electronic display screen. A monitor can be that of the display screen plus all enabling electronic components and the housing. As used herein someone that is sitting or standing "in front" of an exhaled air purification unit is that of someone sitting or standing at a table as depicted in the figures included with this invention disclosure.

An electronic display screen can be recessed if 1 or more of the 4 sides has a height that is higher than that of the outer front surface of the electronic display screen. An electronic display screen can be an exhaled air blocking surface. When 1 or more of the 4 sides of the electronic display screen is higher than (thus superior to or said another way forward to) the outer front surface of the electronic display screen (the exhaled air blocking surface) is referred to as a recessed exhaled air blocking surface. An exhaled air blocking surface can be flat for a monitor having a flat electronic display screen. An exhaled air blocking surface can be curved for a monitor having a curved electronic display screen.

An attached or integrated exhaled air collector can be curved so as to partially or fully align with a curved electronic display screen. An attached or integrated exhaled air catch basin can be curved so as to partially or fully align with a curved electronic display screen. An attached or integrated exhaled air suction intake can be curved so as to partially or fully align with a curved electronic display screen. An attached or integrated exhaled air purification chamber can be curved so as to partially or fully align with the curved electronic display screen. An attached or integrated conventional air purifier can be curved so as to partially or fully align with a curved electronic display screen.

As used herein someone sitting behind a chair, seat, or bench is sitting in the chair, seat, or bench behind that of the chair, seat, or bench that is in front thereof. As used herein the back of a chair, seat, or bench can be the back of the backrest and/or headrest of the chair, seat, or bench.

And as used herein a computer screen can be the screen used with by way of example only one of a monitor, desktop computer, laptop computer, tablet computer, cellphone, mobile phone, or TV. As used herein a computer screen is that of any electronic display screen that involves an associated computer chip. In certain embodiments the computer screen or display screen can be supported by a support member(s) that is attached to the computer screen.

An air suction conduit that connects the exhaled air collector to an air purification chamber can bifurcate into two or more conduits that travel across a right side and a left side of the support member, by way of example. In embodiments when a monitor is integrated with an exhaled air collector and an exhaled air purification chamber, the backside of the computer screen forms one side of an air suction conduit or air flow opening, and the inside side of the back covering of the screen or monitor forms the opposite side of the air suction conduit or air flow opening. In this example the air suction conduit or air flow opening is located within the monitor. With embodiments, such as this, the exhaled air purification chamber is located within the back covering of the monitor (see, e.g., FIGS. 11-12). In embodiments a filter (by way of example only) a HEPA filter is located on the inside side of the back monitor covering and a fan (or fans) are located on the backside side of the back monitor covering. In other embodiments a filter, such as a HEPA filter, and a fan (or fans) are located on the backside side of the back monitor covering (see, e.g., FIGS. 11-12). Air flowing from the air suction intake(s) travels through an open space (air flow opening) or conduit around the display screen or within the monitor covering towards the air purification chamber (see, e.g., FIGS. 11-12). Upon reaching an exhaled air purification chamber portion the air is pulled through a filter, and then through the fan or fans, where it is released into the room's ambient air environment as 99%+ cleaned air.

When a compartment comprising the air filter and fan (or fans) are attached to the back of a monitor or located adjacent to the back of the monitor, the area to which they are attached to or located adjacent to is referred to as the exhaled air purification chamber. The open space to which the air flows from the air suction intake to the exhaled air purification chamber is referred to as an exhaled air suction conduit. The exhaled air suction conduit can be an open space formed between the back of the electronic display and the inside front of the back cover. This open space can be referred to as a channel or a conduit. And can also be referred to as an open space for air flow. The air suction can be provided by a fan or fans located within the open space or conduit. The air suction can be provided by a fan or fans located within or adjacent to the exhaled air purification chamber. The air suction can be provided by a fan or fans on the back side of the exhaled air purification chamber. The air suction can be provided by a fan or fans on the back side monitor cover. The air suction can be provided by a fan or fans within the air flow open space between the back of the electronic display and the inside back of the monitor cover. The air flow open space can be created by attaching a spaced exhaled air collector to the back of a monitor, back of the laptop display screen, back of the tablet, back of a TV, and so on. Such an attachment can be accomplished, by way of example only, by a one adhesive pad or two attracting adhesive pads having a defined thickness, by a magnet or two attracting magnets having a defined thickness, by two connecting Velcro pieces having defined thickness, and so on. Such attachment means provide for not only attaching the exhaled air collector to the back of the monitor, back of the laptop display screen, or back of the tablet, but also provide the proper open space therebetween allowing for the appropriate air flow from the air suction intake(s) to the exhaled air purification chamber(s).

FIG. 27 shows the back of a having an exhaled air collector and air purification chamber. In this embodiment, a front side of the monitor/electronic display screen outer surface can act as an exhaled air blocking surface that can stop or slow down a velocity of respiratory particles so that air suction from one or more air suction intakes and/or an air purification chamber can capture and clean the exhaled air flow, as well as some of the mixed in room air. FIG. 27 also shows an air purification chamber 2701 on the back of a monitor 2702 having two fans 2703 and two HEPA filters 2704. FIG. 27 also shows a universal attachable stand that permits multi-angle and height adjustment 2705. FIG. 28 is similar to FIG. 27, but instead of having one air purification chamber with two fans, it shows the back of the monitor having three air purification chambers 2801, each with its own fan 2802 and HEPA filter(s) 2803. FIG. 29 is similar, but the back of the monitor only has one air purification chamber 2901 with its own fan 2902 and HEPA filter(s) 2903.

In embodiments a port is located within the back cover of the monitor. This port can connect to an exhaled air purification chamber. Such an exhaled air purification chamber can be directly attached to the port or indirectly attached to the port by way of an exhaled air suction conduit.

When a filter is located within the back of the monitor the fan or fans can be attached to the back of the monitor by way of example only, any mechanical means, magnetic, or an adhesive. The exhaled air purification chamber can be sealed to provide an air resistant seal when connected to the back of the monitor or electronic display screen. In embodiments the air purification chamber comprises a filter or filters and a fan or fans. In embodiments a UV light is located within the exhaled air purification chamber and utilized for a period of time prior to removing the filter(s) to sanitize the filter or filters. The air purification chamber can employ any microbicidal chemical, mechanical, thermal, acoustic, light, radiation, or filtering means. The air purification chamber can employ one or multiple filters. The filters can be, by way of example only, a carbon prefilter or HEPA filter. The air purification chamber can be sealed to provide an airtight seal when connected to the back of the monitor or electronic display screen. In embodiments, the air purification chamber comprises a filter or filters and a fan or fans. In aspects, while the fan or fans and a filter are located on or adjacent to the back of the electronic display screen or monitor, the air purification portion can be located at the top, bottom, sides, back, or any combination thereof. In embodiments the fan or fans are attached in a hinged compartment that can be lowered or raised allowing for the filter (e.g., HEPA filter or carbon filter) to be changed/replaced. Upon replacing the filter (s) the compartment or member can be closed and secured by a locking mechanical such as by way of example only, one or more of a mechanical catch, snap, magnet, or hook. This hinged compartment can comprise an airtight or air resistant seal. The compartment comprising the filter can be releasably attached to the monitor, monitor cover, electronic display screen, or monitor support.

In embodiments the monitor, computer screen, or display screen can be supported by an exhaled air purification chamber or a conventional air purifier that is attached to the monitor. In embodiment the electronic display screen or computer screen is integrated with an exhaled air collector and connected to an exhaled air purification chamber.

As used herein the abbreviation CADR is basically a reflection of the air flow (CFM—cubic feet per minute) times the efficiency of the air filter. So, if, for example only, an air filter has 100 cfm and 100% efficiency the CADR would be 100. If, for example only, the exhaled air purification chamber has a 75% efficiency rate the CADR would be 75. As used herein CFM means cubic feet per minute of air flow. CADR means clean air delivery rate out of the exhaled air purification chamber(s). CFM is the air suction in cubic feet per minute into the air suction intake(s).

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention.

FIG. 31 is an illustration of an embodiment of the current invention as described herein.

FIGS. 86A and 86B are illustrations of embodiments of the current invention as described herein.

FIGS. 87A and 87B are illustrations of embodiments of the current invention as described herein.

DETAILED DESCRIPTION OF THE INVENTION

Figure 1:
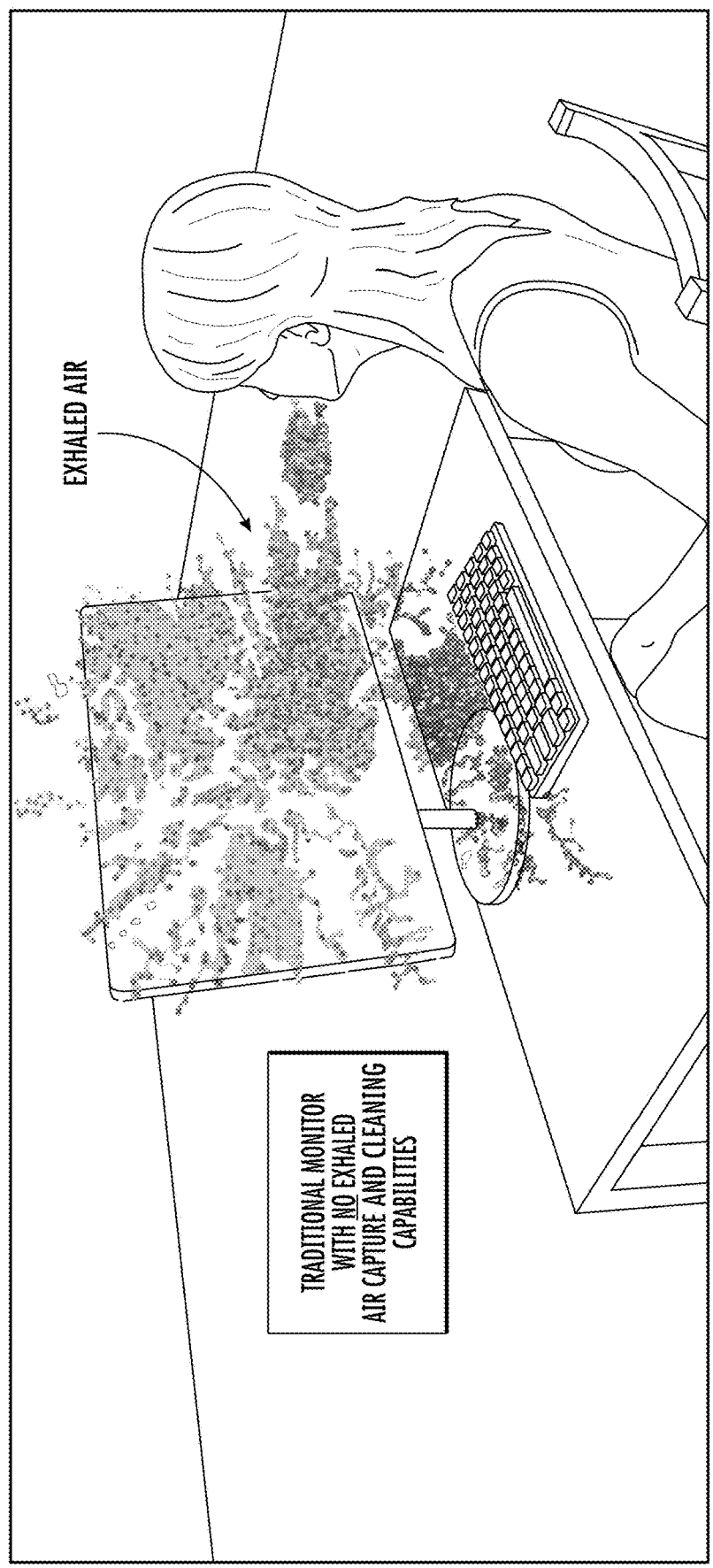
FIG. 1 is an illustration showing a computer model of a cough towards a traditional computer monitor without the invention described herein.
Figure 2:
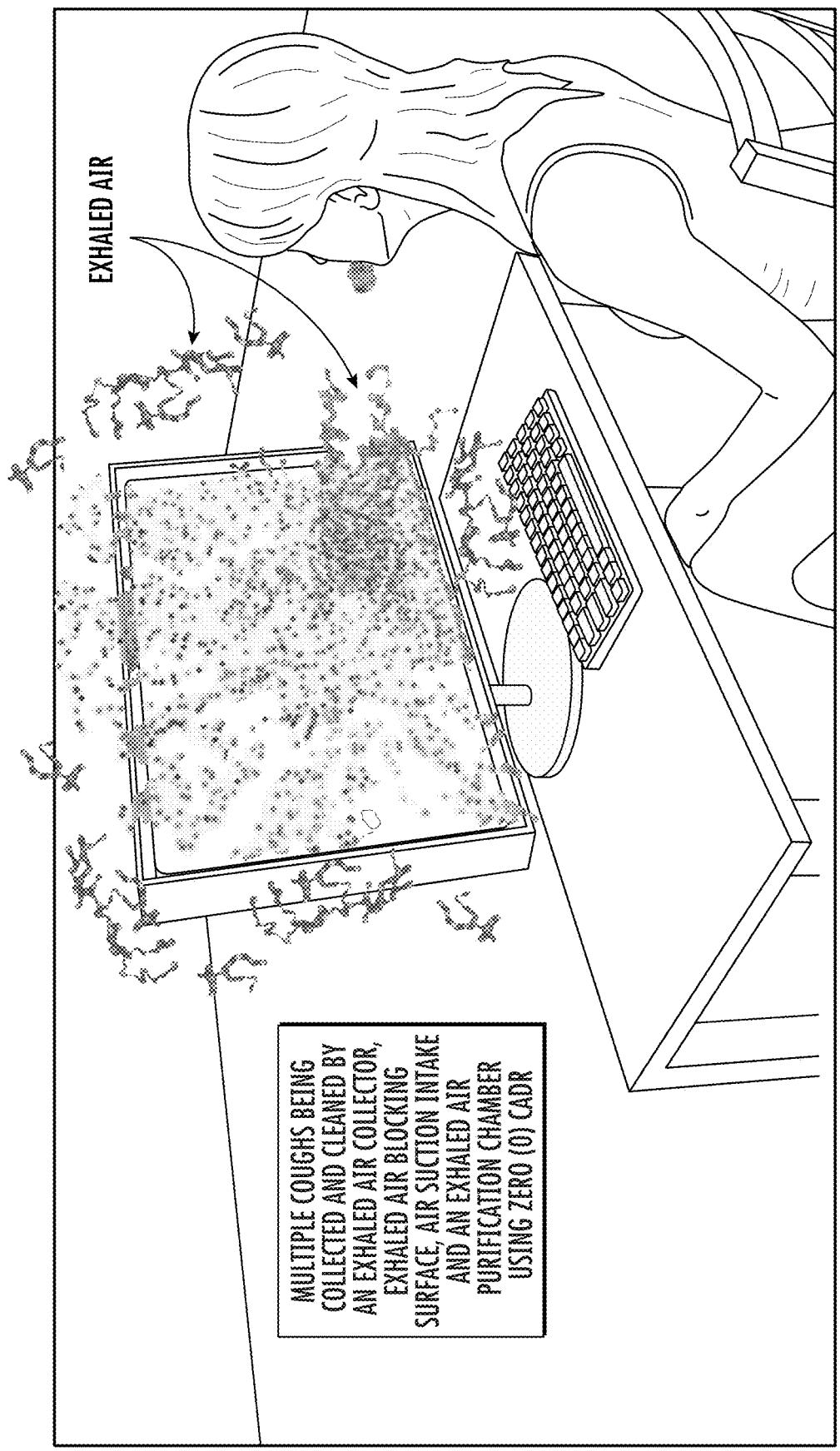
FIG. 2 is a computer-modeled illustration of an embodiment according to the current invention but with 0 CADR.
Figure 3:
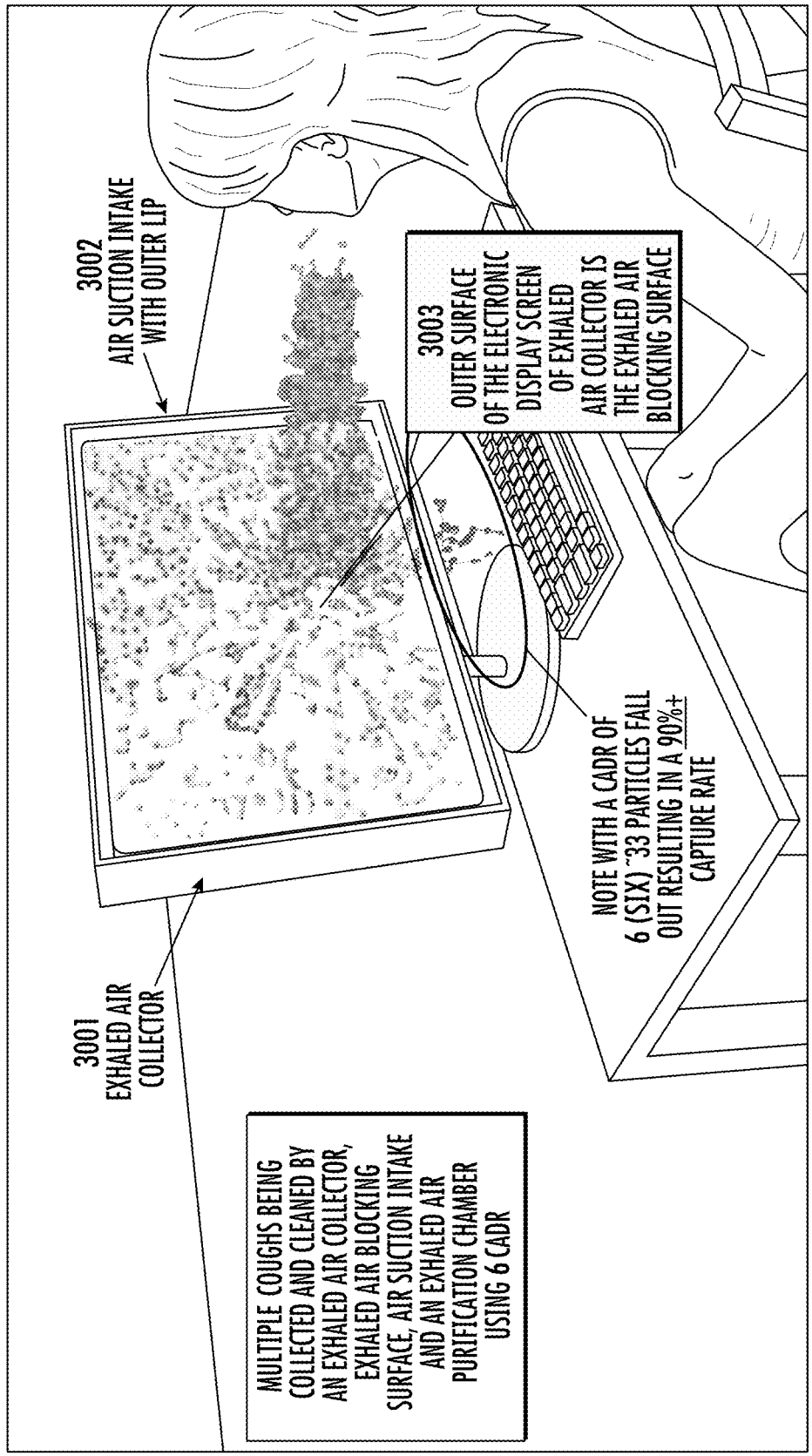
FIG. 3 is an illustration of an embodiment according to the current invention showing a computer modeling.
Figure 4:
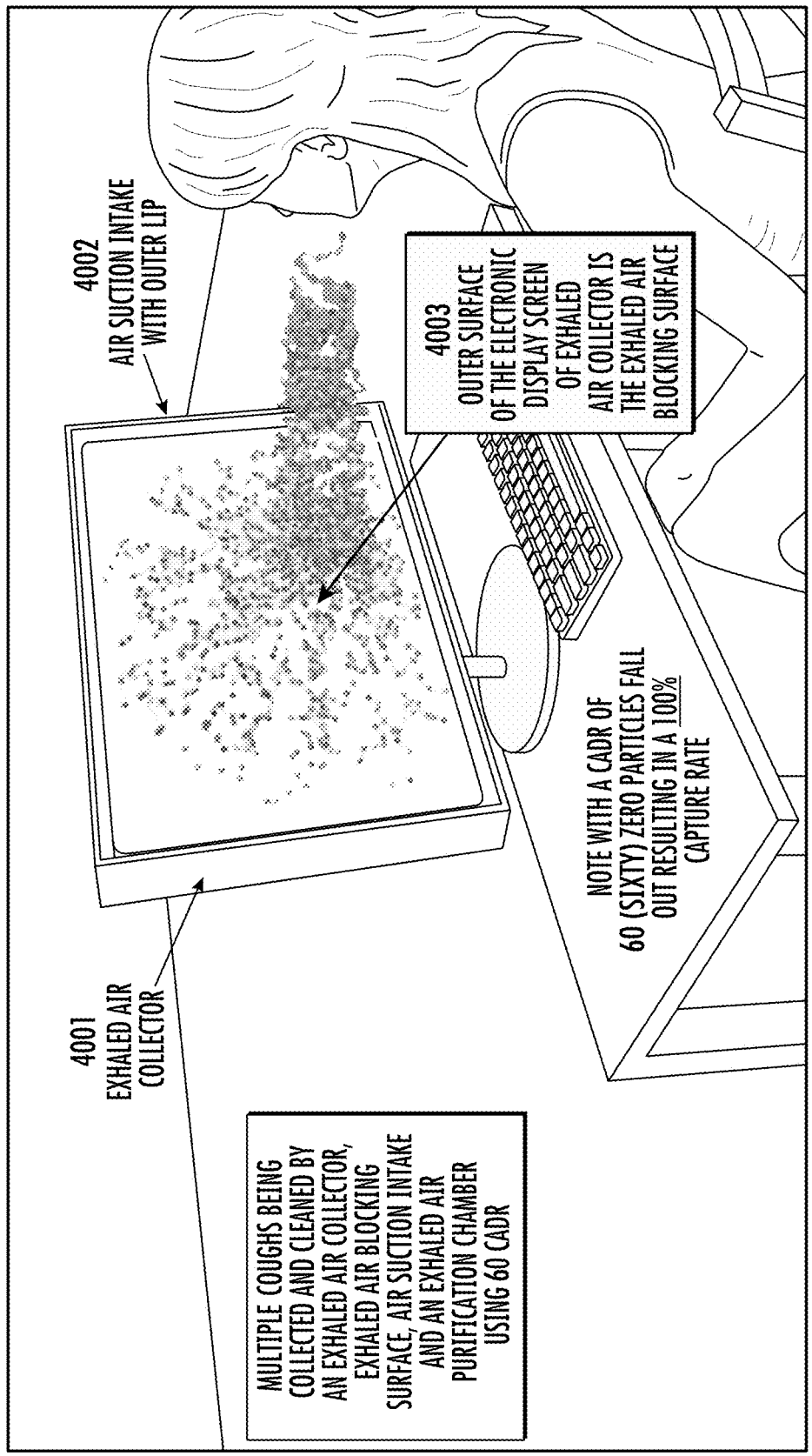
FIG. 4 is an illustration of an embodiment according to the current invention showing a computer modeling.
Figure 5:
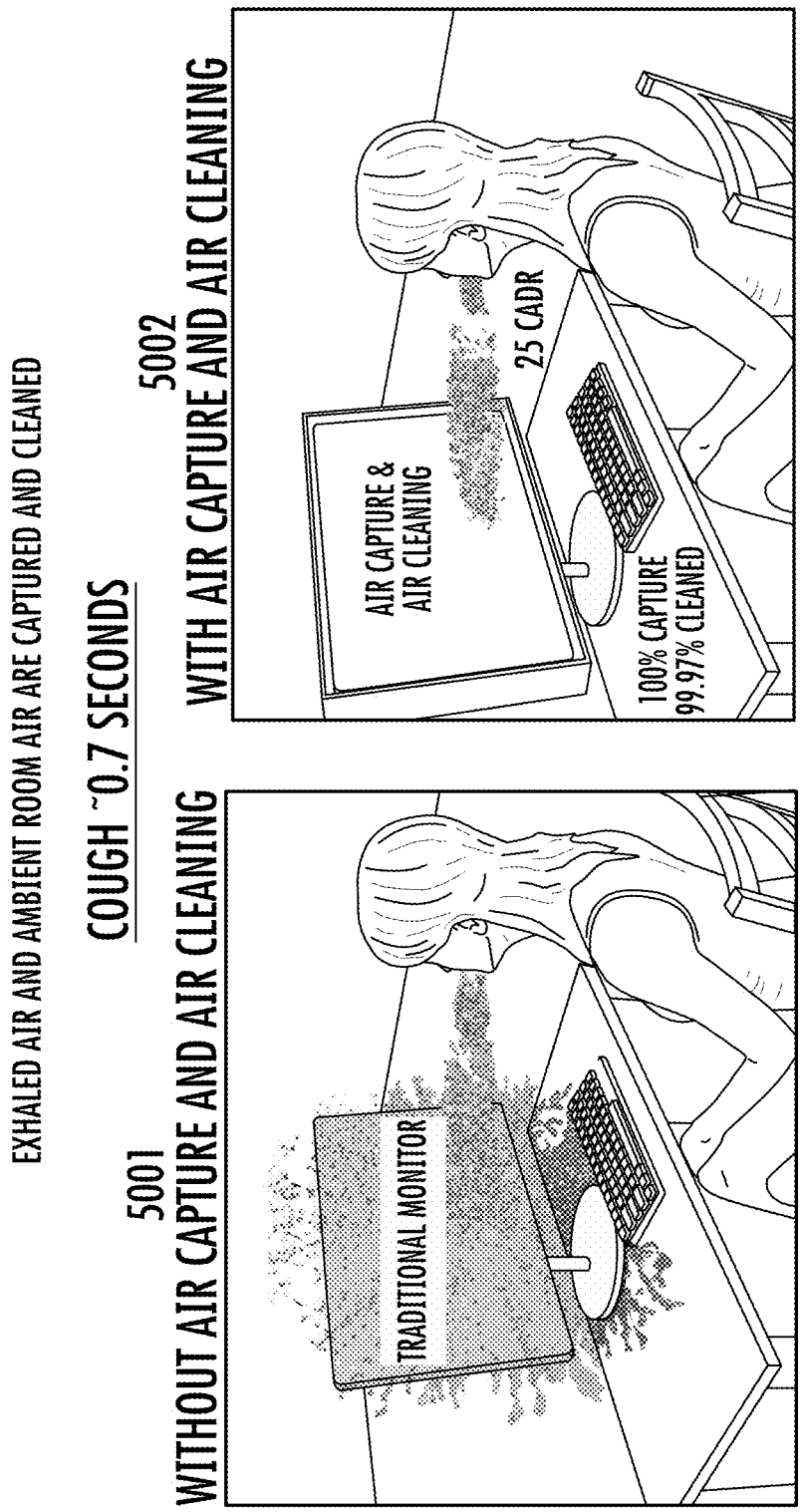
FIG. 5 is an illustration of an embodiment according to the current invention showing a computer modeling.
Figure 6:
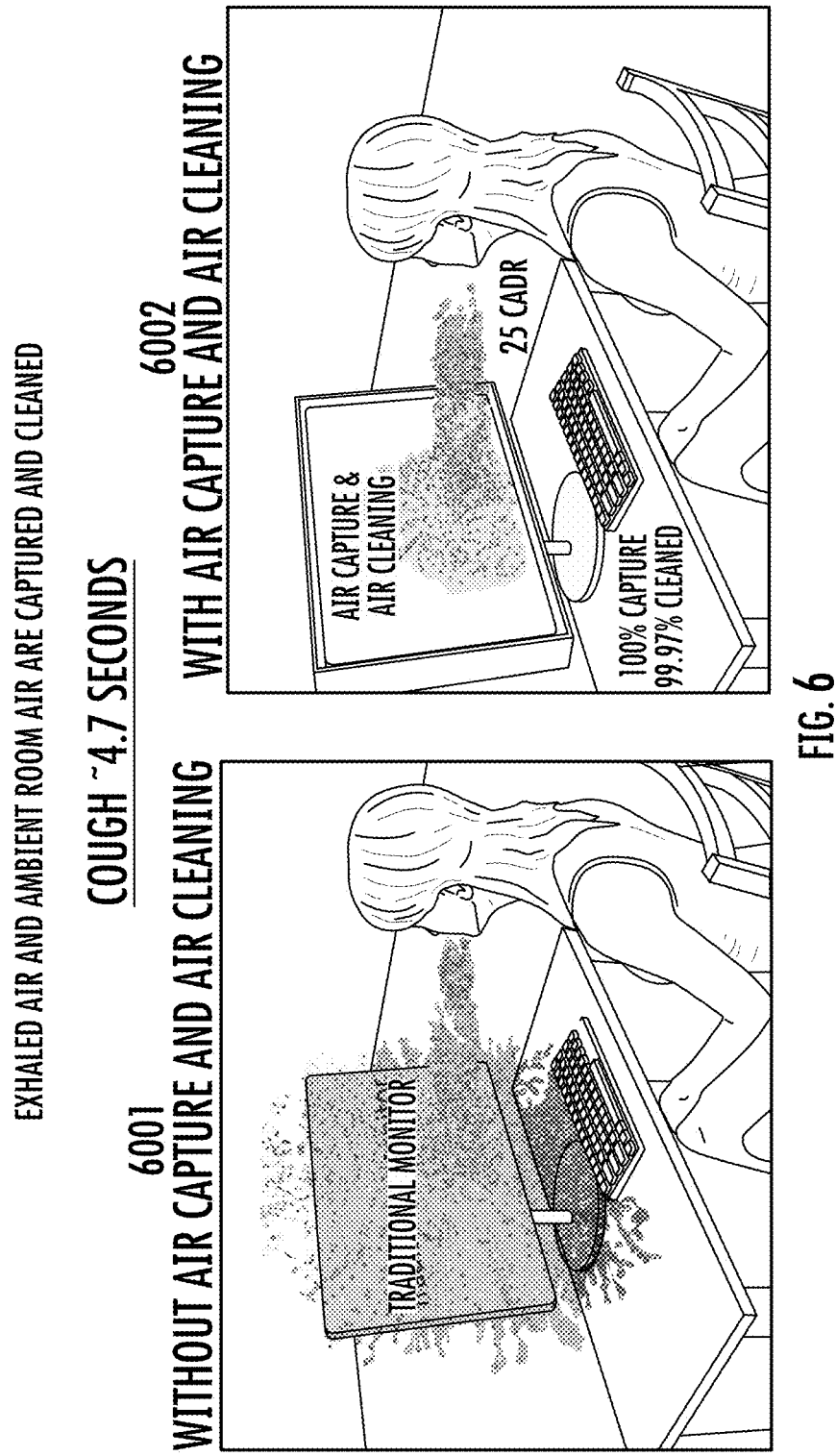
FIG. 6 is an illustration of an embodiment according to the current invention showing a computer modeling.
Figure 7:
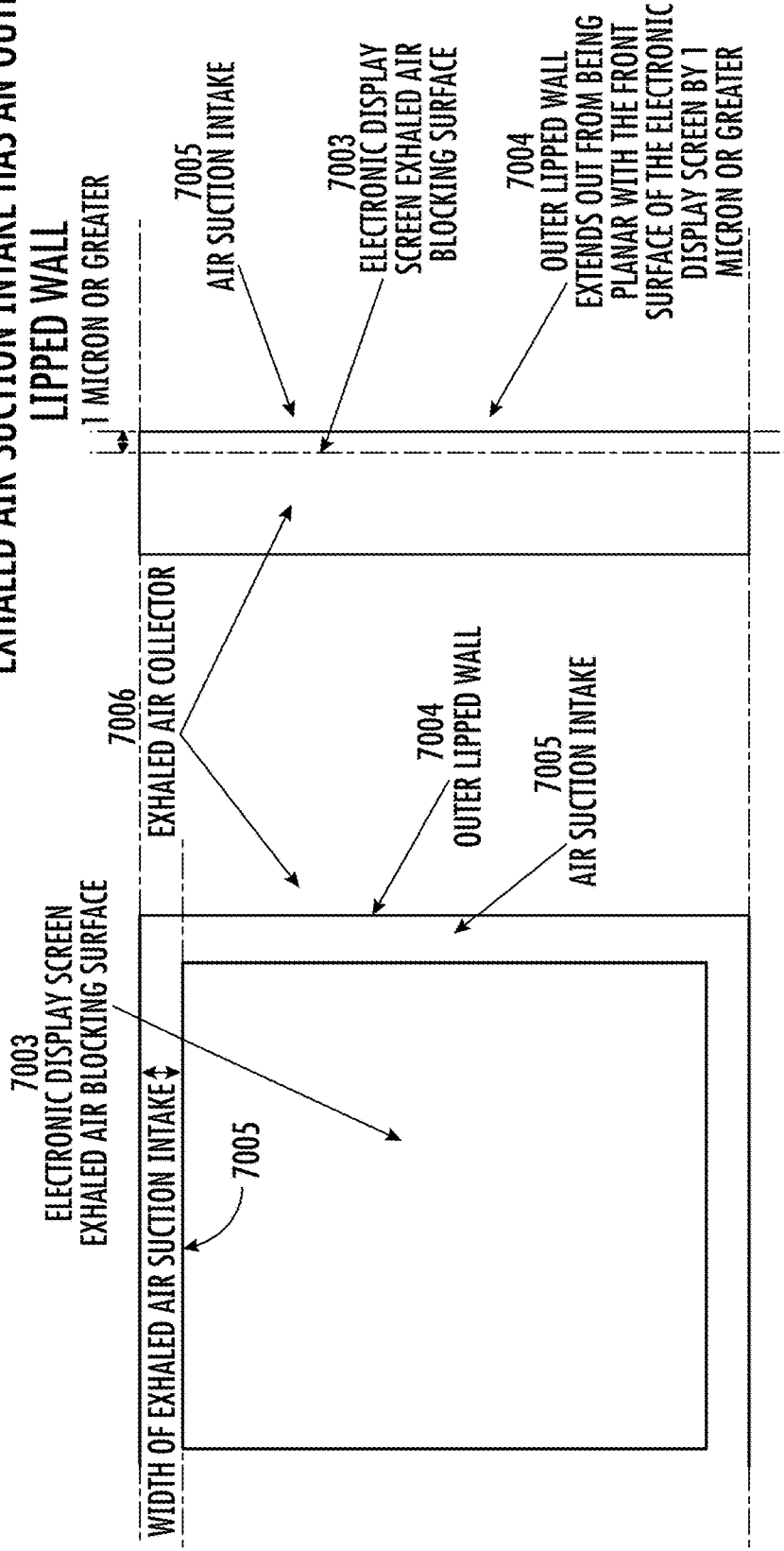
FIG. 7 is an illustration of an embodiment(s) of the current invention as described herein.
Figure 8:
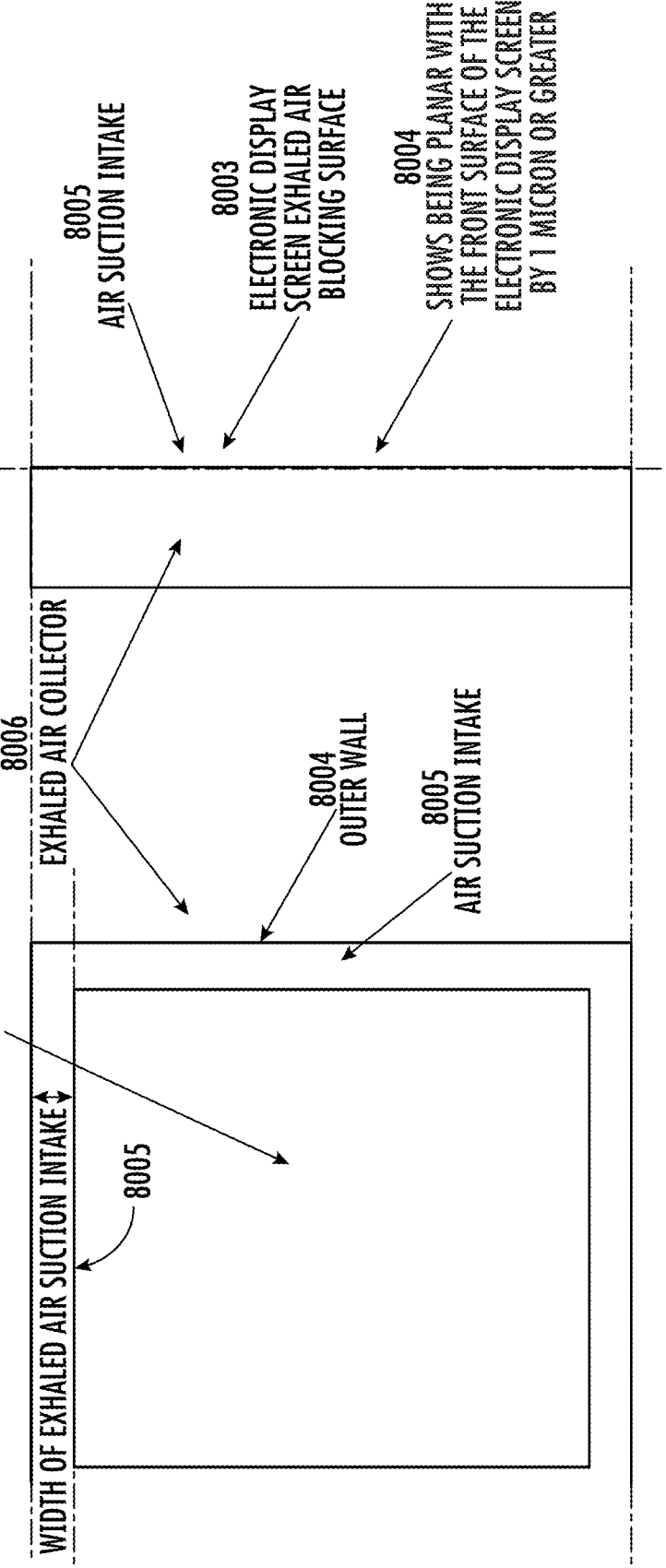
FIG. 8 is an illustration of an embodiment(s) of the current invention as described herein.
Figure 9:
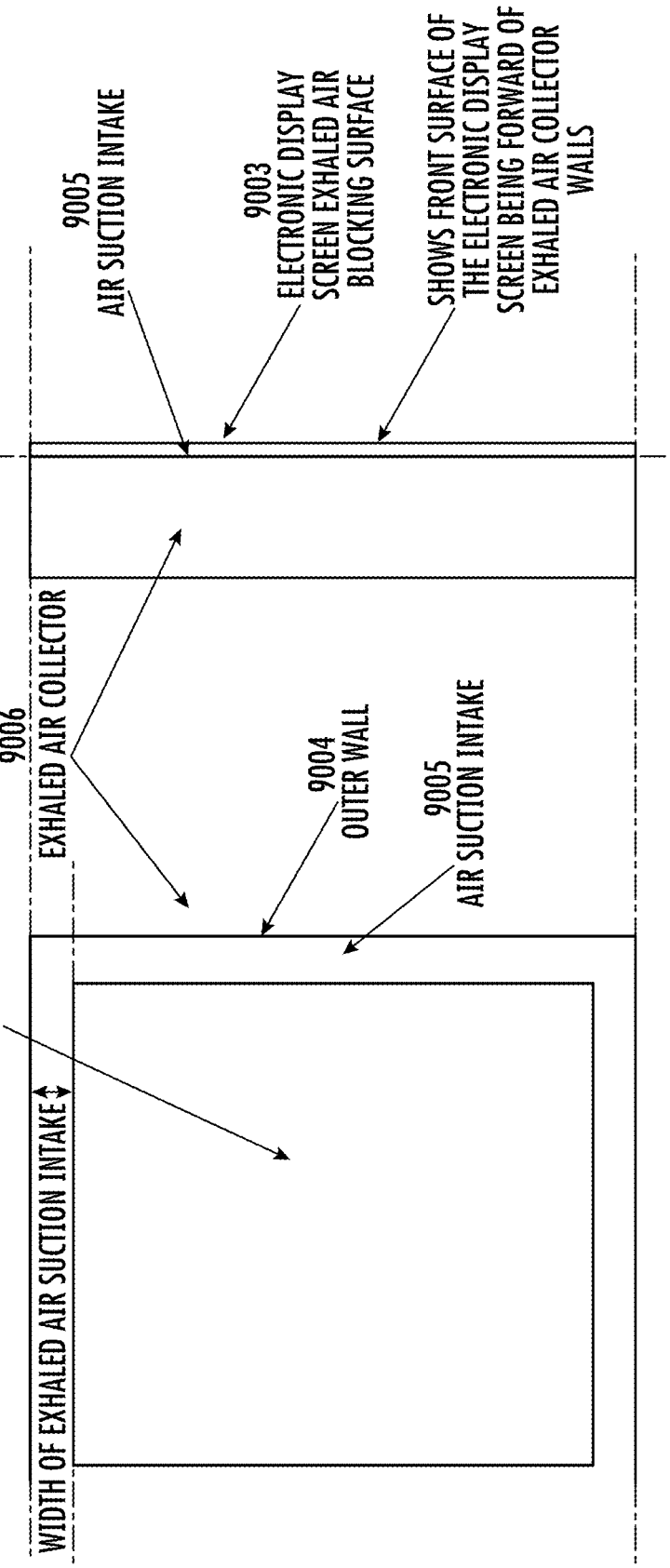
FIG. 9 is an illustration of an embodiment(s) of the current invention as described herein.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

An embodiment of the invention is that of a computer screen, monitor, or electronic display screen (used interchangeably herein), wherein the computer screen, monitor, or electronic display screen, in addition to displaying one or more of images, words, and/or data, makes up a portion of an exhaled air collector, and wherein the exhaled all collector collects exhaled air, and wherein the electronic display screen can one or more of: block, deflect, and direct, exhaled air towards an exhaled air suction intake. An embodiment is that of a monitor, laptop, tablet, TV, or other computer device that comprises an exhaled air collector, electronic display screen which acts as an exhaled air blocking surface, at least one or more air suction intake(s), and an air purification chamber(s). The enabled computer device can capture exhaled air and ambient room air, clean and/or purify the exhaled air and ambient room air and release the cleaned air back into the indoor venue or room.

The exhaled air collector can comprise one or more air suction intake(s). The exhaled air collector can comprise an exhaled air blocking surface. The exhaled air blocking surface can be planar in comparison to the perimeter of the exhaled air collector. The exhaled air collector can be planar on its front. The exhaled air collector can comprise and open front. The monitor front surface perimeter can form the open front surface of the exhaled air collector. The exhaled air collector can partially or fully surround an exhaled air blocking surface. When stating that the exhaled air collector comprises a planar front it is meant that an imaginary line pulled across the open front of the exhaled air blocking surface would be mostly a straight line from left to right or top to bottom. When stating that the exhaled air collector comprises a forward exhaled air blocking surface it is meant that an imaginary line pulled across the open front of the exhaled air blocking surface would be forward that of the walls of the exhaled air collector. When the exhaled air collector comprises a recessed exhaled air blocking surface, a mostly straight imaginary line cannot be positioned across the front of the exhaled air collector. In fact, the imaginary straight line if drawn from left to right or top to bottom would not touch the surface of a recessed exhaled air blocking surface. Depending upon the tilt of the monitor, the exhaled air blocking surface can be within a 45-degree arc to being perpendicular to the floor. The exhaled air blocking surface can be perpendicular to the floor. In embodiments the monitor can be a curved monitor. When the front of a curved monitor forms or portion of the open front of the exhaled air collector the exhaled air blocking surface can be curved.

In embodiments a first exhaled air blocking surface can be in front of a second exhaled air blocking surface. In embodiments the exhaled air blocking surface is not recessed but is forward of the open front of the exhaled air collector. In still other embodiments the exhaled blocking surface is planar with the open front of the exhaled air collector.

An electronic display screen can act as an exhaled air blocking surface for (exhaled air) such as, by way of example only, an exhaled air breath, talk, cough, or sneeze, blocking the stream of exhaled air along the Z-axis from the individual exhaling air and deflecting it (along with other various respiratory particles) towards one or more air suction intakes. In embodiments an exhaled air suction intake is located at one of beneath the bottom edge, bottom front edge, or bottom back edge, of a computer screen or monitor.

In other embodiments an air suction intake is at the bottom of the computer screen (or monitor), at the right side of the computer screen (or monitor), at the left side of the computer screen (or monitor), at the bottom of the computer screen (or monitor), or any combination thereof. The exhaled air suction intake(s) (by way of example only) can be located on the side edges, on the front side in the periphery, between the electronic display screen and the monitor frame, within the frame surrounding the electronic display screen, or any location peripheral to the electronic display screen. One or more exhaled air suction intakes can be located within the frame that surrounds the monitor. One or more exhaled air suction intakes can be located within the monitor cover that covers part or all sides and all the back of the electronic display screen.

The exhaled air suction intake can be located within the bottom ⅓ of the exhaled air collector. In other cases, the exhaled air suction intake can be located around the perimeter of the computer screen or computer monitor (which can be that of a desktop, laptop, or tablet). In still other cases, four exhaled air suction intakes are located such that one is on the front bottom, one at the front bottom, and one on each front side, adjacent to the screen or to the monitor housing. The multiple exhaled air suction intakes can be separated from each other. The multiple exhaled air suction intakes can be connected to each other. In still other cases four exhaled air suction intakes are located such that one is on the front bottom, one is on the top, and one is on each of the two sides of the screen or monitor housing. In still other embodiments three exhaled air suction intakes are located such that one is on the front bottom, and one is on each of the front of both sides adjacent to the screen or to the monitor housing. One or more exhaled air suction intakes can be located within the frame that surrounds the monitor. One or more exhaled air suction intakes can be located within the monitor cover that covers part or all the sides and back of the electronic display screen. In embodiments one exhaled air suction intake can be located beneath the computer screen or monitor. In other embodiments multiple exhaled air suction intakes can be located beneath but attached to the computer screen or monitor. In other embodiments multiple exhaled air suction intakes can be located beneath but distance separated from the computer screen or monitor.

The front opening of one or more exhaled air suction intake(s) (also referred to as an air intake(s) herein) can be planar with the outer front surface of the electronic display screen, slightly behind the outer front surface of the electronic display screen, behind the outer front surface of the electronic display screen, or in front of the outer front surface of the electronic display screen. The outer front surface of an electronic display screen can act as an exhaled air blocking surface which deflects and/or directs exhaled air towards one or more air suction intake(s). Such an exhaled air blocking surface is important when capturing the cone of exhaled air for an exhaled air breath, and even more important for capturing exhaled air from talking, whistling, singing, and when capturing some or all of the exhaled air from a sneeze or a cough.

Figure 30:
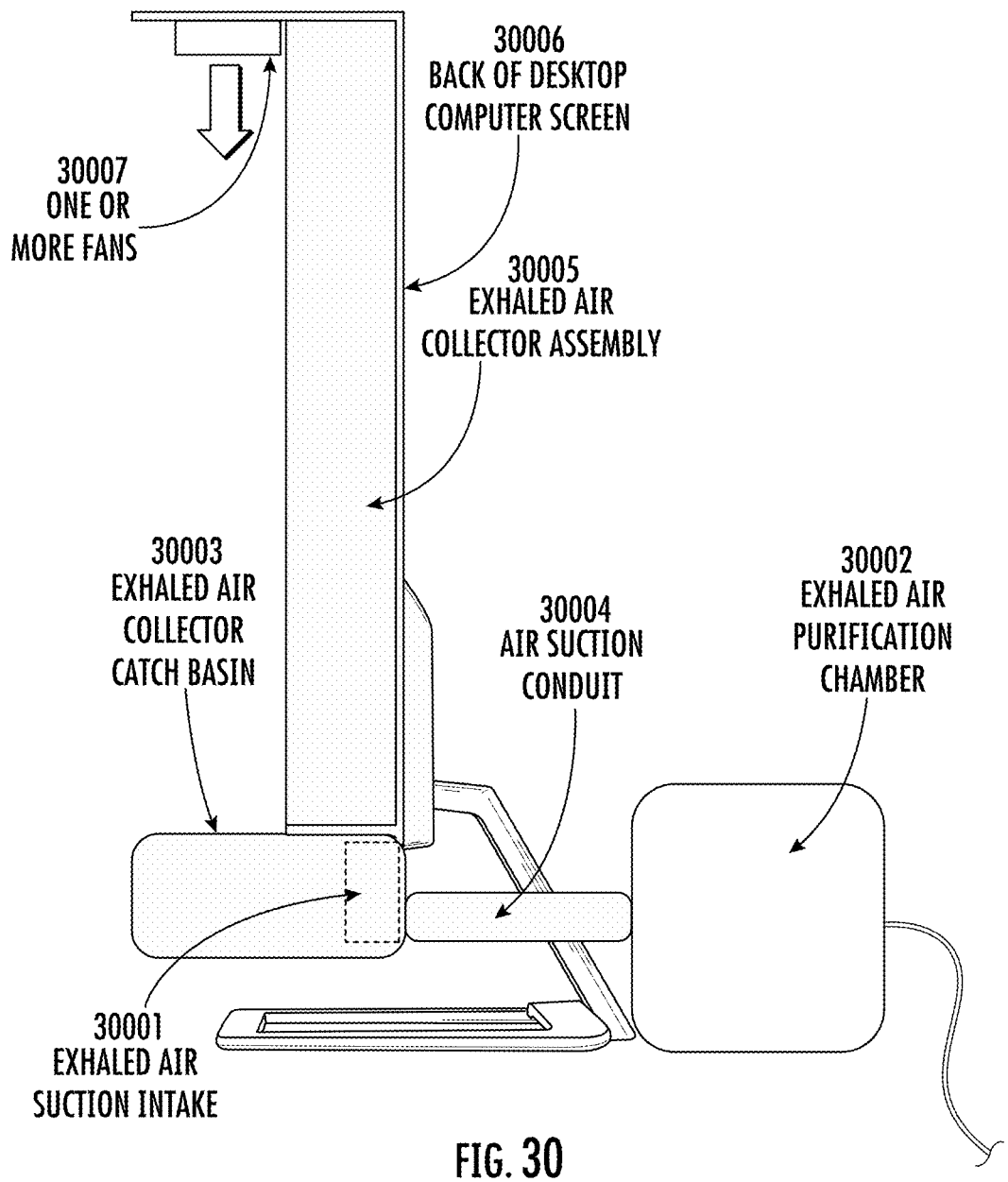
FIG. 30 is an illustration of an embodiment of the current invention as described herein.
Figure 32:
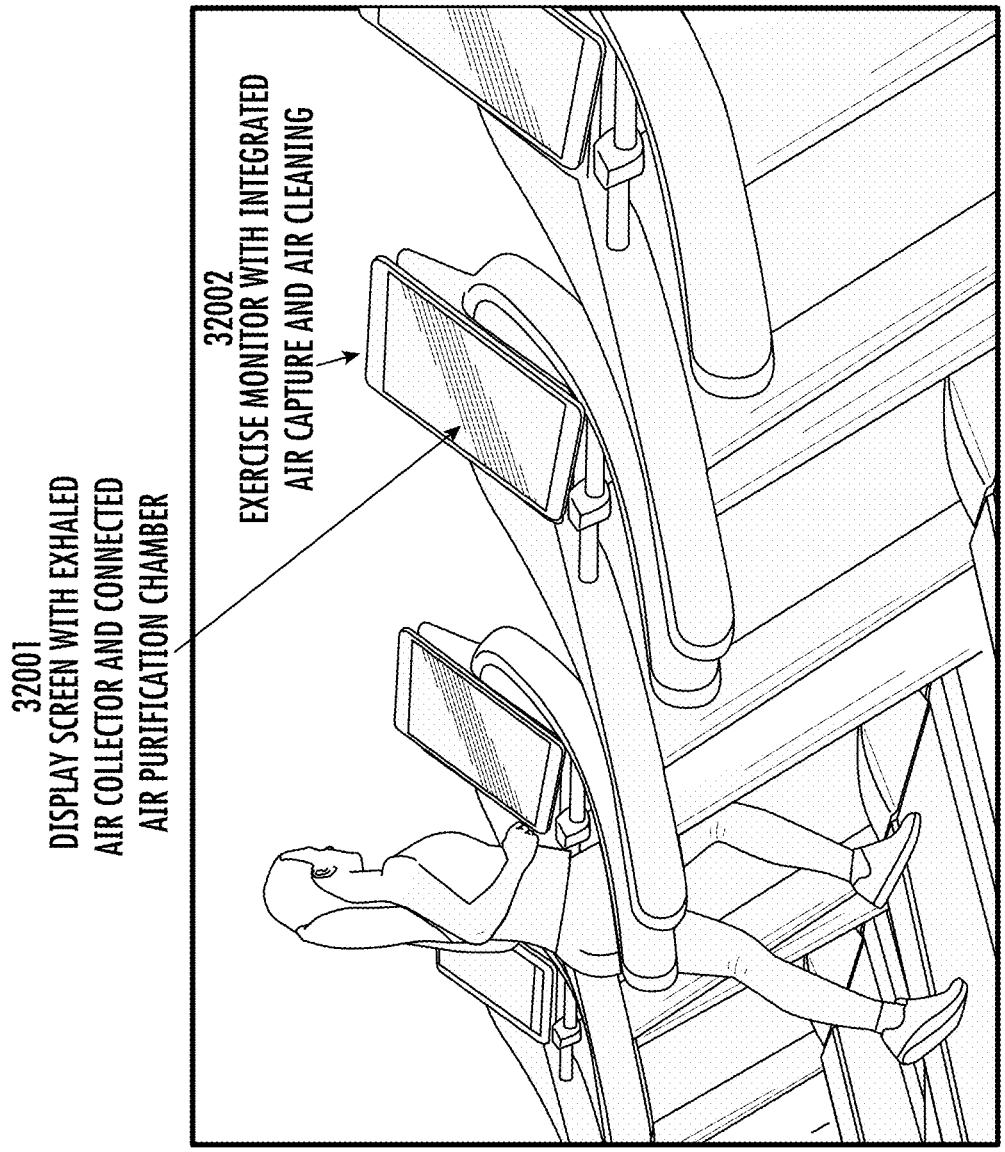
FIG. 32 is an illustration of an embodiment of the current invention as described herein.
Figure 33:
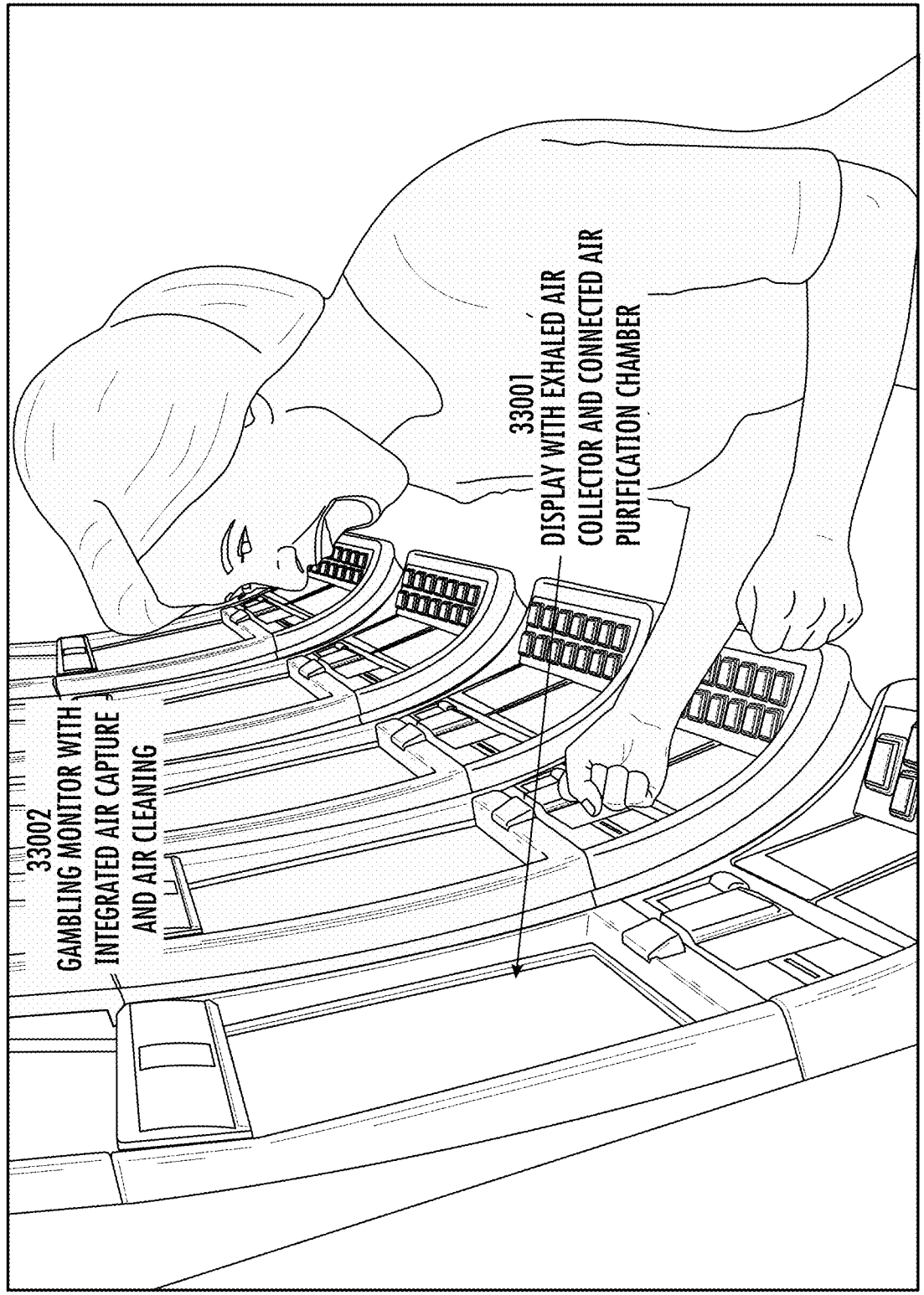
FIG. 33 is an illustration of an embodiment of the current invention as described herein.

As shown in FIG. 30, the exhaled air suction intake 30001 can connect to an air purification chamber 30002. The exhaled air suction intake can be located within an exhaled air catch basin 30003. The exhaled air suction intake can be located at a junction of where the exhaled air collector meets with an exhaled air purification chamber or the exhaled air suction intake can be connected to the exhaled air purification by an air suction conduit 30004, as shown in FIG. 30. In embodiments no exhaled air catch basin is present.

The air suction intake can connect to an air suction conduit 30004. The air suction conduit 30004 can connect the exhaled air collector 30005 to an exhaled air purification chamber 30002. The air-suction conduit can begin as one conduit that connects to the exhaled air collector and then bifurcates into two conduits which connect to an exhaled air purification chamber or multiple exhaled air purification chambers. The air-suction conduit can begin as one conduit that connects to the exhaled air collector and then bifurcates into two conduits which then come together to become one conduit which connects to an exhaled air purification chamber. The air-suction conduit can begin as two or more conduits that connect to the exhaled air collector which then come together to become one conduit that connects to an air purification chamber.

The exhaled air collector can be integrated with the computer screen or monitor 30006. In aspects, one or more fans 30007 at or towards the top of the exhaled air collector 30005 can blow air downward, such as blowing exhaled air towards the air catch basin 30003 and/or exhaled air suction intake 30001. (See FIG. 30.) The exhaled air collector can be designed into a computer screen or monitor's periphery. The exhaled air collector can be an assembly that is attachable to, such as releasably attachable to, a computer screen or monitor, or a computer, such as a laptop or tablet computer. The exhaled air collector and the computer screen or monitor can be supported by a portion of, or all of, an exhaled air purification chamber. The exhaled air collector and the computer screen or monitor can be supported by a portion of, or all of, a conventional air purifier. In embodiments a computer screen and an exhaled air purification unit can be an integrated unit.

In embodiments an exhaled air purification chamber or a conventional air purifier can be attached to, supported by, or integrated within a monitor stand. The exhaled air purification chamber can be connected to the monitor by way of a conduit. The exhaled air purification chamber can be connected to a port on or within the monitor. The connection can be by way of an indirect connection, such as by way of a conduit. The connection can be by way of a direct connection. In embodiments the monitor stand support can comprise a hollow support member that also acts as a conduit.

In embodiments the exhaled air purification unit is comprised of a monitor or computer screen comprising an exhaled air collector with the exhaled air blocking surface being that of the outermost front surface of the electronic display screen, and a distance removed, and separated, air suction intake that connects to an air purification chamber. In aspects, when the air suction intake is distance removed and separated from the monitor or computer screen the air suction intake is located beneath a lower edge of the monitor or computer screen.

In embodiments the exhaled air purification unit is comprised of a monitor or computer screen comprising an exhaled air collector with the exhaled air blocking surface being that of the outermost front surface of the electronic display screen, and a distance removed, but attached, air suction intake that connects to an air purification chamber. When the air suction intake is distance removed, but attached, the attached air suction intake can be located beneath a lower edge of the monitor or computer screen.

In embodiments an exhaled air purification system is comprised of a monitor comprising an exhaled air collector with the exhaled air blocking surface being that of the outermost surface of the electronic display screen and a distance removed, and separated, air suction intake that is part of a conventional air purifier. When the air suction intake is distance removed and separated from the monitor or computer screen the air suction intake of the conventional air purifier can be located beneath a lower edge of the monitor or computer screen.

In embodiments the exhaled air purification system is comprised of a monitor or computer screen comprising an exhaled air collector with the exhaled air blocking surface being that of the outermost front surface of the electronic display screen, and a distance removed, but attached, conventional air purifier. The air purifier comprises the air suction intake and an air purification chamber. With such an exhaled air purification system the air suction intake of the attached conventional air purifier can be located beneath a lower edge of the monitor or computer screen.

In embodiments a monitor or computer screen, exhaled air collector, and exhaled air purification chamber, can be an integrated unit. The monitor can be that of a desktop monitor. The monitor can be that of a laptop. The monitor can be that of a tablet. The monitor can be that of a TV. An embodiment can be that of a monitor that can capture exhaled air and room air and clean the captured air to a 90%+ level prior to releasing it into the room's environment where the monitor is located. An embodiment can be that of a laptop that can capture exhaled air and room air and clean the captured air to a 90%+ level prior to releasing it into the room's environment where the monitor is located. An embodiment can be that of a tablet that can capture exhaled air and room air and clean the captured air to a 90%+ level prior to releasing it into the room's environment where the monitor is located. An embodiment can be that of a TV that can capture exhaled air and room air and clean the captured air to a 90%+ level prior to releasing it into the room's environment where the monitor is located.

When the monitor, laptop, tablet, or TV is located within 3 to 4 feet of the face of an individual whose exhaled air is being captured and cleaned, the capture rate of exhaled air can be 90% or greater. In the case of a TV/monitor located farther away than 4 feet, the capture rate of exhaled air diminishes, however the capture rate of ambient room air increases. In embodiments the TV can be located up to 15 feet away, and when this occurs, the TV comprising an exhaled air suction intake and air purification chamber is, in examples, capturing and cleaning exhaled air already mixed with room air.

An exhaled air collector can be connected to an exhaled air purification chamber by, for example, a conduit and/or open space within the monitor, laptop, or tablet. As referred to herein the open space within a monitor, laptop, or tablet can be the same as a conduit or air flow space. In aspects, the exhaled air collector opens to the conduit by way of one or more air suction intakes. The conduit or open space within the monitor, laptop, tablet, or TV can connect the exhaled air collector to the exhaled air purification chamber. An exhaled air purification chamber can be located behind the monitor, laptop, tablet, electronic display screen, or TV. An exhaled air purification chamber can be located beneath the monitor, laptop, tablet, electronic display screen, or TV. An exhaled air purification chamber can be located within the housing or cover of a monitor, laptop, tablet, electronic display screen, or TV.

As used herein an exhaled air purification chamber can be the same as an air purification chamber. In embodiments an air suction conduit is added within or to exterior of the monitor, laptop, tablet, electronic display screen, or TV. In other embodiments the space between an electronic display screen and the covering of the electronic display screen can be expanded to form an open space for air to travel from the exhaled air collector to the exhaled air purification chamber.

One or more air suction intake(s) can be designed into, formed, or fabricated within the side of a monitor. In certain cases, the one or more air suction intakes can be located on a side or sides closer to the front of the monitor. In other cases, the one or more air suction intakes can be located on the front of the monitor. In still other cases, the one or more air suction intakes can be located partially or fully around the outer front of the monitor. In embodiments, the one or more air suction intakes are located peripheral to the exhaled air blocking surface.

An exhaled air purification chamber can be integral with the back cover of the monitor or electronic display screen allowing for the open space between the back of the electronic display screen and the covering of the electronic display screen to be the air suction conduit that connects to the exhaled air purification chamber. One or more exhaled air purification chamber(s) can be attached to or integral with the back cover of a monitor. The one or more air purification chambers can be separated to allow for a universal support 16006 to attach to the back cover of the monitor. The one or more air purification chambers can be separated to allow for a universal support stand to attach to a retrofit that then attaches to the back of a monitor. (See, e.g., FIG. 16.)

Figure 16:
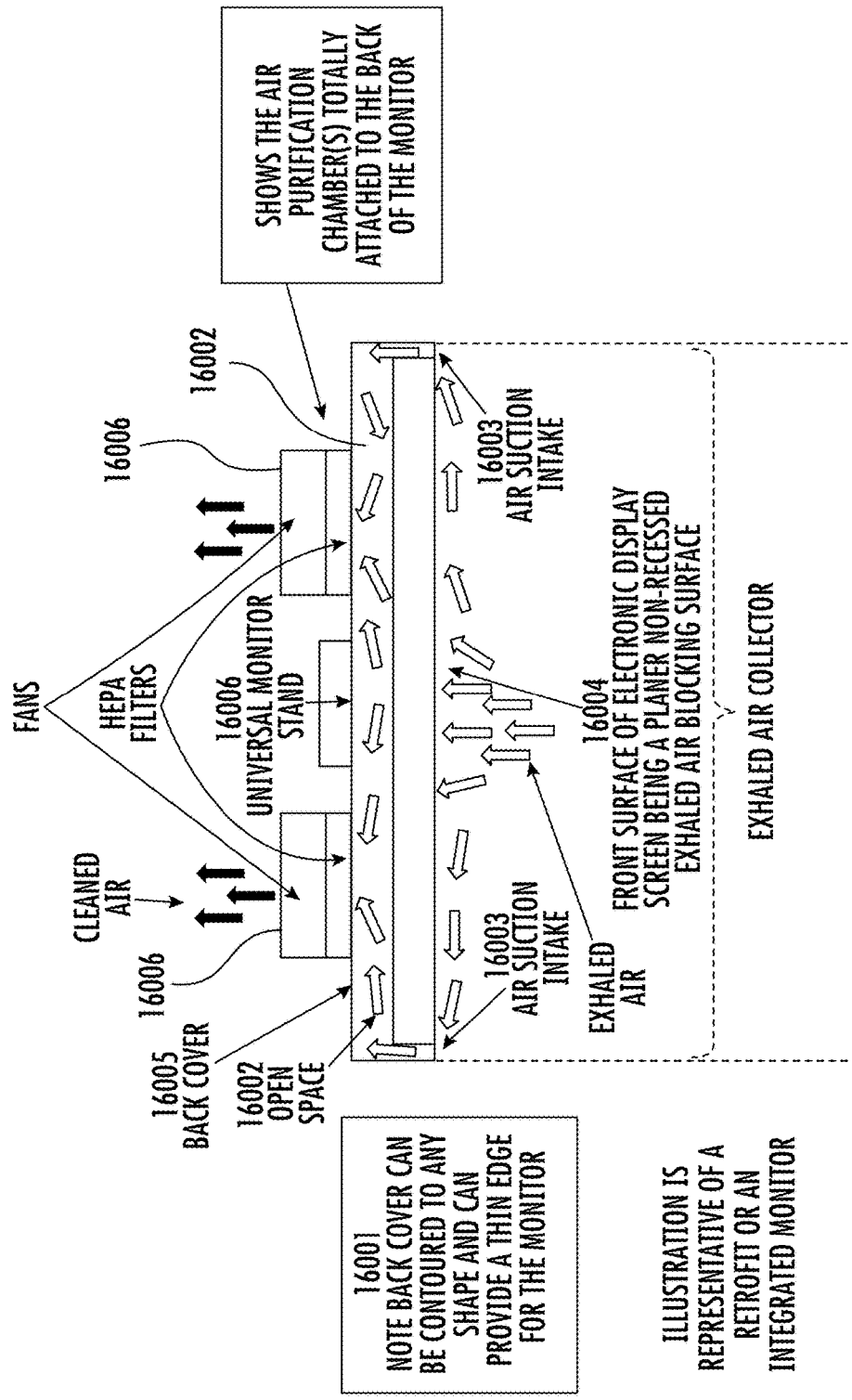
FIG. 16 is an illustration of an embodiment of the current invention as described herein.
Figure 17:
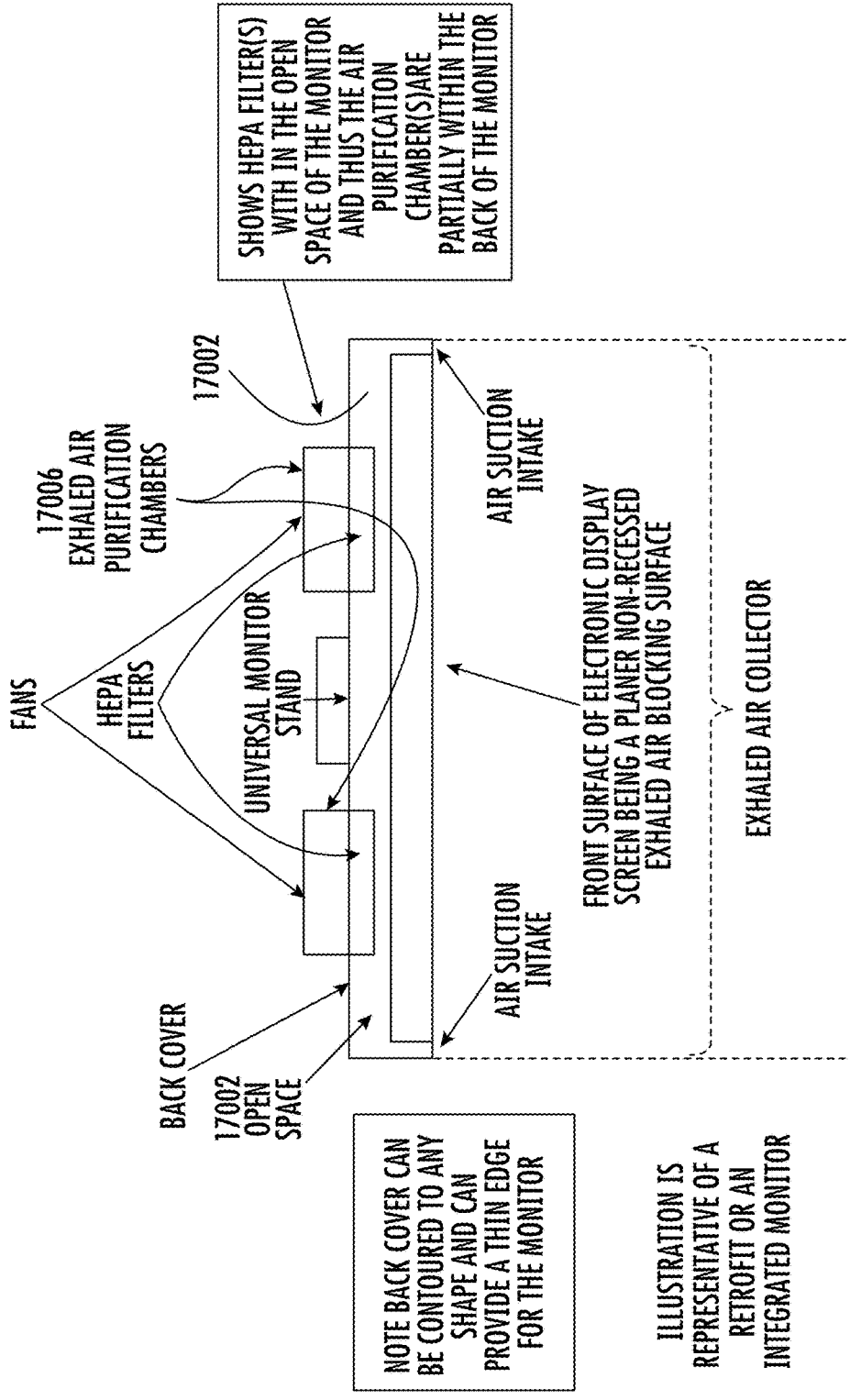
FIG. 17 is an illustration of an embodiment of the current invention as described herein.
Figure 18:
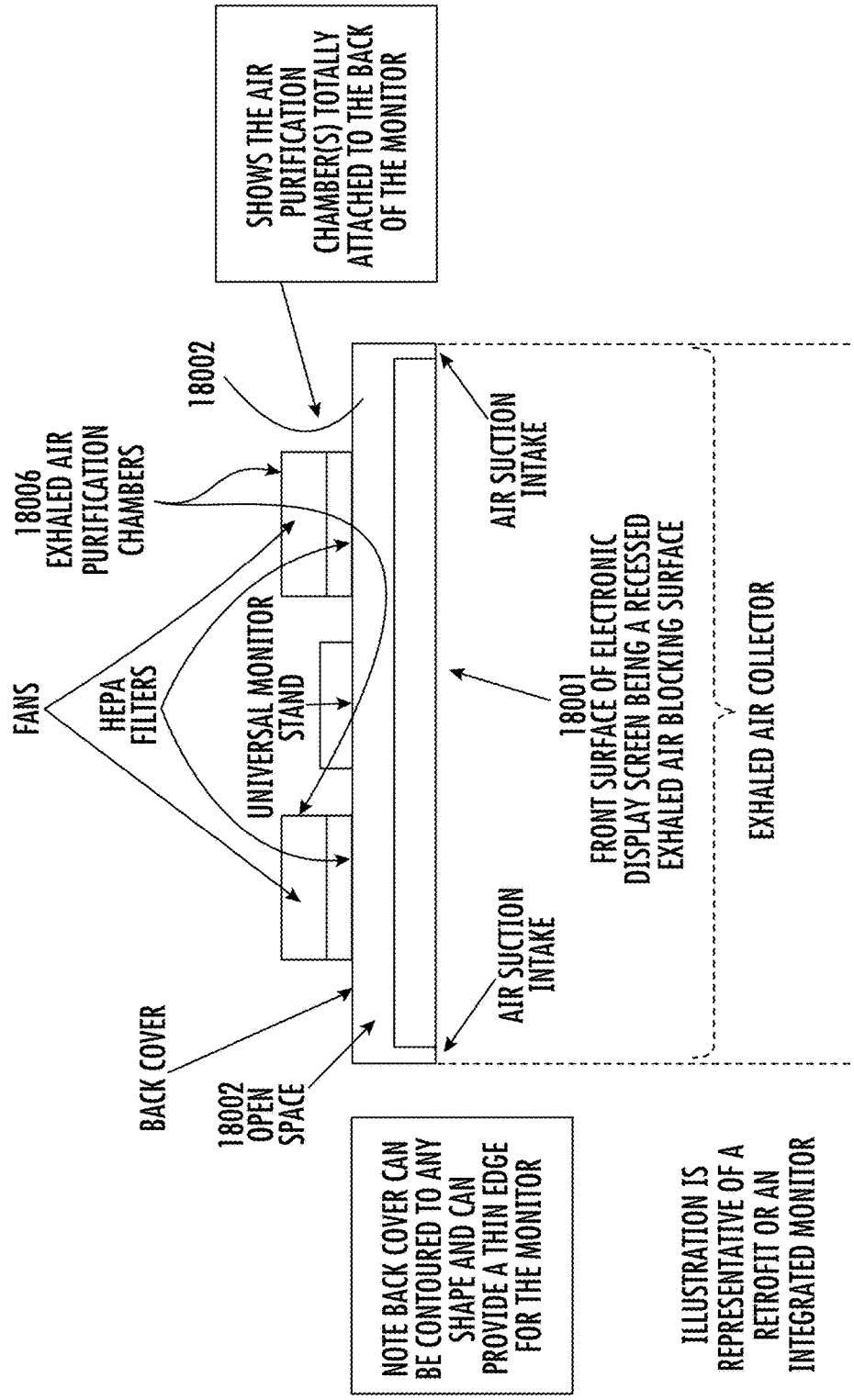
FIG. 18 is an illustration of an embodiment of the current invention as described herein.
Figure 19:
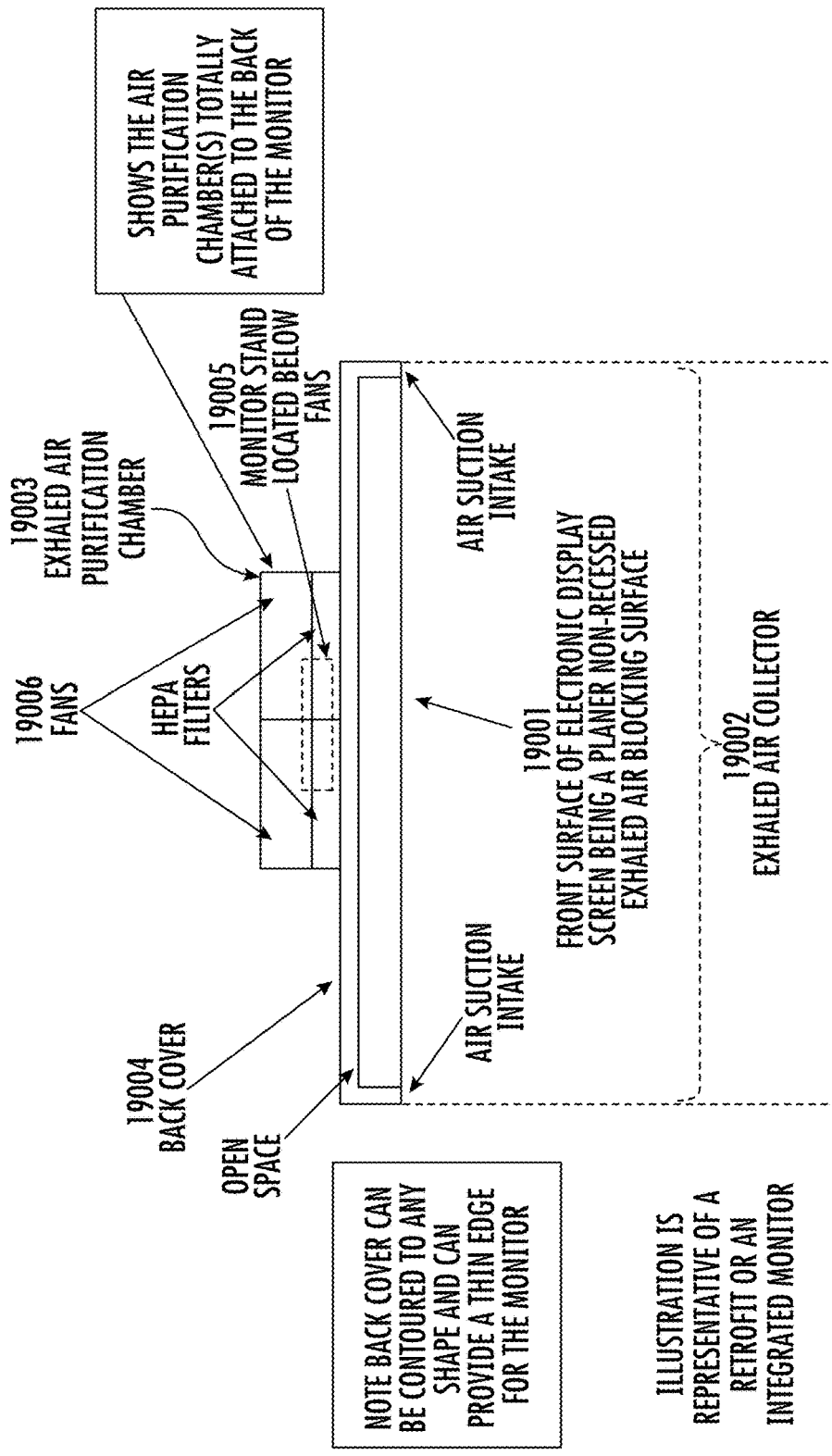
FIG. 19 is an illustration of an embodiment of the current invention as described herein.

As shown in FIG. 16, the back cover of the monitor can be a shell-like member that provides an open space between it and the back and edges of the electronic display screen or monitor, such as a back cover contoured to any shape and providing an edge, such as a thin edge, for the monitor 16001. The shell-like member can resemble a box with short sides and no top. The electronic display screen or monitor can fit within and be spaced apart from the shell-like member. The shell-like member can wrap around a portion of or all the side edges of the electronic display screen or monitor forming an open space 16002 that becomes one or more of the air suction intakes 16003. In aspects, the front surface of the electronic display screen can be a planar, non-recessed exhaled air blocking surface 16004. The shell-like member can be separated from the back of the monitor or electronic display screen by a spacer such as, by way of example only, a magnet, magnets, Velcro, or adhesive pad. The back cover of a monitor can be of any shape or contour desired. A retrofit exhaled air collector can be designed so that once attached and spaced apart it follows the contour of the back cover of the monitor or electronic display screen and be spaced apart from the back and sides thereof. In FIG. 16, the one or more exhaled air suction intakes 16003 pulls the exhaled air into the open space between the display screen and for example a back cover of the monitor, TV, computer, etc. 16005. The exhaled air can pass to one or more air purification chambers 16006, comprising one or more fans and one or more filters, and where cleaned air is then exhausted. In FIG. 16, the air purification chambers 16006 are attached to the back of the monitor and not within the open space 16002. FIG. 17 is similar to FIG. 16, but the HEPA filter(s) are within the open space 17002 and thus part of the air purification chamber(s) 17006 is in the open space. FIG. 18 is similar but the electronic display screen/exhaled air blocking surface is recessed 18001, and the air purification chambers 18006 are attached to the back of the monitor and not within the open space 18002. FIG. 19 is similar but the front surface of the electronic display screen is planar with a non-recessed exhaled air blocking surface 19001 and planar with a front of the exhaled air collector 19002 (e.g., outer walls). In FIG. 19, the air purification chambers 19003 are shown attached to the back of the monitor 19004; it also shows a monitor stand 19005 located below the fans 19006, for example.

Figure 10:
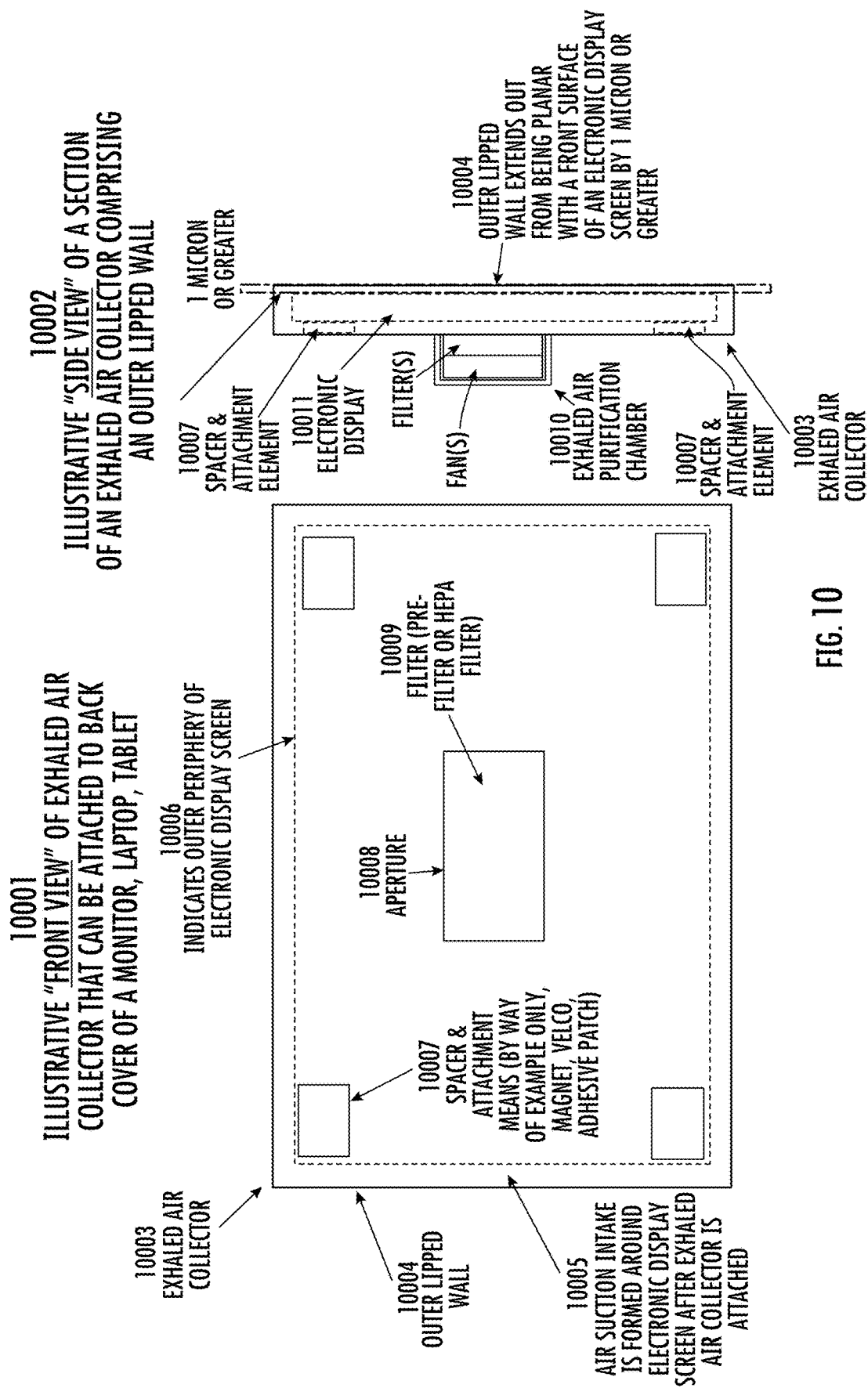
FIG. 10 is an illustration of an embodiment(s) of the current invention as described herein.

FIG. 10 shows an illustrative front view 10001 of an exhaled air collector 10003 that can be attached to a back cover of a monitor, laptop, or tablet, by way of example. As shown in this embodiment, the exhaled air collector has an outer lipped wall 10004, wherein one or more air suction intakes 10005 can be formed around the electronic display screen after the exhaled air collector is attached to the electronic display screen. (A dotted line indicates the outer periphery of the electronic display screen 10006.) In aspects, one or more spacers or attachment means/mechanisms/structures 10007 can be used between the exhaled air collector and the computer, monitor, television, or electronic display screen. In aspects there can be an aperture 10008 at the back of the exhaled air collector to exhaust clean air from the air purification chamber, where in the air is cleaned by, e.g., a filter, pre-filter, or HEPA filter 10009. A side view 10002 shows a section of an exhaled air collector 10003 comprising an outer lipped wall 10004 so the exhaled air blocking surface (e.g., electronic display screen 10011 is recessed). The outer lipped wall 10004 can extend out from being planar with a front surface of the electronic display screen by around 1 micron or more. The embodiment also shows the spacer/attachment element and an air purification chamber comprising one or more fans and one or more filters.

Figure 14:
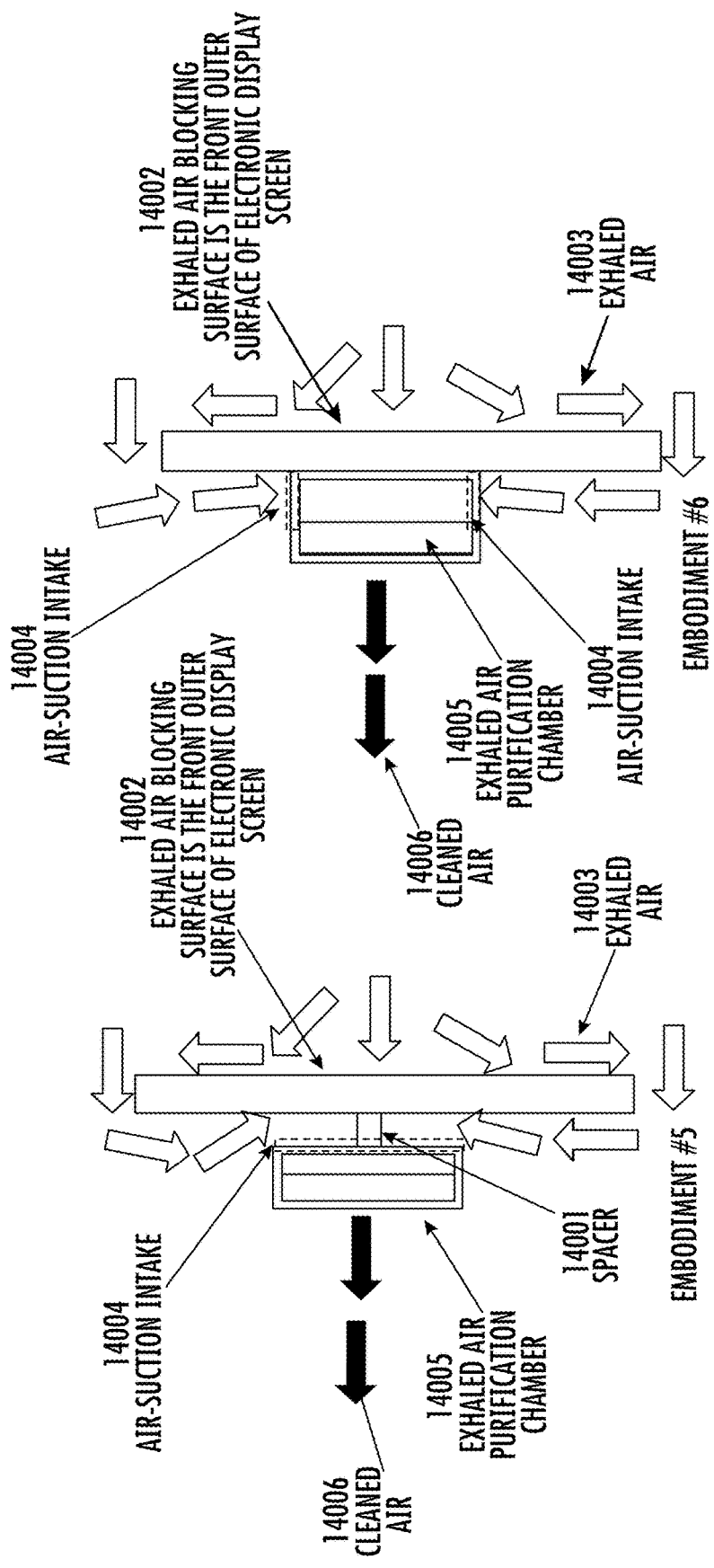
FIG. 14 is an illustration of several embodiments of the current invention as described herein.

FIG. 14 shows an embodiment of the current invention with and without a spacer. In particular, this Figure shows a side view perspective of an exhaled air blocking surface relative to a front surface of an air suction intake. On the left of the Figure, in embodiment #1, a spacer 140001 is provided between the exhaled air blocking surface 14002 (which in aspects is the front, outer surface of an electronic display screen). As shown in the Figure, exhaled air 14003 flows around the exhaled air blocking surface into an open space created by the spacer 14001, where an air suction intake(s) 14004 pulls or pushes the exhaled air into an air purification chamber 14005 where it is cleaned and exhausted 14006. In embodiment #2 on the right side of the page, there is no spacer. The exhaled air 14003 flows around the exhaled air blocking surface 14002 (e.g., electronic display screen) and air suction intakes 14004 on the top and/or bottom of the air purification chamber 14005 push or pull exhaled air into the air purification chamber where it is cleaned and exhausted 14006.

By attaching or being integral to the back of the monitor or electronic display screen, it is possible to minimize any added thickness to the monitor or electronic display screen. The exhaled air purification chamber can be within the back cover of the monitor or electronic display screen allowing the open space between the electronic display screen and the covering of the electronic display screen to be the air suction conduit that connects to the exhaled air purification chamber. The exhaled air purification chamber can be within the monitor or electronic display screen. The exhaled air purification chamber can connect by way of the open space between the electronic display screen and the covering of the electronic display screen or the covering of the monitor and the back of the electronic display screen. This open space can be that of a conduit or channel that connects the exhaled air purification chamber with the exhaled air collector and allows for air flow through, beginning with the air suction intake(s), then through the open space behind the electronic display screen, and then exiting through the air purification chamber(s).

Figure 11:
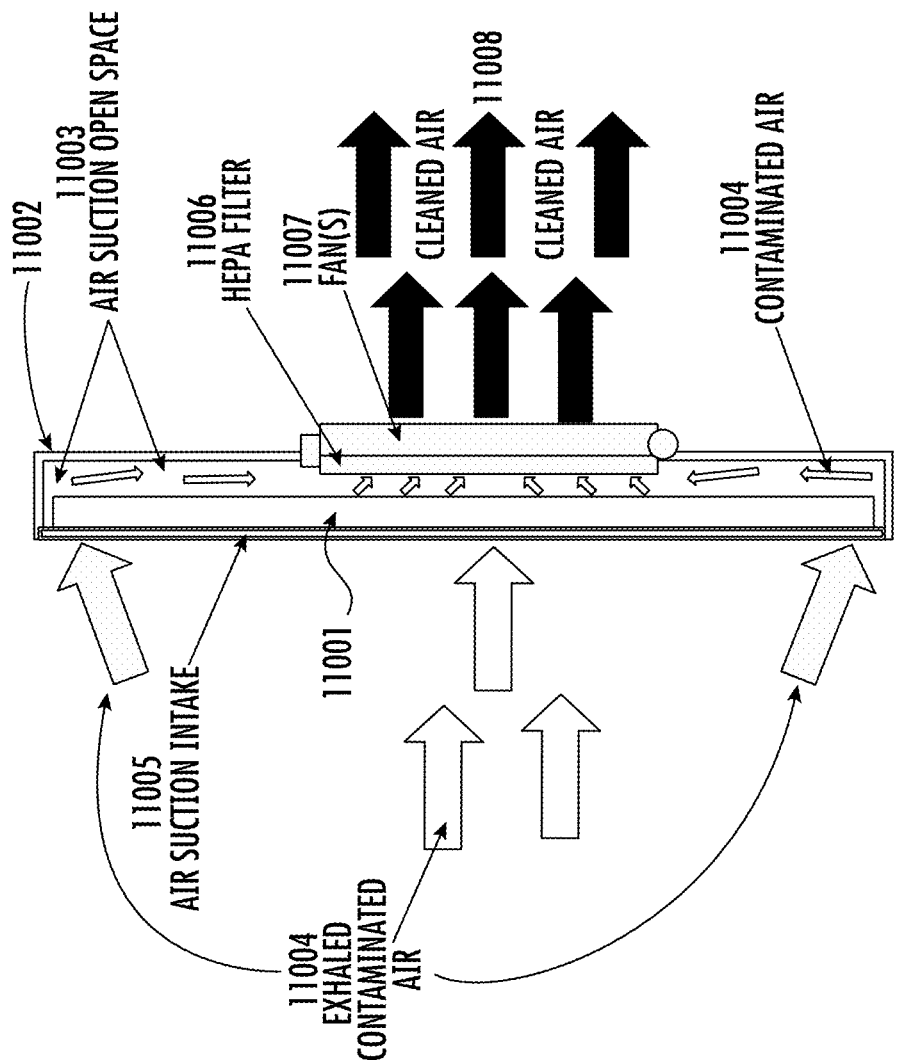
FIG. 11 is an illustration of an embodiment(s) of the current invention as described herein, showing integrated Option A.

For example, FIG. 11 shows integrated option "A," showing an open space/air suction open space 11003 between an electronic display screen 11001 and a cover 11002 of the monitor, computer, television, electronic display screen, etc. This figure shows exhaled contaminated air being 11004 sucked into the open space 11003 by one or more air suction intakes 11005. The contaminated air 11004 is led towards and into the air purification chamber wherein the air is cleaned using, e.g., filters or HEPA filters 11006 and exhausted using one or more fans 11007. Cleaned air is returned to the room 11008.

Figure 12:
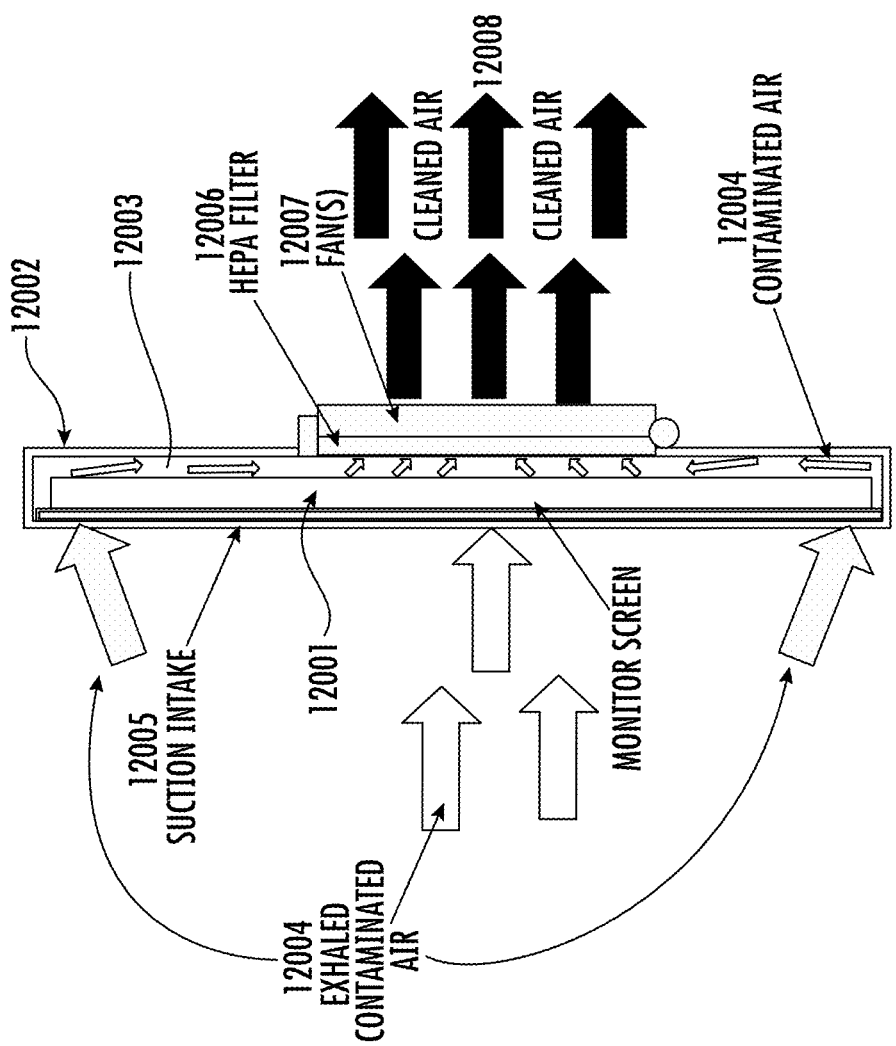
FIG. 12 is an illustration of an embodiment(s) of the current invention as described herein, showing integrated Option B.
Figure 13:
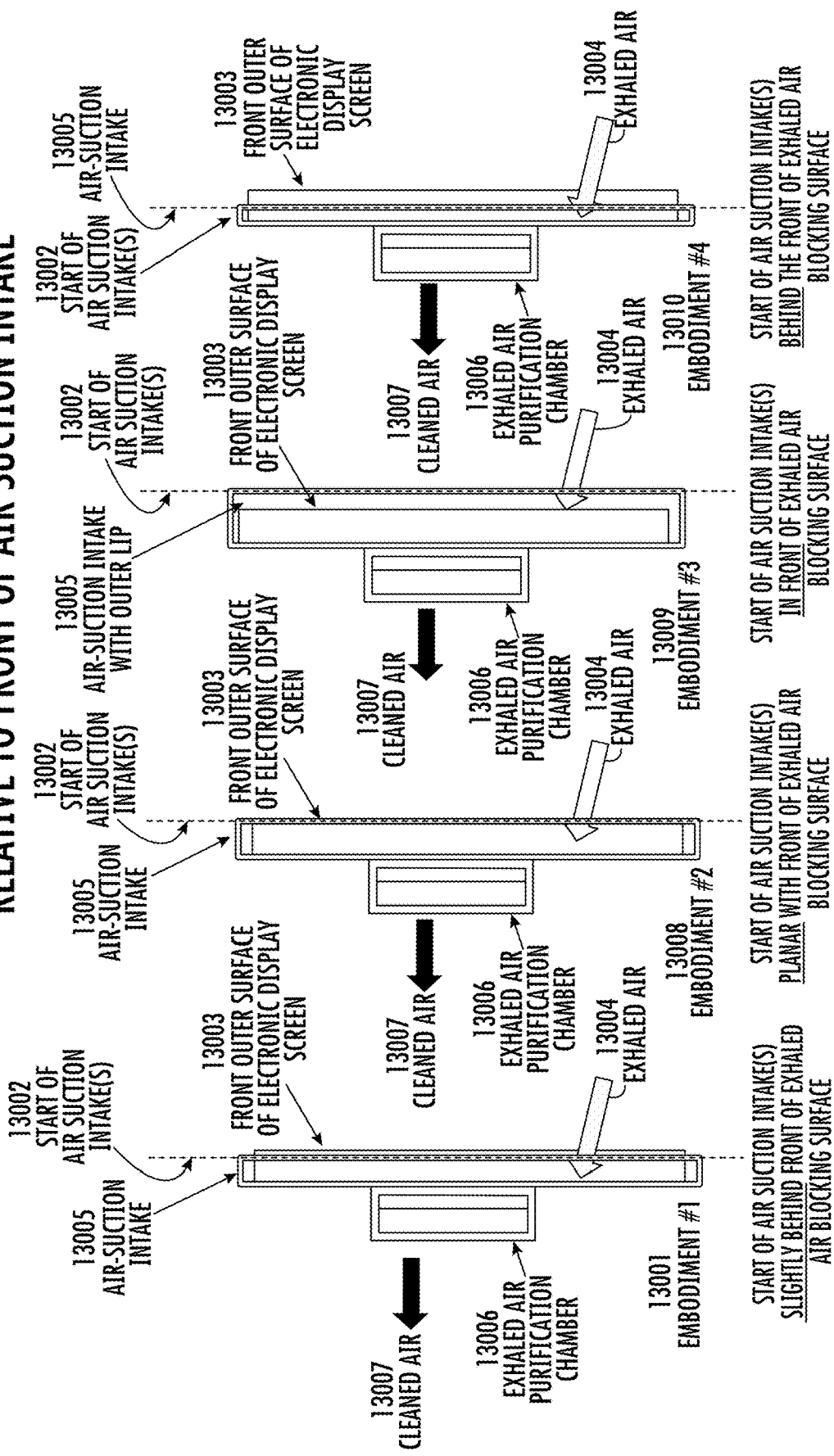
FIG. 13 is an illustration of several embodiments of the current invention as described herein.

FIG. 12 shows another option, Option "B," for integrating the monitor and exhaled air collector and utilizing an empty space between for example the monitor, computer, TV, or electronic display screen and a cover. While Option "A" shows the HEPA filter within the open space, in Option "B" the HEPA filter is located outside the back cover of the monitor. Thus, in FIG. 11, the air purification chamber is located partially within the monitor/open space, whereas FIG. 12 shows the air purification chamber adjacent to but located behind the monitor. FIG. 12 shows the open space/air suction open space 12003 between an electronic display screen 12001 and a cover 12002 of the monitor, computer, television, electronic display screen, etc. This figure shows exhaled contaminated air 12004 being sucked into the open space 12003 by one or more air suction intakes 12005. The contaminated air 12004 is led towards and into the air purification chamber wherein the air is cleaned using, e.g., filters or HEPA filters 12006 and exhausted using one or more fans 12007. Cleaned air is returned to the room 12008.

Figure 20:
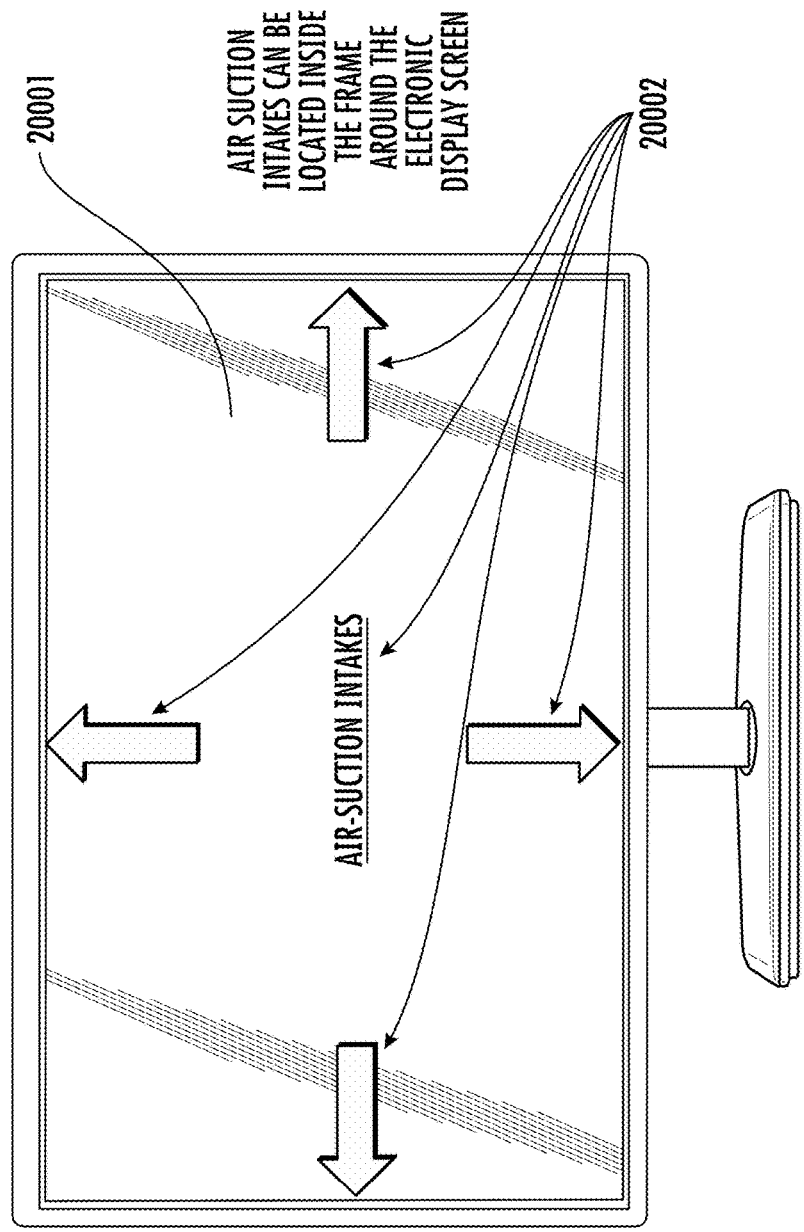
FIG. 20 is an illustration of an embodiment of the current invention as described herein.
Figure 21:
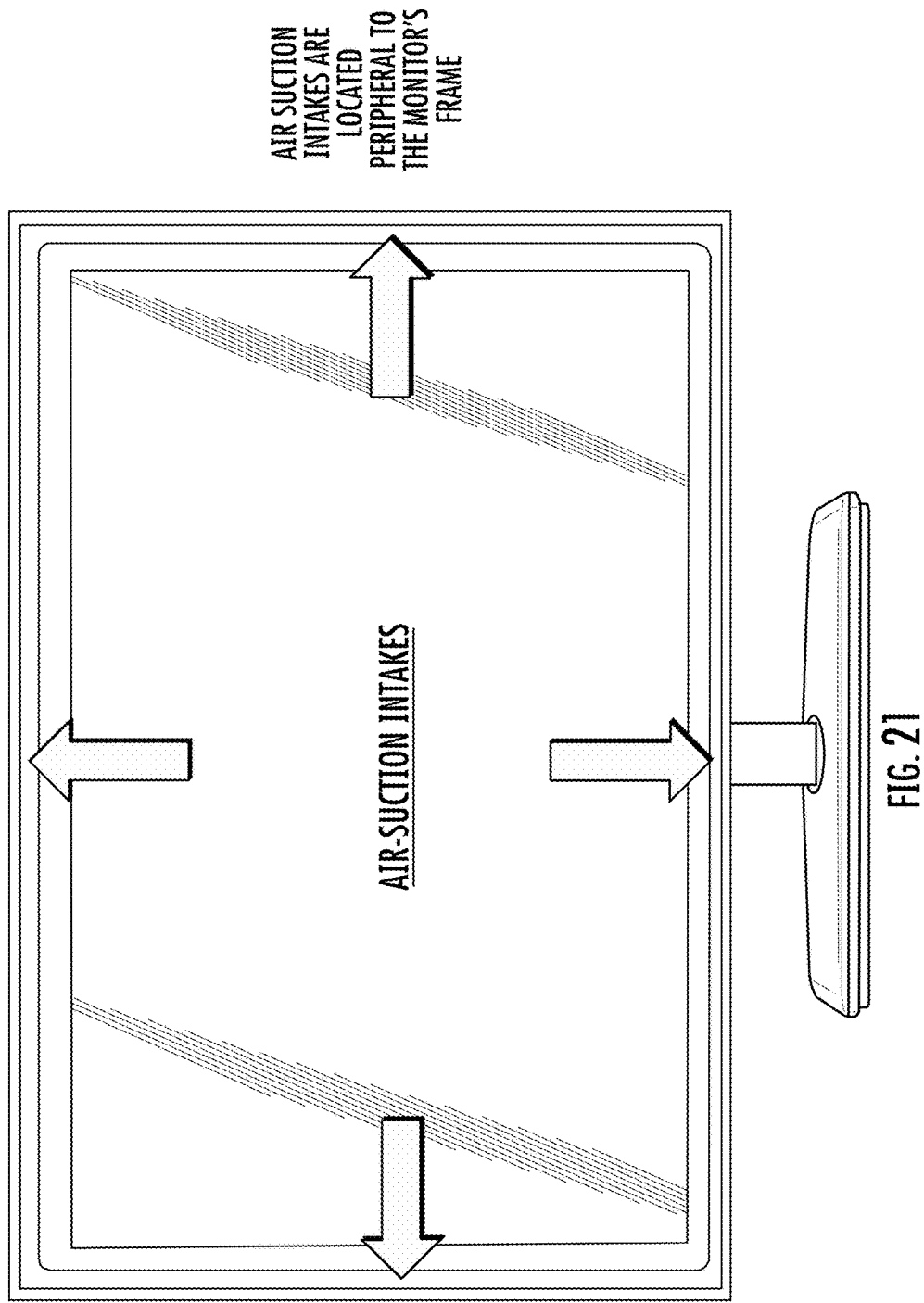
FIG. 21 is an illustration of an embodiment of the current invention as described herein.
Figure 22:
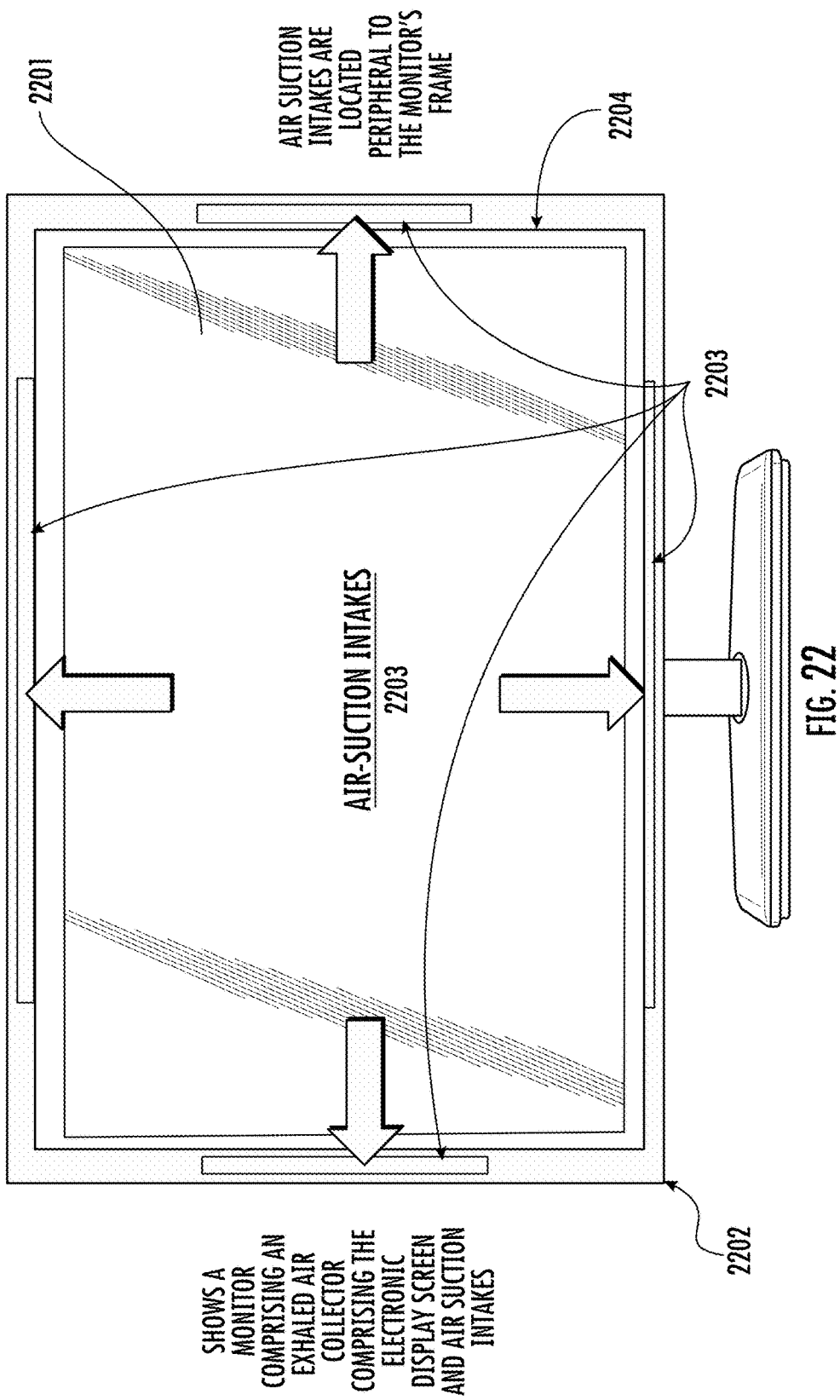
FIG. 22 is an illustration of an embodiment of the current invention as described herein.
Figure 23:
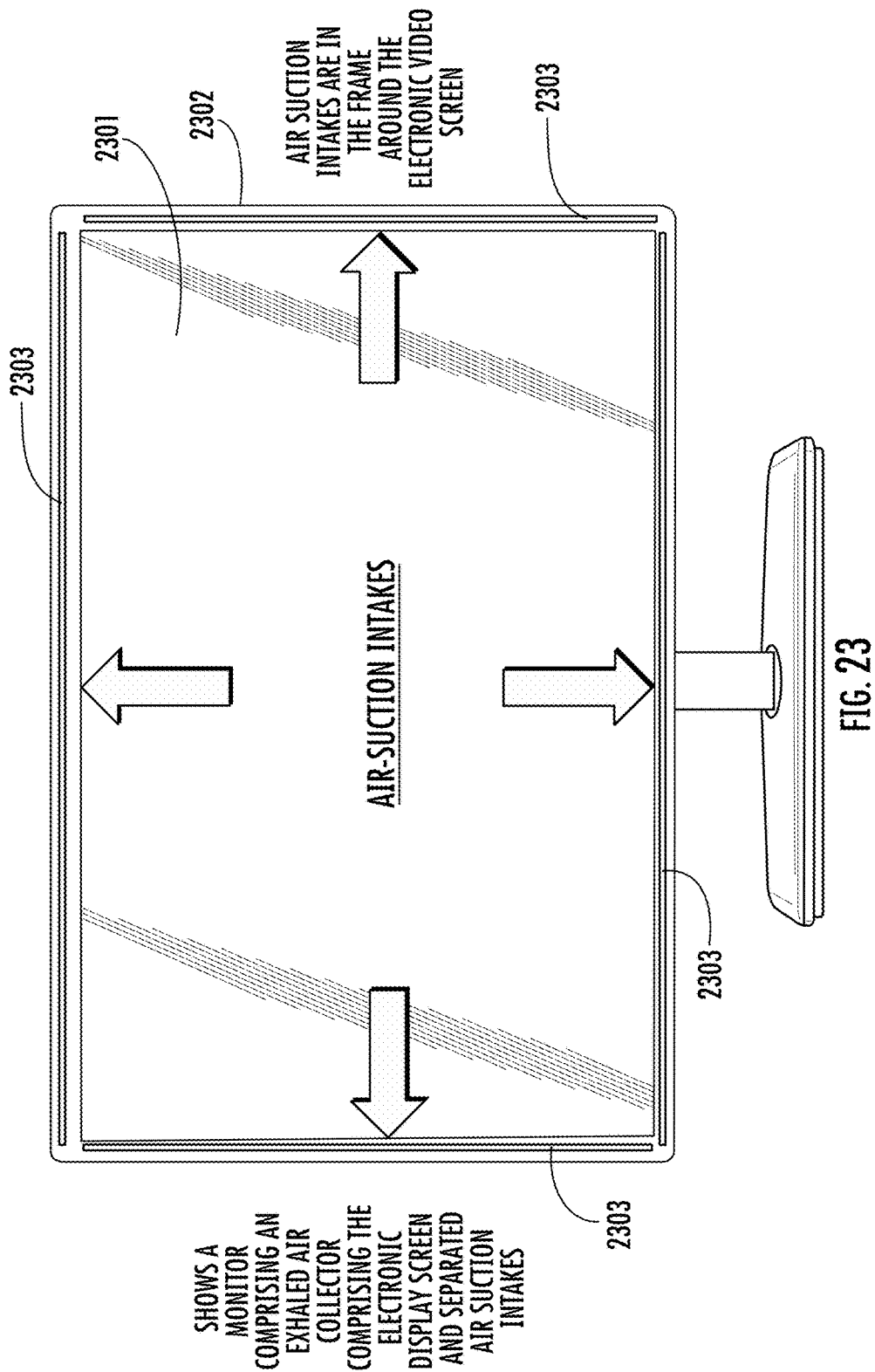
FIG. 23 is an illustration of an embodiment of the current invention as described herein.
Figure 24:
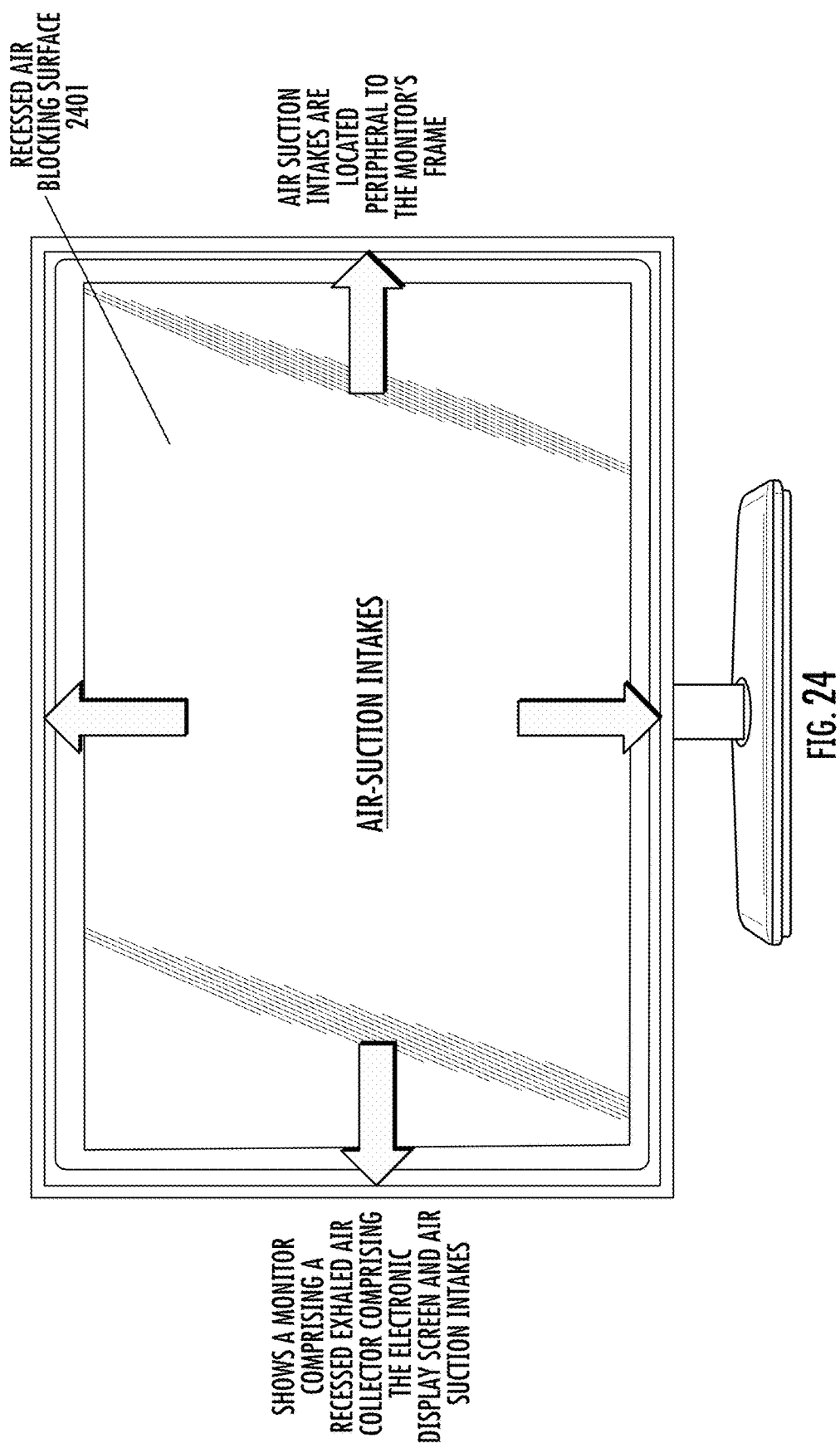
FIG. 24 is an illustration of an embodiment of the current invention as described herein.
Figure 25:
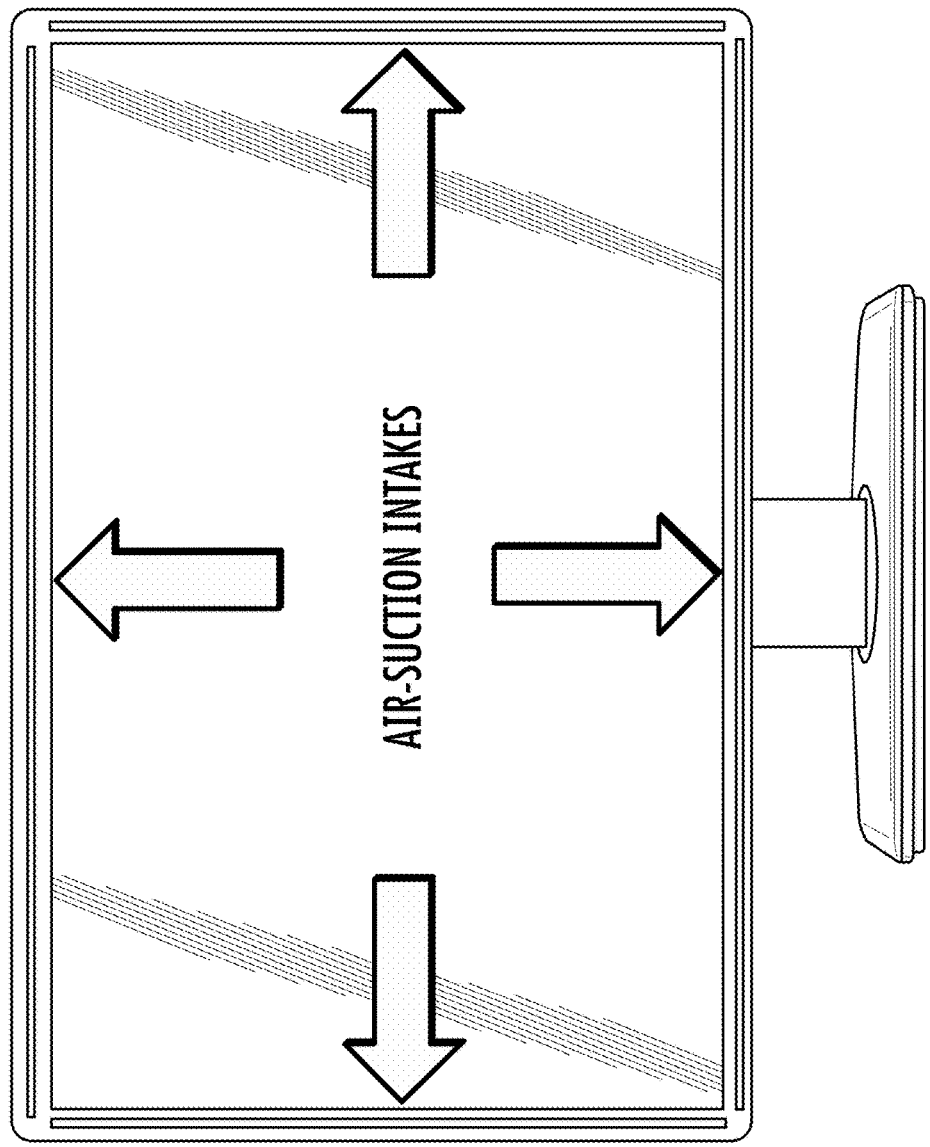
FIG. 25 is an illustration of an embodiment of the current invention as described herein.
Figure 26:
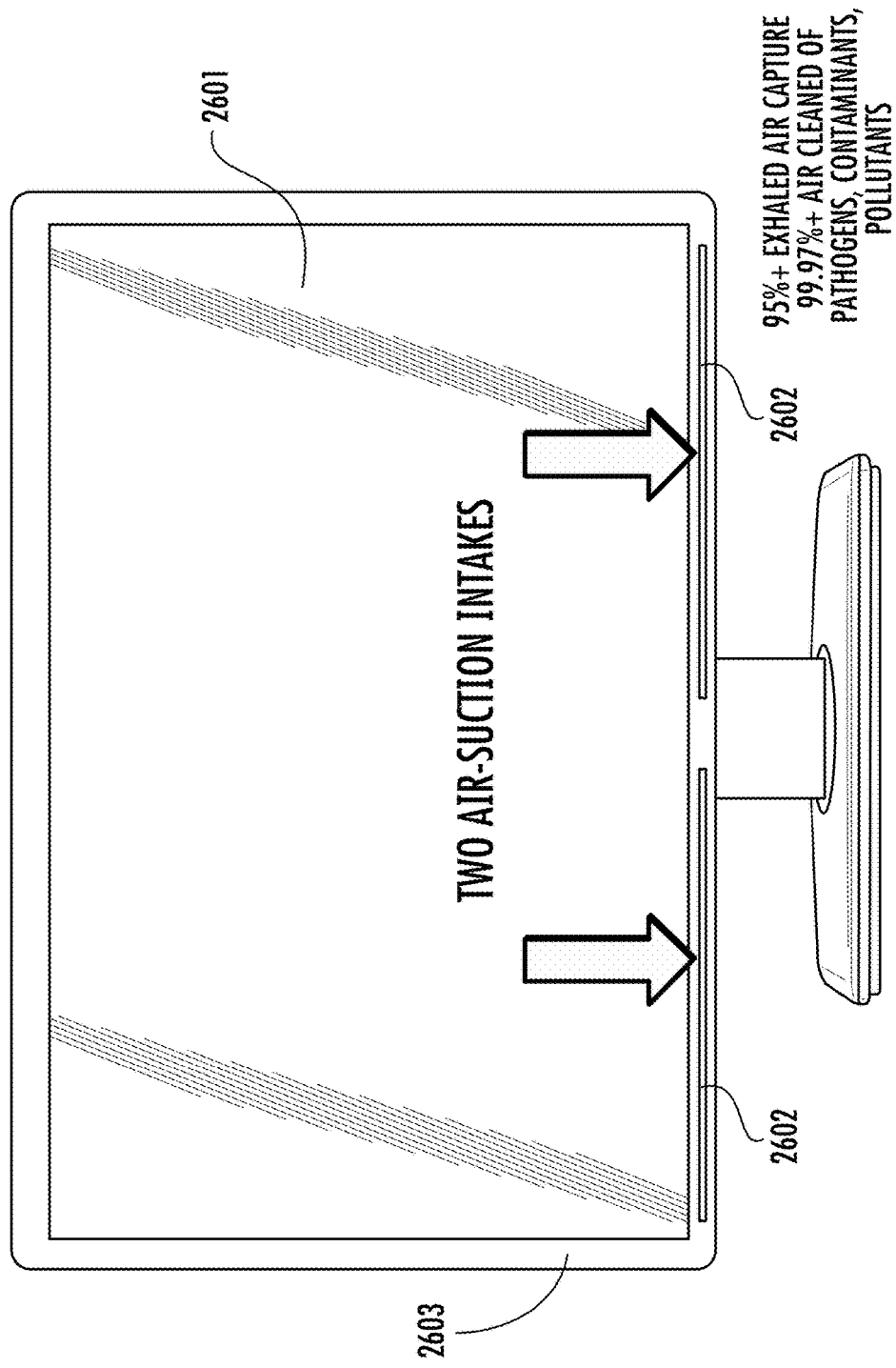
FIG. 26 is an illustration of an embodiment of the current invention as described herein.
Figure 27:
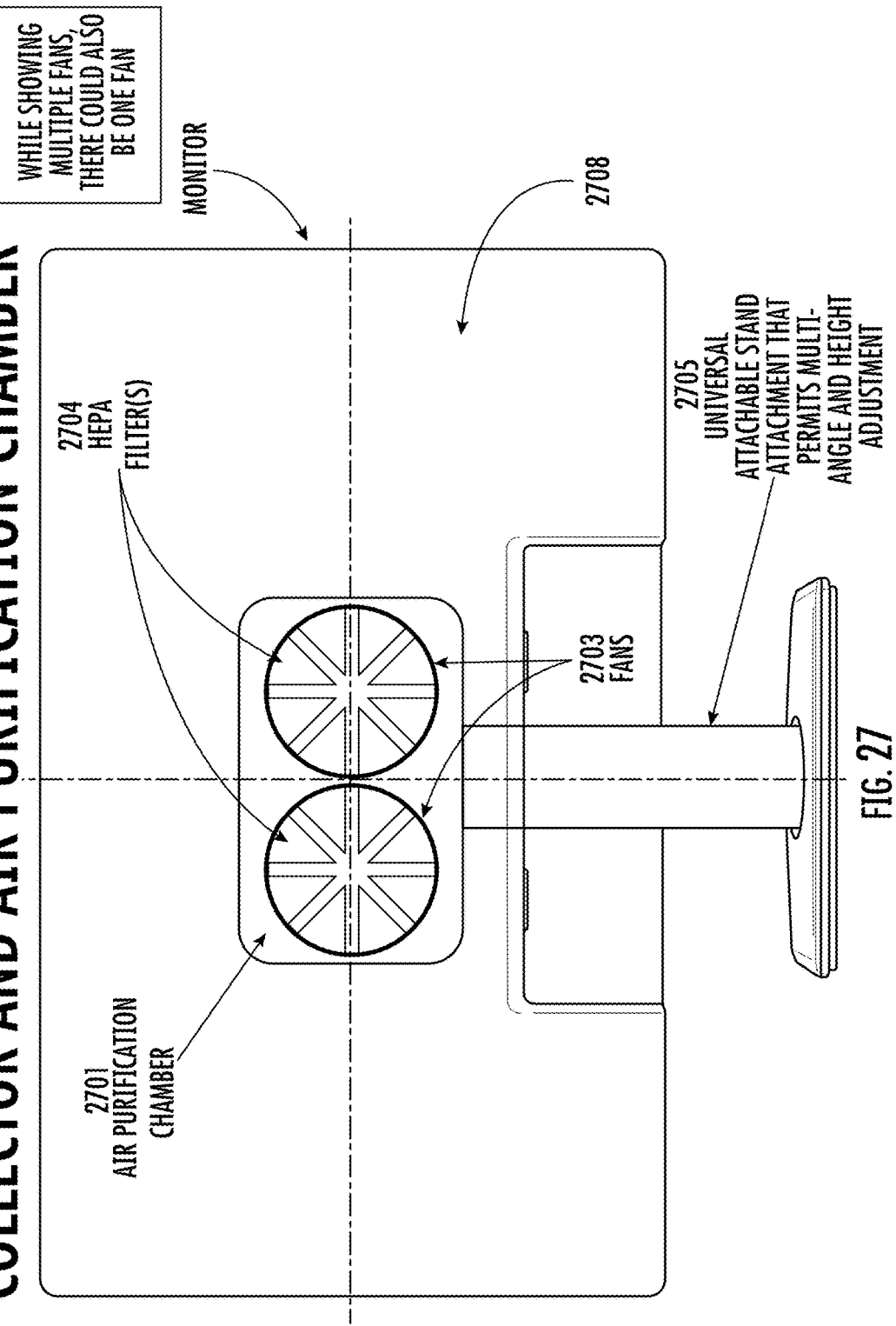
FIG. 27 is an illustration of an embodiment of the current invention as described herein.
Figure 28:
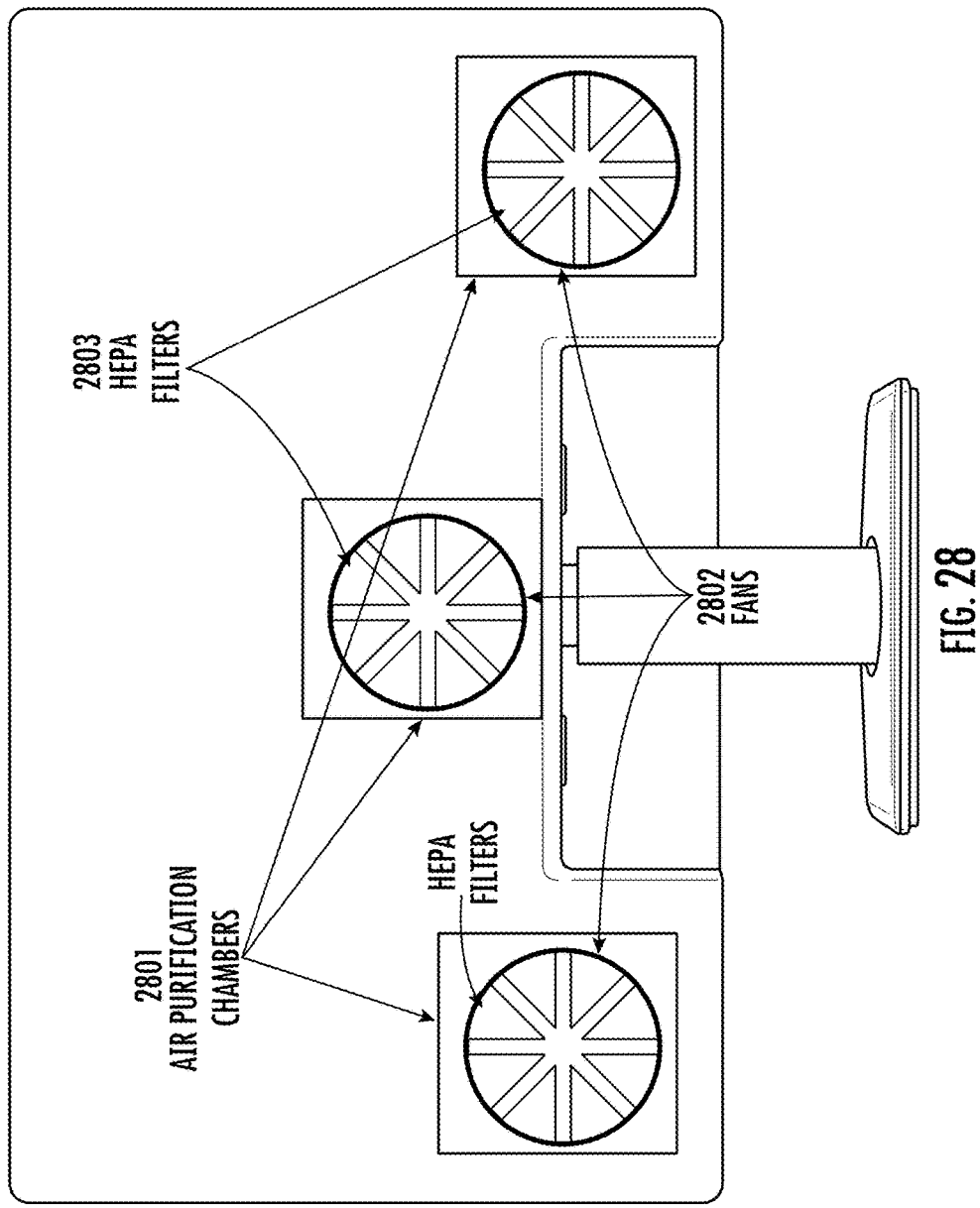
FIG. 28 is an illustration of an embodiment of the current invention as described herein.
Figure 29:
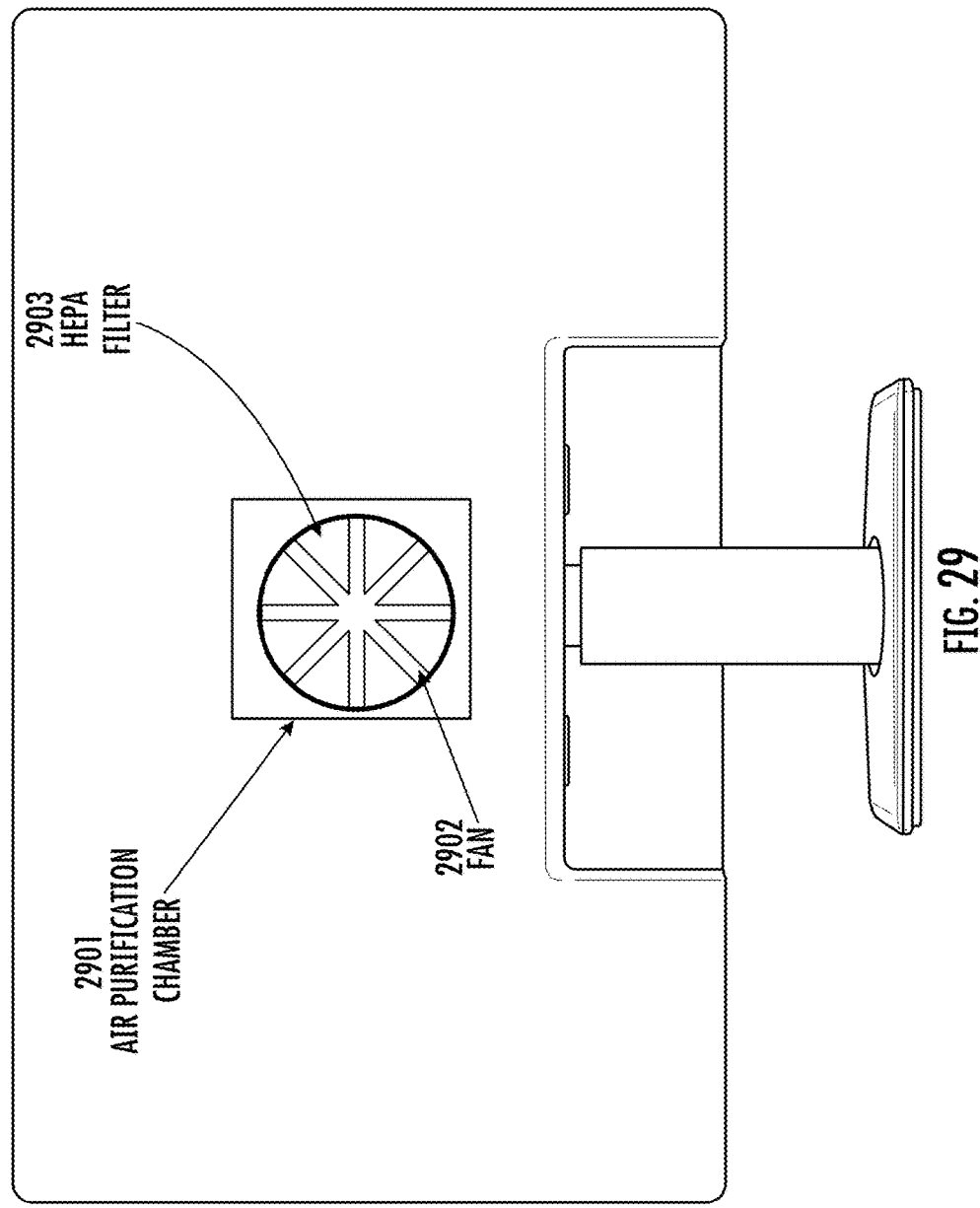
FIG. 29 is an illustration of an embodiment of the current invention as described herein.

FIG. 20 also shows an exhaled air collector and air purification chamber integrated with, e.g., a monitor. FIG. 20 shows a monitor comprising an exhaled air collector comprising the electronic display screen 20001 and air suction intakes 20002. In aspects, there can be one air suction intake that encircles all or part of the display screen. In aspects, there can be one air suction intake on each side, on one side, on two sides, or on three sides. In aspects, there can be four separated air suction intakes. In aspects, there can be three separated air suction intakes. In aspects, there can be two separated air suction intakes. In aspects, there can be one air suction intake; the one air suction intake can be located at the bottom of the display screen, underneath the display screen, or adjacent to the bottom of the display screen, in aspects. Further, one connected air suction intake can surround four or less sides of the display screen. One connected air suction intake can surround three or less sides of the display screen. One connected air suction intake can surround two or less sides of the display screen. One connected air suction intake can fully or partially surround one side of the display screen. FIG. 20 shows one air suction intake encircling the electronic display screen. FIG. 21 shows one or more air suction intakes located peripheral to the monitor/electronic display screen's frame. FIG. 22 shows a monitor/electronic display screen 2201 comprising an exhaled air collector 2202 comprising the electronic display screen 2201 and one or more air suction intakes 2203, wherein the one or more air suction intakes can be located peripheral to the monitor/electronic display screen frame 2204. FIG. 23 is similar, showing a monitor/electronic display screen 2301 comprising an exhaled air collector comprising the electronic display screen and one or more separated air suction intakes. In FIG. 23, the air suction intakes 2303 are in the frame 2302 around the electronic display screen 2301. FIG. 24 shows air suction intakes located peripheral to the monitor's frame (see arrows in FIG. 24). In FIG. 24, the electronic display screen acts as a recessed exhaled air blocking surface 2401. In FIG. 25, a monitor/electronic display screen is shown comprising an exhaled air collector and one or more exhaled air suction intakes, wherein the monitor also comprises a port on its back for attaching to an air suction conduit that connects to a distance separated exhaled air purification chamber. FIG. 26 shows an exhaled air collector integrated with a monitor/electronic display screen 2601 having two air suction intakes 2602 located in a frame 2603 of the monitor/electronic display screen. In embodiments, such a configuration can result in 95%+ exhaled air capture with 99.97% of that captured air cleaned of pathogens, contaminations, and/or pollutants.

Figure 34:
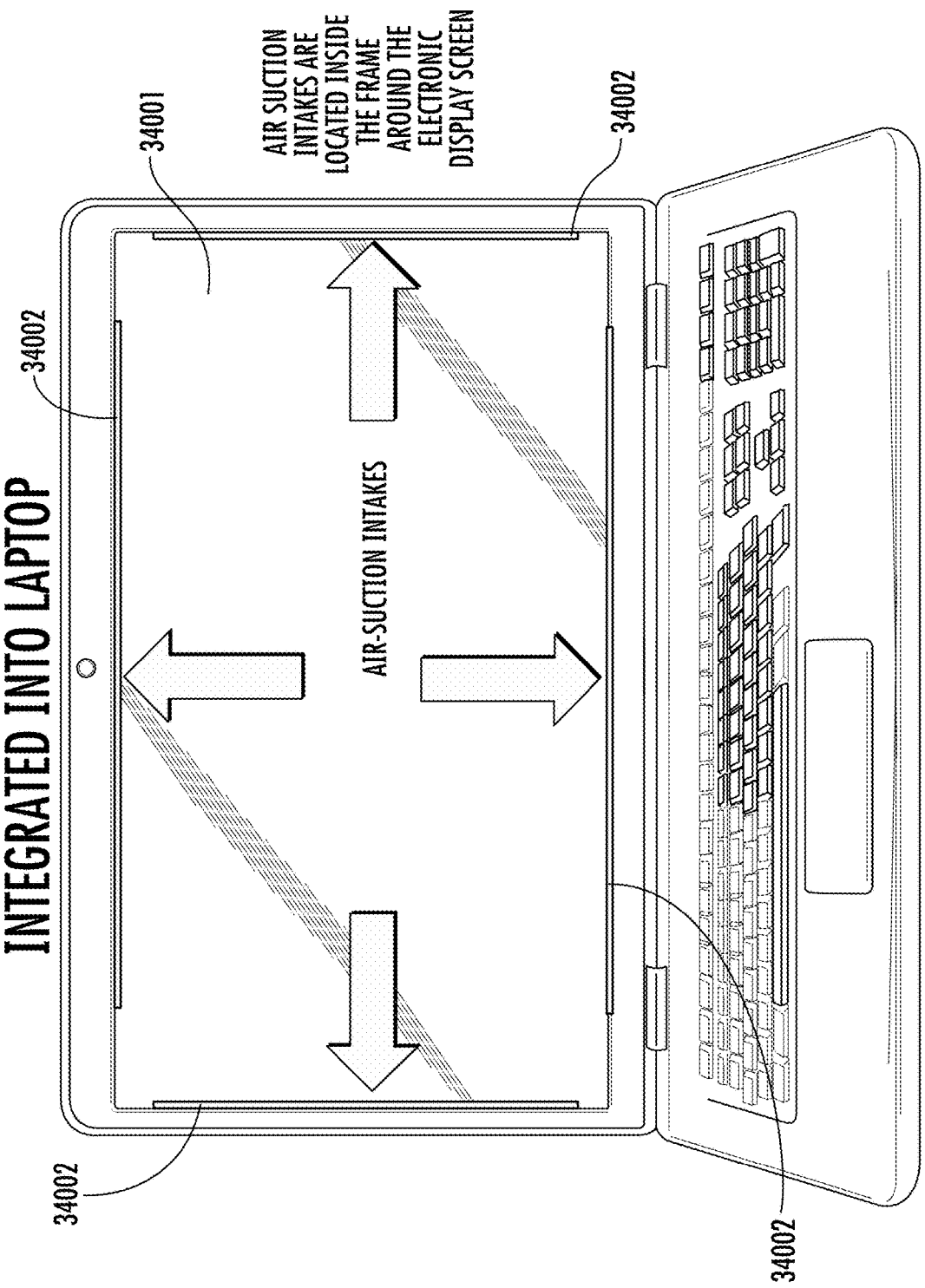
FIG. 34 is an illustration of an embodiment of the current invention as described herein.
Figure 35:
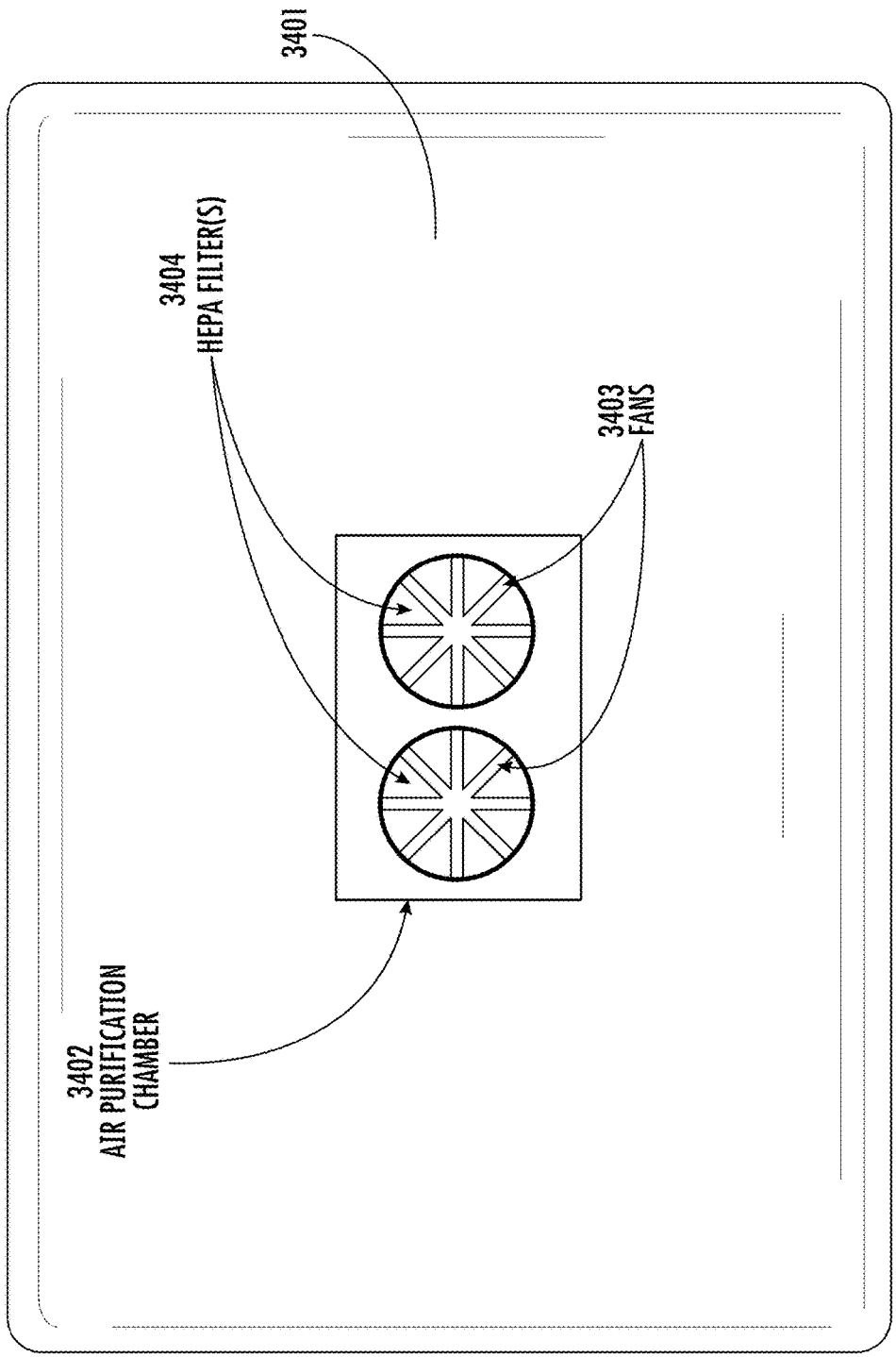
FIG. 35 is an illustration of an embodiment of the current invention as described herein.
Figure 37:
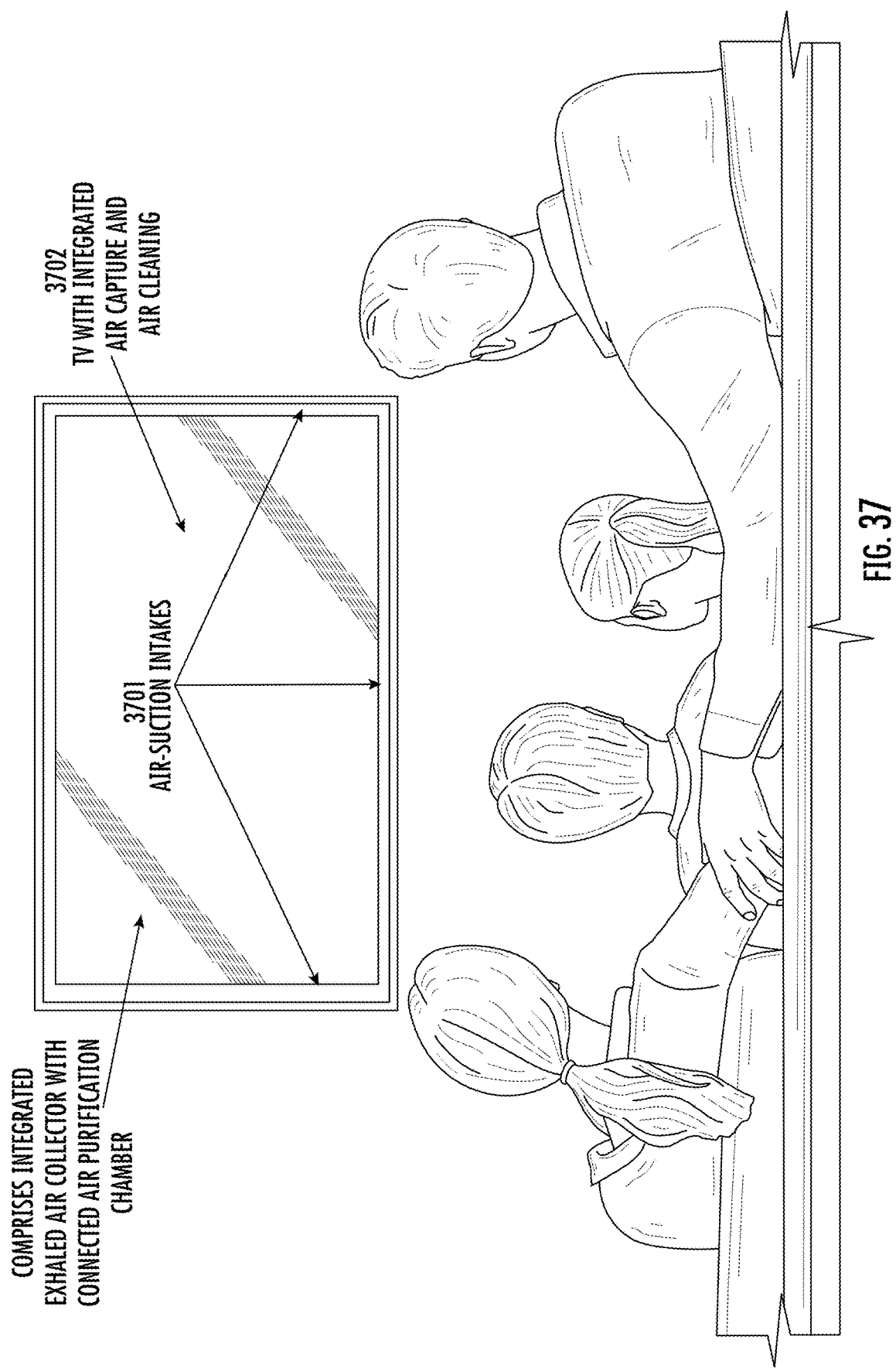
FIG. 37 is an illustration of an embodiment of the current invention as described herein.

FIG. 34 shows an exhaled air collector and air purification chamber integrated with a laptop computer. FIG. 34 shows a laptop computer comprising an exhaled air collector comprising the electronic display screen 34001 and air suction intakes 34002. In aspects, there can be one air suction intake that encircles all or part of the display screen. In aspects, there can be one air suction intake on each side, on one side, on two sides, or on three sides. In aspects, there can be four separated air suction intakes. In aspects, there can be three separated air suction intakes. In aspects, there can be two separated air suction intakes. In aspects, there can be one air suction intakes; the one air suction intake can be located at the bottom of the display screen, underneath the display screen, or adjacent to the bottom of the display screen, in aspects. Further, one connected air suction intake can surround four or less sides of the display screen. One connected air suction intake can surround three or less sides of the display screen. One connected air suction intake can surround two or less sides of the display screen. One connected air suction intake can fully or partially surround one side of the display screen. FIG. 34 shows air suction intakes located inside the frame around the electronic display screen of the laptop computer. FIG. 35 shows the back of the laptop computer of, for example, FIG. 34, wherein the back of the laptop's screen 3401 includes or is attached to an air purification chamber 3402 with fans 3403 and HEPA filters 3404. FIG. 37 shows a television with an integrated exhaled air collector and with a connected air purification chamber, meaning a television having integrated air capture and air cleaning 3702. In this example, three air suction intakes 3701 are used at a bottom and two sides of the television, although other configurations/exhaled air suction intake locations are contemplated as described elsewhere herein.

In embodiments an air suction port is present within the monitor, laptop, tablet, or TV. The air suction port can be in the back of the monitor, the backside of the top cover of the laptop that comprises the electronic display screen, or the back of a tablet or a TV. For example, FIG. 31 shows a back of a monitor having an air suction port 31001. This embodiment shows the back of the monitor associated with an exhaled air collector, wherein the back of the monitor includes an air suction conduit port for attaching an air suction conduit that would connect on another end to an exhaled air purification chamber. The air suction port can provide a port where an exhaled air suction conduit can attach and/or connect an exhaled air purification chamber. Such an exhaled air purification chamber can be directly connected by way of directly attaching or can be indirectly attached by way of the utilization of a conduit to a remote or distance separated air purification chamber.

By utilizing an air suction port in association with exhaled air suction intakes and the open space already present between the side and/or backside of the electronic display screen and the inside back cover of the monitor, it is possible to fabricate a monitor, laptop, tablet, etc. that is of the same or around the same thickness as currently-available monitors, laptops, or tablets, or within around 0.50 inches of currently-available electronic display screen and computer thickness. Such a monitor, laptop or tablet, in aspects, would be exhaled air capture and air clean ready, but would then need to be attached to a peripheral device that comprises an air purification chamber and air suction conduit that would (by way of example only) snap, plug, be inserted, attached, or connected to the air suction port in the monitor, laptop, tablet, or TV. Such attachment or connection can be facilitated (by way of example only), mechanically, magnetically or a combination of both. The port can provide for an air resistant connection. The port can provide for an airtight connection.

By utilizing an air suction port in the monitor, laptop, tablet, or TV and a connecting air suction conduit, it is possible to eliminate the added thickness of the air purification chamber that would then be remote or peripheral to that of the monitor, laptop, or tablet. The air purification chamber can then be connected to the air suction port by way of the air suction conduit. In embodiments, the manufacturers of the monitor, laptop, tablet, or TV would then need only provide during the design, fabrication, and assembly of the monitor, laptop, tablet or TV, the exhaled air suction intake(s) on, for example, (a) the side edges, (b) on the front side in the periphery, (c) between the electronic display screen and the monitor frame, (d) within the frame surrounding the electronic display screen, or (e) any location peripheral to the electronic display screen, as well as an open space from the air suction intake(s) that leads to the air suction port. In embodiments, one common air suction port is utilized. In other cases, two or more air suction ports are utilized.

Exhaled air and ambient room air can be pulled directly into the exhaled air suction intake(s). Exhaled air and ambient air can be deflected and moved towards and into an exhaled air suction intake due to the velocity of the exhaled air event (such as, by way of example only, a cough or sneeze).

The total required CFM (cubic feet per minute) of air suction and total CADR (clean air delivery rate) for an air capture and air cleaning system can depend on the size of the display screen being used as the exhaled air blocking surface, the design of the exhaled air collector, and the distance of the individual exhaling from the exhaled air collector. In examples, The "total" CFM or "total CADR is the total of all air suction CFM of a fan or fans pulling air through one or more exhaled air suction intakes. In examples, the "total" CADR is the total of all exiting air flow from one or more air purification chambers.

When an exhaled air blocking surface is "recessed," such that it is partially or fully surrounded by an exhaled air suction intake comprising an outer wall that is of a height or depth dimension that is 1 micron or greater in height or depth compared to the outer front surface of the electronic display screen (thus the reason why it can be referred to herein as a lipped outer wall), the total CFM and total CADR of such an air handling system embodiment can in cases be between 20 CFM or more, with a CADR of 13 CADR or more. Such an exhaled air collector design can achieve an exhaled air capture rate for a breath, talk, or cough of 90% or greater with an exhaled air cleaning level of 99%+. The noise level dB of the fan(s) can be as low as 40 dB or less.

For air handling systems where the outer front exhaled air blocking surface is "planar" with the outer wall of an exhaled air suction intake, or where the outer front exhaled air blocking surface is in front of ("forward to") that of the exhaled air suction intake's outer wall(s), the required total CFM air intake to achieve a 90%+ air capture rate for an exhaled breath or cough, with a 99%+ air cleaned level can be around 25 CFM or more, with the total CADR of the exiting air flow out of an exhaled air purification chamber being around 16 CADR or more. The noise level dB of the fan(s) can be as low as 60 dB or less.

In aspects, a precise CFM and CADR required to achieve a 90%+ exhaled air capture rate with a 99%+ cleaning depends upon 1) the size of the exhaled air blocking surface or the outer dimensions of the exhaled air collector, 2) the design of the exhaled air collector, 3) the distance from the individual whose exhaled air is being captured and cleaned, and 4) the type of exhaled air being captured and cleaned (meaning by way of example only, exhaled air breath, talk, cough, or sneeze). In aspects, for a monitor the CFM can range between 25 CFM and 150 CFM with the CADR ranging between 16 CADR and 100 CADR. In aspects, for a laptop the CFM can range between 40 CFM and 100 CFM with the CADR can range between 25 CADR and 70 CADR. In aspects, for a tablet the CFM can range between 20 CFM and 75 CFM with the CADR ranging between 13 CADR and 50 CADR. In aspects, for a TV the CFM can range between 50 CFM and 250 CFM with the CADR ranging between 33 CADR and 170 CADR.

Such an air handling system comprising a "recessed" air blocking system has the advantages of, in cases, needing lower energy, needing smaller fan(s), emitting less noise, being thinner, being lighter weight, and/or being less expensive. Such a system when connected to a laptop or tablet can be powered in many cases by the USB port of a laptop or tablet.

The use of the word total is to denote the total CFM additive effect if one or more fans are utilized or the total CADR effect if one or more filter stations are present.

When following the flow of exhaled air and/or ambient room air after entering one or more air suction intakes, the exhaled air and/or ambient room air is pulled around one or more of the bottom, one or both sides, and top of the electronic display screen or monitor. Once being pulled around a side, a bottom, a top, or any combination thereof of the electronic display screen or monitor, the exhaled air and/or ambient room air can be moved through an open space that can be, by way of example only, a conduit or open space between the back of the electronic display screen and the inside surface of the back cover of the monitor, and then towards and into one or more air purification chamber(s). In embodiments multiple conduits are utilized. In other embodiments only one conduit is utilized. The conduit(s) can be within the monitor. The conduit can be external to the monitor. In other embodiments an air suction port or ports can be in the back cover of the monitor. Should there be an air suction port or ports, in aspects, one or more air suction conduits can connect a remote or peripheral exhaled air purification chamber to the monitor.

In embodiments, the flow of exhaled air+ambient room air can flow as follows (by way of examples only):

A) exhaled air+ambient room air>exhaled air blocking surface being that of the front surface of the electronic display screen>air suction intake(s)>within air suction intake(s) around one or more edges (sides) of the electronic display screen or monitor>into an open cavity between the back of the electronic display screen and the inside surface of the back cover>into an air purification chamber>released back into the room after being cleaned or purified.

B) exhaled air+ambient room air>exhaled air blocking surface being that of the front surface of the electronic display screen>air suction intake(s)>within air suction intake(s) around one or more edges (sides) of the electronic display screen or monitor>into an open cavity between the back of the electronic display screen and the inside surface of the back cover>through a port in in the back cover>into an air suction conduit>and into an air purification chamber>released back into the room after being cleaned or purified.

C) exhaled air+ or ambient room air>exhaled air blocking surface being that of the front surface of the electronic display screen>air suction intake(s)>within air suction intake(s) around one or more edges (sides) of the electronic display screen or monitor>into conduit or conduits located between the back of the electronic display screen and the inside surface of the back cover>into an air purification chamber>released back into the room after being cleaned or purified.

D) exhaled air+ambient room air>exhaled air blocking surface being that of the front surface of the electronic display screen>air suction intake(s)>within air suction intake(s) around one or more edges (sides) of the electronic display screen or monitor>into a conduit(s) between the back of the electronic display screen and the inside surface of the back cover>through a port in the back cover>into an air suction conduit>and into an air purification chamber>released back into the room after being cleaned or purified E) exhaled air+ambient room air>exhaled air blocking surface being that of the front surface of the electronic display screen>air suction intake(s)>within air suction intake(s) around one or more edges (sides) of the electronic display screen or monitor>into air suction conduit or conduits located external to the back of the back cover>into an air purification chamber>released back into the room after being cleaned or purified.

F) exhaled air and/or ambient room air>exhaled air blocking surface being that of the front surface of the electronic display screen>air suction intake(s)>within air suction intake(s) around one or more edges (sides) of the electronic display screen or monitor>into an open space located between the back cover and the back of the electronic display>through a port located within the back cover>into an air purification chamber>released back into the room after being cleaned or purified.

G) exhaled air+ambient room air>exhaled air blocking surface being that of the front surface of the electronic display screen>air suction intake(s)>within air suction intake(s) around one or more edges (sides) of the electronic display screen or monitor>into an open space located between the back cover and the back of the electronic display screen>through a port located within the back cover>into an air suction conduit>into an air purification chamber>released back into the room after being cleaned or purified.

H) exhaled air+ambient room air>exhaled air blocking surface being that of the front surface of the electronic display screen>air suction intake(s)>within air suction intake(s) around one or more edges (sides) of the electronic display screen or monitor>into an open space located between the back cover and the back of the electronic display screen>through a port located within the back cover>into an air suction conduit within or attached to a support stand>into an air purification chamber>released back into the room after being cleaned or purified.

I) exhaled air+ambient room air>first exhaled air blocking surface being that of the front surface of the electronic display screen>around one or more edges (sides) of the electronic display screen or monitor>second exhaled air blocking surface>air suction intake(s)>into air suction conduit or conduits located external to the back of the back cover>into an air purification chamber>released back into the room after being cleaned or purified.

J) exhaled air+ambient room air>first exhaled air blocking surface being that of the front surface of the electronic display screen>around one or more edges (sides) of the electronic display screen or monitor>second exhaled air blocking surface>air suction intake(s)>through an aperture in the back of the back cover>into an air purification chamber>released back into the room after being cleaned or purified.

K) exhaled air+ambient room air>exhaled air blocking surface being that of the front surface of the electronic display screen>around one or more edges (sides) of the electronic display screen or monitor>into an open space located between the back cover and the back of the electronic display>into an air suction intake>into a conduit>into an air purification chamber>released back into the room after being cleaned or purified.

L) exhaled air+ambient room air>exhaled air blocking surface being that of the front surface of the electronic display screen>around one or more edges (sides) of the electronic display screen or monitor>into an open space located between the back cover and the back of the electronic display>into an air suction intake>into an air purification chamber>released back into the room after being cleaned or purified.

M) exhaled air+ambient room air>exhaled air blocking surface being that of the front surface of the electronic display screen>into an air suction intake located beneath the electronic display screen or monitor>into an air purification chamber>released back into the room after being cleaned or purified.

N) exhaled air+ambient room air>exhaled air blocking surface being that of the front surface of the electronic display screen>into an air catch basin located beneath the electronic display screen or monitor>into an air suction intake>into an air purification chamber>released back into the room after being cleaned or purified.
O) exhaled air+ambient room air>exhaled air blocking surface being that of the front surface of the electronic display screen>into a distance separated air suction intake located beneath the electronic display screen or monitor>into an air purification chamber>released back into the room after being cleaned or purified.
P) exhaled air+ambient room air>exhaled air blocking surface being that of the front surface of the electronic display screen>into an attached air suction intake located beneath the electronic display screen or monitor>into an air purification chamber>released back into the room after being cleaned or purified.
Q) exhaled air+ambient room air>exhaled air blocking surface being that of the front surface of the electronic display screen>into a distance separated conventional air purifier located beneath the electronic display screen or monitor>into an air purification chamber>released back into the room after being cleaned or purified.
R) exhaled air+ambient room air>exhaled air blocking surface being that of the front surface of the electronic display screen>into an attached conventional air purifier located beneath the electronic display screen or monitor>into an air purification chamber>released back into the room after being cleaned or purified.

The terms sides or edges as used above is meant to be one or more, or any combination thereof, of a top side or top edge, a bottom side or bottom edge, a right side or right edge, or a left side or left edge. Said another way a side can be an edge. In embodiments the exhaled air collector can comprise two panels separated from one another by walls on three or four sides forming an open space between the two panels that allows exhaled air to flow. In other embodiments the exhaled air collector can comprise a single panel that is distant separated from the back of the monitor cover allowing air to flow between the back of the monitor cover and the front of the single panel. In still other embodiments the exhaled air collector can comprise a single panel that comprises air suction intake(s) through it that open into an open space formed behind the electronic display screen and the back cover of the monitor or electronic display screen.

An embodiment of the invention disclosed herein can be that of one or more of a monitor, laptop, tablet, or TV, wherein the monitor, laptop, tablet, or TV comprise an exhaled air collector, an electronic display screen, and one or more air suction intakes, and wherein the exhaled air collector comprises an open front, wherein the electronic display screen is located within a perimeter of the exhaled air collector, wherein exhaled air in the form of a cough, sneeze, talk or exhaled air breath is blocked by the electronic display screen and deflected towards an air suction intake, wherein the monitor, laptop, tablet, or TV further comprise or are connected to an air purification chamber, and wherein air entering the air suction intake travels towards and through the air purification chamber. An exhaled air suction intake can connect to an air purification chamber. An air-suction intake can be located within an exhaled air-catch basin. An air suction intake can be located around an electronic display screen. An air suction intake can be located around the perimeter of an electronic display screen. An air-suction intake can connect to an air suction conduit. An exhaled air collector can be integrated with the electronic display screen. An exhaled air collector can be designed into an electronic display screen's periphery. An exhaled air collector can be adjacent to the electronic display screen. An exhaled air collector can house the electronic display screen. An exhaled air collector can encircle the electronic display screen. An exhaled air collector and electronic display screen can be supported by a portion of, or all of, an exhaled air purification chamber or a conventional air purifier. One or more air suction intakes can be located below the electronic display screen. One or more of the air suction intakes can be located to the right and/or left of the electronic display screen.

One or more air suction intakes can be located above, to the right of, to the left of, and/or below the electronic display screen. The exhaled air collector can comprise one or more fans. The electronic display screen can be attached wirelessly or wired to a laptop. The electronic display screen can be attached wirelessly or wired to a desktop computer. The electronic display screen can be attached wirelessly or wired to a tablet. The exhaled air collector or electronic display screen can comprise a sensor, wherein the sensor is capable of sensing when an individual is sitting or standing in front of the electronic display screen or monitor. The exhaled air collector can be connected to an exhaled air purification chamber. The electronic display screen can be connected to an air purification unit. The exhaled air purification chamber can comprise a HEPA filter. The exhaled air purification chamber can comprise one or more of filtration, a HEPA filter, a carbon filter, activated carbon filter, ultrasound, ionization, chemical microbicidal purification, light microbicidal purification (such as, by way of example only, UVC light), radioactive microbicidal purification, mechanical microbicidal purification, thermal microbicidal purification, microbicidal agents, microbicidal materials, and/or a $CO_2$ reducing agent or means. The exhaled air purification chamber can comprise an exhaled air purification chamber located behind the electronic display screen. The exhaled air purification chamber can be connected to an air suction conduit, wherein the air suction conduit travels under or around a portion of the electronic display screen. The exhaled air collector can comprise an exhaled air catch basin, wherein the exhaled air catch basin is located at or under the electronic display screen. The exhaled air collector can be attached to the electronic display screen. The exhaled air collector can be attached to a monitor. The exhaled air collector can be integrated with the monitor. The exhaled air collector can be integrated with the electronic display screen.

The exhaled air collector can encircle the electronic display screen's periphery and be connected to an exhaled air purification chamber by an air suction conduit. The exhaled air collector can comprise one or more fans. The electronic display screen and a computer device can work together forming a system to compute and display data or images, wherein a portion of the electronic display screen provides an exhaled air blocking surface of the exhaled air collector. The front outer surface of the electronic display screen can be recessed within a perimeter of the exhaled air collector. The electronic display screen can be planar to the perimeter of the exhaled air collector. The front outer surface of the electronic display screen can be forward to the perimeter of the exhaled air collector. Air entering the open front exhaled air collector can pass through an open contained space around one or more sides of the electronic display screen as it travels towards the air purification chamber.

A laptop can comprise an opening under the electronic display screen and above the keyboard so that exhaled air and room air can travel through the opening to an air suction intake and into an exhaled air purification chamber. The laptop's keyboard can be coated with a microbicidal coating.

Figure 36:
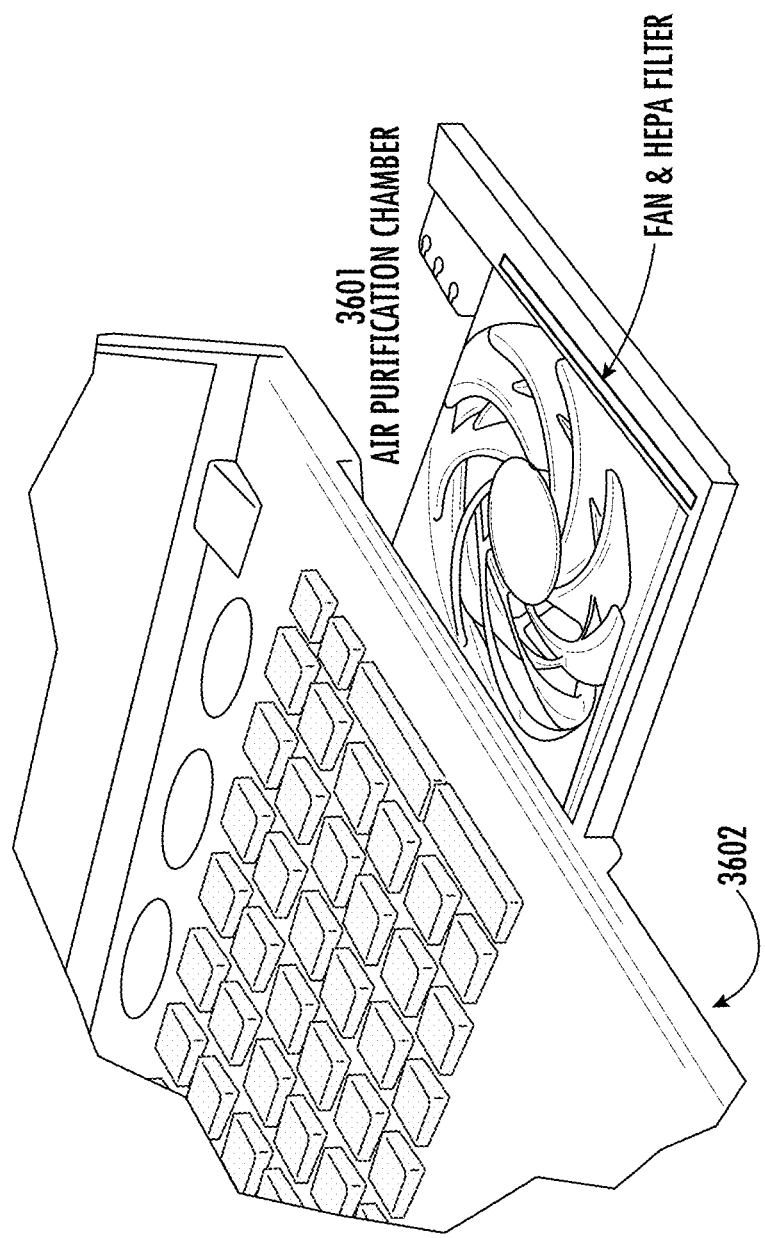
FIG. 36 is an illustration of an embodiment of the current invention as described herein.

A monitor, laptop, tablet, or TV can comprise one or more apertures that are exhaled air suction intakes in the form of a plurality of apertures. The exhaled air purification chamber of one of the monitor, laptop, tablet, or TV can snap in and out of one or more of the monitor, laptop, tablet, or TV, allowing for changing a filter or replacing a part within the exhaled air purification chamber. FIG. 36 shows an air purification chamber 3601 that snaps into a laptop computer 3602 or is connectable to a laptop computer. In embodiments, the snap in air purification chamber is the primary air purification chamber for the laptop computer that creates air suction, uses a filter, and cleans exhaled air. In other embodiments, the snap in air purification chamber is an attached or connected secondary air purification chamber that helps capture and clean respiratory particles, for example, those left on the keyboard. In still other embodiments, both a primary air purification chamber and a secondary air purification chamber are used alone or together.

A portable monitor such as, by way of example only, a laptop, tablet, or TV can accommodate a portable exhaled air collector and air purification chamber that attaches to the monitor. Such attachment can be by way of example only, mechanical, pressure, magnetic, or adhesive. Such attachment can be a releasable attachment that can attach, release, and reattach multiple times. The portable exhaled air collector and air purification chamber can utilize its own rechargeable battery for power and/or obtain power from the USB port of, by way of example only, the portable laptop, tablet, or TV.

A monitor, laptop, tablet, or TV can comprise two or more exhaled air purification chambers. A laptop can comprise a secondary air purification chamber, wherein the secondary air purification chamber comprises a fan(s) and a filter(s), and/or microbicidal means. The laptop can comprise a secondary air purification chamber, wherein the secondary air purification chamber comprises a fan(s) and a filter(s) and wherein the primary air purification chamber is located apart from the laptop. The laptop can comprise a secondary air purification chamber, wherein the secondary air purification chamber comprises a fan(s) and a filter(s), and wherein the primary air purification chamber is located on a platform to or on which the laptop rests. The laptop can comprise a plurality of apertures either below the screen or in the keyboard, and wherein the plurality of apertures form air suction intakes. The laptop can comprise an aperture either below the screen or in the keyboard or where the keyboard meets the screen, and wherein the aperture forms an air suction intake.

A monitor, laptop, tablet, or TV can comprise an antimicrobial or microbicidal agent or coating that is on the electronic display screen and/or keyboard.

In an embodiment, the monitor (screen) surface, the docking station, and any other surface of the unit/system can be coated with transparent antimicrobial coating, such as but not limited to coatings containing Cu ion, Ag ion, or photocatalytic $TiO_2$, which upon light and moisture is activated and destroys different pathogens.

In another embodiment, the monitor (screen) surface, a docking station, monitor stand or support, and any other surface of the exhaled air collector and/or exhaled air purification chamber can be coated with transparent biocidal-containing coatings, such as but not limited to those presented in Tables 1-3 included herein.

In yet another embodiment, the surfaces can be sprayed and/or wiped with an antimicrobial agent before each use or are sprayed/wiped in certain time intervals (daily, weekly, or monthly).

In some embodiments, the screen surface can be made to be liquid- and/or oil-repellent, i.e. hydrophobic and/or oleophobic in nature. As an example only, this can be accomplished using low-surface-energy materials, such as but not limited to wax, Teflon, PDMS, etc., which give rise to large water contact angles of greater than 90°. The liquid and oil droplets on such surfaces do not attach to them, but rather roll-up and slide, especially if the surface is inclined under angle or is a vertical surface.

In other embodiments, one or more of the electronic display screen's surface, the exhaled air collector, the exhaled air suction intake, the exhaled air catch basin surface, and/or the exhaled air purification chamber, can be made of hydrophobic or superhydrophobic structural elements, preferably multi-scaled periodic structures which do not interfere with the transparency but enable water contact angles of greater than 90°. It is known that such surfaces also yield to reduced contact times to bouncing droplets and aerosols (Ref: L. Wang et al., Compact nanoscale textures reduce contact time of bouncing droplets, Sci. Adv. 2020; 6: eabb2307; F. Yu, et al., Durable Super-repellent Surfaces: From Solid-Liquid Interaction to Applications, Acc. Mater. Res. 2021, 2, 920-932).

In another embodiment, the surface of one or more of the electronic display screen, the exhaled air collector, the exhaled air suction intake, the exhaled air catch basin surface, and/or the exhaled air purification chamber, can be made repellent by applying a hydrophobic or superhydrophobic coating before each use or periodically (daily, weekly, monthly), like those provided by Surfactis Technologies (Hydrophobic Coating for Optics—Surfactis), nano-Care Company (Durable water repellent»hydrophobic coating|nanoCare (nano-care.com)), Prosoco (Masonry Water Repellents|Water Repellent Coatings—PROSOCO) and others.

TABLE 1

Various Disinfectants and their role

| S No | Disinfectant | Role |
| --- | --- | --- |
| 1. | Air disinfectants | A disinfectant can be used as an aerosol or vapour with sufficient concentration to kill airborne microorganisms. |
| 2. | Alcohols | Alcohol and alcohol-based compounds are hospital-grade disinfectants approved by the Center for Disease Control (CDC) and Environmental Protection Agency (EPA)[18]. It is found that high concentration mixture of ethanol (80%) and isopropanol (5%) are very effective against the viruses like Human Immunodeficiency Virus (HIV), Hepatitis B, and Hepatitis C. |
| 3. | Aldehydes | These are sporicidal and fungicidal and inactivate the organic matter partially. |

TABLE 1-continued

Various Disinfectants and their role

| S No | Disinfectant | Role |
|---|---|---|
| 4. | Oxidising agents | The mechanism involves the oxidising of the cell membrane, which leads the virus to death or in the activity. Chlorine and oxygen are powerful oxidisers. |
| 5. | Peroxy and. Peroxo acids | These are also very good oxidants and effective in disinfection of viruses and bacteria. |
| 6. | Phenolic | These are the ingredients of disinfectants and found in mouth wash, soap and hand wash. |
| 7. | Quaternary ammonium compounds | Also known as "quats" and shows a very high tendency with alcohol to kill viruses like norovirus, rotavirus, or poliovirus, which are non-enveloped. |
| 8. | Inorganic compounds | It has the solution of chlorine, hypochlorite, or hypochlorous acid which is capable of destroying the viruses, bacteria, mycobacteria and the spores, 'Chlorine is considered as an excellent disinfectant of water, whether it is drinking water, pool water or wastewater. |

TABLE II

Inactivation of coronaviruses by different types of biocidal agents in suspension tests

| Biocidal agent | Concentration | Virus | Strain/isolate | Exposure time | Reduction of viral infectivity ($\log_{10}$) |
|---|---|---|---|---|---|
| Ethanol | 95% | SARS-CoV | Isolate FFM-1 | 30 s | ≥5.5 |
|  | 85% | SARS-CoV | Isolate FFM-1 | 30 s | ≥5.5 |
|  | 80% | SARS-CoV | Isolate FFM-1 | 30 s | ≥4.3 |
|  | 80% | MERS-CoV | Strain EMC | 30 s | >4.0 |
|  | 78% | SARS-CoV | Isolate FFM-1 | 30 s | ≥5.0 |
|  | 70% | MHV | Strains MHV-2 and MHV-N | 10 min | >3.9 |
|  | 70% | CCV | Strain I-71 | 10 min | >3.3 |
| 2-Propanol | 100% | SARS-CoV | Isolate FFM-1 | 30 s | ≥3.3 |
|  | 75% | SARS-CoV | Isolate FFM-1 | 30 s | ≥4.0 |
|  | 75% | MERS-CoV | Strain EMC | 30 s | ≥4.0 |
|  | 70% | SARS-CoV | Isolate FFM-1 | 30 s | ≥3.3 |
|  | 50% | MHV | Strains MHV-2 and MHV-N | 10 min | >3.7 |
|  | 50% | CCV | Strain I-71 | 10 min | >3.7 |
| 2-Propanol and 1-propanol | 45% and 30% | SARS-CoV | Isolate FFM-1 | 30 s | ≥4.3 |
|  |  | SARS-CoV | Isolate FFM-1 | 30 s | ≥2.8 |
| Benzalkonium chloride | 0.2% | HCoV | ATCC VR-759 (strain 0C43) | 10 min | 0.0 |
|  | 0.05% | MHV | Strains MHV-2 and MHV-N | 10 min | >3.7 |
|  | 0.05% | CCV | Strain I-71 | 10 min | >3.7 |
|  | 0.00175% | CCV | Strain S378 | 3 d | 3.0 |
| Didecyldimethyl ammonium chloride | 0.0025% | CCV | Strain S378 | 3 d | >4.0 |
| Chlorhexidine digluconate | 0.02% | MHV | Strains MHV-2 and MHV-N | 10 min | 0.7-0.8 |
|  | 0.02% | CCV | Strain I-71 | 10 min | 0.3 |
| Sodium hypochlorite | 0.21% | MHV | Strain MHV-1 | 30 s | ≥4.0 |
|  | 0.01% | MHV | Strains MHV-2 and MHV-N | 10 min | 2.3-2.8 |
|  | 0.01% | CCV | Strain I-71 | 10 min | 1.1 |
|  | 0.001% | MHV | Strains MHV-2 and MHV-N | 10 min | 0.3-0.6 |
|  | 0.001% | CCV | Strain I-71 | 10 min | 0.9 |
| Hydrogen peroxide | 0.5% | HCoV | Strain 229E | 1 min | >4.0 |
| Formaldehyde | 1% | SARS-CoV | Isolate FFM-1 | 2 min | >3.0 |
|  | 0.7% | SARS-CoV | Isolate FFM-1 | 2 min | >3.0 |
|  | 0.7% | MHV |  | 10 min | >3.5 |
|  | 0.7% | CCV | Strain I-71 | 10 min | >3.7 |
|  | 0.009% | CCV |  | 24 h | >4.0 |
| Glutardialdehyde | 2.5% | SARS-CoV | Hanoi strain | 5 min | >4.0 |
|  | 0.5% | SARS-CoV | Isolate FFM-1 | 2 min | >4.0 |
| Povidone iodine | 7.5% | MERS-CoV | Isolate HCoV-EMC/2012 | 15 s | 4.6 |
|  | 4% | MERS-CoV | Isolate HCoV-EMC/2012 | 15 s | 5.0 |
|  | 1% | SARS-CoV | Hanoi strain | 1 min | >4.0 |
|  | 1% | MERS-CoV | Isolate HCoV-EMC/2012 | 15 s | 4.3 |
|  | 0.47% | SARS-CoV | Hanoi strain | 1 min | 3.8 |
|  | 0.25% | SARS-CoV | Hanoi strain | 1 min | >4.0 |

TABLE II-continued

Inactivation of coronaviruses by different types of biocidal agents in suspension tests

| Biocidal agent | Concentration | Virus | Strain/isolate | Exposure time | Reduction of viral infectivity ($\log_{10}$) |
|---|---|---|---|---|---|
| | 0.23% | SARS-CoV | Hanoi strain | 1 min | >4.0 |
| | 0.23% | SARS-CoV | Isolate FFM-1 | 15 s | ≥4.4 |
| | 0.23% | MERS-CoV | Isolate HCoV-EMC/2012 | 15 s | ≥4.4 |

TABLE III

Inactivation of coronaviruses by different types of biocidal agents in carrier tests

| Biocidal agent | Concentration | Virus | Strain/Isolate | Volume/material | Organic load | Exposure time | Reduction of viral infectivity ($\log_{10}$) |
|---|---|---|---|---|---|---|---|
| Ethanol | 71% | TGEV | Unknown | 50 μl/stainless | None | 1 min | 3.5 |
| | 71% | MHV | Unknown | 50 μl/stainless | None | 1 min | 2.0 |
| | 70% | TGEV | Unknown | 50 μl/stainless | None | 1 min | 3.2 |
| | 70% | MHV | Unknown | 50 μl/stainless | None | 1 min | 3.9 |
| | 70% | HCoV | Strain 229E | 20 μl/stainless | 5% serum | 1 min | >3.0 |
| | 62% | TGEV | Unknown | 50 μl/stainless | None | 1 min | 4.0 |
| | 62% | MHV | Unknown | 50 μl/stainless | None | 1 min | 2.7 |
| Benzalkoniumhloride | 0.04% | HCoV | Strain 229E | 20 μl/stainless | 5% serum | 1 min | <3.0 |
| Sodium hypochlorite | 0.5% | HCoV | Strain 229E | 20 μl/stainless | 5% serum | 1 min | >3.0 |
| | 0.1% | HCoV | Strain 229E | 20 μl/stainless | 5% serum | 1 min | >3.0 |
| | 0.06% | TGEV | Unknown | 50 μl/stainless | None | 1 min | 0.4 |
| | 0.06% | MHV | Unknown | 50 μl/stainless | None | 1 min | 0.6 |
| | 0.01% | HCoV | Strain 229E | 20 μl/stainless | 5% serum | 1 min | <3.0 |
| Glutardialdehyde | 2% | HCoV | Strain 229E | 20 μl/stainless | 5% serum | 1 min | >3.0 |
| Ortho-phtalaldehyde | 0.55% | TGEV | Unknown | 50 μl/stainless | None | 1 min | 2.3 |
| | 0.55% | MHV | Unknown | 50 μl/stainless | None | 1 min | 1.7 |
| Hydrogen peroxide | Vapor of unknown concentration | TGEV | Purdue strain type 1 | 20 μl/stainless steel | None | 2-3 h | 4.9-5.3* |

TGEV = transmissible gastroenteritis virus; MHV = mouse hepatitis virus; HCoV = human coronavirus;
*depending on the volume of injected hydrogen peroxide.

In embodiments, when the exhaled air collector is an attachable or releasably attachable assembly to a monitor or electronic display screen, a flexible or compressible gasket can be used to ensure the attached peripheral exhaled air collector assembly is airtight or substantially airtight when fitted to the electronic display screen or electronic device (e.g., computer). In addition, a plastic or rubberized sealing tape can be used.

In embodiments the exhaled air collector can be a folded assembly that is attachable to a computer screen/electronic display screen and when attached and unfolded becomes an exhaled air collector. When the exhaled air collector is an assembly for a laptop or tablet computer screen, the assembly can comprise an additional foldable flap that permits the exhaled air blocking surface to not only include the electronic display screen, but also a portion of a surface of a flap that extends in a superior position above that of the electronic display screen once it is applied to the monitor. This increases the vertical dimension of the exhaled air blocking surface of the attached exhaled air collector for a laptop or tablet computer screen. In most cases, an electronic display screen already has the necessary vertical dimension and thus this additional superior surface area is not required.

In an embodiment, when attaching the exhaled air collector to a monitor or electronic display screen a portion of the exhaled air collector can be pulled over a portion of the monitor or electronic display screen, wherein once attached a portion of the exhaled air collector covers a portion of the back of the monitor or electronic display screen, and wherein a portion of the exhaled air collector covers one or more sides of the monitor or electronic display screen. The exhaled air collector can comprise one or more fans.

In embodiments a monitor, laptop, tablet, or TV can comprise an exhaled air collector and a port. The port can be on a side of a monitor, laptop, tablet, or TV. The port can on one end open to an air flow space that connects to an exhaled air collector and on the other end connect directly or indirectly to a remote air purification chamber. The remote air purification chamber can be portable and comprise its own rechargeable battery and/or it can be portable and receive power from the USB port of the monitor, laptop, tablet, or TV. The remote air purification chamber can be stationary and receive its power from an AC outlet directly or indirectly.

An electronic display screen can be connected wirelessly or wired to a laptop. The electronic display screen can be connected wirelessly or wired to a desktop computer. The electronic display screen can be attached wirelessly or wired to a tablet. The exhaled air collector or computer screen can comprise a sensor, wherein the sensor is capable of sensing when an individual is sitting or standing in front of the computer screen. The exhaled air collector or computer screen can comprise a $CO_2$ sensor, wherein the sensor can determine the quality of air ventilation in the room. The $CO_2$ sensor can cause ad increase or decrease in the CFM or CADR of the air purification unit depending upon the level of $CO_2$ the $CO_2$ sensors senses.

The invention can be that of an operational computer and wired or wireless connected electronic display screen, wherein the display screen comprises an attached or integrated exhaled air collector. The electronic display screen can be that of an exhaled air blocking surface. The exhaled air collector can be indirectly connected to an exhaled air purification chamber. The exhaled air collector can be directly attached to an exhaled air purification chamber. The exhaled air collector can be distance separated from an exhaled air purification chamber. The display screen can be indirectly connected to an exhaled air purification unit. The display screen can be distance separated from an exhaled air purification unit. The computer and screen can be that of a desktop monitor. The computer and screen can be that of a laptop computer and electronic display screen. The computer and screen can be that of a tablet computer and electronic display screen. The computer and screen can be that of a TV.

As used herein an exhaled air purification unit comprises both an exhaled air collector and an exhaled air purification chamber. An exhaled air purification unit can comprise each of an exhaled air collector, an exhaled air blocking surface, an optional exhaled air catch basin, an exhaled air suction intake, an optional exhaled air suction conduit, and/or an exhaled air purification chamber. An exhaled air purification unit can comprise a HEPA filter. The exhaled air purification chamber can comprise any type of an air filter and/or any type of microbicidal agent, material, or means (including by way of example only, heat, ultrasound, chemical agent, ionization, UV light, UVC light, or HEPA filter), and/or radiation, for capturing and/or destroying airborne pathogens, contaminants, pollution, and/or allergens. The exhaled air purification unit can comprise an exhaled air purification chamber located behind, under, on top of, or besides a monitor and/or electronic display screen.

The exhaled air purification unit can comprise an air suction conduit, wherein the air suction conduit travels under or around a portion of the electronic display screen or monitor. The exhaled air purification unit can optionally comprise an exhaled air catch basin, wherein the exhaled air catch basin can be located at or under the electronic display screen or monitor. The exhaled air purification unit can optionally comprise an exhaled air catch basin, wherein the exhaled air catch basin can be located at or directly under the electronic display screen or monitor. The exhaled air purification unit can optionally comprise an exhaled air catch basin, wherein the exhaled air catch basin can be located at or under the lower front surface of an electronic display screen or monitor. The exhaled air collector can be integrated into the electronic display screen or monitor. The exhaled air collector can be designed into the display screen or monitor's periphery and can be connected to an exhaled air purification chamber. The exhaled air collector can be distance separated from an exhaled air catch basin comprising an air suction intake and connected directly or indirectly to an air purification chamber. The exhaled air collector can be distance separated from a conventional air purifier.

The exhaled air collector can be an attachable assembly, and wherein the attachable assembly is attachable to an electronic display screen or monitor. The exhaled air collector can be a releasably attachable assembly, and wherein the attachable assembly is attachable and releasable to and from an electronic display screen or monitor. The exhaled air collector can comprise one or more fans. The exhaled air collector can be devoid of a fan. The exhaled air purification chamber can comprise one or more fans. In embodiments the exhaled air purification chamber comprises a fan array comprising 2 or more fans. In embodiments the exhaled air purification chamber comprises a fan array comprising 3 or more fans. In embodiments the exhaled air purification chamber comprises a fan array comprising 4 or more fans.

An embodiment can be that of one or more of an exhaled air capture and air cleaning docking station that connects to or supports a monitor, laptop, tablet, or TV. The electronic display screen of the monitor, laptop, tablet, or TV can serve as the exhaled air blocking surface and the docking station can serve as the exhaled air collector capturing exhaled air and directing it through one or more air suction intakes into a directly connected or indirectly connected air purification chamber. The exhaled air capture and air cleaning docking station can be portable and comprise its own rechargeable battery and/or can connect to the USB port of the monitor, laptop, tablet, or TV. The air capture and air cleaning docking station can be stationary and connect to an AC outlet.

An embodiment can be that of one or more of an exhaled air capture and air cleaning support tray that connects to or supports a monitor, laptop, tablet, or TV. The electronic display screen of the monitor, laptop, tablet, or TV can serve as the exhaled air blocking surface and the support tray can serve as the exhaled air collector capturing exhaled air and directing it through one or more air suction intakes into a directly connected or indirectly connected air purification chamber. The exhaled air capture and air cleaning support tray can be portable and comprise its own rechargeable battery and/or can connect to the USB port of the monitor, laptop, tablet, or TV. The air capture and air cleaning support tray can be stationary and connect to an AC outlet.

An embodiment can be that of one or more of an exhaled air capture and air cleaning attachable member that connects to or supports a monitor, laptop, tablet, or TV. The electronic display screen of the monitor, laptop, tablet, or TV can serve as the exhaled air blocking surface and the attachable member can serve as the exhaled air collector capturing exhaled air and directing it through one or more air suction intakes into a directly connected or indirectly connected air purification chamber. The exhaled air capture and air cleaning attachable member can be portable and comprise its own rechargeable battery and/or can connect to the USB port of the monitor, laptop, tablet, or TV. The air capture and air cleaning attachable member can be stationary and connect to an AC outlet An embodiment can be that of one or more of an exhaled air capture and air cleaning backstop screen that connects to, supports, or can be adjacent to a monitor, laptop, tablet, or TV. The electronic display screen of the monitor, laptop, tablet, or TV can serve as the exhaled air blocking surface and the backstop screen can serve as the exhaled air collector capturing exhaled air and directing it through one or more air suction intakes into a directly connected or indirectly connected air purification chamber. The exhaled air capture and air cleaning backstop screen can be portable and comprise its own rechargeable battery and/or can connect to the USB port of the monitor, laptop, tablet, or TV. The air capture and air cleaning backstop screen can be stationary and connect to an AC outlet.

An operational computer and electronic display screen and exhaled air collector can work together to compute and display data or images, wherein a portion of the display screen provides an exhaled air blocking surface of the exhaled air collector. The exhaled air blocking surface can be one of: recessed, planar, and forward with respect to the most forward outer wall of the exhaled air collector. The operational computer, display screen, and exhaled air collector can work together as a system to compute, display data and/or images, and capture exhaled air, wherein a portion of the electronic display screen acts to deflect and/or direct exhaled air, wherein the exhaled air collector captures exhaled air, and wherein the exhaled air is then further cleaned by an exhaled air purification chamber that is connected directly to, connected indirectly to, or distance separated from the exhaled air collector. As used herein an electronic display screen can be that of a computer screen.

In an embodiment an electronic display screen can be integrated with an exhaled air collector. In an embodiment a monitor can be integrated with an exhaled air collector. In an embodiment an electronic display screen can comprise one or more exhaled air suction intake(s) in its periphery. In an embodiment a monitor can comprise one or more exhaled air suction intake(s) in its periphery.

In embodiments the monitor support stand can be hollow and provide for both support and serve as an air suction conduit that connects a remote or peripheral exhaled air purification chamber to an exhaled air capture and clean readied monitor or tablet. In embodiments the monitor support can be hollow and provide for both support and serve as an air suction conduit that connects a remote or peripheral exhaled air purification chamber to a monitor or tablet that comprises an exhaled air collector, exhaled air suction intake(s), air flow open space, and/or conduit, and port.

In embodiments, upon reaching an air purification chamber portion, the air is pulled through a filter and then through the fan or fans as it is released into the room's ambient air environment as 99%+ cleaned air. The fan or fans can be located within or on the back of the air purification chamber, by way of example only, by any mechanical means or an adhesive. While the fan or fans and a filter(s) are located on or adjacent to the back, the air purification portion can be located at the top, bottom, or back, or any combination thereof. In embodiments a fan can be in front of a filter located within the air purification chamber which pushes air through the filter. In embodiments fans can be in front of and behind a filter(s) located within the air purification chamber which push and pull air through the filter(s). The filter can be that of an HEPA filter. The filter can be that of an activated carbon filter for removing odors. The filter can be that of a pre-filter.

The fan or fans or the air purification chamber can be attached or part of a hinged compartment or member that can be lowered or raised allowing for the filter(s) to be changed/replaced. Upon replacing the filter(s), the compartment or member can be closed and secured by a locking mechanical means, such as by way of example only, one or more of a mechanical catch, snap, magnet, and hook. The hinged compartment or member can be attached to the back of a monitor. The hinged compartment or member can be attached to the back of a laptop. The hinged compartment or member can be attached to the back of a laptop air capture and cleaning docking station. The hinged compartment or member can be attached to the back of a laptop air capture and cleaning Snap-On member. The hinged compartment or member can be attached to the back of a tablet. The hinged compartment or member can be attached to the back of a tablet air capture and cleaning Snap-On member. The hinged compartment or member can be attached to the back of a TV.

In an embodiment an exhaled air purification system is comprised of a plurality of air purification units comprising computer screens having attached exhaled air collectors connected to air purification chambers that are utilized within, by way of example only, a room of an office, workplace, school classroom, conference room, auditorium, etc. In another embodiment an exhaled air purification system comprises a plurality of air purification units comprising computer screens having integrated exhaled air collectors connected to air purification chambers that are utilized within, by way of example only, a room of an office, workplace, school classroom, conference room, auditorium, etc. In still another embodiment two ventilation modalities can be utilized: 1) a plurality of individual exhaled air collectors with a plurality of associated exhaled air purification chambers attached or integrated with a plurality of individual monitors, wherein the plurality of monitors can be utilized together with 2) the room's HVAC system. The combination of both ventilation modalities cleans the air in the room.

In an embodiment a laptop comprising an aperture capable of becoming an air suction intake can be attached to, connected to, or supported by an exhaled air collector, or can be positioned in front of an exhaled air collector. The exhaled air collector can be connected to or attached to an exhaled air purification chamber. The aperture can be located under the electronic display screen of the laptop. The aperture can be located between the bottom of the electronic display screen and a back portion of a laptop's keyboard, or within the upper area of the keyboard near the bottom of the laptop screen. The aperture can be an air suction intake. This opening can serve to help pull exhaled air and room air through the laptop into the exhaled air purification chamber, thus reducing the number of particles left on the laptop keyboard following an exhalation in the form of a cough, a sneeze, an exhaled air breath, a spoken word(s), etc.

An exhaled air collector and associated exhaled air purification chamber can be portable. An exhaled air collector and associated exhaled air purification chamber can be mobile. A portable or mobile laptop, tablet, monitor, or TV can be used with one of the following embodiments: 1) laptop, tablet, monitor, or TV "docking station" comprising an exhaled air collector and an exhaled air purification chamber, 2) laptop, tablet, monitor, or TV "backstop" comprising an exhaled air collector and an exhaled air purification chamber, 3) laptop, tablet, monitor, or TV air cleaning "tray" comprising an exhaled air collector and an exhaled air purification chamber, 4) laptop, tablet, monitor, or TV "snap on back member" comprising an exhaled air collector and an exhaled air purification chamber.

Each of the above four embodiments can be portable. Each of the above four embodiments can be mobile. Each of the four above embodiments can be attachable to a laptop, tablet, monitor, or TV. Each of the four above embodiments can be releasably attachable to a laptop, tablet, monitor, or TV. Such attachment whether permanently attached or releasably attached can provide for an open space for air flow between the back of the laptop, tablet, monitor, or TV, and the front of the back of any of the four above mentioned embodiments. Such an air flow space can permit air flow from the exhaled air collector to be moved towards and/or into the exhaled air purification chamber. A releasable attachment member or members for such attachment can, by way of example only, be that of one or more of: magnet, magnets, Velcro, adhesive pad, screen and bolt, and clamp. Should a magnet be utilized the magnet or magnets can be covered to not scratch the outer cover of the laptop, tablet, monitor, or TV. Such a cover can be by way of example only, coated with a thin layer of plastic, enclosed in a plastic, and/or covered with a thin fabric, such as felt. A permanent attachment member or members for such attachment can, by way of example only, be that of one or more of a mechanical connection and/or adhesive. Each of the four above embodiments can provide support for a laptop, tablet, monitor, or TV. Each of the four above embodiments can have an extension back portion that can be raised or lowered to extend the height of the back to increase or be additive to the height of an exhaled air blocking surface. Such an extension member can have a portion that is transparent. Each of the above four embodiments can be powered by a rechargeable battery. Each of the above four embodiments can be powered by the USB port of the connected or attached laptop, tablet, monitor, or TV.

The embodiments of 1) laptop, tablet, monitor, or TV "docking station" comprising an exhaled air collector and an exhaled air purification chamber, 2) laptop, tablet, monitor, or TV "backstop" comprising an exhaled air collector and an exhaled air purification chamber, 3) laptop, tablet, monitor, or TV air cleaning "tray" comprising an exhaled air collector and exhaled air purification chamber, 4) laptop, tablet, monitor, TV "snap on back member" comprising an exhaled air collector and exhaled air purification chamber, can further comprise one or more of an air suction intake(s); a power source, such as a rechargeable battery, USB charging capability, or AC power source or connector; and/or a sensor (by way of example only) a motion sensor, photosensor, accelerometer, and/or CO2 sensor. Any of the four above embodiments can automatically turn on when a laptop is placed therein and automatically turn off when the laptop is removed, or such automatic control can be turned off.

The embodiments of 1) laptop, tablet, monitor, or TV "docking station" comprising an exhaled air collector, 2) laptop, tablet, monitor, or TV "backstop" comprising an exhaled air collector, 3) laptop, tablet, monitor, or TV air cleaning "tray" comprising an exhaled air collector, 4) laptop, tablet, monitor, or TV "snap on back member" comprising an exhaled air collector; can comprise a port which can be connected to an air suction conduit that connects to a remote air purification chamber.

The embodiments of 1) laptop, tablet, monitor, or TV "docking station" comprising an exhaled air collector, 2) laptop, tablet, monitor, or TV "backstop" comprising an exhaled air collector, 3) laptop, tablet, monitor, or TV air cleaning "tray" comprising an exhaled air collector, 4) laptop, tablet, monitor, or TV "snap on back member" comprising an exhaled air collector can comprise a port or other connection which can be connected to a support stand that connects or attaches to a remote air purification chamber. Such a support stand can have a hollow portion for permitting air to be transferred from the exhaled air collector to the air purification chamber.

The embodiments of 1) laptop, tablet, monitor, or TV "docking station" comprising an exhaled air collector, 2) laptop, tablet, monitor, or TV "backstop" comprising an exhaled air collector, 3) laptop, tablet, monitor, or TV air cleaning "tray" comprising an exhaled air collector, 4) laptop, tablet, monitor, or TV "snap on back member" comprising an exhaled air collector, can each comprise one or two rotational or foldable partial side walls or one or two fixed partial side walls. The one or two rotational or foldable partial side walls or one or two fixed partial side walls can be located on each lower side of the four embodiments noted above where the embodiments touch a tabletop to which they would rest upon. Thus, a rotational or foldable partial side wall can be located on the bottom right side and/or bottom left side of each of the four embodiments above. Or a fixed partial side wall can be located on the bottom right side and or bottom left side of the four embodiments above. The purpose of the rotational partial side walls, foldable partial side walls or fixed partial side walls is to further improve the air suction air flow when the laptop, tablet, monitor, or TV is angled backward with its top being further way from a user than its bottom. These partial side walls provide a reduction of room air that could be pulled into an air suction intake and improve the air flow of exhaled air through the air suction intake when a laptop, tablet, monitor, or TV is tilted backwards on a tabletop or desktop. The partial side walls can be designed into any one or all of the above four embodiments. The partial side walls can be integrated into any one or all of the above four embodiments. The partial side walls can be attached to any one or all of the above four embodiments.

Figure 57:
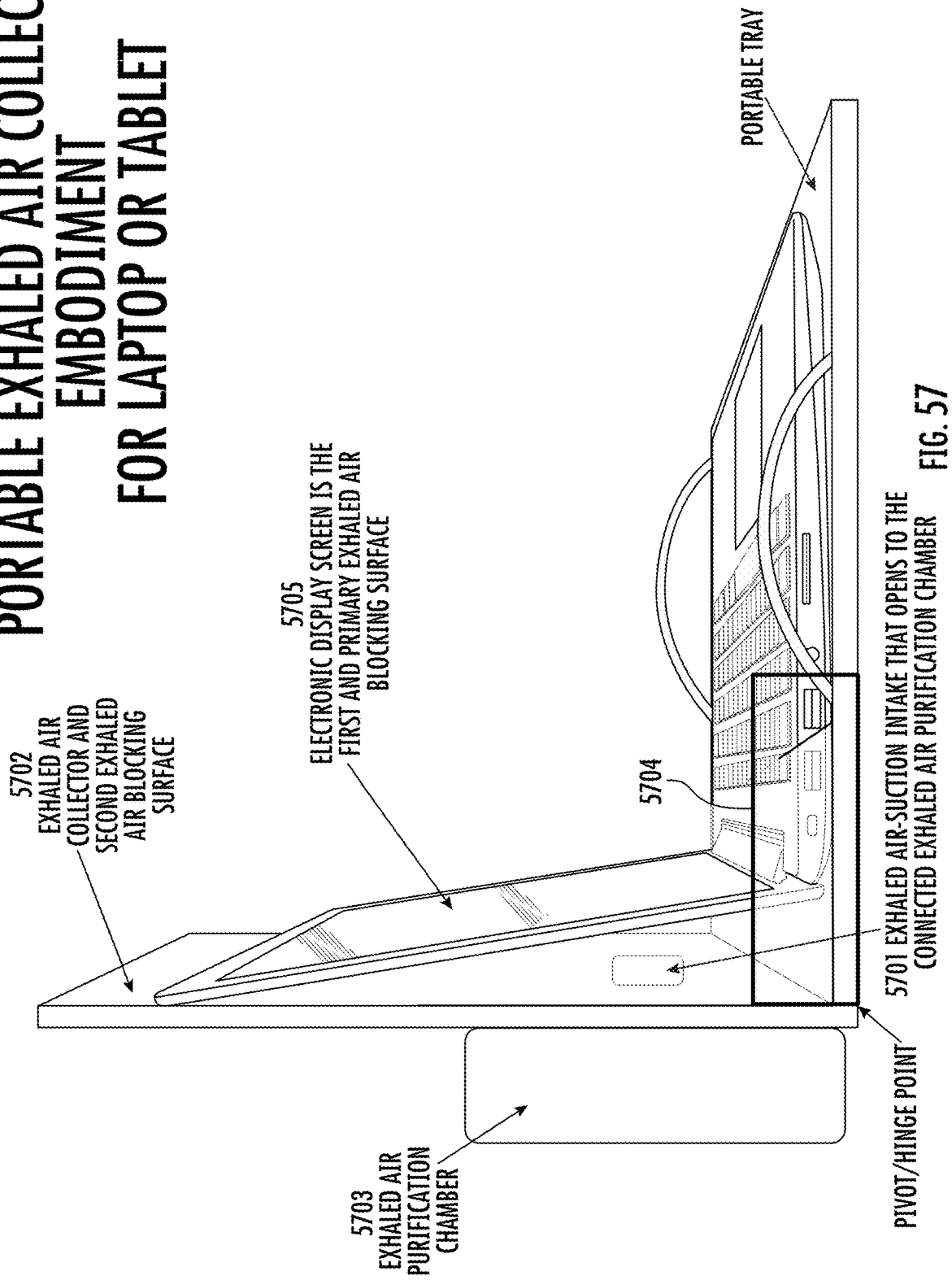
FIG. 57 is an illustration of an embodiment of the current invention as described herein.

FIG. 57 shows a laptop computer associated with an air purification unit having an air suction intake 5701 located in a back exhaled air collector 5702 that opens into an exhaled air purification chamber 5703. The exhaled air collector and air purification chamber is formed in part as that of a portable tray. In aspects, this embodiment can include a partial side wall 5704 that allows for continued contact with a tabletop as the laptop is angled backward (in aspects, there can be for example two side walls; one on the right side and one on the left side). In aspects, the electronic display screen if the first and primary exhaled air blocking surface 5705 and the exhaled air collector 5702 can be considered a secondary air blocking surface.

Figure 58:
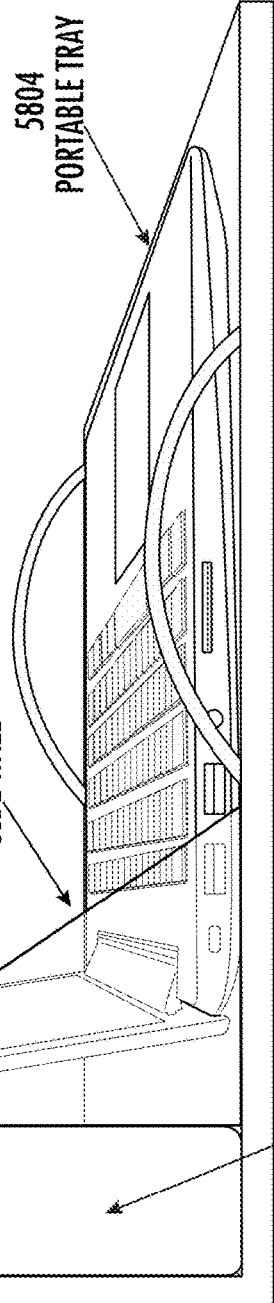
FIG. 58 is an illustration of an embodiment of the current invention as described herein.

FIG. 58 shows a laptop computer associated with an air purification unit having an air suction intake 5806, in aspects peripheral to the display screen/air blocking surface/collector 5805, and an air suction connection port 5801 on the back of the laptop. The port is connected to an air suction conduit 5802 that connects to an exhaled air purification chamber 5803. The laptop can be resting on a portable tray 5804. The exhaled air collector and air purification chamber can be formed in part as that of a portable tray, meaning the air purification unit can be integrated into or built into the tray so the tray and unit are integrated and together portable. In aspects, this embodiment can include a partial side wall 5807 that allows for continued contact with a tabletop as the laptop is angled backward (in aspects, there can be for example two side walls; one on the right side and one on the left side).

Figure 59:
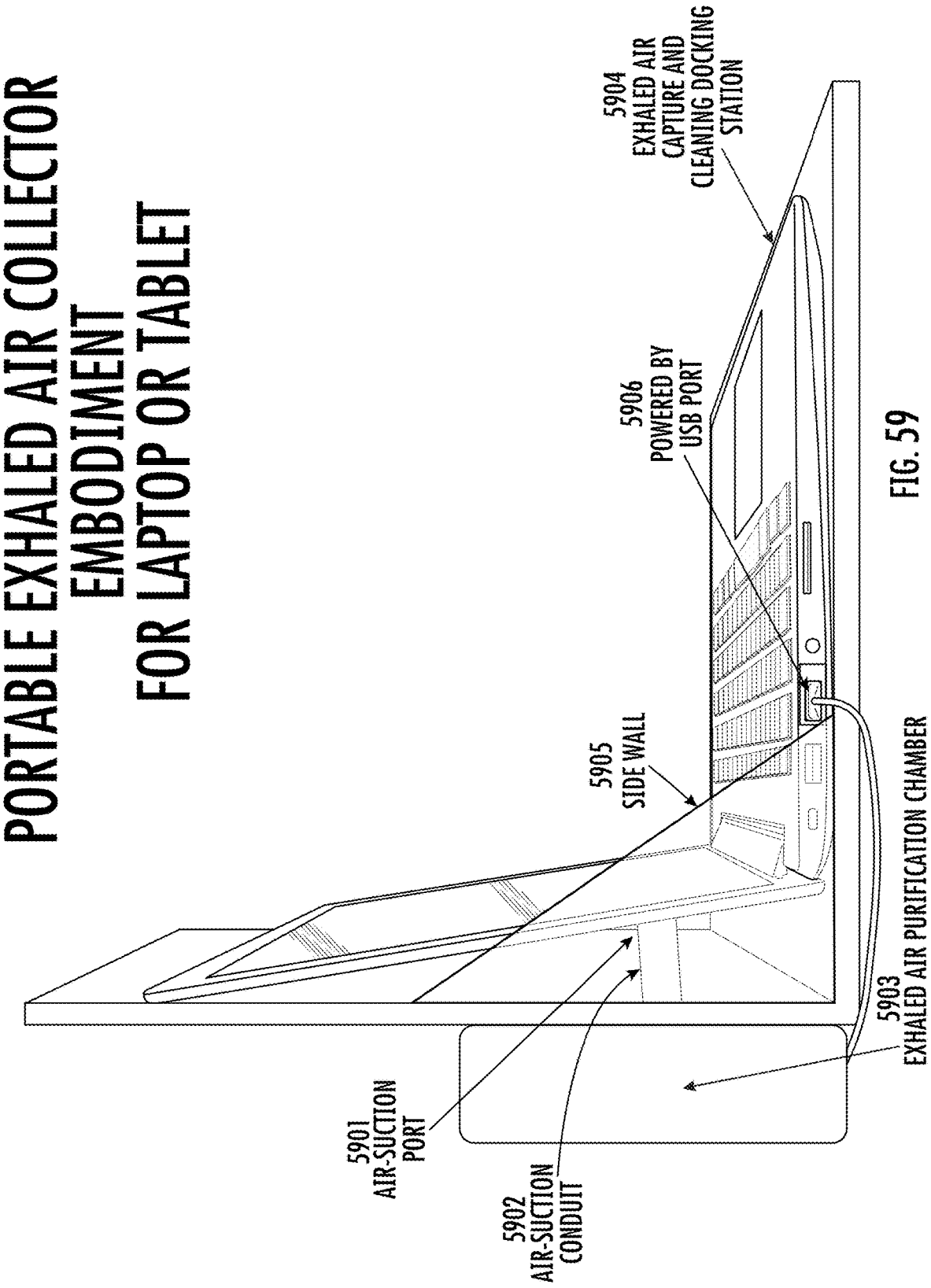
FIG. 59 is an illustration of an embodiment of the current invention as described herein.

FIG. 59 shows a laptop computer associated with an air purification unit having an exhaled air suction intakes, and an air suction connection port on the back of the laptop 5901. The port is connected to an air suction conduit 5902 that connects to an exhaled air purification chamber 5903. The laptop in this embodiment is resting in or on an exhaled air collector docking station 5904. The exhaled air collector and air purification chamber can be formed in part as that of the docking station, meaning the air purification unit can be integrated into or built into the station. In aspects, this embodiment can include a partial side wall 5905 that allows for continued contact with a tabletop as the laptop is angled backward (in aspects, there can be for example two side walls; one on the right side and one on the left side). In aspects, the air purification unit can be powered by the USB powered port on the laptop computer 5906.

Figure 60:
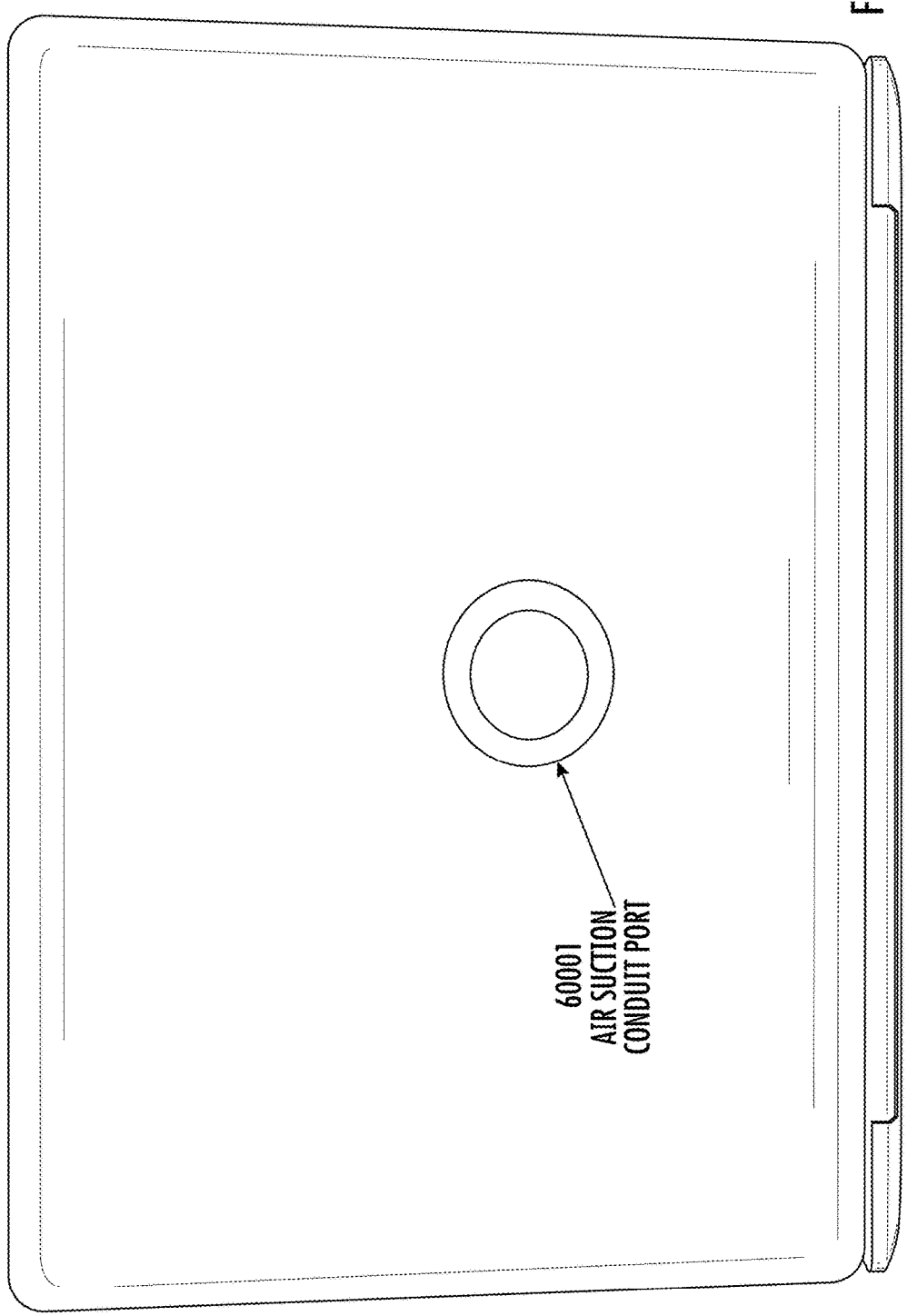
FIG. 60 is an illustration of an embodiment of the current invention as described herein.

FIG. 60 shows how a separate or distance-separated remote exhaled air purification chamber utilizing a conduit can be connected and disconnected to and from the laptop air suction conduit port 60001, enabling the laptop to be used with an air purification unit. In aspects, the laptop can comprise an integrated exhaled air collector with air suction intakes. In aspects, the air purification unit provides the exhaled air collector and air suction intakes. In aspects, the laptop's display screen will serve as the only or the primary exhaled air blocking surface. In aspects, the laptop display screen will serve as the exhaled air collector.

Figure 61:
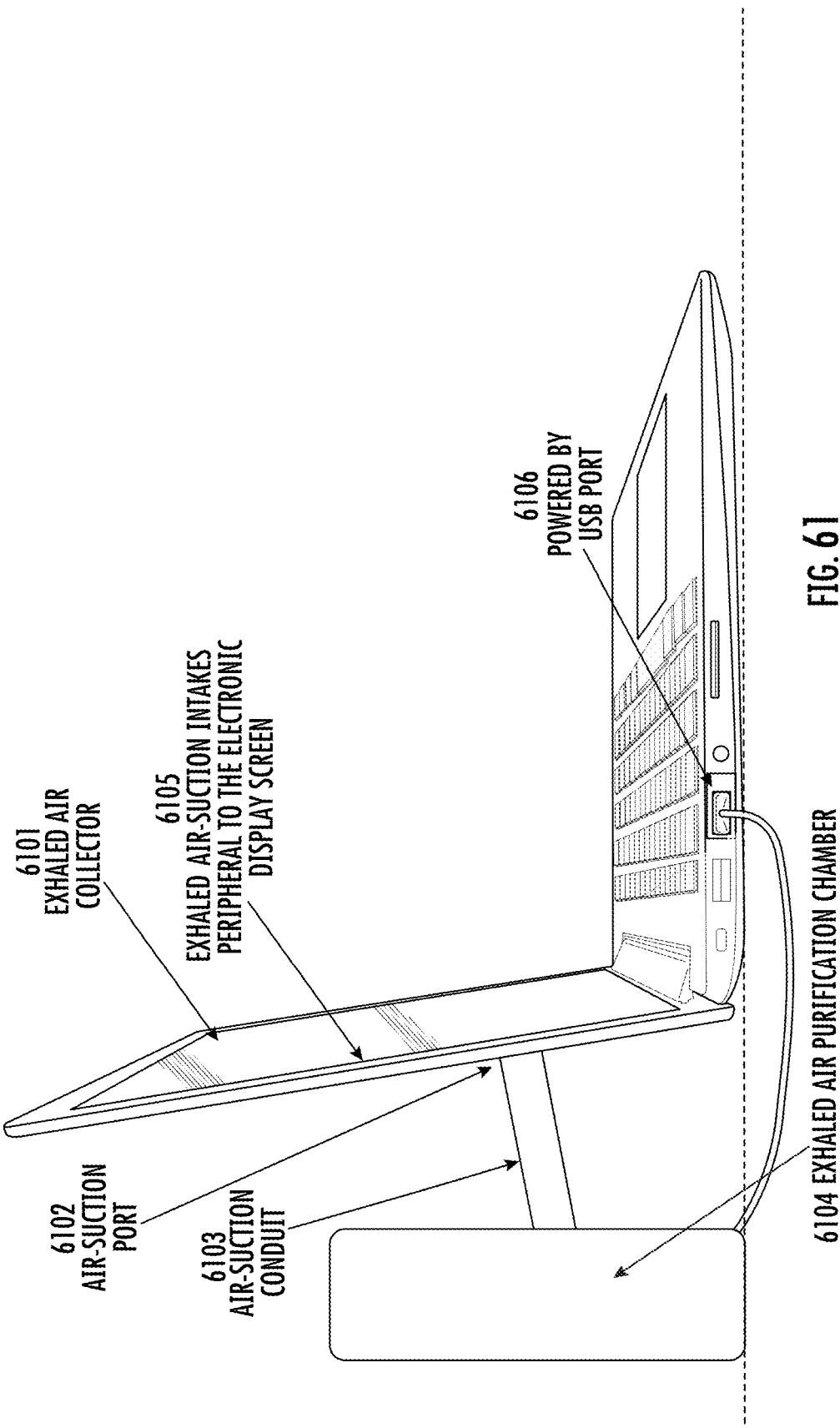
FIG. 61 is an illustration of an embodiment of the current invention as described herein.
Figure 62:
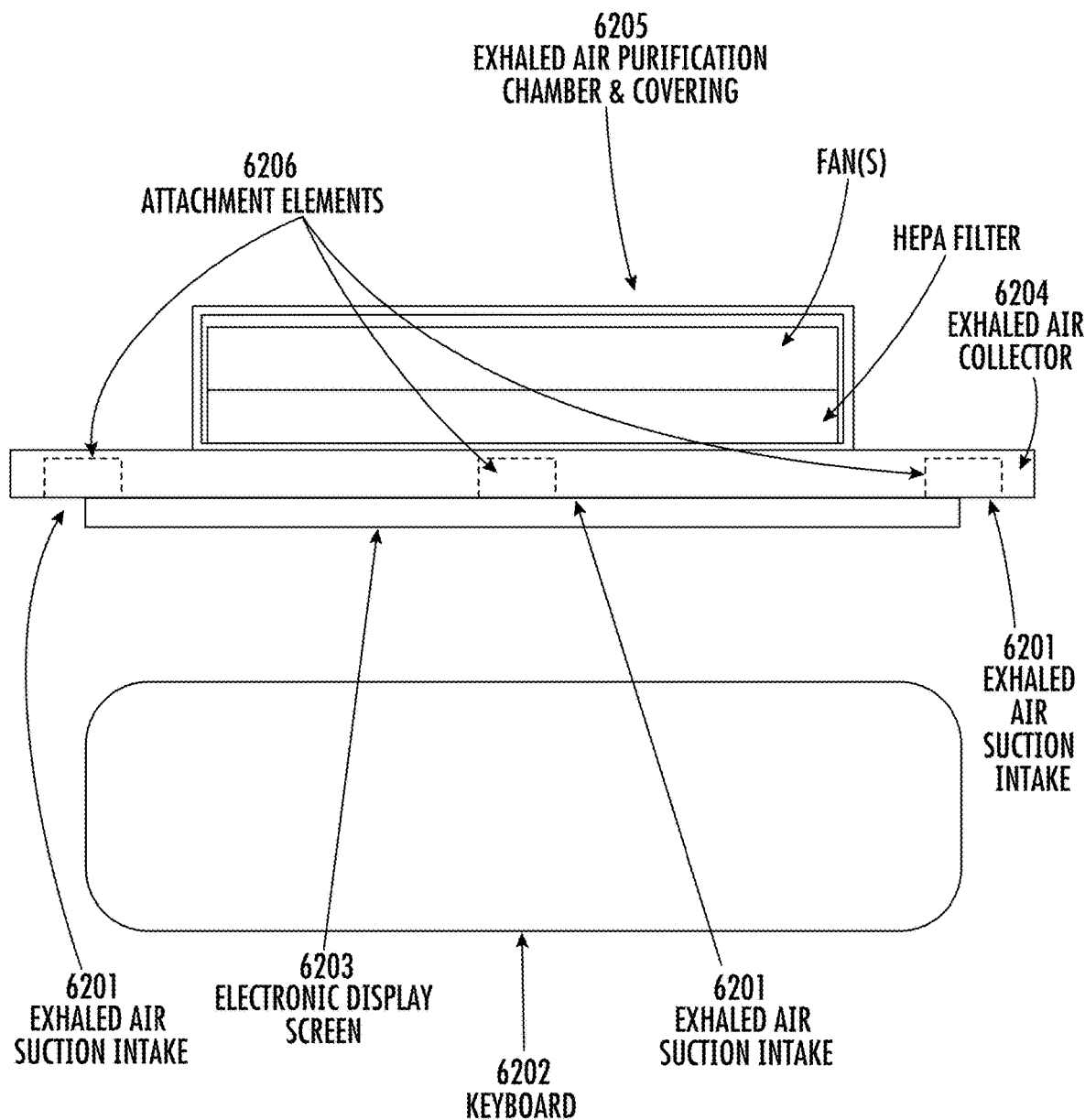
FIG. 62 is an illustration of an embodiment of the current invention as described herein.

FIG. 61 shows a portable exhaled air collector embodiment for a laptop or tablet having an exhaled air collector (e.g., screen of display) 6101, air suction port 6102 in the back of the laptop connected to an air suction conduit 6103 that connects to an air purification chamber 6104. This embodiment includes exhaled air suction intakes 6105 peripheral to the electronic display screen. In aspects, the air purification unit can be powered by the USB powered port on the laptop computer 6106. In aspects, the Figure shows a laptop comprising exhaled air suction intakes and an air suction connection port on the back of the laptop. The port is connected to an air suction conduit that connects to the air purification chamber. FIG. 62 is a top-down view of a releasably attachable back portable exhaled air collector embodiment showing exhaled air suction intakes 6201, the keyboard 6202 of a computer, the electronic display screen/computer monitor 6203, the portable/releasably attachable exhaled air collector 6204, the exhaled air purification chamber and covering 6205, having fans and a filter, and attachment elements 6206 for attaching the exhaled air collector of the air purification unit to the electronic display screen/computer monitor.

Figure 63:
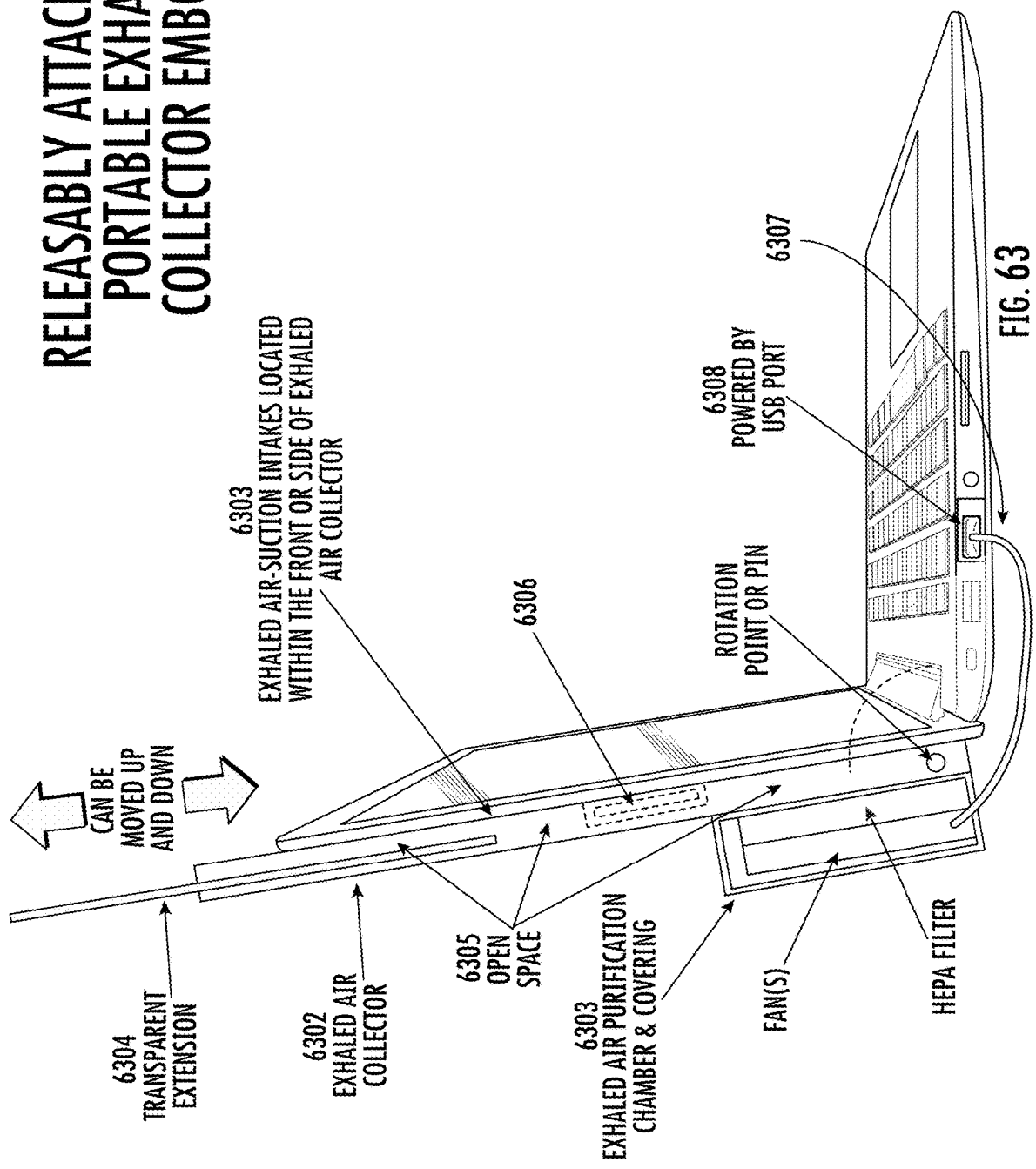
FIG. 63 is an illustration of an embodiment of the current invention as described herein.
Figure 64:
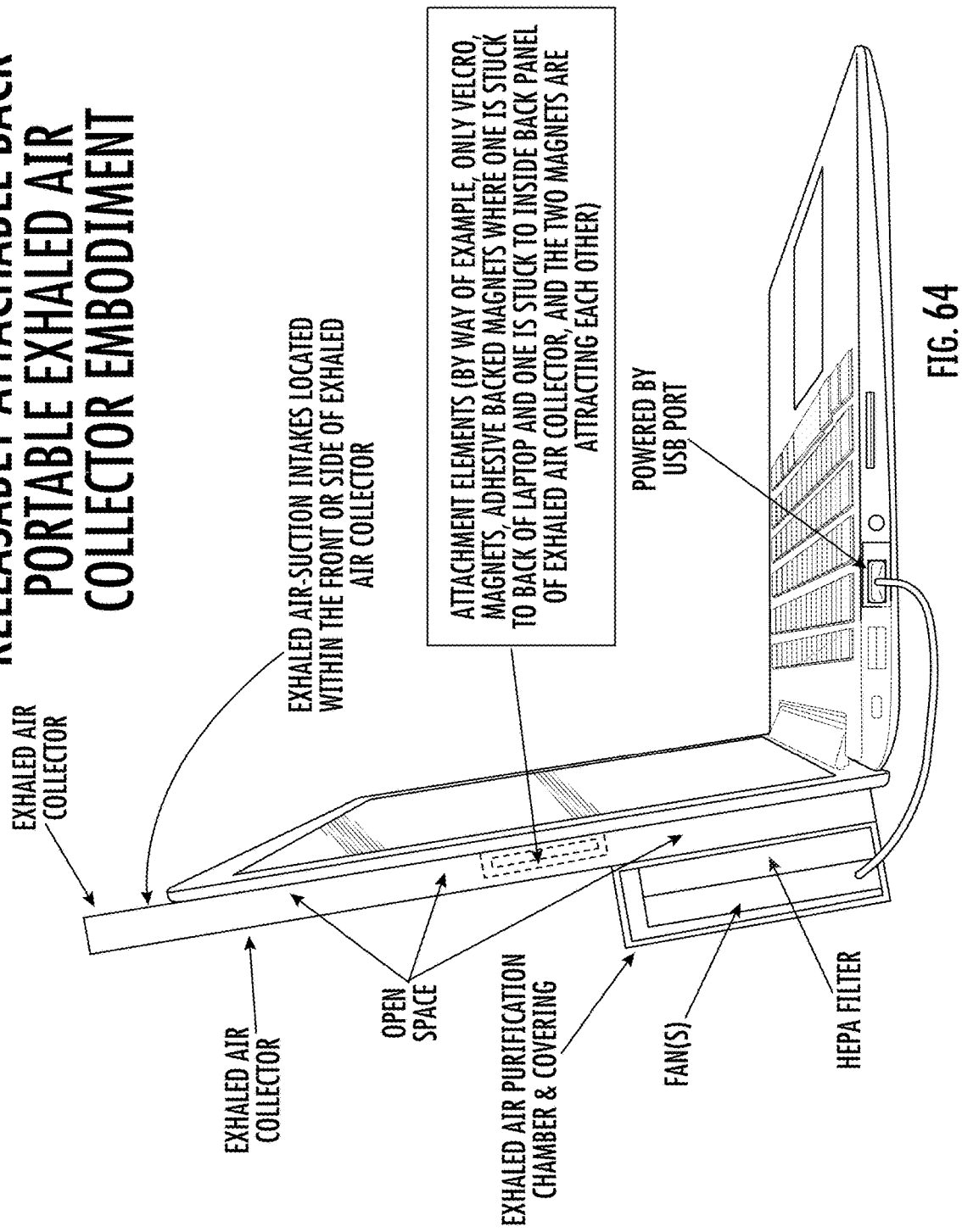
FIG. 64 is an illustration of an embodiment of the current invention as described herein.
Figure 65:
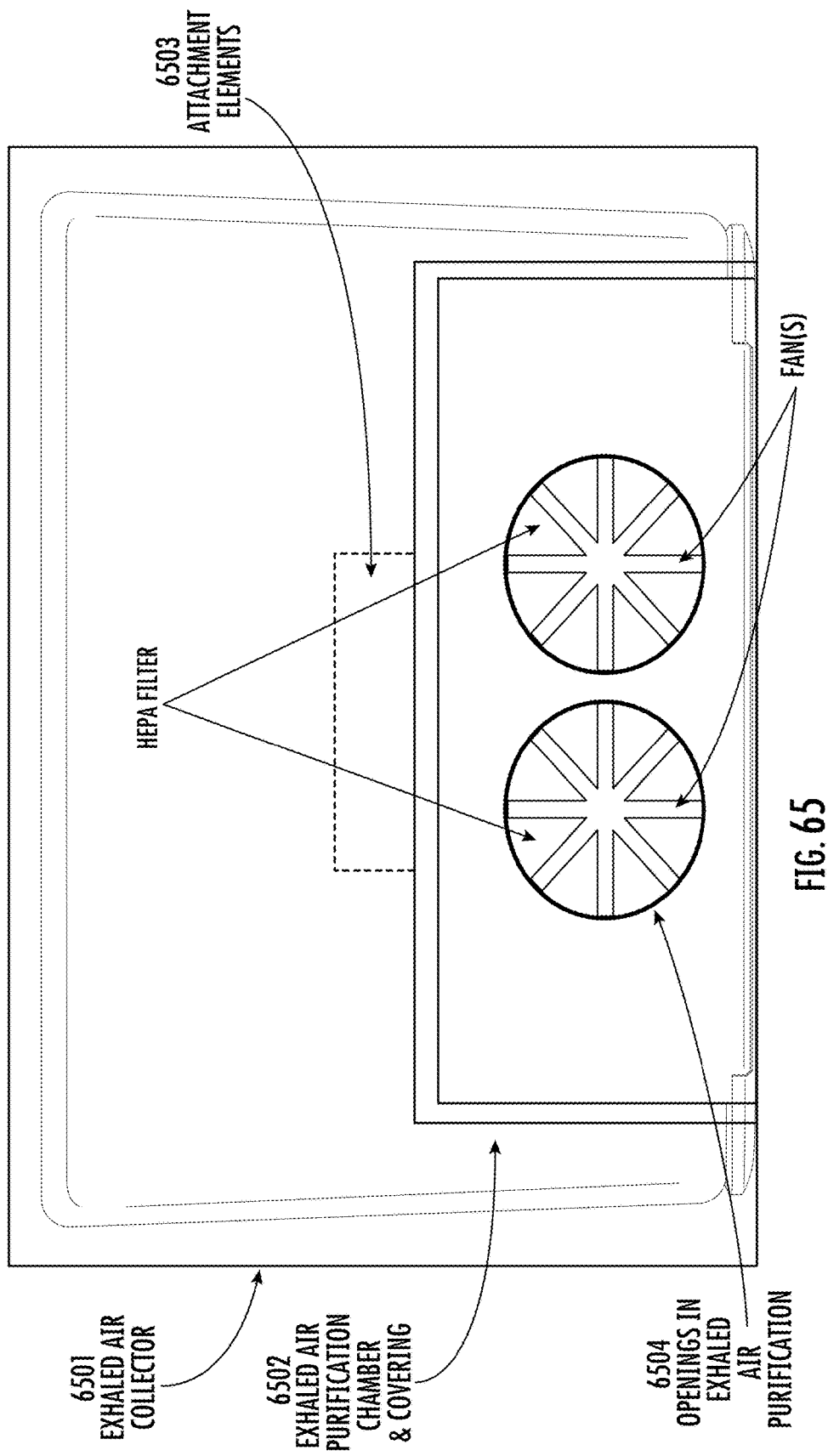
FIG. 65 is an illustration of an embodiment of the current invention as described herein.
Figure 66:
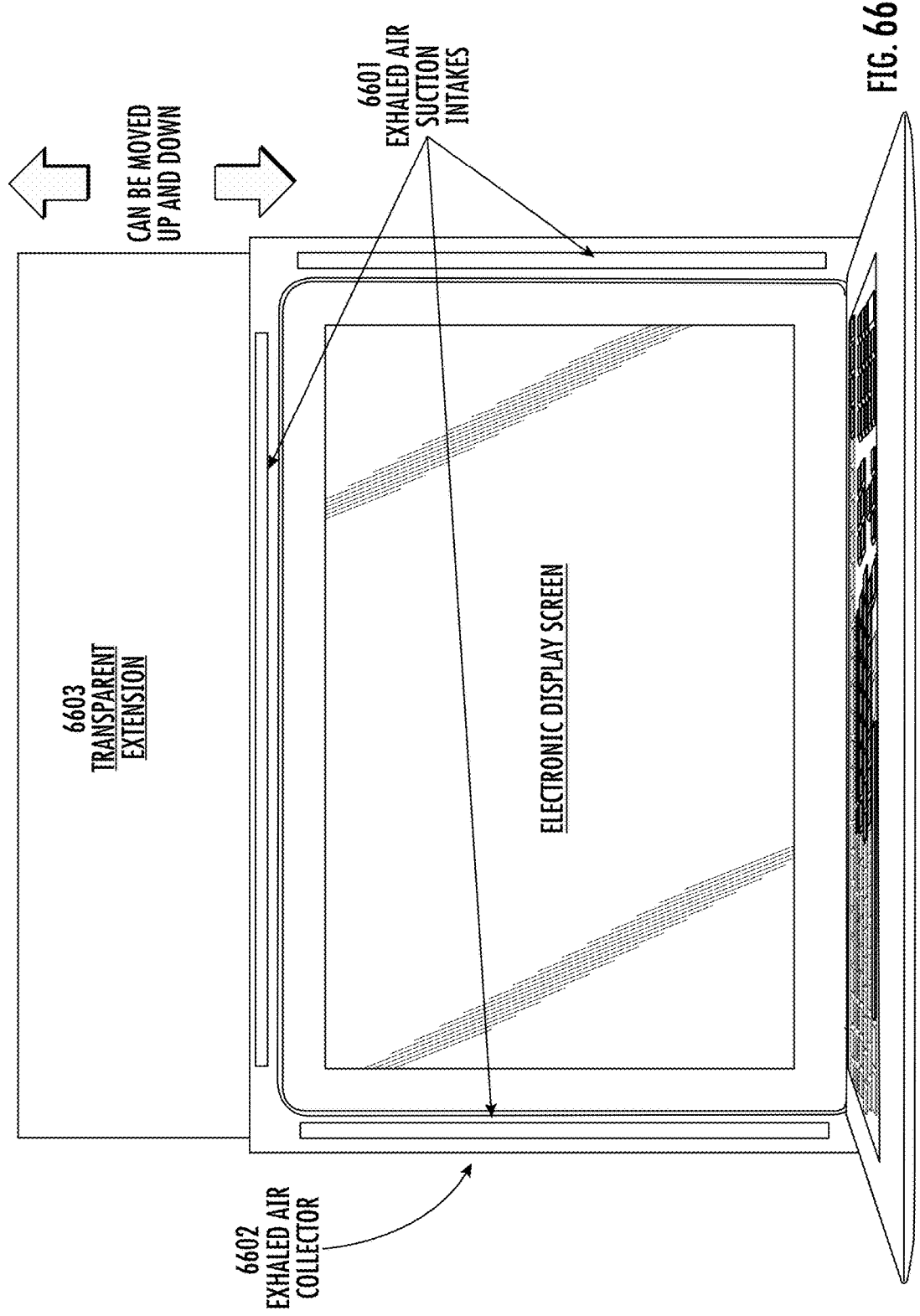
FIG. 66 is an illustration of an embodiment of the current invention as described herein.
Figure 67:
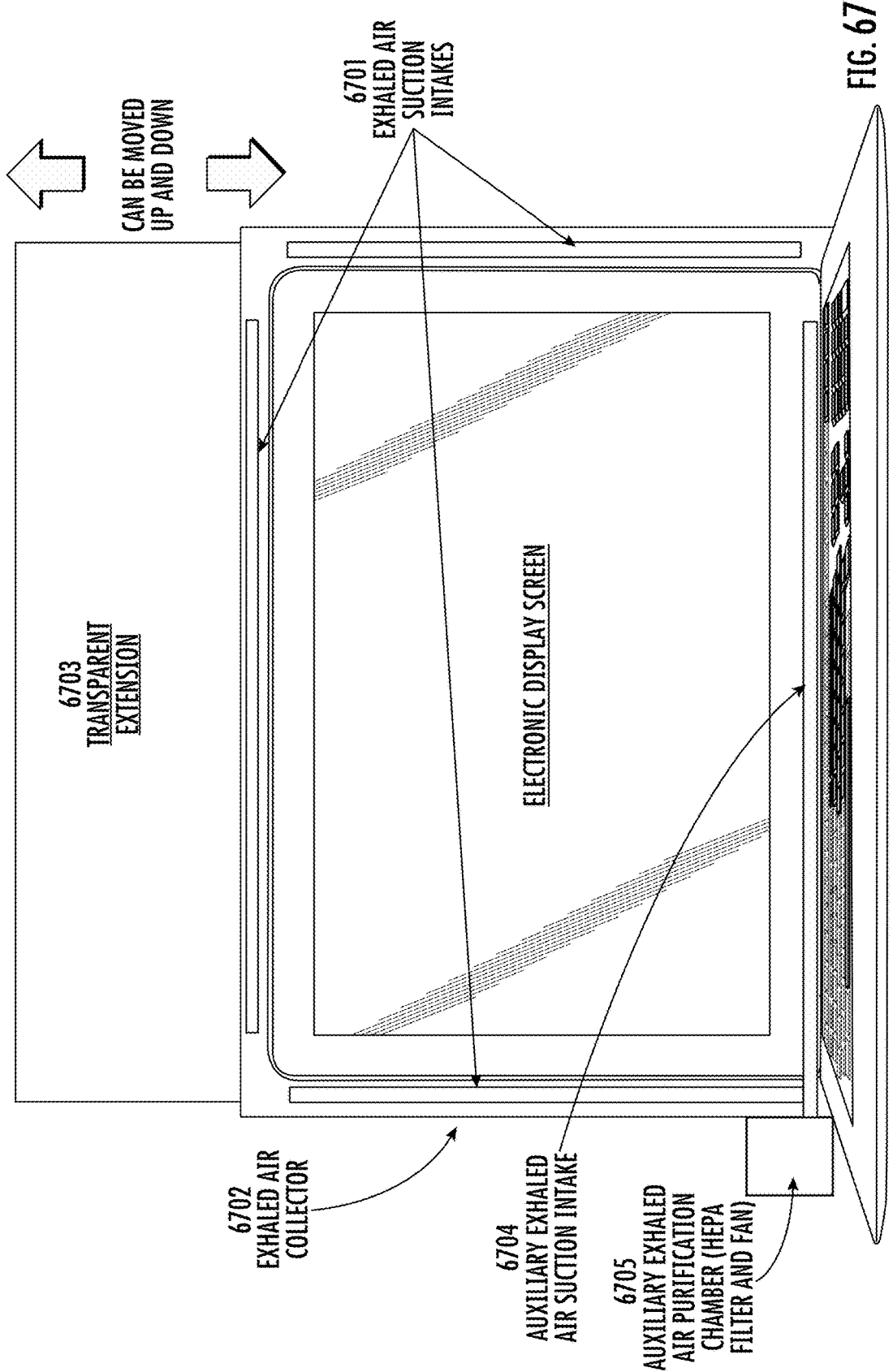
FIG. 67 is an illustration of an embodiment of the current invention as described herein.
Figure 68:
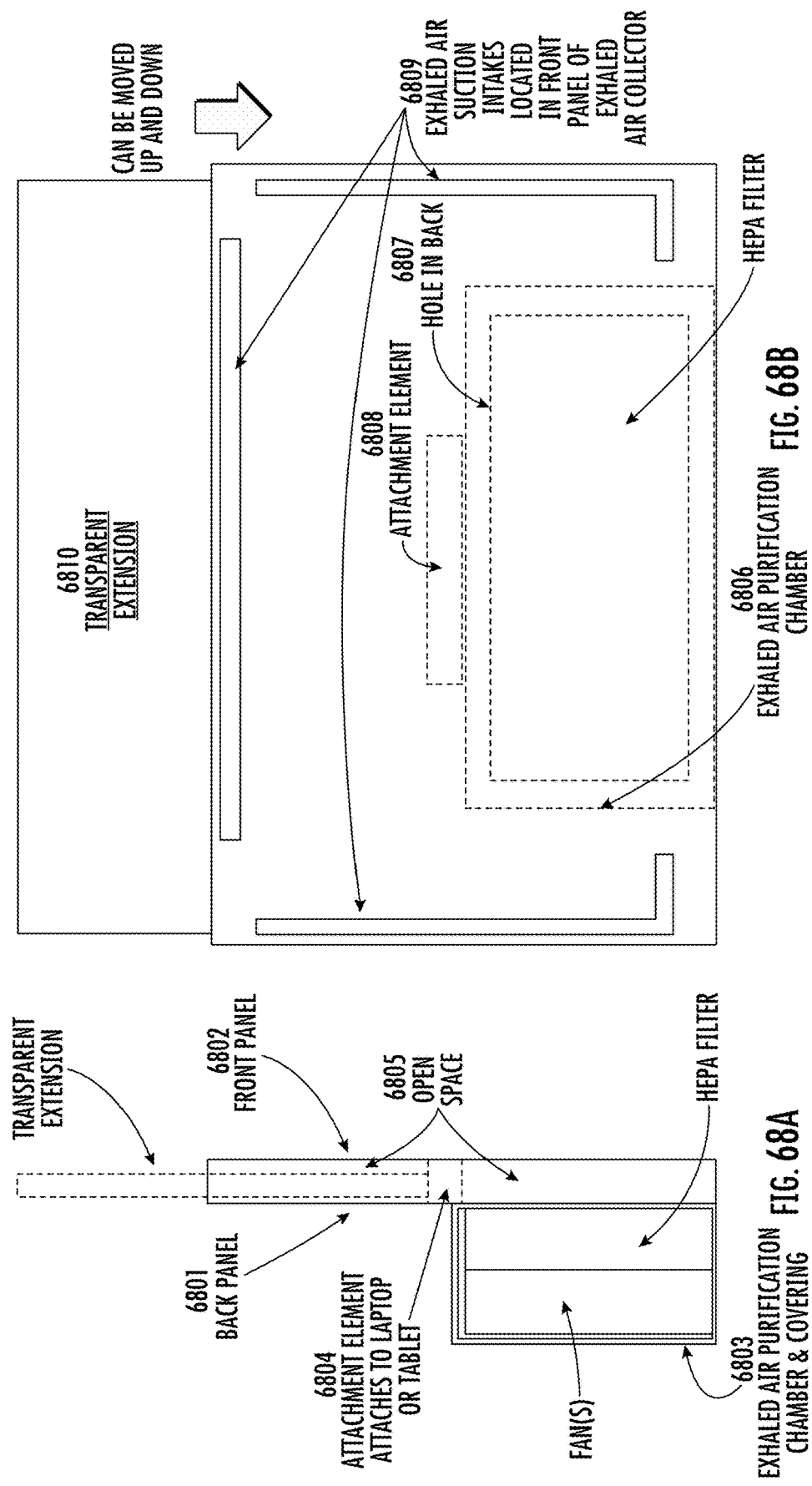
FIGS. 68A and 68B are illustrations of embodiments of the current invention as described herein.

FIG. 63 shows a side view of a releasably attachable back portable exhaled air collector embodiment showing exhaled air suction intakes 6301 located within a front or a side, or both, of the exhaled air collector, the portable/releasably attachable exhaled air collector 6302, the exhaled air purification chamber and covering 6303, having fans and a filter, and attachment elements 6306 for attaching the exhaled air collector of the air purification unit to the electronic display screen/computer monitor, wherein the attachment elements can be, by way of example only, Velcro, magnets, adhesive backed magnets where is stuck to the back of the laptop and the other is stuck to an inside back panel of the exhaled air collector and the two magnets attract one another. In this embodiment a transparent extension 6304 can be adjusted up and down. In aspects there can be an open space 6305 between the monitor back and the exhaled air collector. In aspects there can be rotational partial side walls 6307 that allow for continuing contact with a desktop as a laptop is angled backwards; there can be two side walls, one on each side. In aspects, the air purification unit can be powered by the USB powered port on the laptop computer 6308. FIG. 64 is the same as FIG. 63 but there are no partial side walls, and there is no transparent extension. FIG. 63 is a back view of FIG. 65 showing the exhaled air collector 6501, the exhaled air purification and covering 6502, the attachment elements 6503 (which would not be visible as they are between the exhaled air collector and back of the laptop/monitor), and opening in the exhaled air purification chamber 6504. In this Figure, the back of the portable exhaled air collector is shown transparent so that the back of the laptop screen/monitor shows through. FIG. 66 shows a front view of the portable exhaled air collector, showing locations of the exhaled air suction intakes 6601 in the exhaled air collector 6602. This Figure also shows the optional transparent extension 6603 that can be moved up and down. FIG. 67 shows a front view of the portable exhaled air collector, showing locations of the exhaled air suction intakes 6701 in the exhaled air collector 6702. This Figure also shows the optional transparent extension 6703 that can be moved up and down. This Figure also shows an optional secondary auxiliary exhaled air suction intake 6704, and an optional secondary or tertiary exhaled air purification chamber 6705 (e.g., with HEPA filter and fan(s)). FIG. 68A shows a side view (on the left of the Figure) of the releasably attachable back portable exhaled air collector embodiment showing a back panel 6801 and a front panel 6802 of the exhaled air collector, the exhaled air purification chamber and covering 6803 having fans and a filter, and an attachment element 6804 for attaching the exhaled air collector of the air purification unit to the electronic display screen/computer monitor of, for example, a laptop or tablet computer. In this embodiment, a transparent extension 6804 can be adjusted up and down. The Figure shows open space 6805 in the exhaled air collector. FIG. 68B, on the right of the Figure, is a front view of the portable exhaled air collector releasably attachable to a laptop or tablet, having two separated back panels. This embodiment shows the exhaled air purification chamber and covering 6806 having fans and a filter, a hole in the back 6807 for exhaled air to enter the air purification chamber, and an attachment element 6808 for attaching the exhaled air collector of the air purification unit to the electronic display screen/computer monitor of, for example, a laptop or tablet computer, and air suction intakes 6809 located in the front panel of the exhaled air collector. In this embodiment a transparent extension 6810 can be adjusted up and down.

Figure 69:
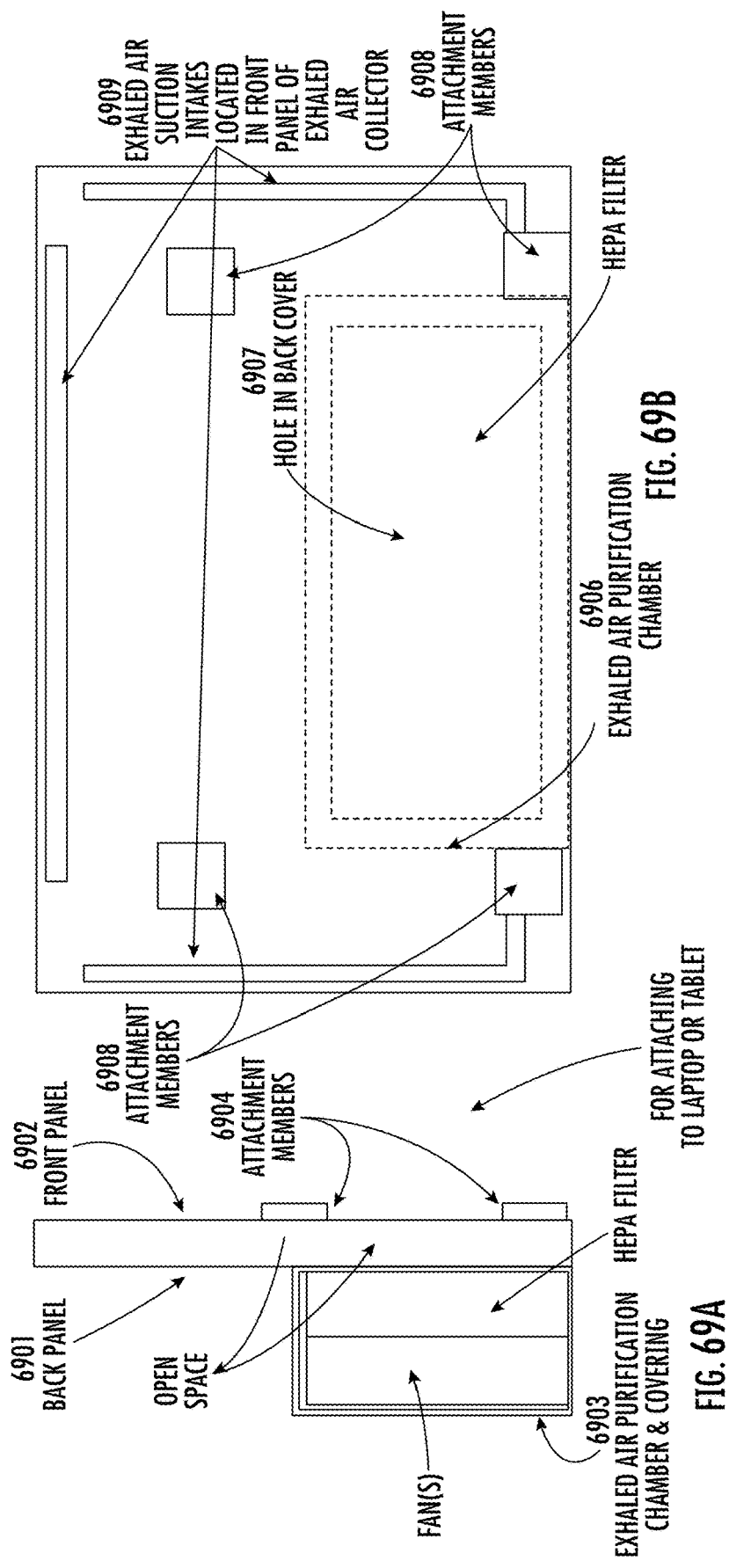
FIGS. 69A and 69B are illustrations of embodiments of the current invention as described herein.

FIG. 69A shows a side view (on the left of the Figure) of the releasably attachable back portable exhaled air collector embodiment showing a back panel 6901 and a front panel 6902 of the exhaled air collector, the exhaled air purification chamber and covering 6903 having fans and a filter, and attachment elements/members 6904 for attaching the exhaled air collector of the air purification unit to the electronic display screen/computer monitor of, for example, a laptop or tablet computer. FIG. 69B, on the right of the Figure, is a front view of the portable exhaled air collector releasably attachable to a laptop or tablet, having two separated back panels. This embodiment shows the exhaled air purification chamber and covering 6906 having fans and a filter, a hole in the back 6907 for exhaled air to enter the air purification chamber, and attachment elements/members 6908 for attaching the exhaled air collector of the air purification unit to the electronic display screen/computer monitor of, for example, a laptop or tablet computer, and air suction intakes 6909 located in the front panel of the exhaled air collector.

Figure 70:
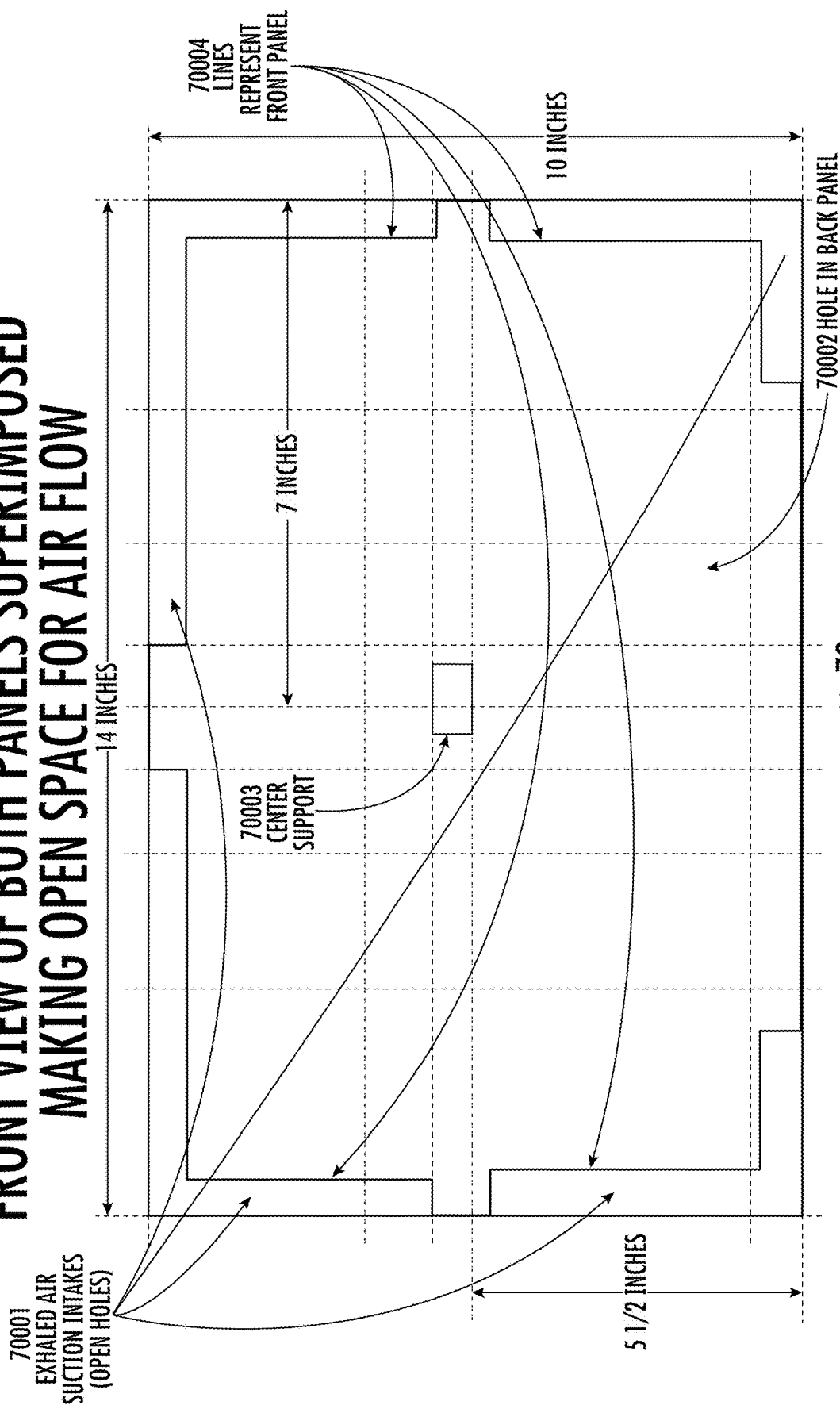
FIG. 70 is an illustration of an embodiment of the current invention as described herein.

FIG. 70 shows a front view of both panels superimposed, making open space for air flow. The Figure includes dimensions, which are non-limiting examples only. Shown in the Figure are exhaled air suction intakes (open holes) 70001, a hole in the back panel 70002, a center support 70003, wherein lines represent the front panel of the exhaled air collector 70004. In aspects, the front and back panels of the exhaled air collector can be separated (such as by ¾ inch) forming an open space.

Figure 71:
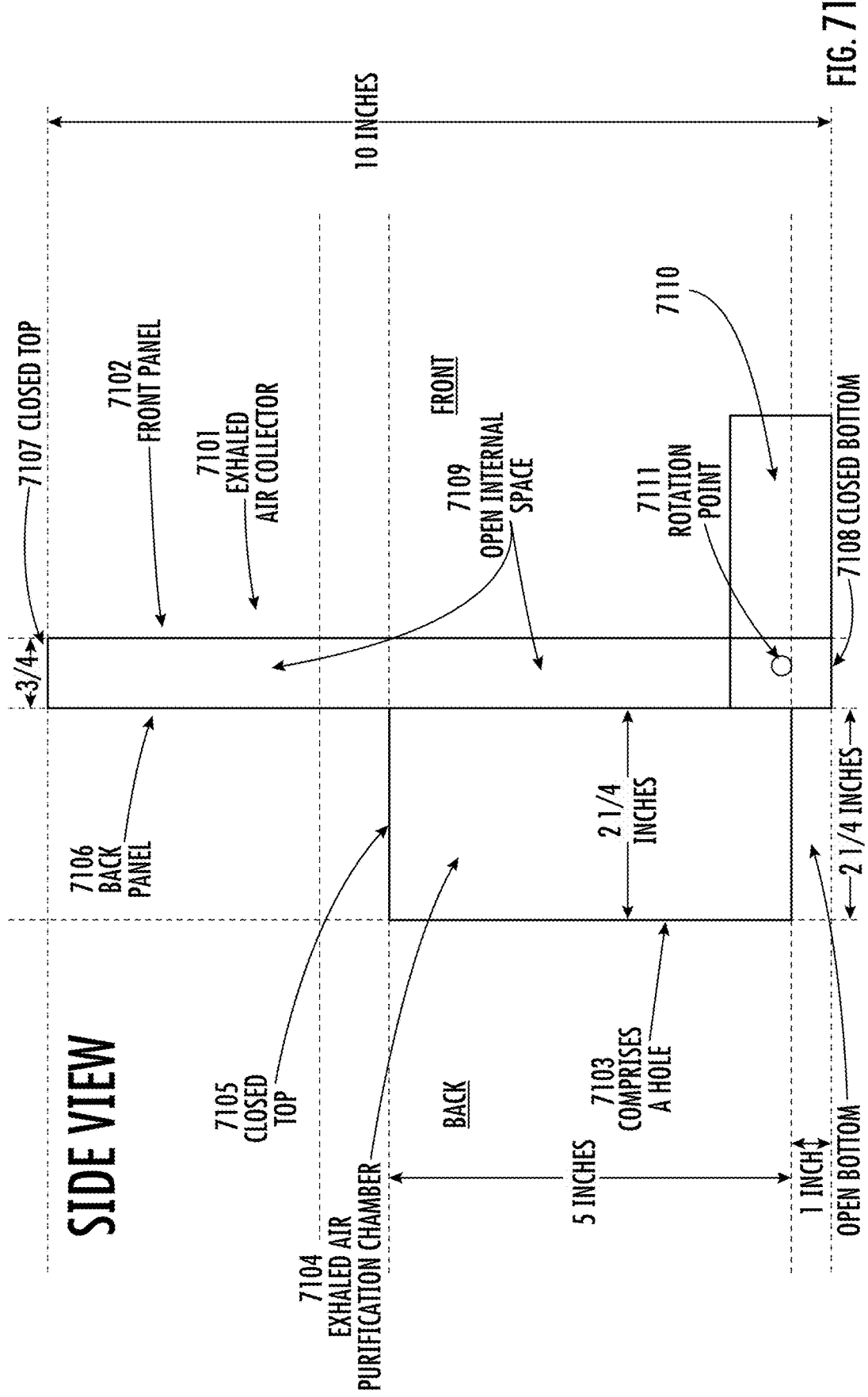
FIG. 71 is an illustration of an embodiment of the current invention as described herein.

FIG. 71 shows a side view of the portable exhaled air collector releasably attachable to a laptop or tablet computer, having two separate back panels. The Figure includes dimensions, which are non-limiting examples only. Shown in the Figure are the exhaled air collector 7101, the front panel 7102, a hole for exhausting clean air 7103 from the air purification chamber 7104 having a closed top 7105, the back panel 7106, a closed top 7107 and a closed bottom 7108 of the exhaled air collector 7101, open internal space of the exhaled air collector 7109, and rotational side walls 7110 that allow for continuing contact with a desktop as the laptop is angled backwards, wherein the side walls have rotation/hinge point 7111. In aspects, the front and back panels of the exhaled air collector can be separated (such as by ¾ inch) forming an open space.

Figure 72:
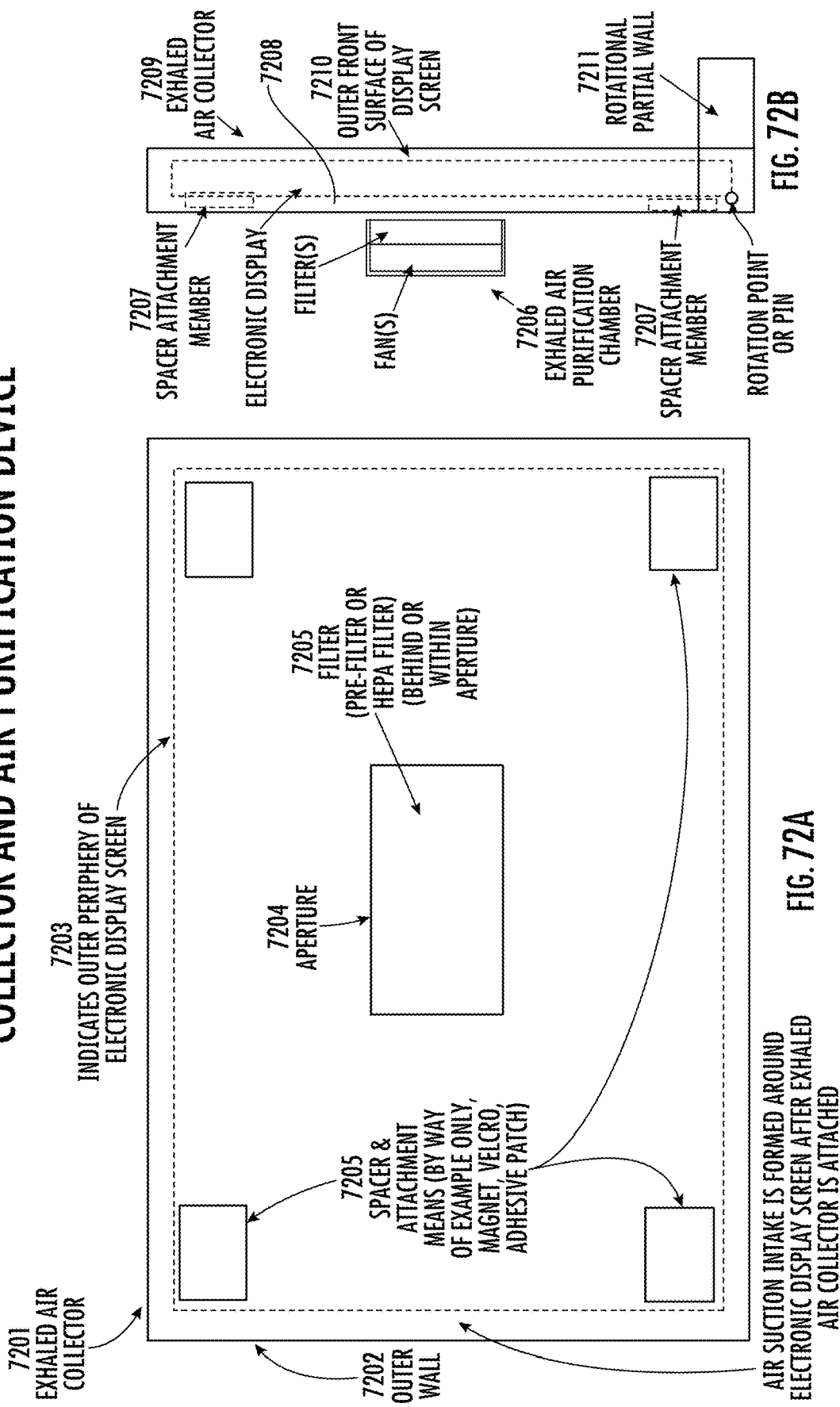
FIGS. 72A and 72B are illustrations of embodiments of the current invention as described herein.

FIG. 72A shows a front view of a releasably attached "single" panel exhaled air collector and air purification device. It shows the exhaled air collector 7201 and its outer wall 7202, wherein it is indicated where an outer periphery of the electronic display 7203 may be located inside the periphery of the exhaled air collector 7201. The exhaled air collector has an aperture 7204 with a filter 7205 (pre-filter and/or HEPA filter) leading to the air purification chamber (not pictured). This embodiment shows one or more spacer attachments members 7205 (by way of example only, magnet(s), Velcro, adhesive, or adhesive patch). FIG. 72B is an illustrative side view of a section of an exhaled air collector with air purification chamber 7206, spacer attachment member(s) 7207 providing for an open space 7208 for air flow from the exhaled air collector 7209 to the air purification chamber 7206. This embodiment also shows the outer front surface of the electronic display screen 7210 and an optional rotational partial side wall 7211.

Figure 73:
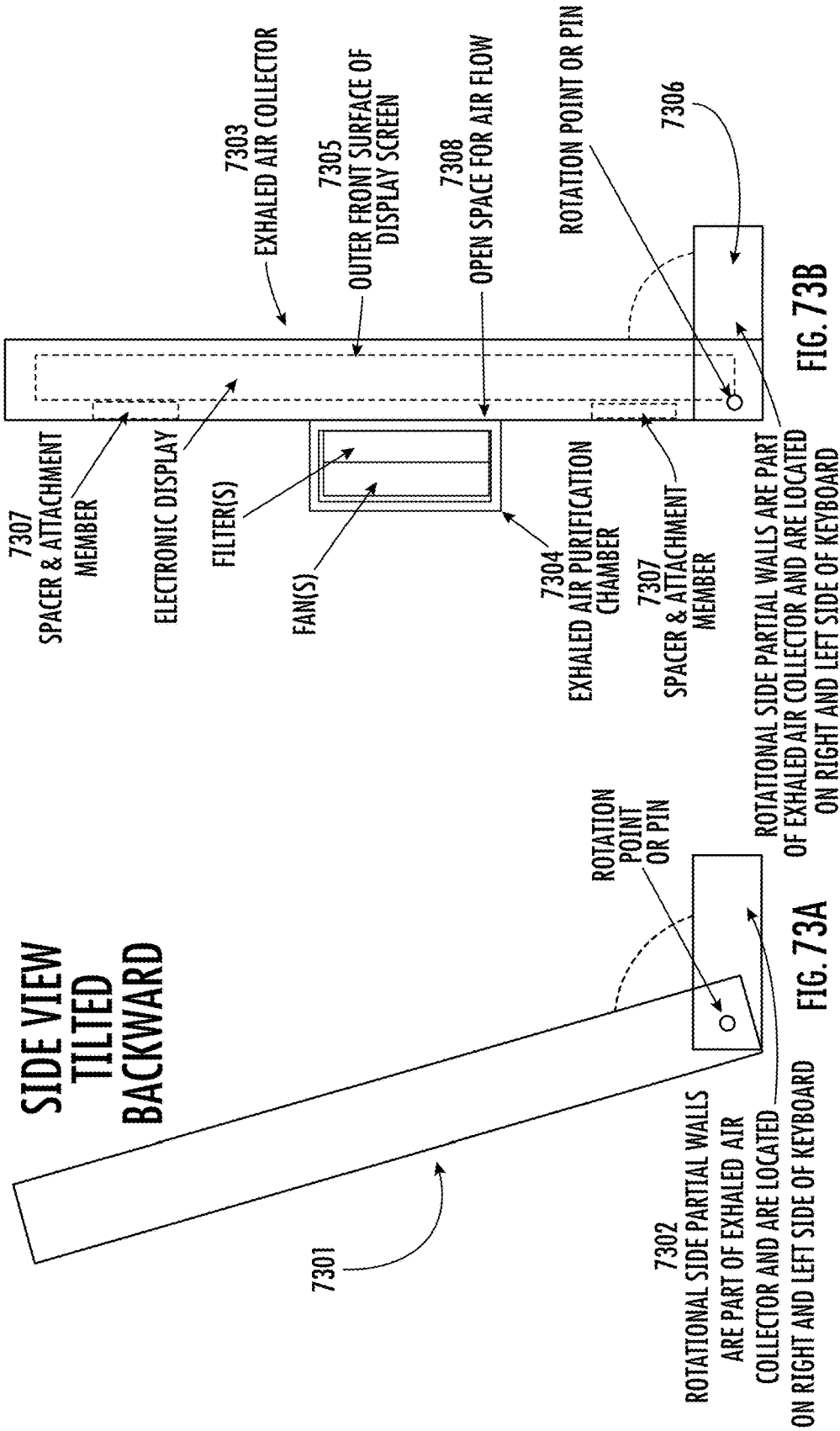
FIGS. 73A and 73B are illustrations of embodiments of the current invention as described herein.

FIG. 73A shows a side a side view of a releasably attachable single panel exhaled air collector and air purification device. In this example the exhaled air collector 7301 is tilted backwards and it has rotational partial side walls 7302 located on the right and left side of a keyboard, for example. FIG. 73B is an illustrative side view of a section of an exhaled air collector 7303 comprising an outer lipped wall, exhaled air collector with air purification chamber 7304, spacer attachment member(s) 7307 providing for an open space 7308 for air flow from the exhaled air collector 7303 to the air purification chamber 7304. This embodiment also shows the outer front surface of the electronic display screen 7305 and an optional rotational partial side wall 7306 allowing for the wall to contact the desktop when the laptop is angled backward, thereby permitting the side walls to partially cover the right and left side of the laptop keyboard, for example. These rotational partial side walls can be part of the exhaled air collector and can be located on the right side, the left side, or both sides of the exhaled air collector, and for example a laptop keyboard.

Figure 74:
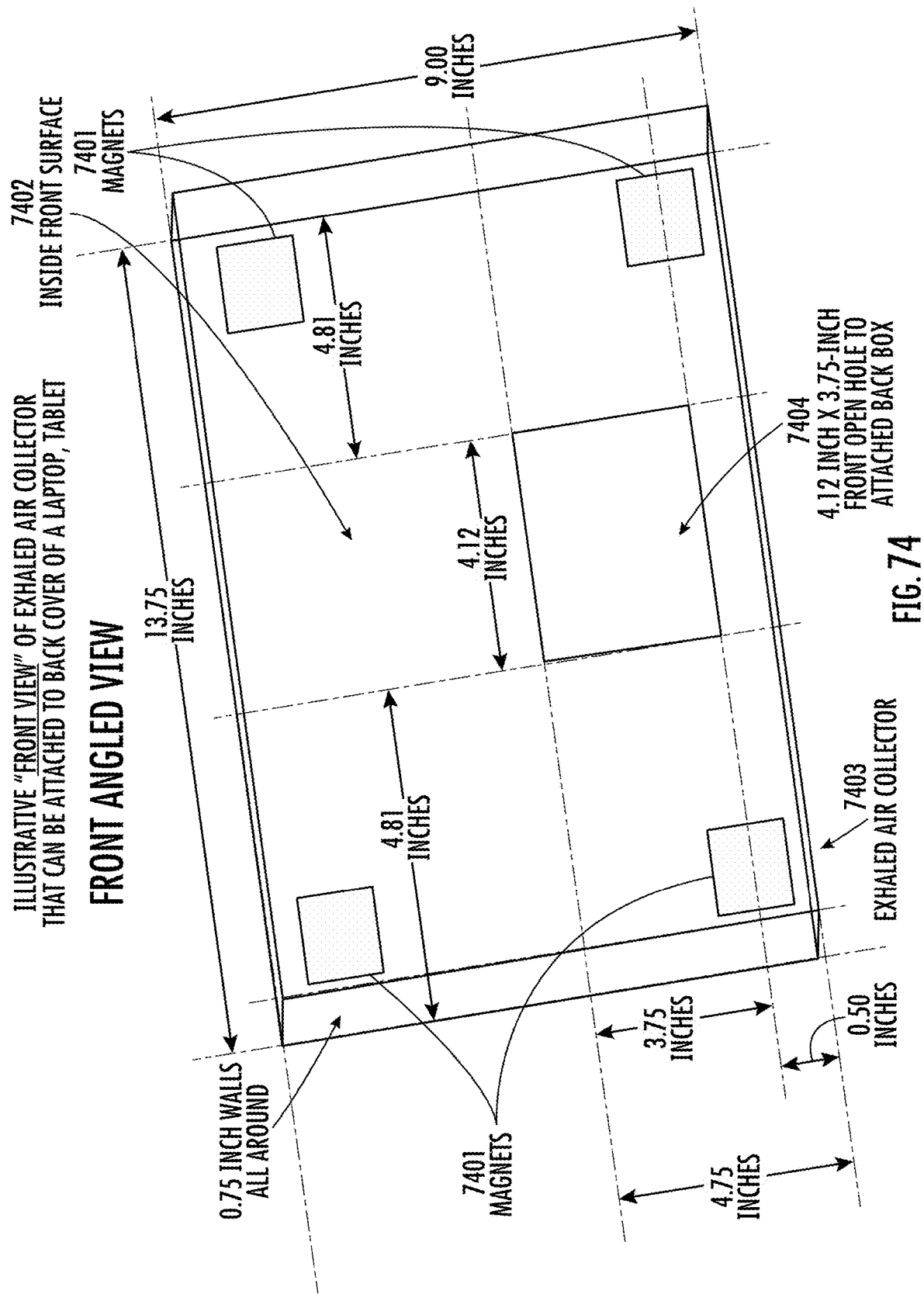
FIG. 74 is an illustration of an embodiment of the current invention as described herein.
Figure 75:
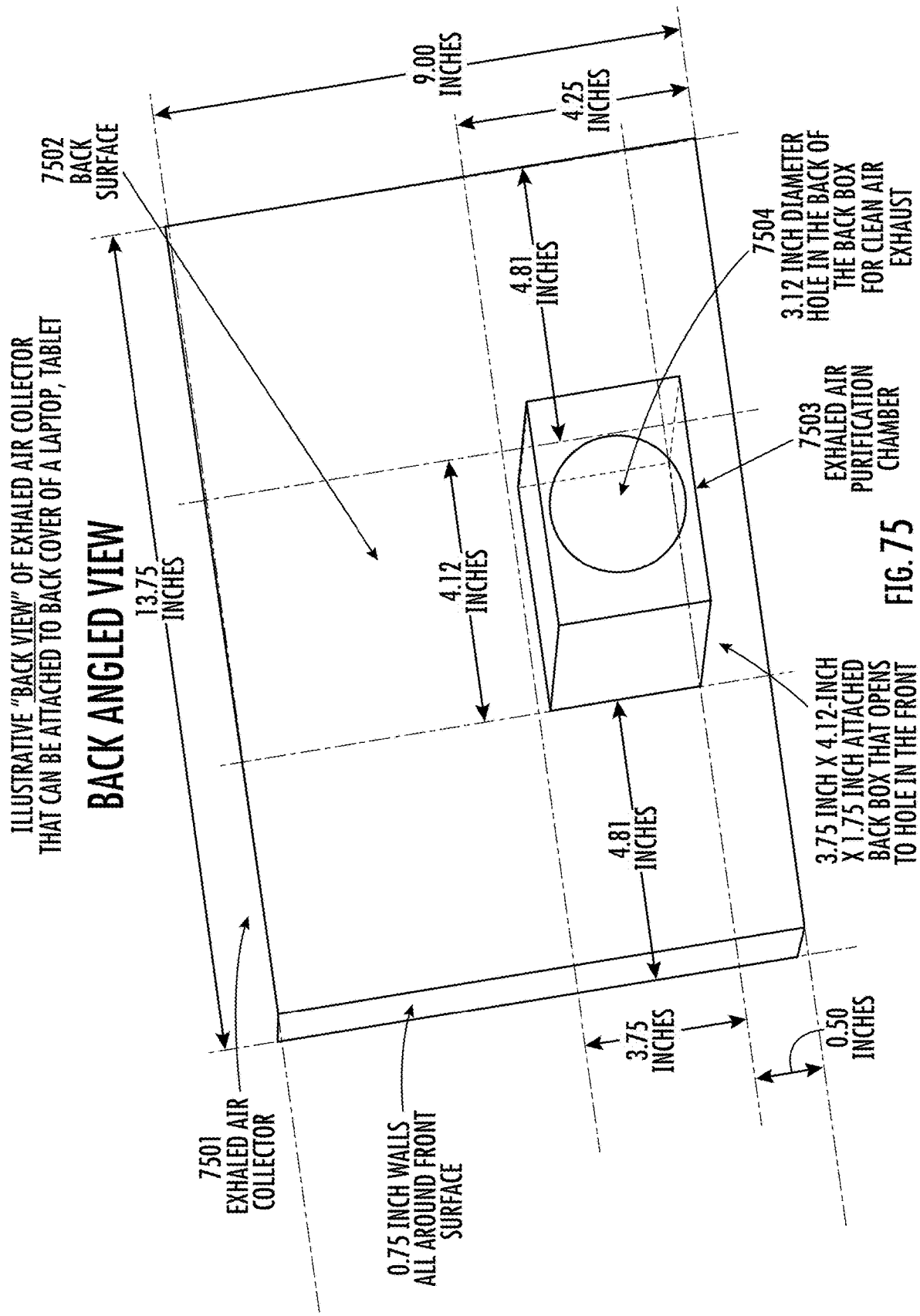
FIG. 75 is an illustration of an embodiment of the current invention as described herein.

FIG. 74 is an illustrative front view of an exhaled air collector 7403 that can be attached to a back cover of a laptop or tablet computer. The device shown can be a releasably attachable single panel air collector and air purification device. The dimensions shown in the Figure are for non-limiting example only. The Figure shows attachment magnets 7401, the inside front surface of the exhaled air collector 7402, and a front open hole 7404 to the attached back box. FIG. 75 is an illustrative back view of the exhaled air collector 7501 that can be attached to a back cover of a laptop or tablet computer. The device shown can be a releasably attachable single panel air collector and air purification device. The dimensions shown in the Figure are for non-limiting example only. The Figure shows the back surface 7502 of the exhaled air collector, an air purification chamber 7503, which opens and/or is attached to a hole shown in FIG. 74 as 7404. The air purification chamber has a hole in the back of the air purification chamber back box for exhausting cleaned air 7504.

Figure 76:
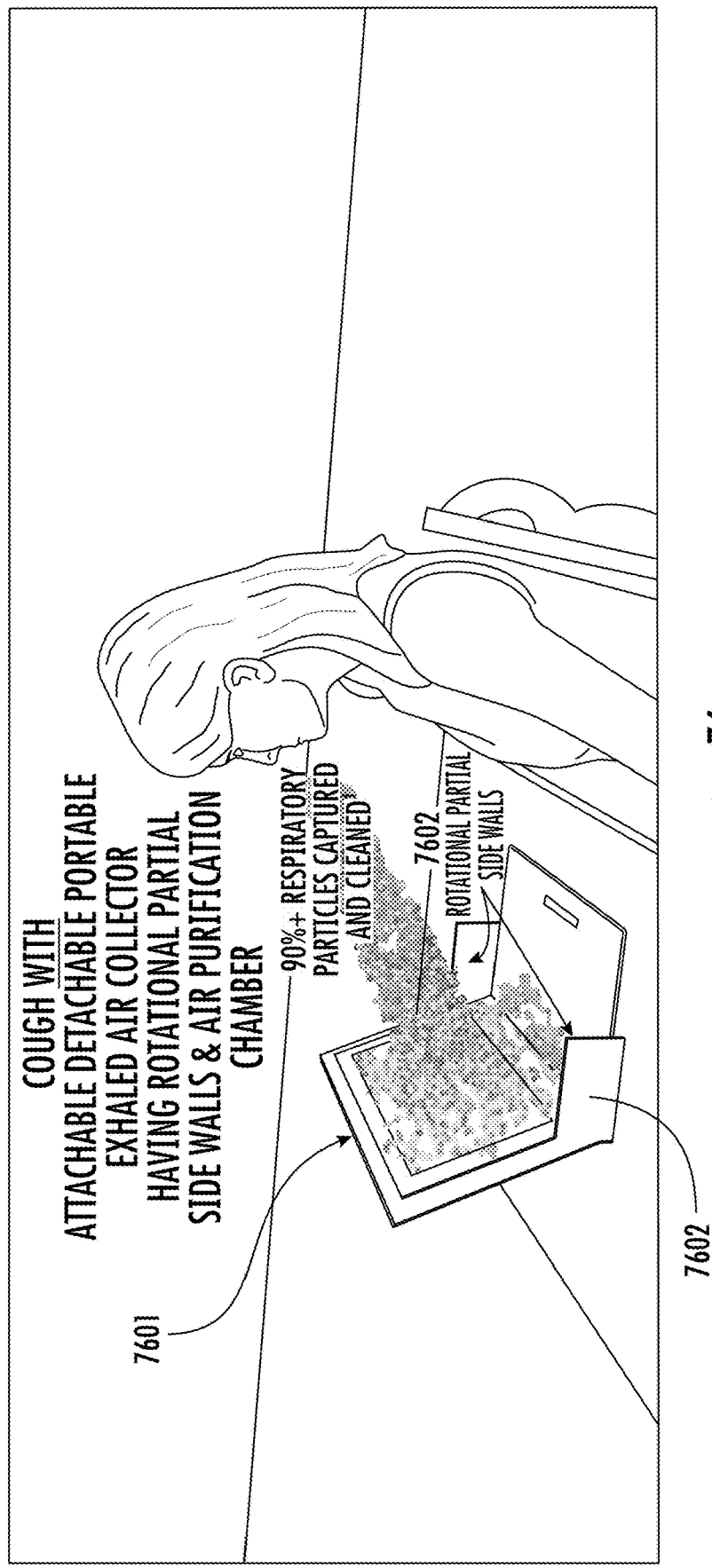
FIG. 76 is an illustration of an embodiment of the current invention as described herein.

FIG. 76 shows the laptop docking station 7601 having an attachable/detachable portable exhaled air collector having rotational partial side walls 7602 and air purification chamber, having a CADR of 40 CADR, wherein particles are sucked into the exhaled air collector around the laptop and below the laptop screen. In this embodiment, the laptop docking station can capture around 90%+ of respiratory particles from a cough using the air capture and cleaning laptop docking station having 40 CADR, by way of example only. In aspects, the non-captured particles end up remaining on the laptop keyboard and pose less of a threat to others; in this case, few, if any, particles remain on the keyboard. (In this model, the figure shows particles around 10 seconds after a cough.)

Figure 77:
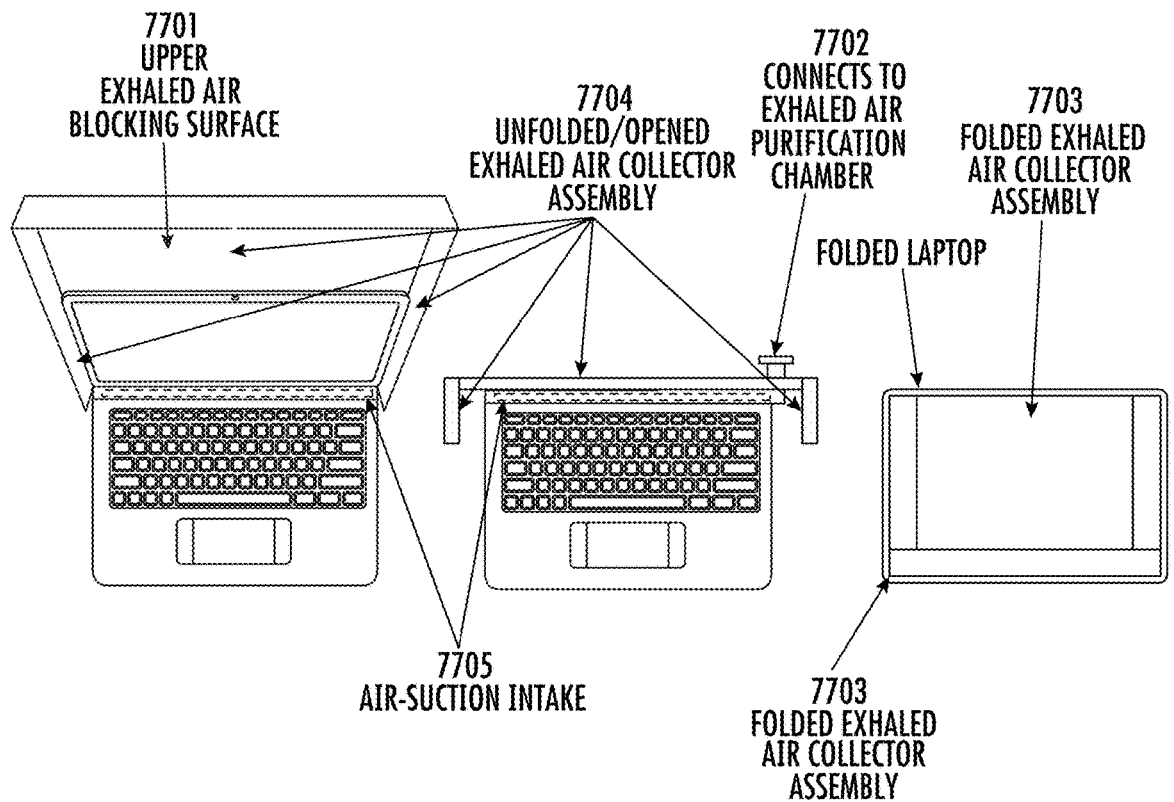
FIG. 77 is illustrations of an embodiment of the current invention as described herein.
Figure 78:
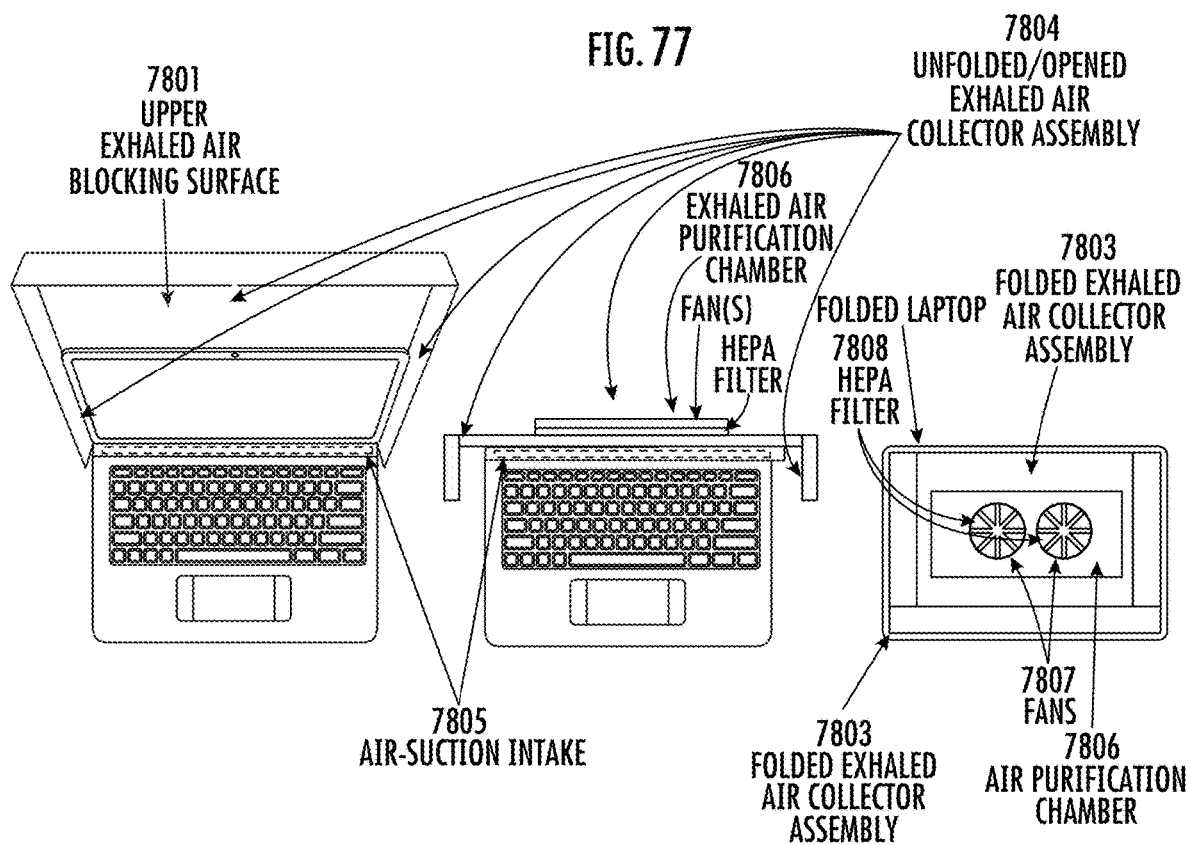
FIG. 78 is illustrations of an embodiment of the current invention as described herein.
Figure 79:
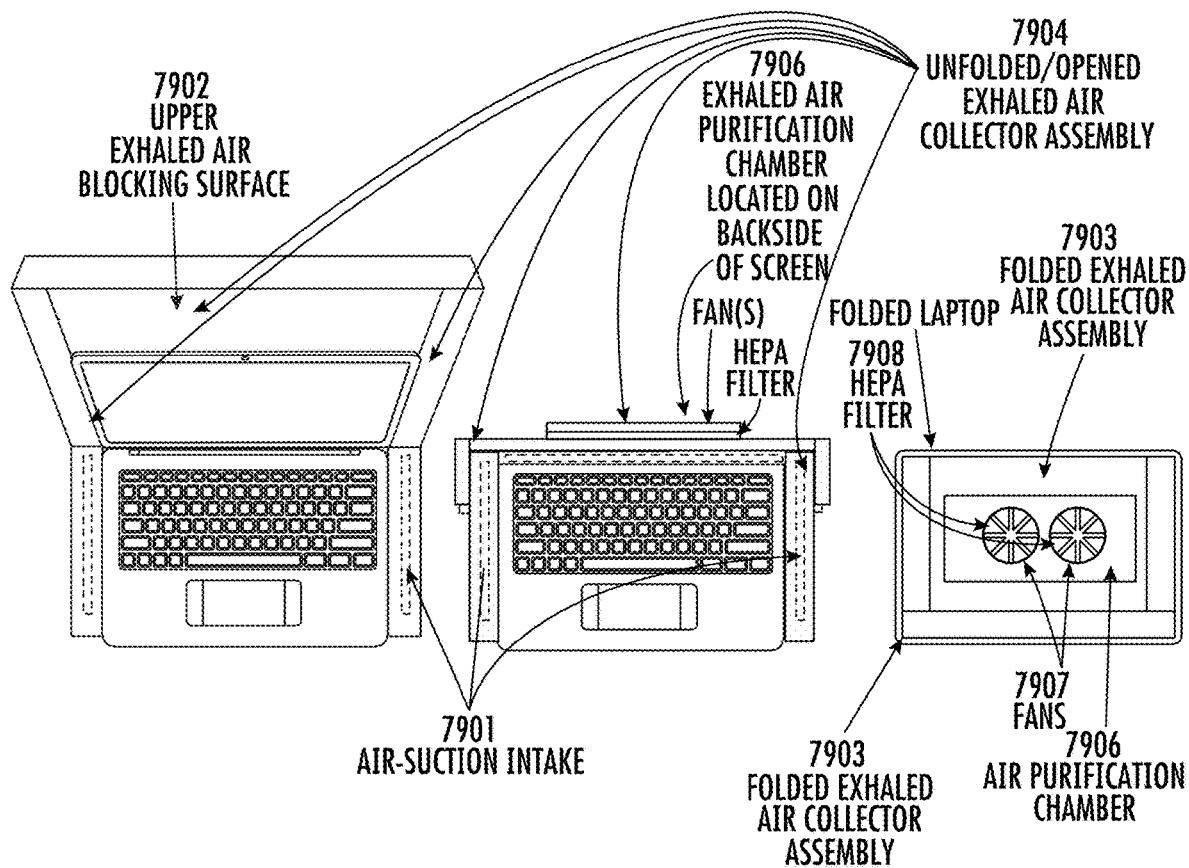
FIG. 79 is illustrations of an embodiment of the current invention as described herein.

FIG. 77 shows the top-down views of attachable/detachable portable exhaled air collector when the laptop screen is tilted backwards and showing the upper exhaled air blocking surface 7701, an example when the laptop screen is straight up and exhaled air purification chamber connector is visible 7702 (for example, this may be a port that connects to an air purification chamber or connects to a conduit that connects to an air purification chamber), and when the laptop is folded and the exhaled air collector assembly is folded 7703. The example on the left and in the middle show the unfolded and opened exhaled air collector assembly 7704 when the exhaled air suction intakes 7705 are visible. FIG. 78 is similar to FIG. 77, but in this embodiment the exhaled air purification chamber 7806 (having a filter and fan(s)) is at the back of the exhaled air collector assembly. When the exhaled air collector assembly is folded/closed, the air purification chamber 7806 can be seen on the back of the exhaled air collector, including in this example the exhaust areas with fan(s) 7807 and HEPA filter 7808. FIG. 78 also shows the upper exhaled air blocking surface 7801, an example when the laptop screen is straight up and exhaled air purification chamber is visible 7806, and when the laptop is folded, and the exhaled air collector assembly is folded 7803. The example on the left and in the middle show the unfolded and opened exhaled air collector assembly 7804 when the exhaled air suction intakes 7805 are visible. FIG. 79 is similar to FIG. 78, but in this embodiment exhaled air suction intakes 7901 are also included on the sides of the exhaled air collector assembly near or adjacent to the bottom sides of the laptop keyboard. The exhaled air purification chamber 7906 (having a filter and fan(s)) is at the back of the exhaled air collector assembly. When the exhaled air collector assembly is folded/closed, the air purification chamber 7906 can be seen on the back of the exhaled air collector, including in this example the exhaust areas with fan(s) 7907 and HEPA filter 7908. FIG. 79 also shows the upper exhaled air blocking surface 7902, an example when the laptop screen is straight up and exhaled air purification chamber is visible 7906, and when the laptop is folded, and the exhaled air collector assembly is folded 7903. The example on the left and in the middle show the unfolded and opened exhaled air collector assembly 7904 when the exhaled air suction intakes 7901 are visible.

Figure 80:
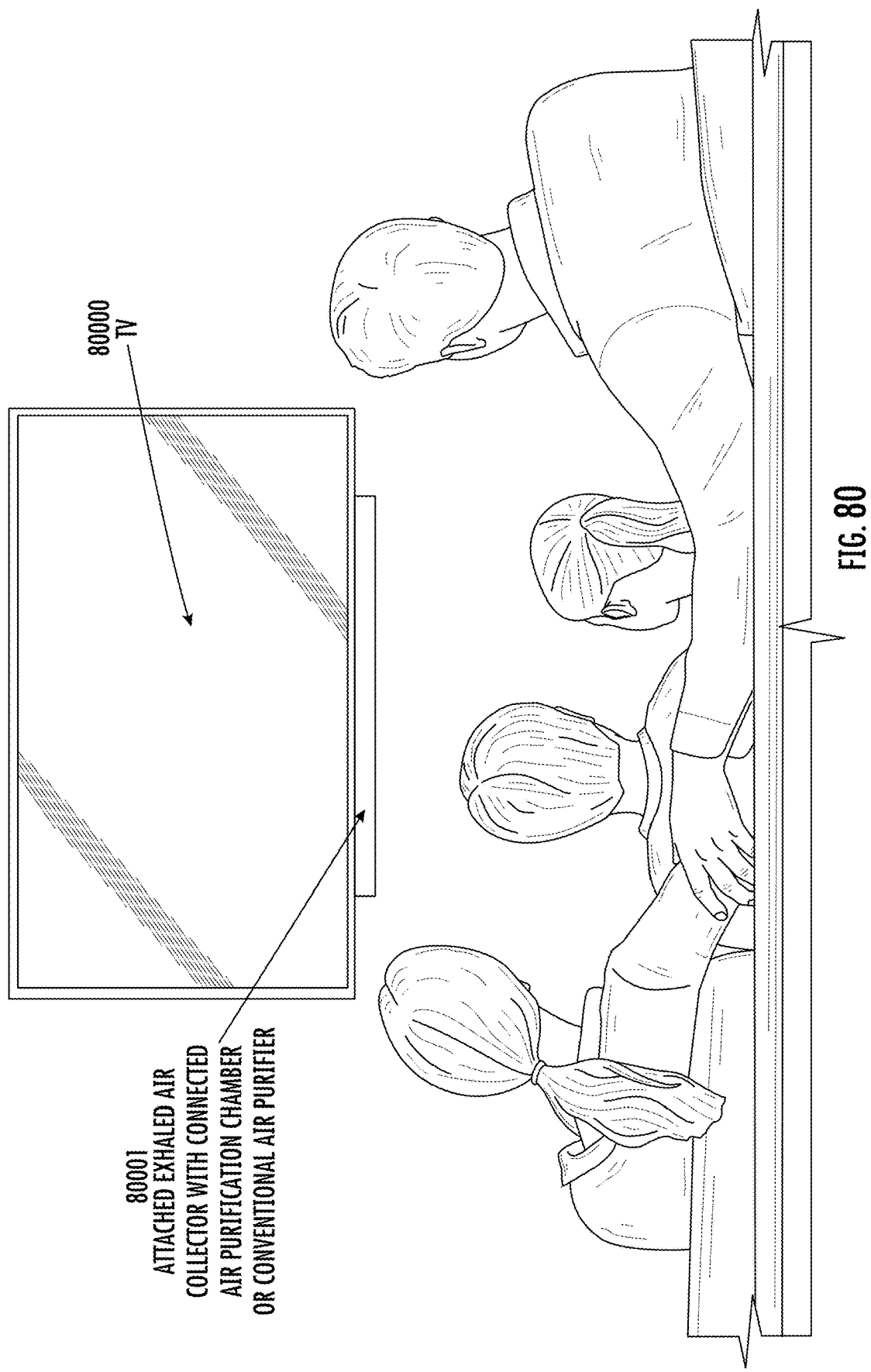
FIG. 80 is an illustration of an embodiment of the current invention as described herein.

FIG. 80 shows a television 80000 having an attached exhaled air collector 80001 with a connected air purification chamber or conventional air purifier.

Figure 81:
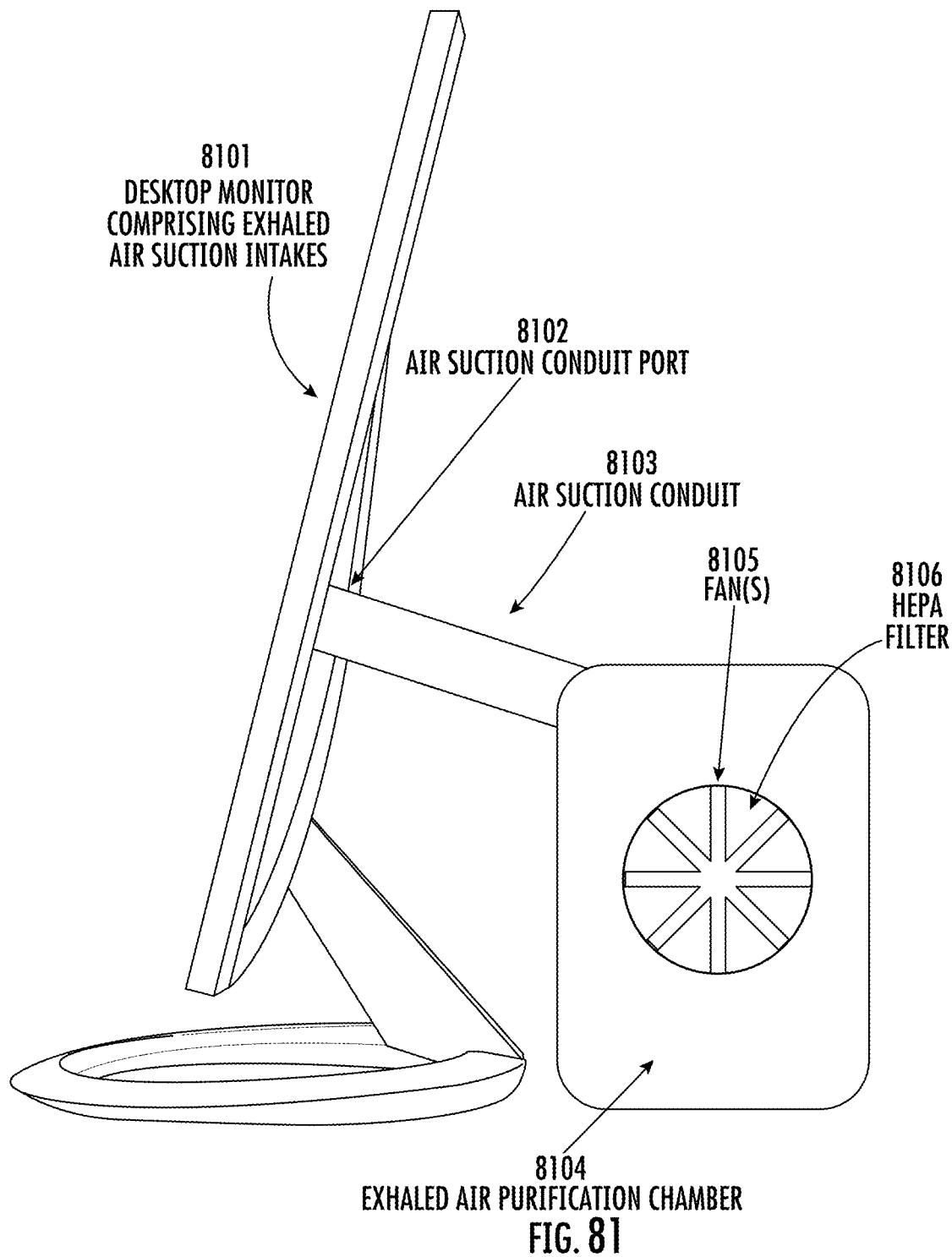
FIG. 81 is an illustration of an embodiment of the current invention as described herein.

FIG. 81 shows a monitor with an integrated exhaled air collector and port to a distance "connected" air purification chamber. This embodiment shows an attachable/detachable air suction conduit attaching into the port in the back of the monitor and connecting to an air purification chamber. In this example the desktop monitor includes/comprises exhaled air suction intakes 8101, wherein an air suction port 8102 on the back of the monitor connects to an air suction conduit 8103 which connects on the other end to an air purification chamber 8104 having one or more fans 8105 and a filter (e.g., HEPA filter) 8106.

Figure 82:
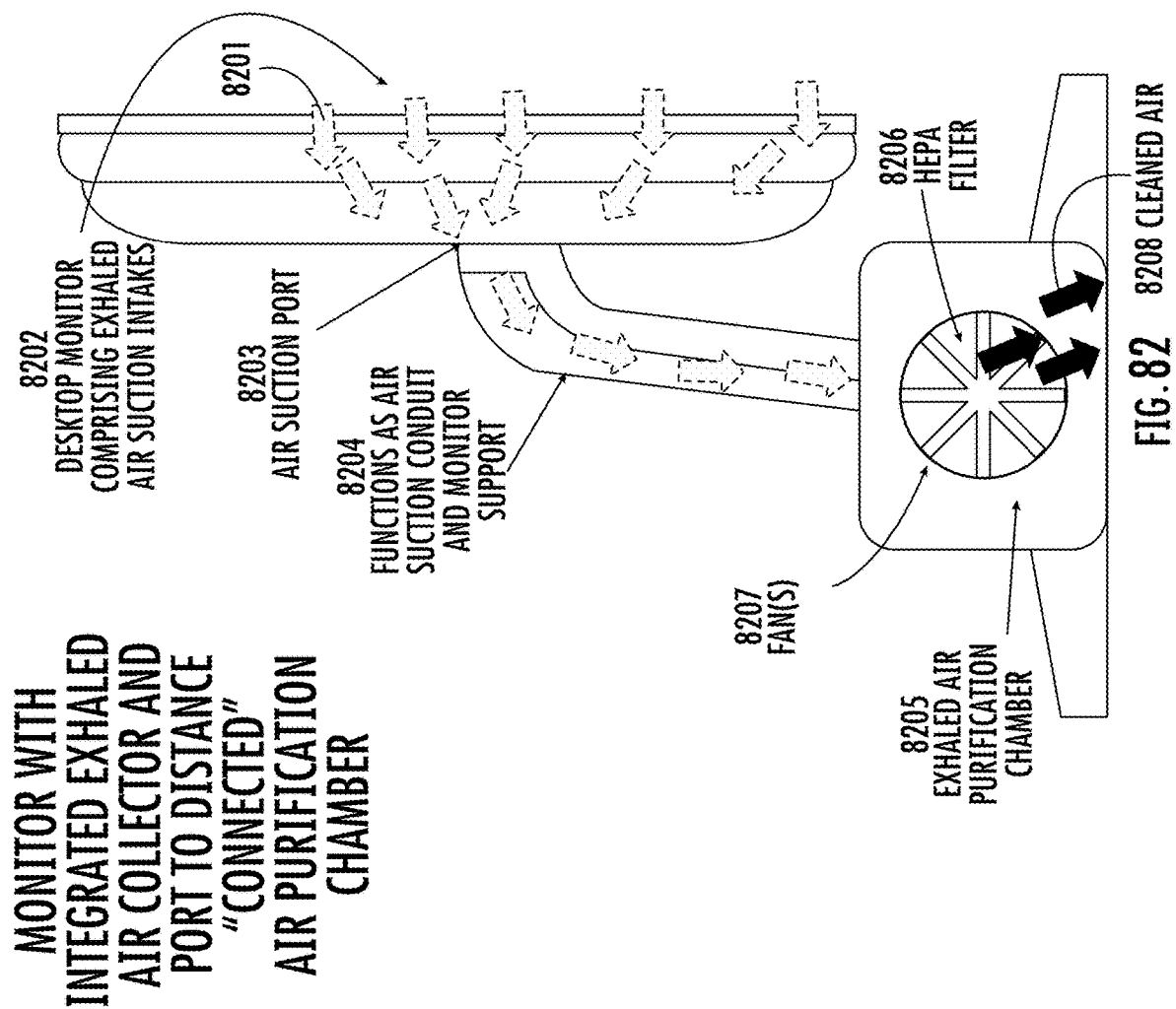
FIG. 82 is an illustration of an embodiment of the current invention as described herein.

FIG. 82 shows side view of a monitor with an integrated exhaled air collector and port to a distance "connected" air purification chamber. This embodiment shows non-cleaned exhaled air 8201 traveling through air suction intake(s) 8202 and interior air suction conduit (connected to air suction port 8203) or open space of monitor 8204 (connected to air suction port 8203) functioning as an air suction conduit and monitor support, and through the air suction conduit or open space to an air purification chamber 8205 having fan(s) 8207 where it is cleaned (e.g., by a HEPA filter 8206) and then cleaned air 8208 is released back into the room.

Figure 83:
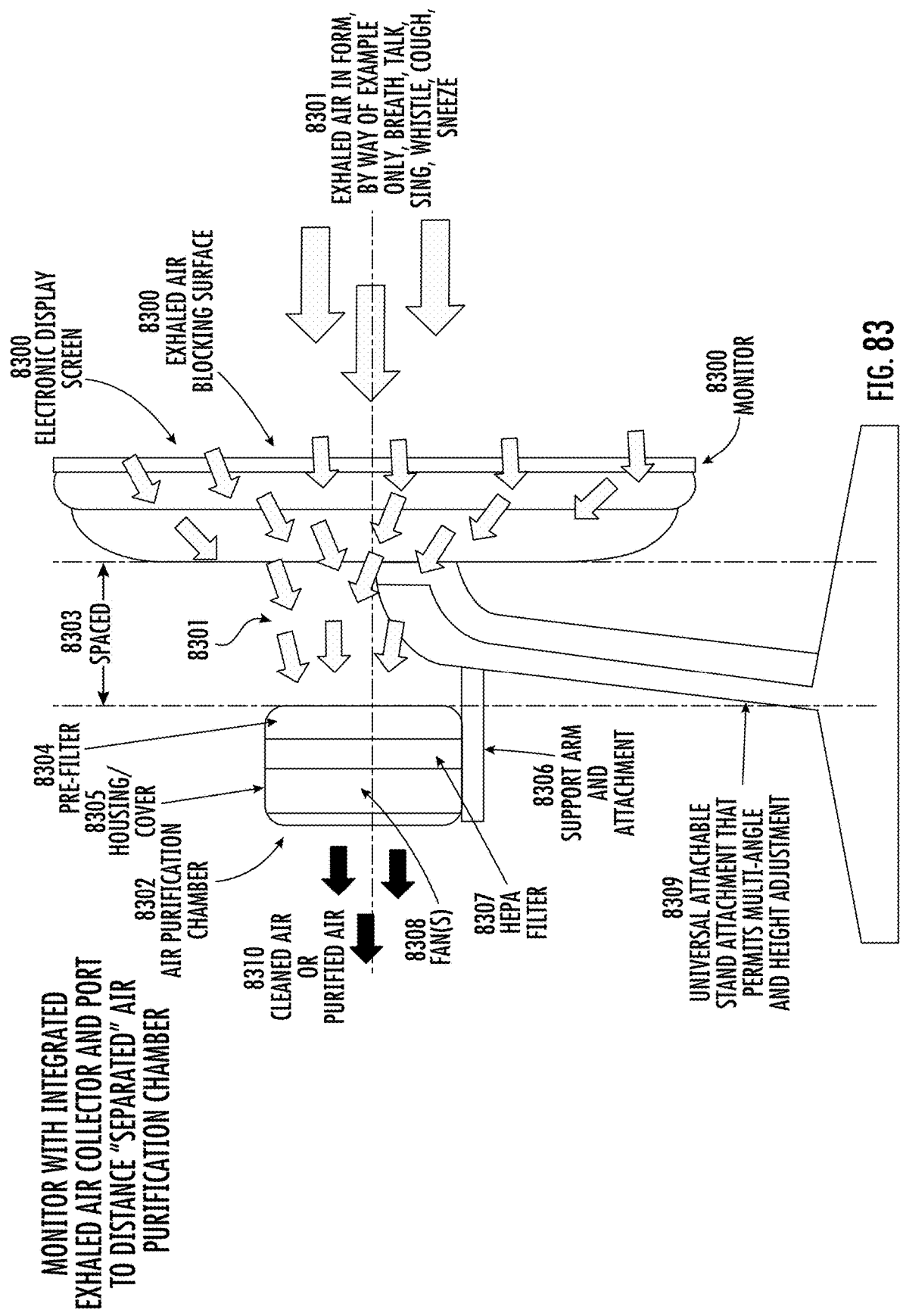
FIG. 83 is an illustration of an embodiment of the current invention as described herein.

FIG. 83 shows side view of a monitor with an integrated exhaled air collector and port to a distance "connected" air purification chamber. This embodiment shows the electronic display screen 8300 front outer surface acting as an exhaled air blocking surface 8300 that slows down the velocity of respiratory particles in non-cleaned exhaled air 8301 so that an air purification chamber 8302 can then capture and clean the exhaled air flow mixed with room air. In this embodiment the air purification chamber is spaced 8303 away from the monitor. The air purification chamber can include a pre-filter 8304, a housing/cover 8305, a support arm and attachment 8306, a HEPA filter or other filter 8307, and one or more fans 8308. The embodiment shows a possibly universal attachable stand attachment that permits multi-angle and height adjustment 8309. After the air purification chamber 8302, cleaned/purified air is returned to the room 8310.

Figure 84:
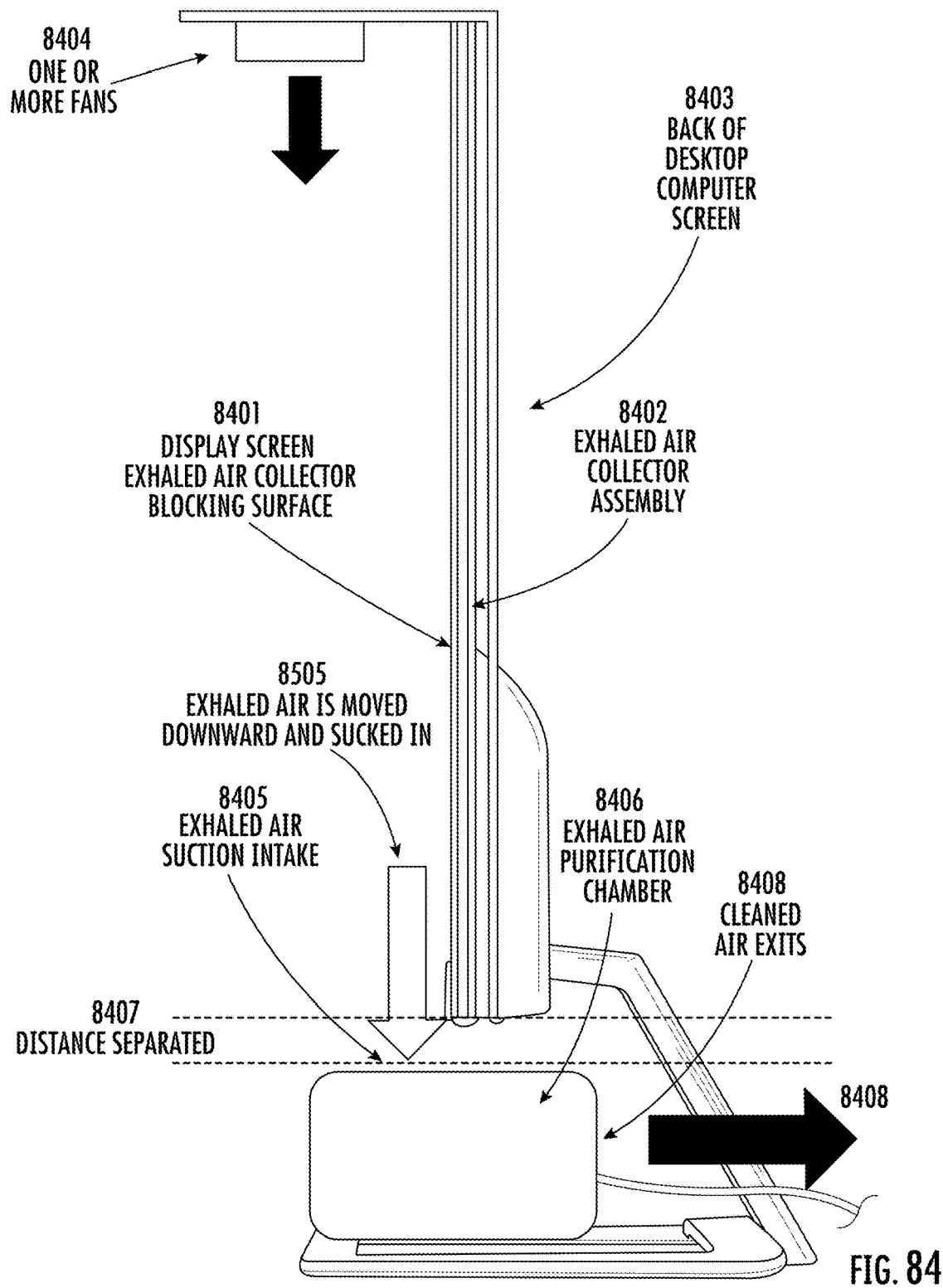
FIG. 84 is an illustration of an embodiment of the current invention as described herein.

FIG. 84 shows a side view of desktop screen with a detached exhaled air suction intake and air purification chamber showing the display screen acting as the exhaled air blocking surface 8401, the exhaled air collector assembly 8402, and the back of the desktop computer screen 8403. In this embodiment one or more fans 8404 at the top of the exhaled air collector assembly, electronic display screen, or both, blow air downwards towards the exhaled air suction intake 8405. Thereby exhaled air is moved downwards and sucked into the air suction intake 8405. The exhaled air purification chamber 8406 is distance separated 8407. The air purification chamber cleans the exhaled air and exhausts it out the back as shown 8408.

Figure 85:
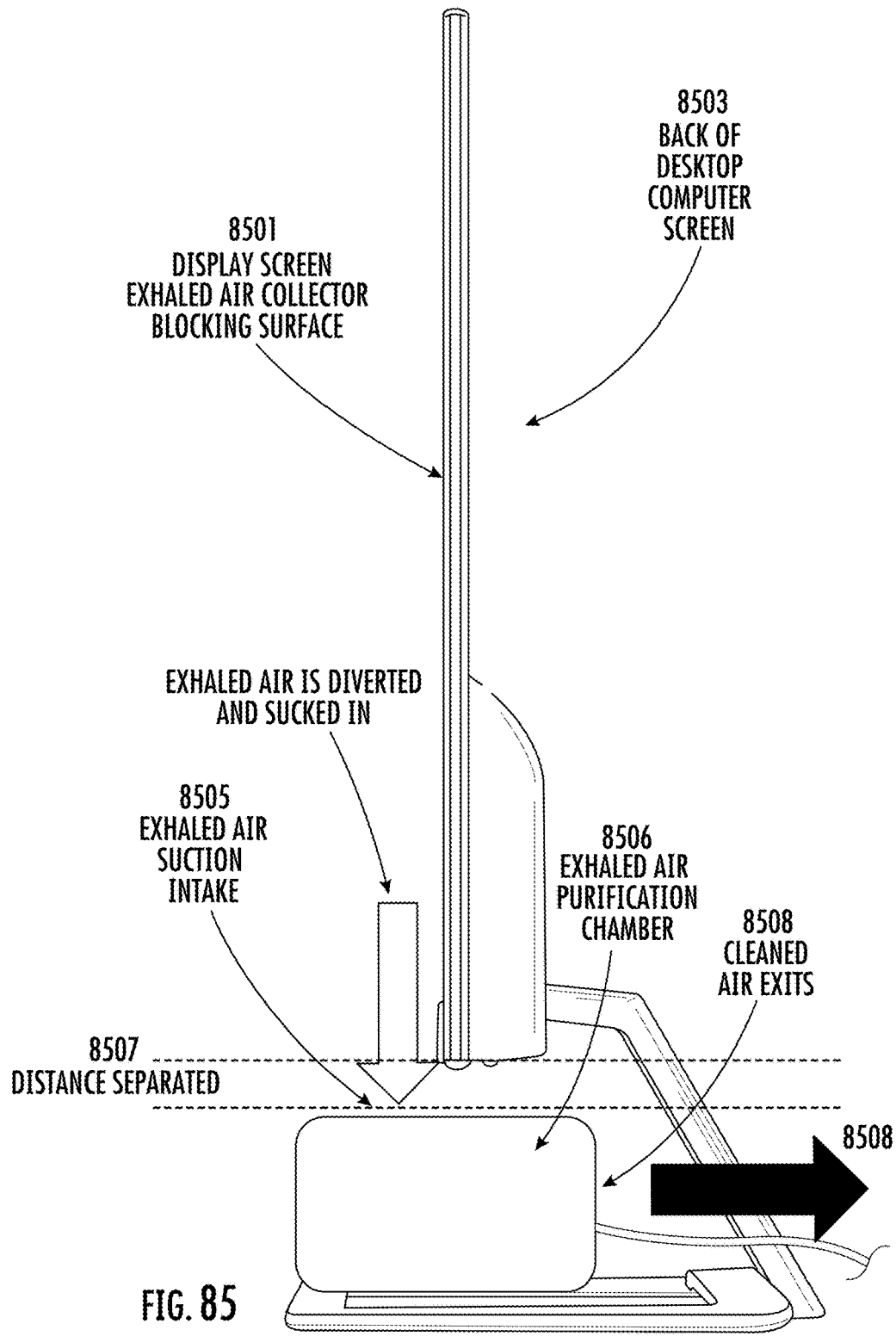
FIG. 85 is an illustration of an embodiment of the current invention as described herein.

FIG. 85 shows a side view of desktop screen with a detached exhaled air suction intake and air purification chamber showing the display screen acting as the exhaled air blocking surface 8501 and the back of the desktop computer screen 8503. In this embodiment, the exhaled air suction intake 8505 suctions in air diverted by the air blocking surface 8501. The exhaled air purification chamber 8506 is distance separated 8507. The air purification chamber cleans the exhaled air and exhausts it out the back as shown 8508.

FIGS. 86A and 86B show a detached exhaled air suction intake and air purification chamber distance separated and sitting beneath the exhaled air blocking surface. FIG. 86A is a top-down view of the detached air purification unit 8601, showing the exhaled air blocking surface is the outer front surface 8603 of the electronic display screen, which deflects or redirects exhaled air towards a distance separated air purifier or air purification unit comprising one or more air suction intakes and one or more air purification chambers. FIG. 86A shows an exhaled air suction intake 8602, and a HEPA filter 8604 and fan 8605 of a distance separated air purification chamber sitting distance separated and underneath the exhaled air blocking surface. FIG. 86B shows a side view of detached air suction intakes and air purification chamber. It shows exhaled air 8606 entering a top of the air purification chamber 8607 though an exhaled air suction intake 8608, which passes the air through a HEPA filter 8609 and fan(s) 8610 and cleaned air is exhausted from the back side of the air purification chamber as shown in the Figure.

FIGS. 87A and 87B show a detached exhaled air suction intake and air purification chamber distance separated and sitting beneath the exhaled air blocking surface. FIG. 87A is a top-down view of two detached air purification chambers 8701, showing the exhaled air blocking surface is the outer front surface 8703 the electronic display screen, which deflects or redirects exhaled air towards an exhaled air suction intake 8711, which can be part of, attached to, or adjacent to a distance separated air purification chamber, air purifier, or air purification unit comprising one or more air suction intakes and one or more air purification chambers. FIG. 87A shows an exhaled air suction intake 8711, and two air purification chambers, each having a HEPA filter 8704 and fan 8705. FIG. 87B shows a side view of detached air suction intakes and air purification chamber. It shows exhaled air 8706 entering a top of the air purification chamber 8707 though an exhaled air suction intake 8711, which passes the air through a HEPA filter 8704 and fan(s) 8705 and cleaned air is exhausted from the back side of the air purification chamber as shown in the Figure.

Figure 88:
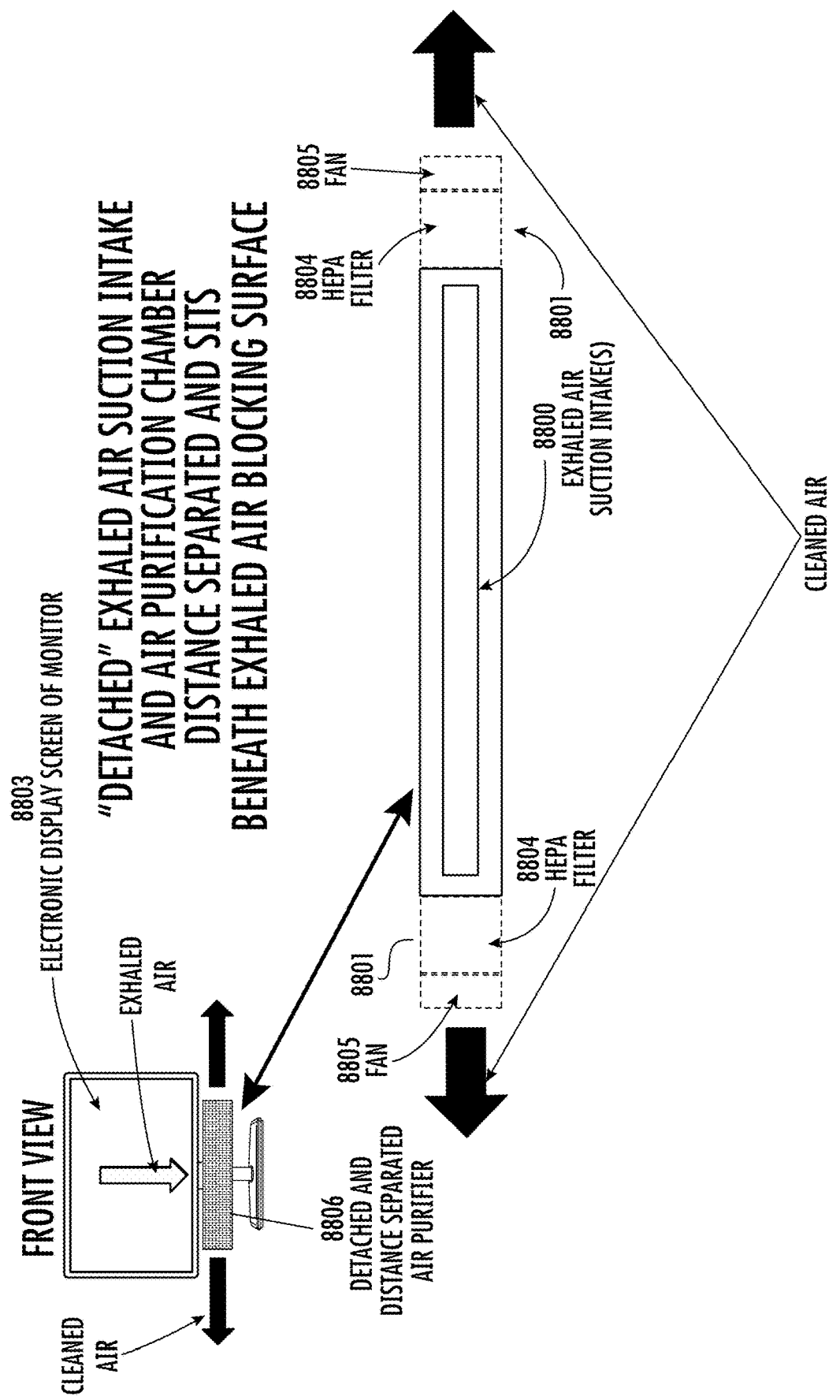
FIG. 88 is an illustration of an embodiment of the current invention as described herein.

FIG. 88 shows a detached exhaled air suction intake and air purification chamber distance separated and sitting beneath the exhaled air blocking surface. FIG. 88 is a top-down view of a detached air suction intake 8800 and two detached air purification chambers or air purifiers 8801, having a HEPA filter 8804 and fan 8805. The Figure shows the exhaled air blocking surface is the outer front surface 8803 of the electronic display screen, which deflects or redirects exhaled air towards an exhaled air suction intake 8800, which can be part of, attached to, or adjacent to a distance separated air purification chamber, air purifier, or air purification unit comprising one or more air suction intakes and one or more air purification chambers. The detached and distance separated air purifier is also shown in relation to the front of a monitor 8806.

Figure 89:
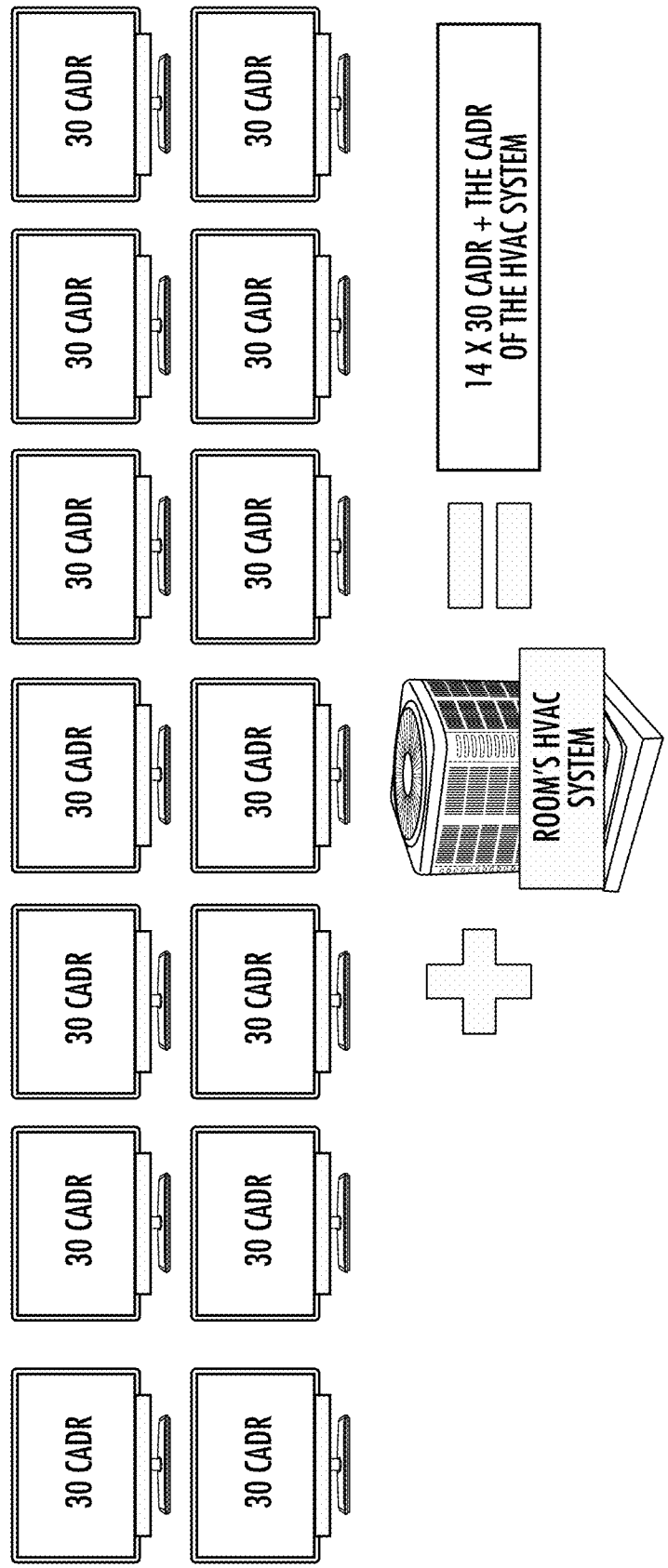
FIG. 89 is an illustration of an embodiment of the current invention as described herein.
Figure 90:
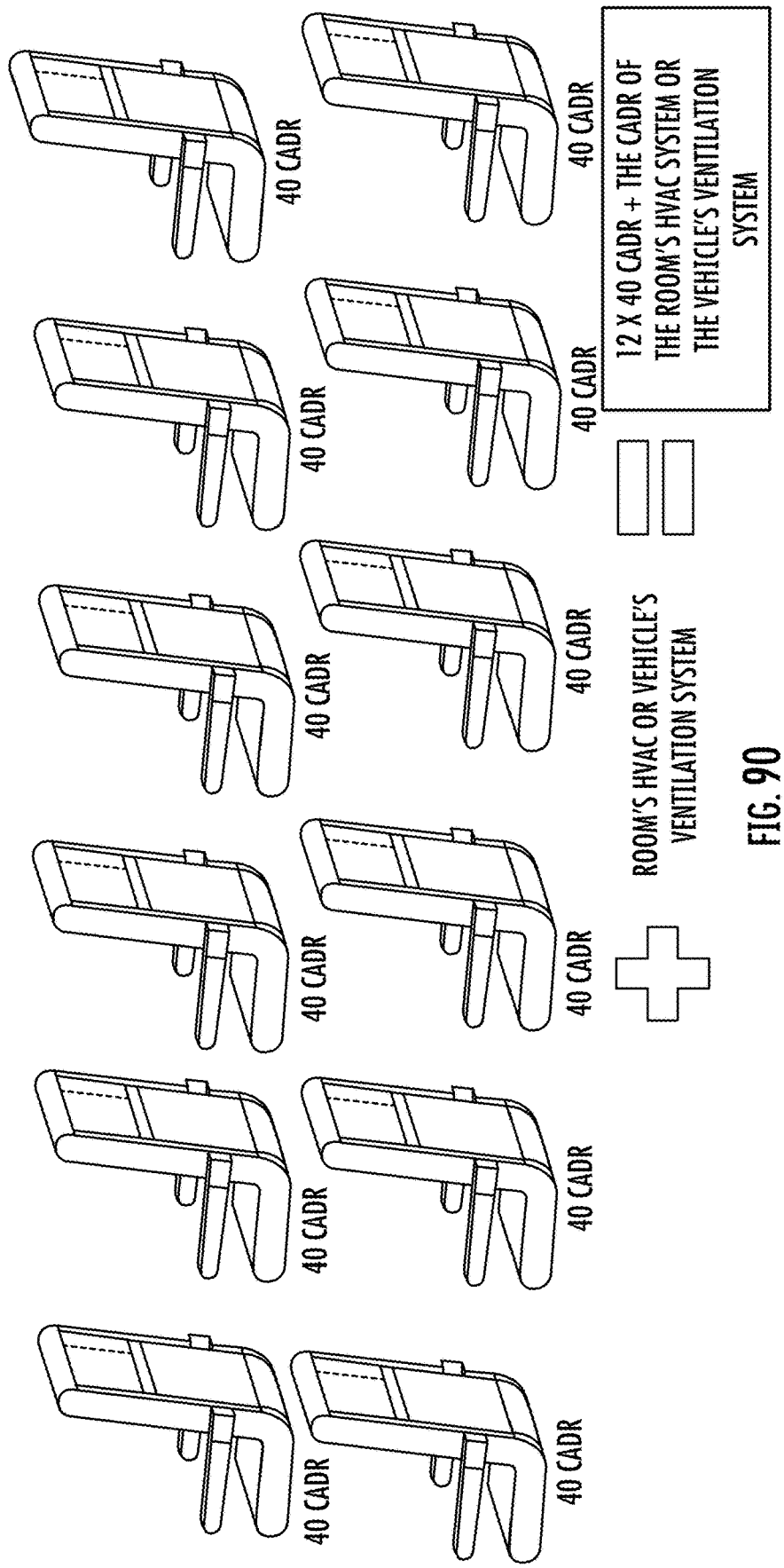
FIG. 90 is an illustration of an embodiment of the current invention as described herein.

FIG. 89 shows an illustration of multiple air capture and air cleaning monitors within the same indoor room, which increases total CADR and room clean air turns per hour. The numbers are non-limiting examples only. FIG. 90 shows an illustration of multiple air capture and air cleaning devices integrated or attached to chairs within the same indoor room or vehicle, which increases total CADR and room clean air turns per hour. The numbers are non-limiting examples only.

In embodiments, an exhaled air catch basin can be attached to one or more of the bottom portion of the monitor or electronic display screen, a front bottom portion of the monitor or electronic display screen electronic display screen, and a back bottom portion of the monitor or electronic display screen, by way of example only, using one or more of an adhesive pad, an adhesive strip, an adhesive, a magnet, magnets, mechanical members, and Velcro. In embodiments, the exhaled air catch basin can be attached to the bottom of the monitor by way of example only, one or more of an adhesive pad, an adhesive strip, an adhesive, a magnet, magnets, mechanical member(s), and Velcro, and can be connected to the exhaled air walls. When exhaled air walls are utilized they can be attached to the side of the monitor by way of, for example only, an adhesive strip, an adhesive pad, an adhesive, a magnet, magnets, Velcro, and mechanical member(s).

Figure 52:
FIG. 52 is an illustration of a computer model of a cough towards a monitor without the current invention as described herein.
Figure 53:
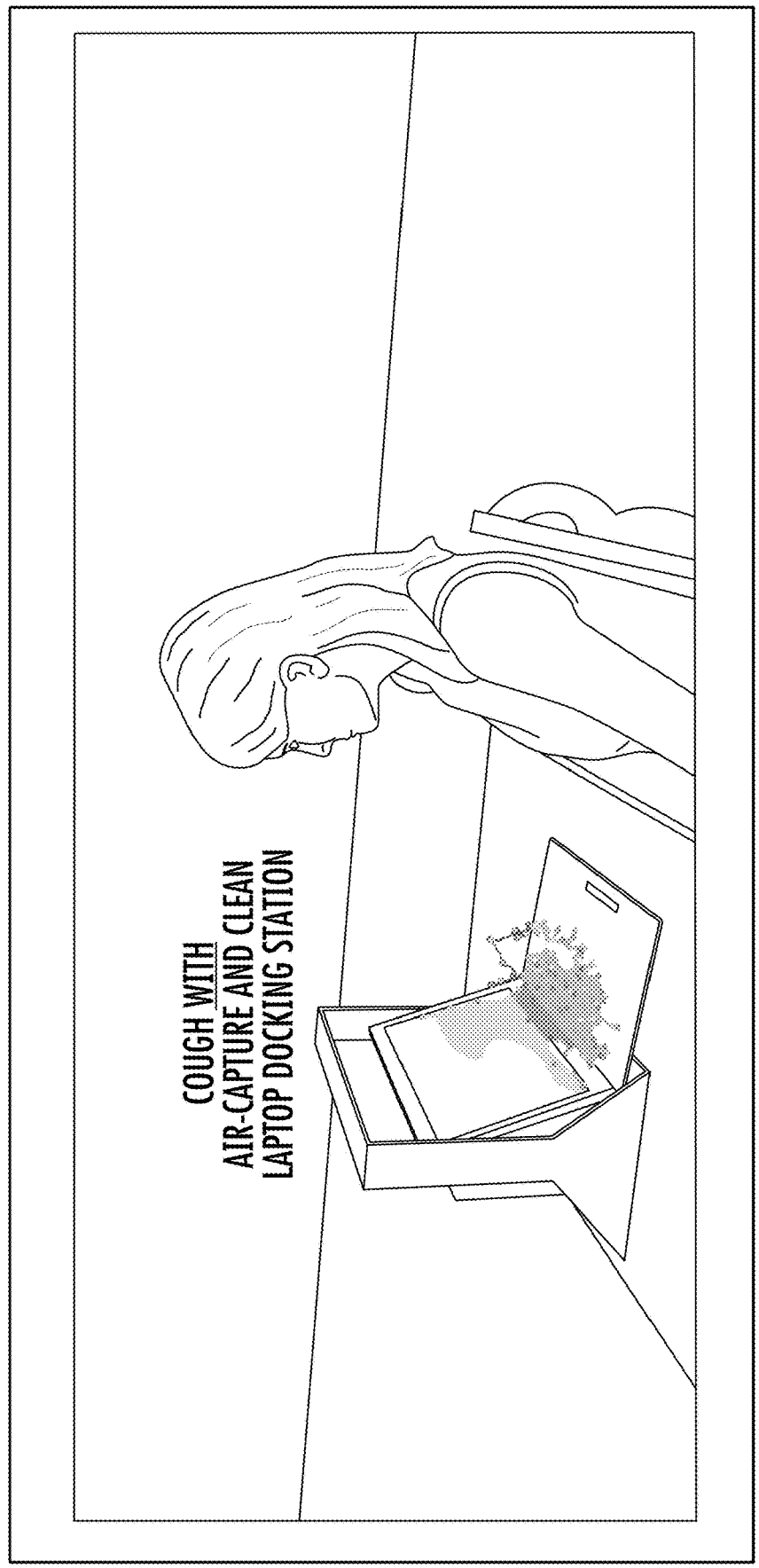
FIG. 53 is an illustration using computer modeling of an embodiment of the current invention as described herein.
Figure 54:
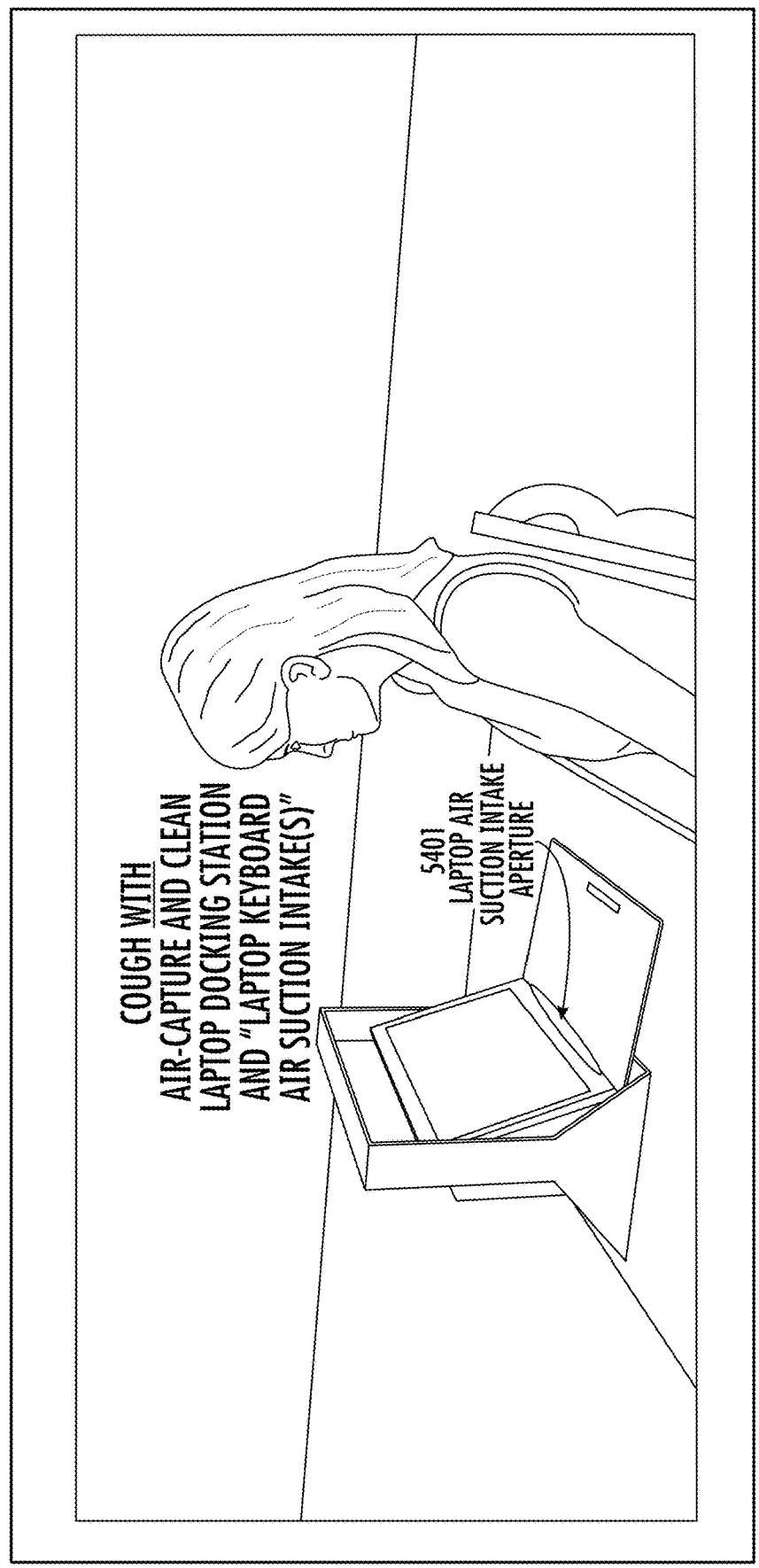
FIG. 54 is an illustration using computer modeling of an embodiment of the current invention as described herein.
Figure 55:
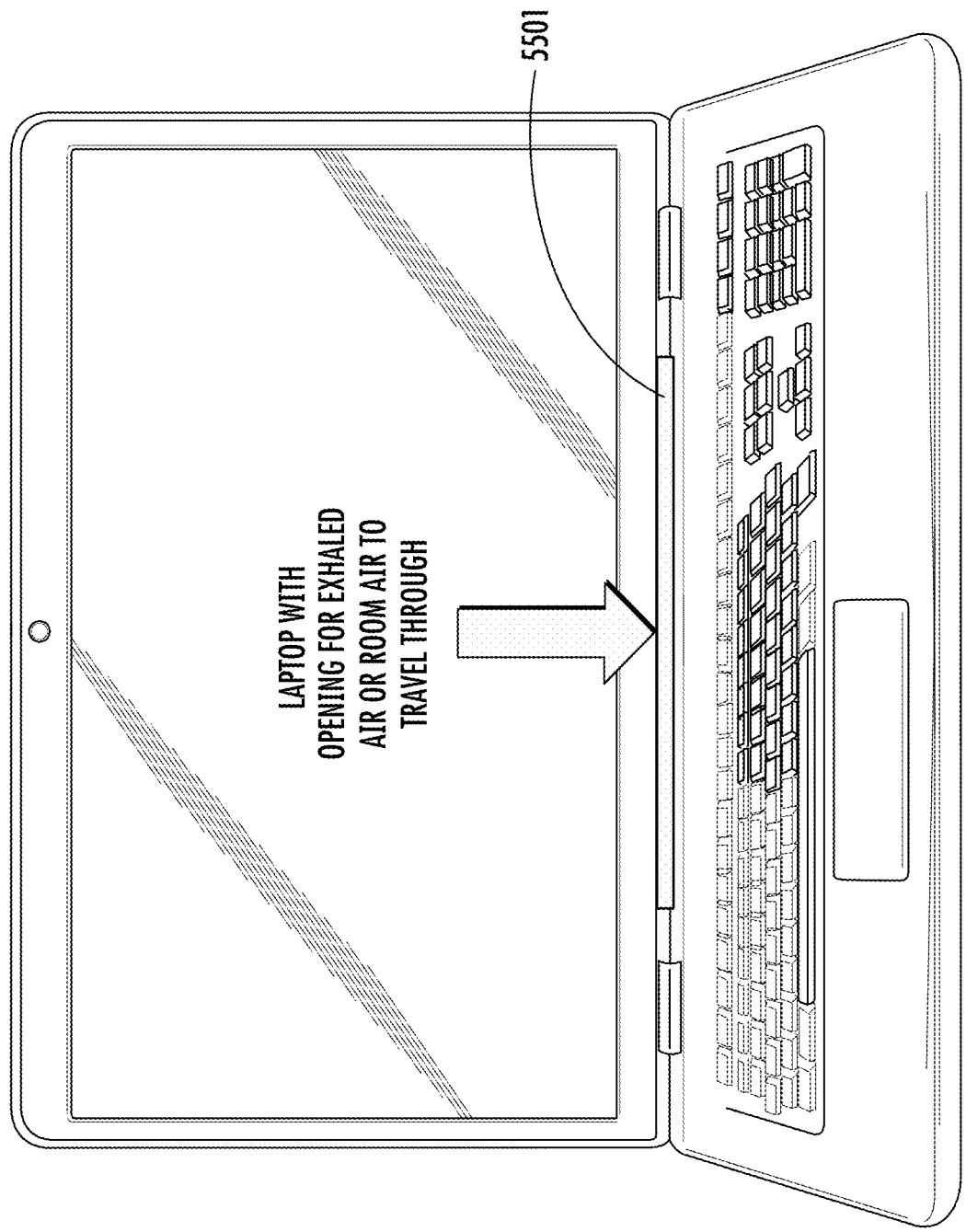
FIG. 55 is an illustration of an embodiment of the current invention as described herein.
Figure 56:
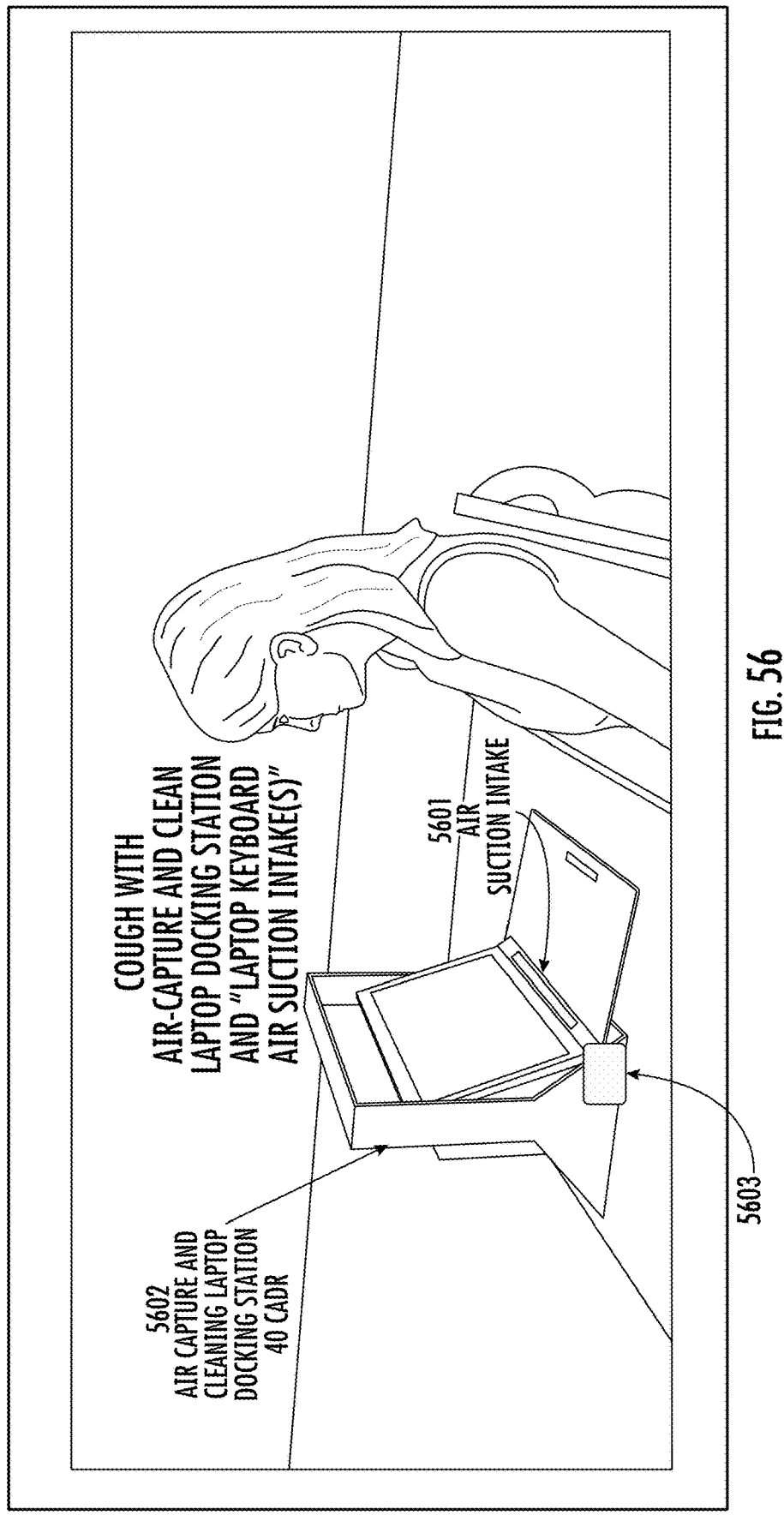
FIG. 56 is an illustration using computer modeling of an embodiment of the current invention as described herein.

In an embodiment, a computer or monitor, such as a laptop computer can be placed or reside partially or completely within the exhaled air collector. FIG. 52 shows a laptop without an air purification unit as taught herein. This figure shows the spread of respiratory particles after a cough without the air capture and cleaning device taught herein, showing the particles freely flowing into the room air for contamination of others. (This is example is around 10 seconds after a cough, the computer model showing no exhaled air capture.) FIG. 53 shows the same computer model but including the air capturing and cleaning device, wherein a laptop computer is placed partially within the device's exhaled air collector. More particularly, this embodiment is the laptop docking station example. In embodiments, the laptop docking station can capture 90%+ of respiratory particles from a cough using the air capture and cleaning laptop docking station having 40 CADR, by way of example only. In aspects, the non-captured particles end up remaining on the laptop keyboard and pose less of a threat to others, such as around 10% or less of the particles from the computer modeled cough remaining on the keyboard. (In this model, the figure shows particles around 10 seconds after a cough.) Thus, rather than spread like in FIG. 52, the particles are sucked into the exhaled air collector and around the laptop screen. FIG. 54 shows the laptop docking station, but this time including laptop keyboard air suction intake(s) 5401, wherein a laptop computer is placed partially within the device's exhaled air collector. In one embodiment, as shown in FIG. 54, a laptop air suction intake aperture 5401 can be located at the bottom of the laptop computer monitor. In this embodiment, the laptop docking station can capture 95%+ of respiratory particles from a cough using the air capture and cleaning laptop docking station having 40 CADR, by way of example only. In aspects, the non-captured particles end up remaining on the laptop keyboard and pose less of a threat to others; in this case, few, if any, particles remain on the keyboard, because exhaled air is suctioned around and below the monitor. (In this model, the figure shows particles around 10 seconds after a cough.) FIG. 55 shows another example of a laptop's exhaled air suction intake 5501 for capturing exhaled air mixed with room air. FIG. 56 shows the laptop docking station including laptop keyboard air suction intake(s) 5601, wherein a laptop computer is placed partially within the device's exhaled air collector. In one embodiment, as shown in FIG. 56, a laptop air suction intake aperture 5601 can be located at the bottom of the laptop computer monitor. In this embodiment, a secondary air purification chamber 5603 is used, which can be around 20 CADR, by way of example only, and can in aspects can be releasably attached to the laptop, monitor, or docking station, such as a snap-in second air purification chamber. In this embodiment, the laptop docking station 5602 can capture around 99% of respiratory particles from a cough using the air capture and cleaning laptop docking station having 40 CADR, by way of example only. In aspects, the non-captured particles end up remaining on the laptop keyboard and pose less of a threat to others; in this case, few, if any, particles remain on the keyboard, because the exhaled air is being suctioned around and below the monitor, and a secondary air purification chamber is used. (In this model, the figure shows particles around 10 seconds after a cough.)

Figure 41:
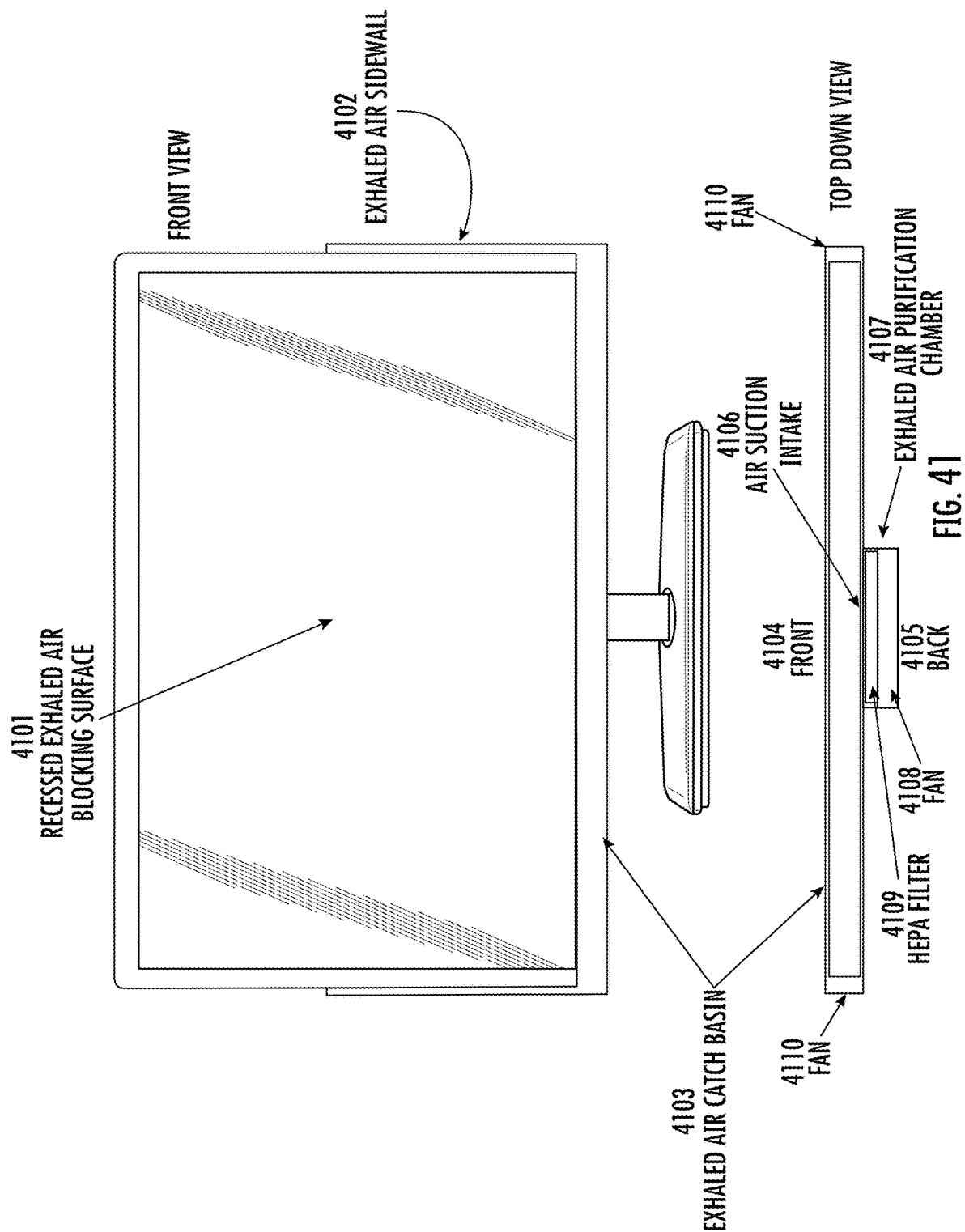
FIG. 41 is an illustration of an embodiment of the current invention as described herein.

FIG. 41 shows an embodiment comprising a recessed exhaled air blocking surface 4101 (which is the outer front surface of an electronic display screen) with exhaled air side walls and a lower exhaled air catch basin having an air suction intake that opens into an air purification chamber. This embodiment can be attached to the monitor post-sale or incorporated into the design of the monitor and thus be fully integrated. In this embodiment one or more exhaled side walls 4102 can attach to one or more sides of the monitor/electronic display screen and thereby provide support for the exhaled air catch basin 4103 and exhaled air purification chamber. In the top-down view, there is shown a front-facing (e.g., user facing) side 4104, and a back side 4105. As shown in FIG. 41, this embodiment uses an air suction intake(s) 4106 which would be located at the bottom of or underneath the electronic display screen as integrated into or adjacent to the exhaled air catch basin, such as at the bottom or back of the exhaled air catch basin. The air suction intake would lead to an adjacent air purification chamber 4107 comprising one or more fans 4108 and one or more filters 4109. In aspects, there can be one or more fans on either end of the basin 4110.

Figure 42:
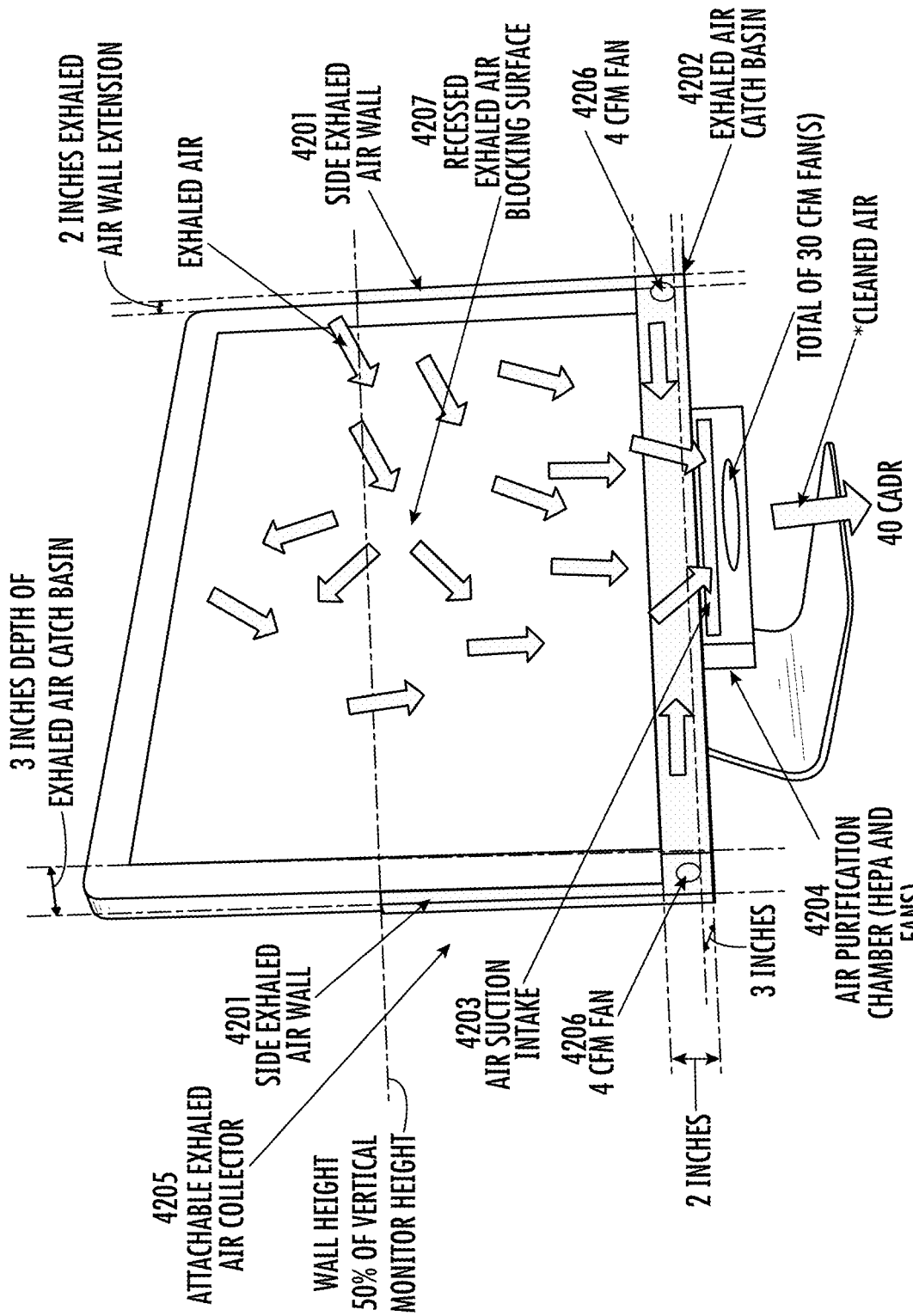
FIG. 42 is an illustration of an embodiment of the current invention as described herein.

FIG. 42 shows an embodiment of an attachable/detachable exhaled air collector 4205 having the exhaled air side walls 4201 and an exhaled air catch basin 4202, wherein underneath the exhaled air catch basin 4202 is an air suction intake 4203 and an air purification chamber 4204 having one or more fans and one or more filters. In this embodiment, cleaned air can be exhausted from the air purification chamber sideways, downwards, or backwards/behind. In aspects, the wall height of the exhaled side walls can be 50% of the vertical monitor height, by way of example only. Other measurements or values in this figure are for illustrative purposes only and are not to be construed as limiting the dimensions the embodiment or the teachings herein. Fans 4206 can be located at either end of the exhaled air catch basin. In this embodiment the exhaled air blocking surface is the electronic display screen 4207. As with other embodiments, exhaled air is stopped by the air blocking surface 4207 and deflected down into the exhaled air catch basin 4202. It is suctioned by the one or more exhaled air suction intakes 4203, cleaned by the air purification chamber 4204, and returned to the room. In this non-limiting example, the total CFM of fans(s) in the air purification chamber are 30 CFM and the unit returns 40 CADR of cleaned air.

Figure 43:
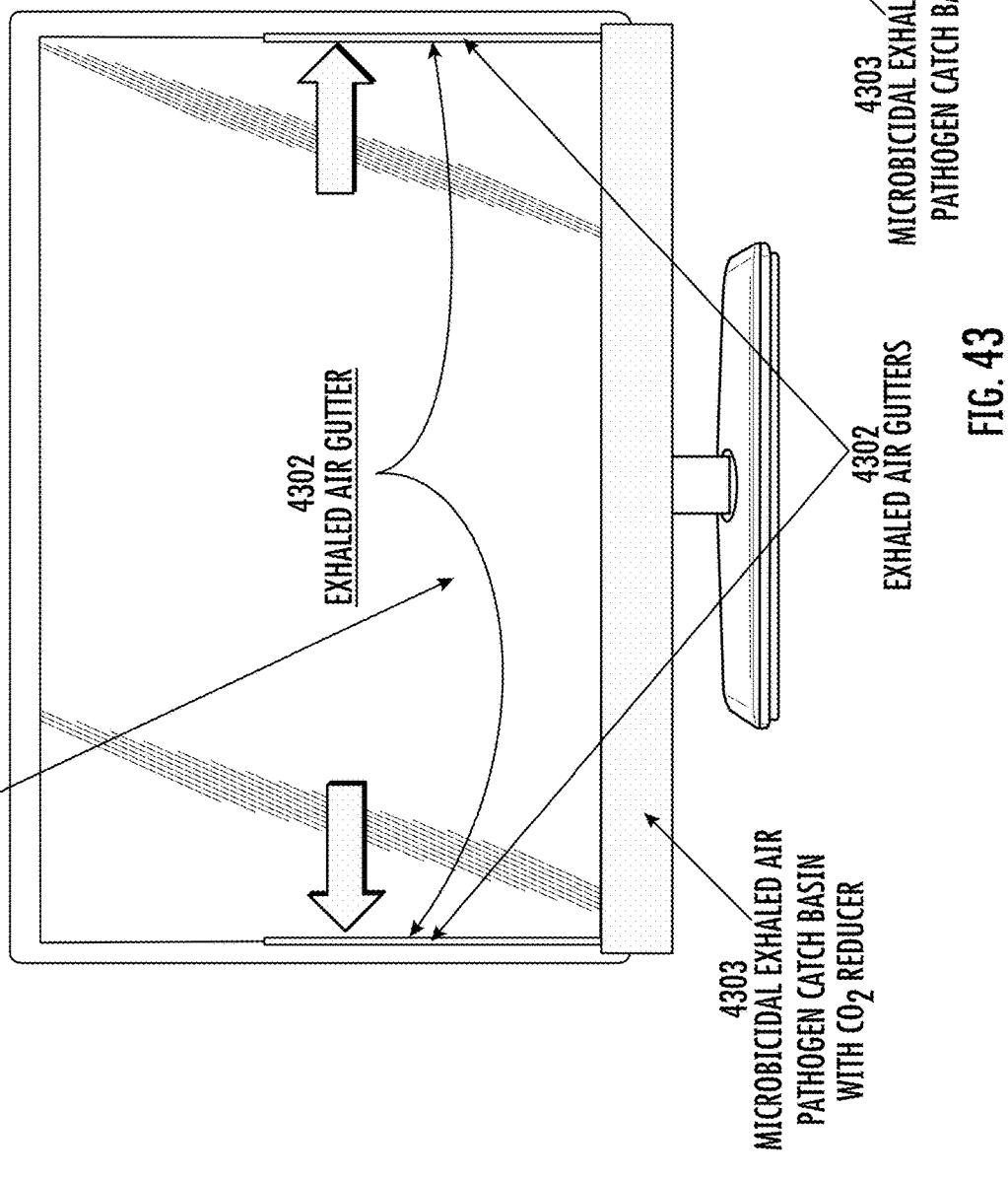
FIG. 43 is an illustration of an embodiment of the current invention as described herein.
Figure 44:
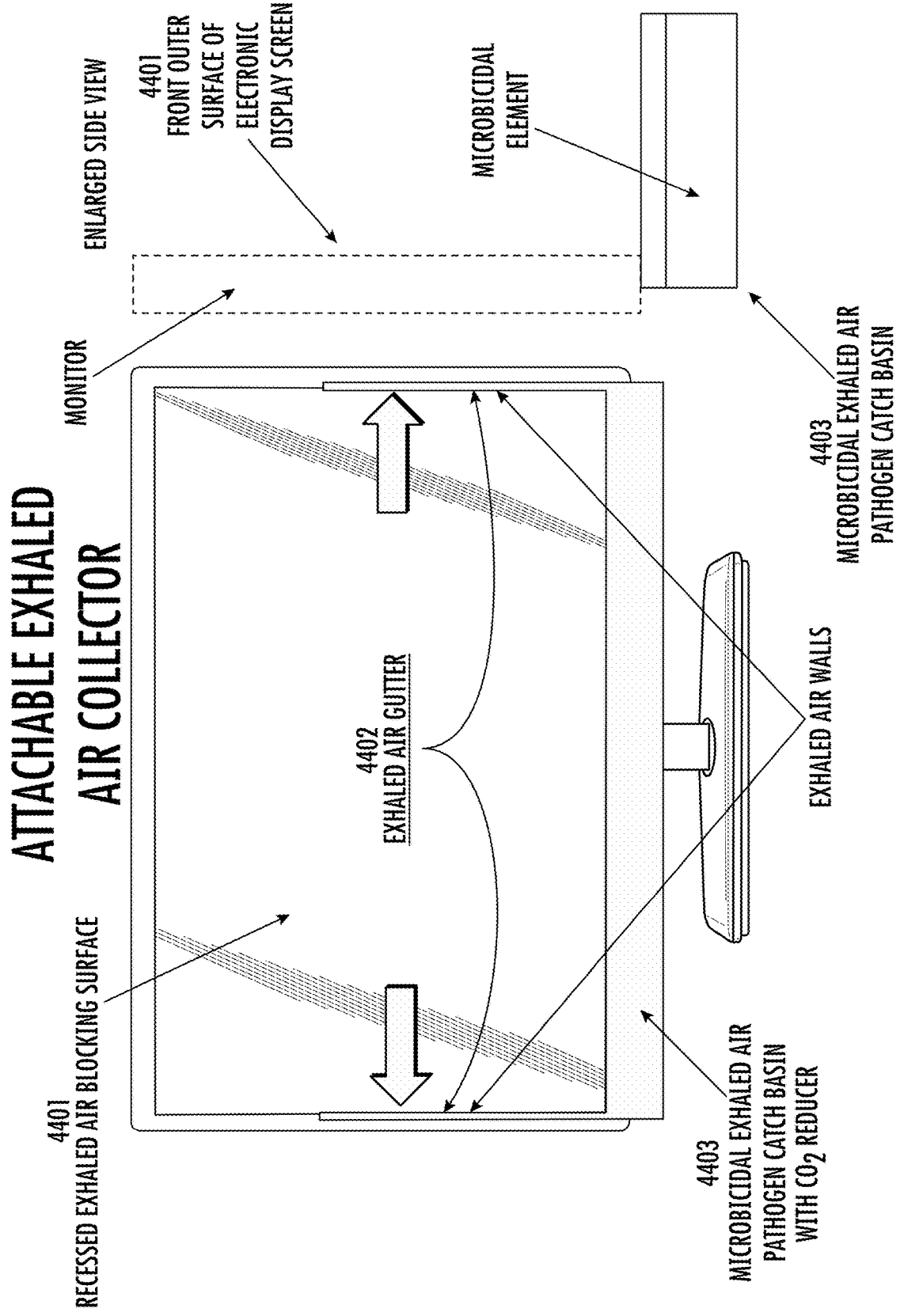
FIG. 44 is an illustration of an embodiment of the current invention as described herein.
Figure 45:
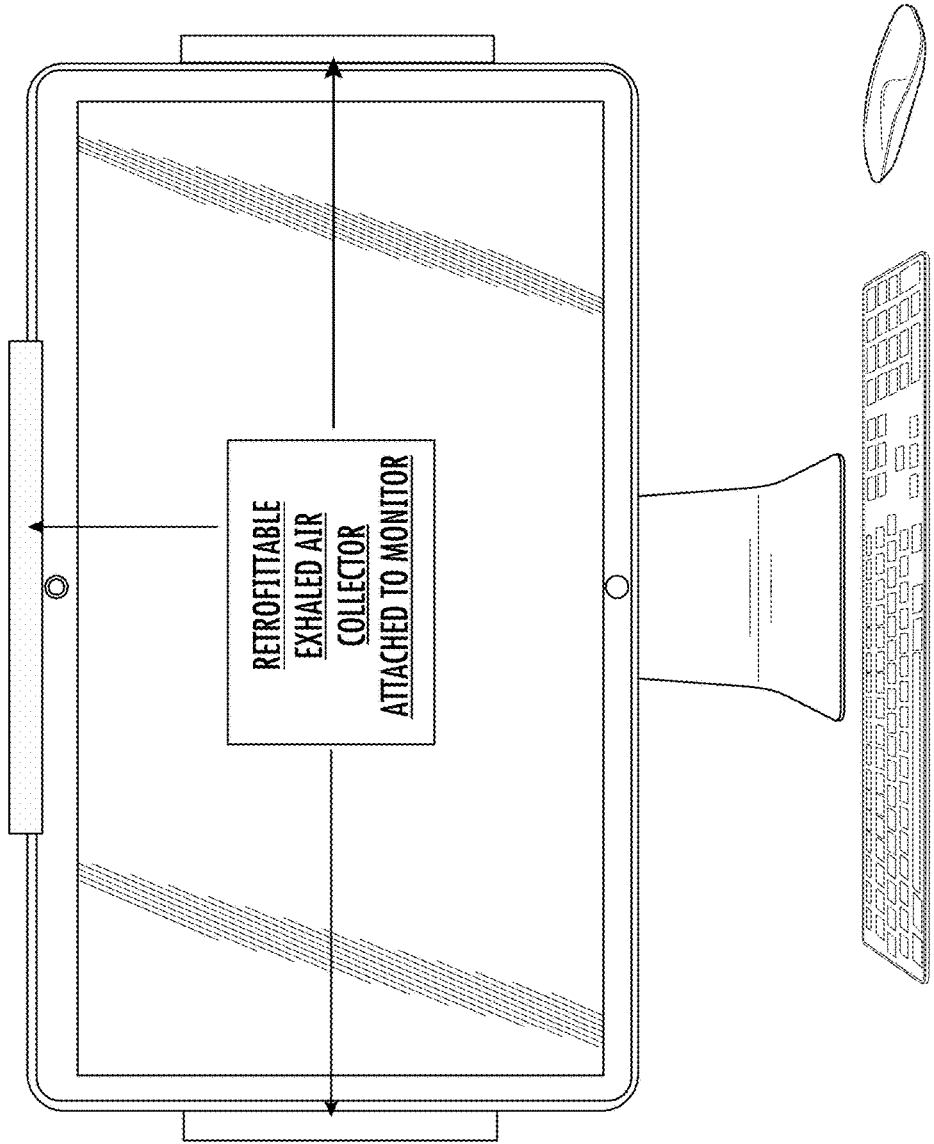
FIG. 45 is an illustration of an embodiment of the current invention as described herein.

FIG. 43 shows an attachable exhaled air collector comprising a recessed exhaled air blocking surface 4301 with a partially surrounding exhaled air gutter 4302 and a lower microbicidal exhaled air pathogen catch basin 4303 (optionally with CO2 reducer). The embodiment shows a monitor comprising the exhaled air blocking surface, and an air purification chamber in the form of an exhaled air pathogen catch basin. FIG. 44 shows an attachable exhaled air collector comprising a recessed exhaled air blocking surface 4401 with a partially surrounding exhaled air gutter 4402 and a lower microbicidal exhaled air pathogen catch basin 4403 (optionally with CO2 reducer). This embodiment does not utilize an air suction intake. The embodiment shows a monitor comprising the exhaled air blocking surface, and an air purification chamber in the form of an exhaled air pathogen catch basin. FIG. 45 shows an adjustable size attachable exhaled air collector, which is designed so that one SKU exhaled air collector can fit a plurality of different sized monitors, TVs, computers, electronic display screens, etc. In this embodiment as shown in FIG. 45, the system utilizes a retrofittable exhaled air collector attached to a monitor.

Figure 91:
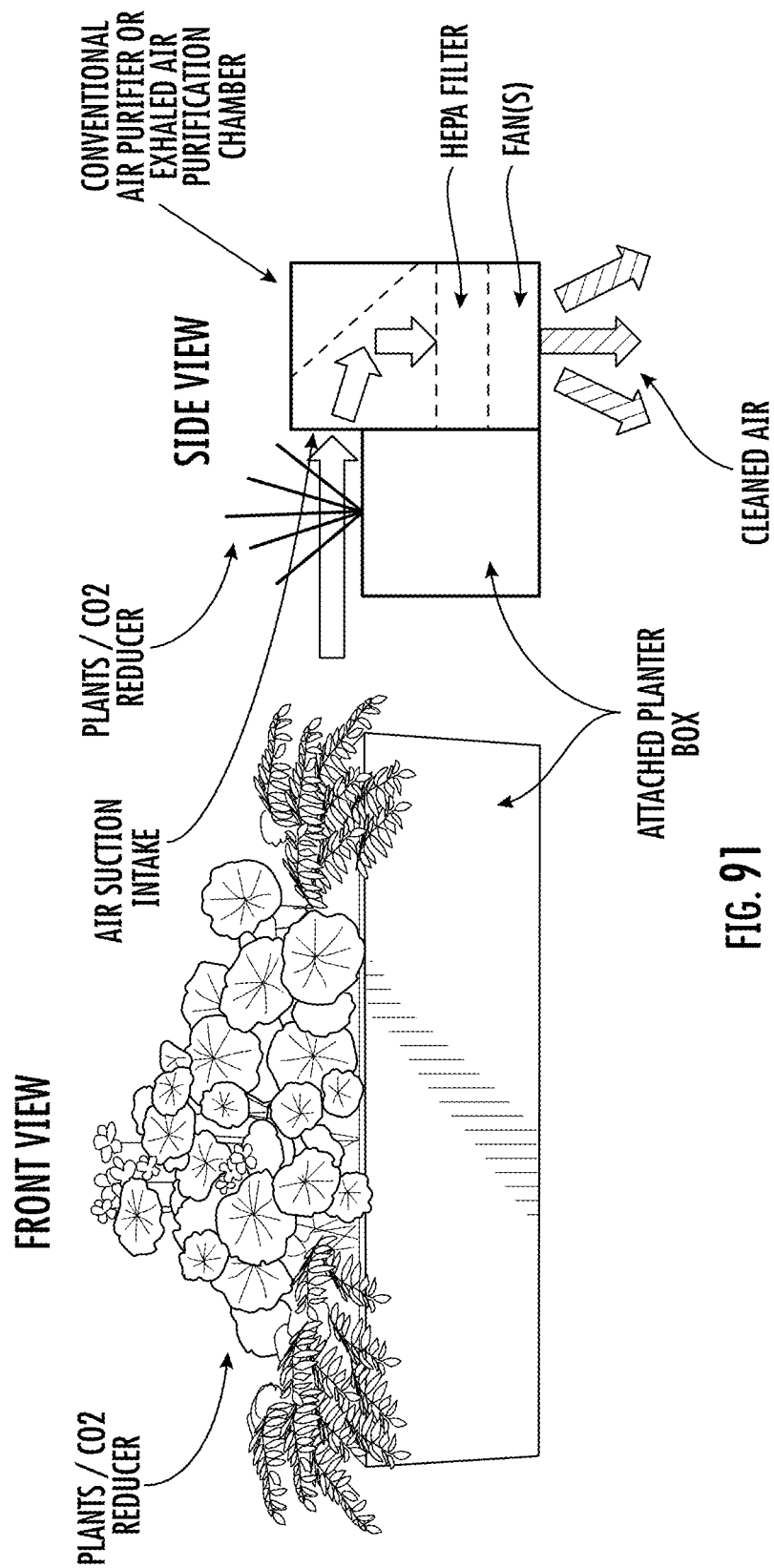
FIG. 91 is an illustration of an embodiment of the current invention as described herein.
Figure 92:
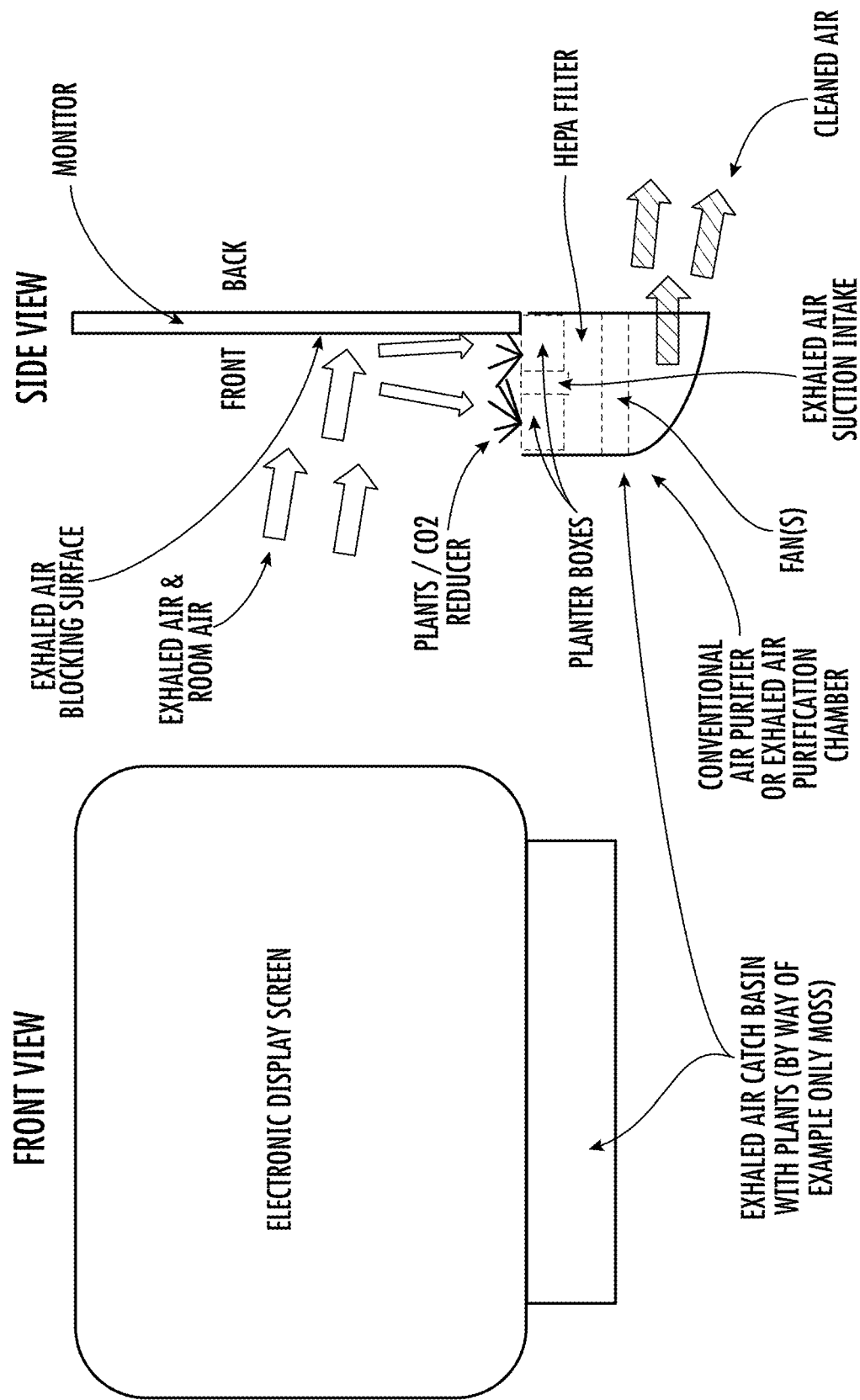
FIG. 92 is an illustration of an embodiment of the current invention as described herein.

FIG. 91 shows a planter box having plants, CO2 reducer(s), or CO2 reducing plants that can be attached to or located in front of a conventional air purifier or exhaled air purification chamber. As shown in FIG. 91, exhaled air moves through the plants, CO2 reducer(s), or CO2 reducing plants before entering the conventional air purifier or exhaled air purification chamber, which cleans the exhaled air using a HEPA filter and a fan or fans, by way of example, and exhausts the cleaned air. FIG. 92 shows an exhaled air catch basin with plants (by way of example only, moss). Further according to FIG. 92, a mixture of exhaled air and room air contacts the exhaled air blocking surface (in this case a monitor), which is directed downwards to the exhaled air catch basin having plants/CO2 reducers. The mixed air travels through an air suction intake, in aspects between planter boxes in the exhaled air catch basin, and into a conventional air purifier or exhaled air purification chamber having a filter and fan(s), which cleans and exhausts the air. The planter box(es) can be waterproof. The planter box can have access to a watering element. A grow lamp can be attached to the planter box, exhaled air collector, monitor, laptop, tablet, or TV.

Figure 46:
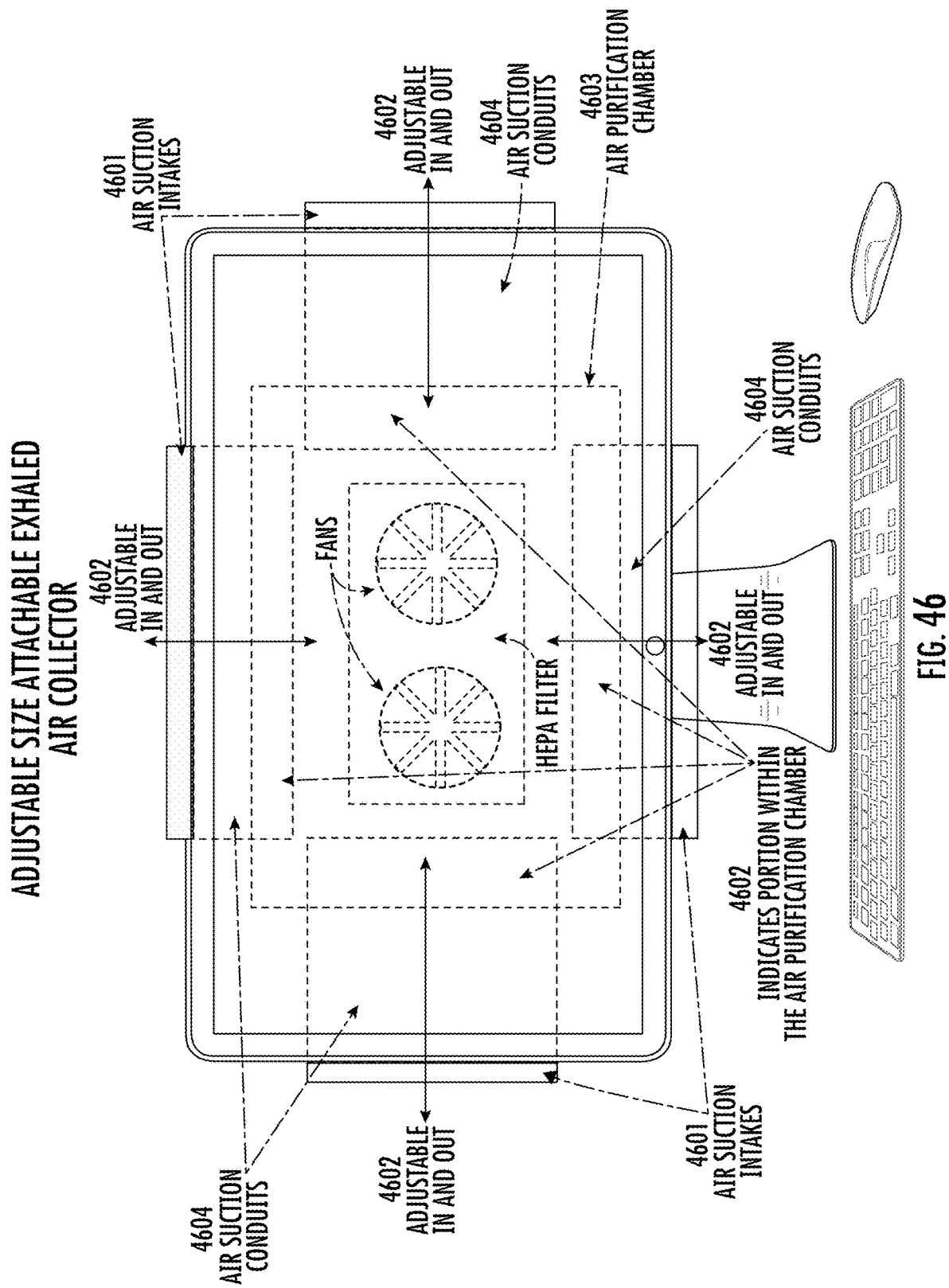
FIG. 46 is an illustration of an embodiment of the current invention as described herein.
Figure 47:
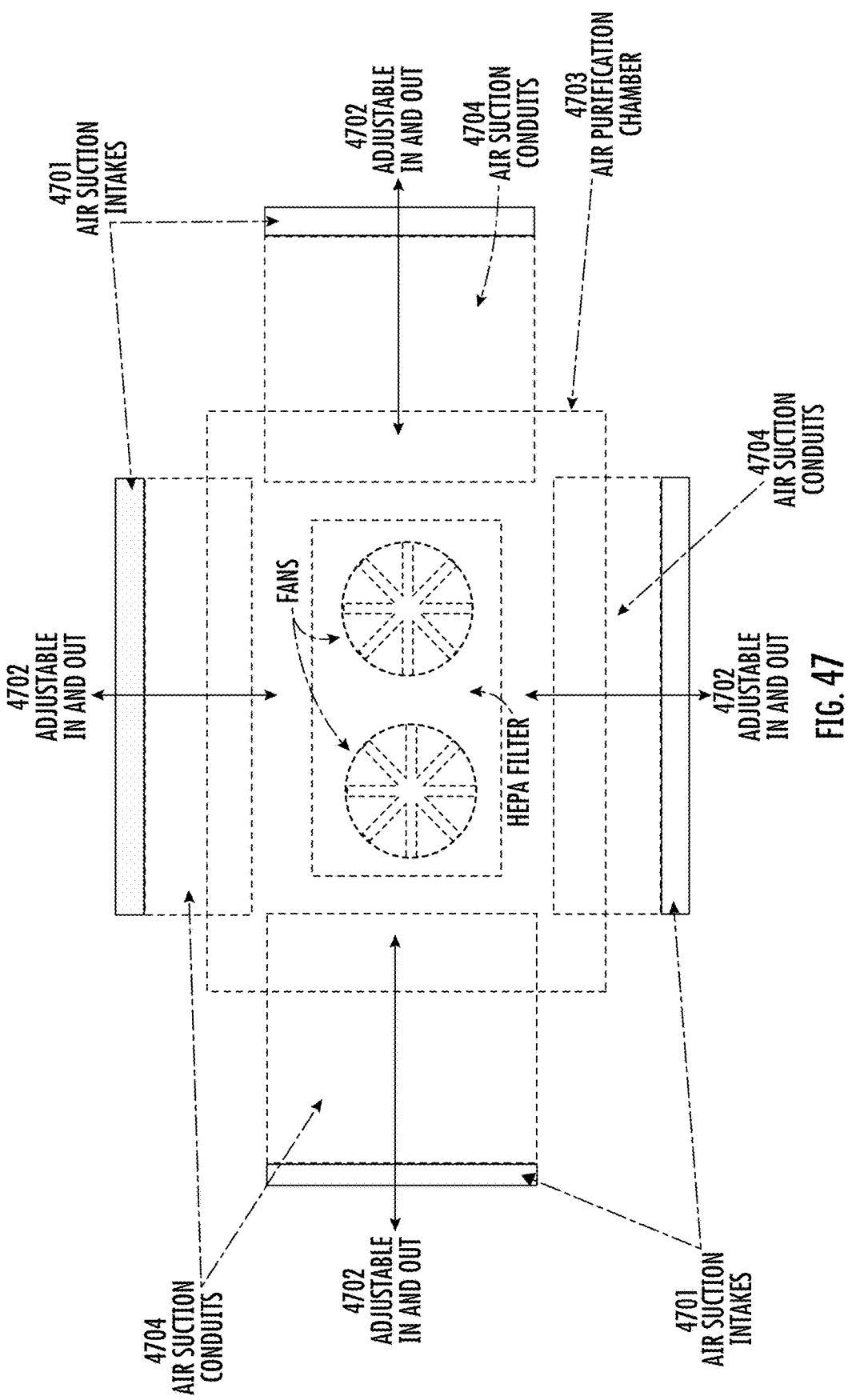
FIG. 47 is an illustration of an embodiment of the current invention as described herein.
Figure 48:
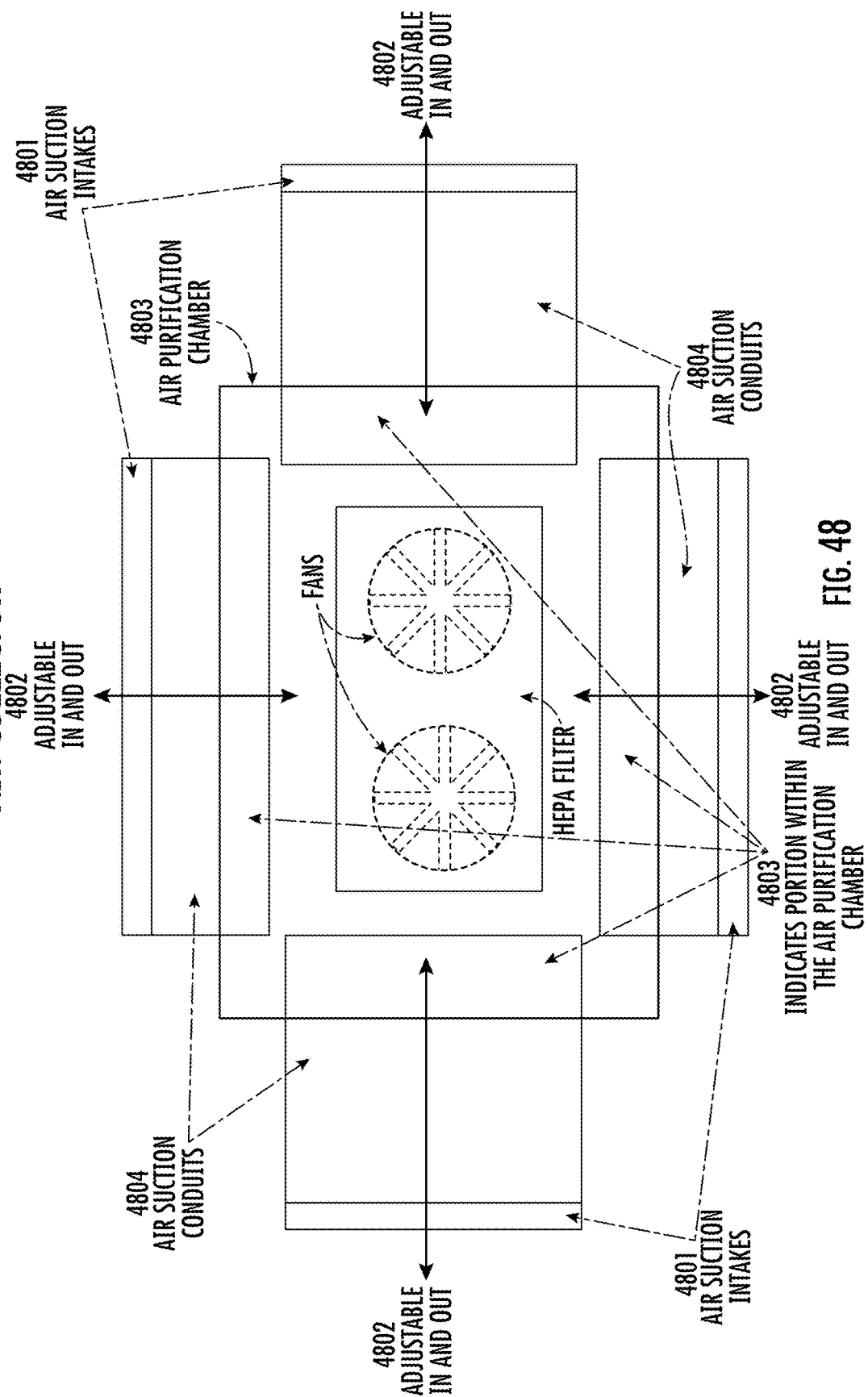
FIG. 48 is an illustration of an embodiment of the current invention as described herein.
Figure 49:
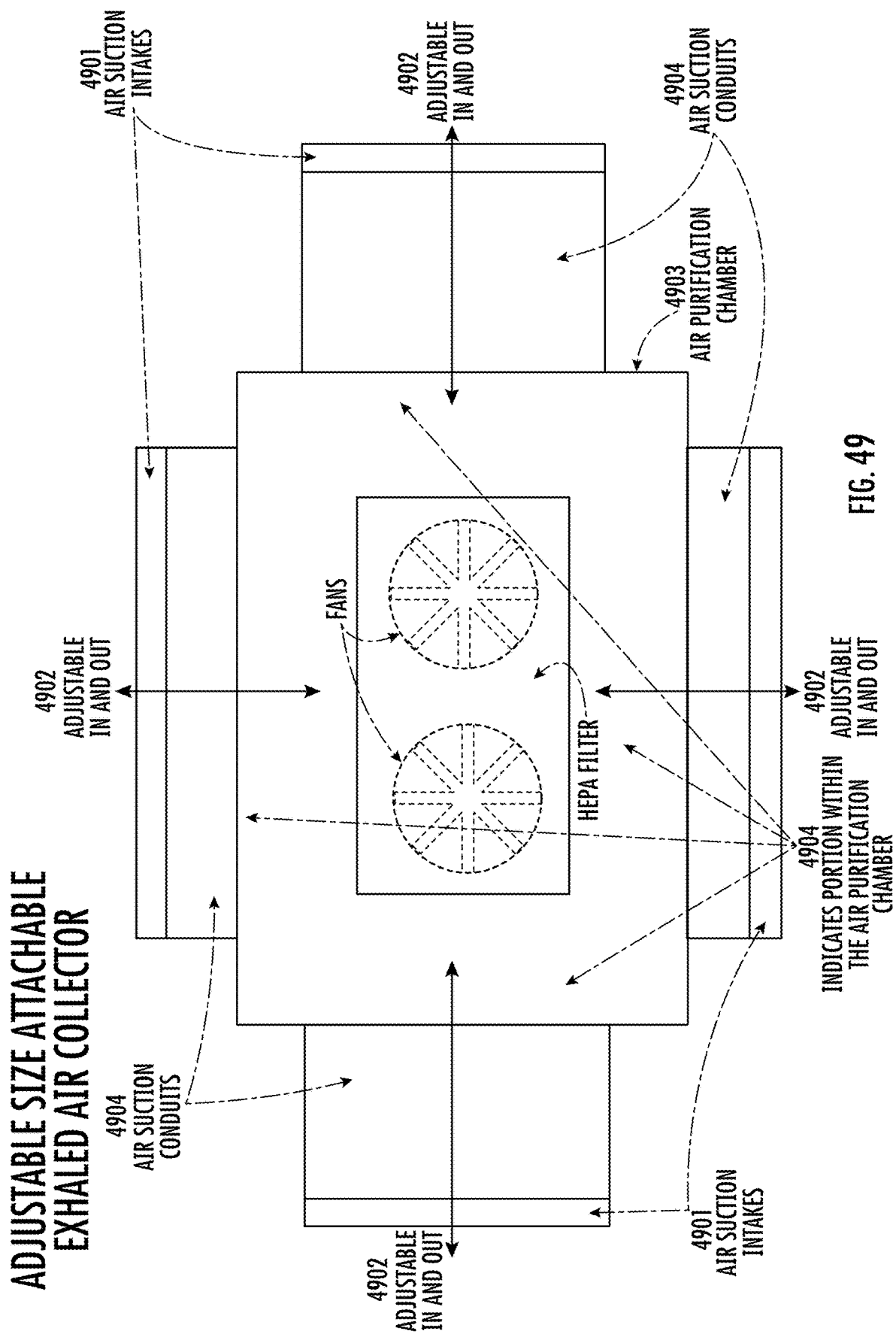
FIG. 49 is an illustration of an embodiment of the current invention as described herein.
Figure 50:
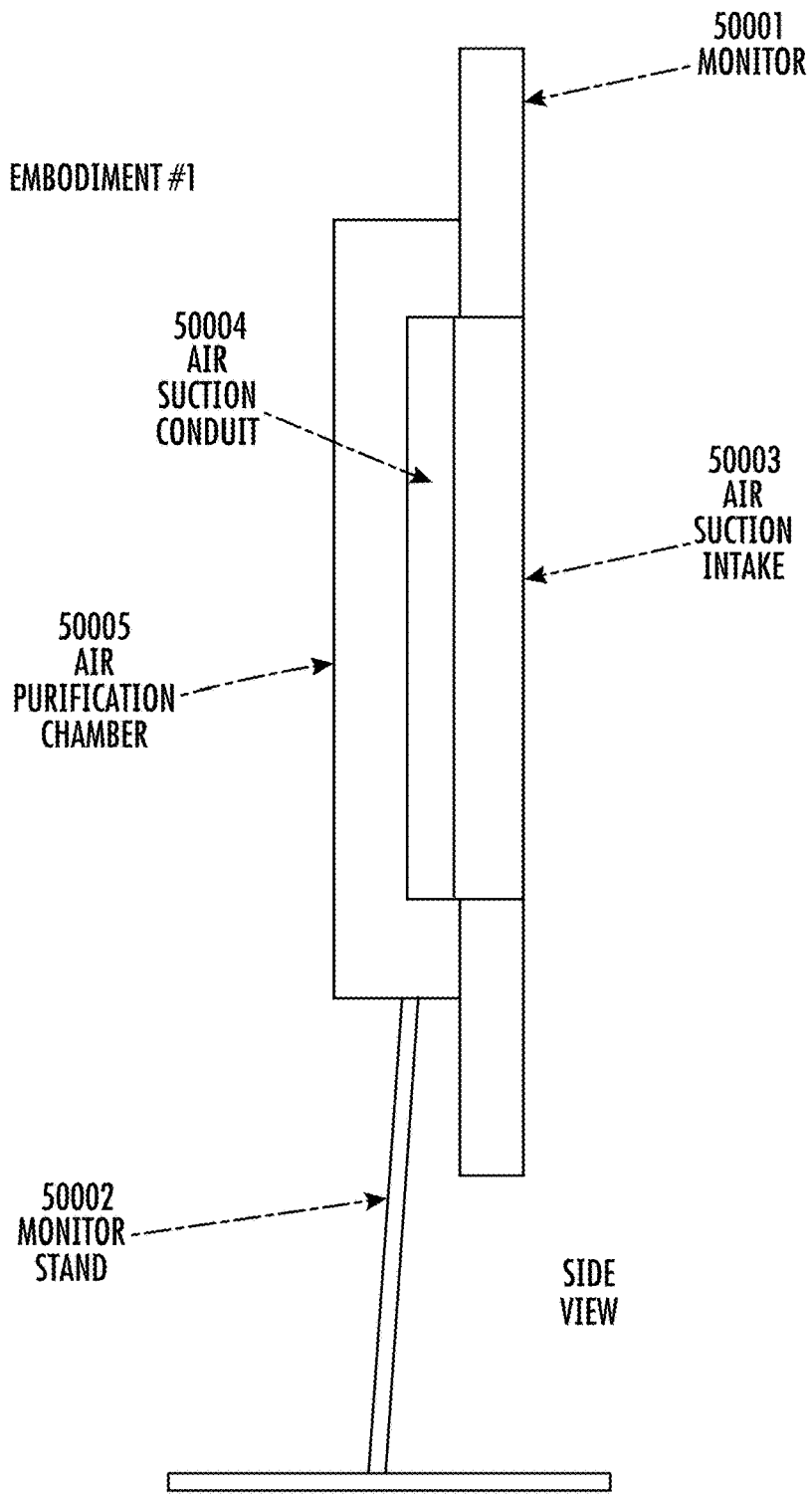
FIG. 50 is an illustration of an embodiment of the current invention as described herein.
Figure 51:
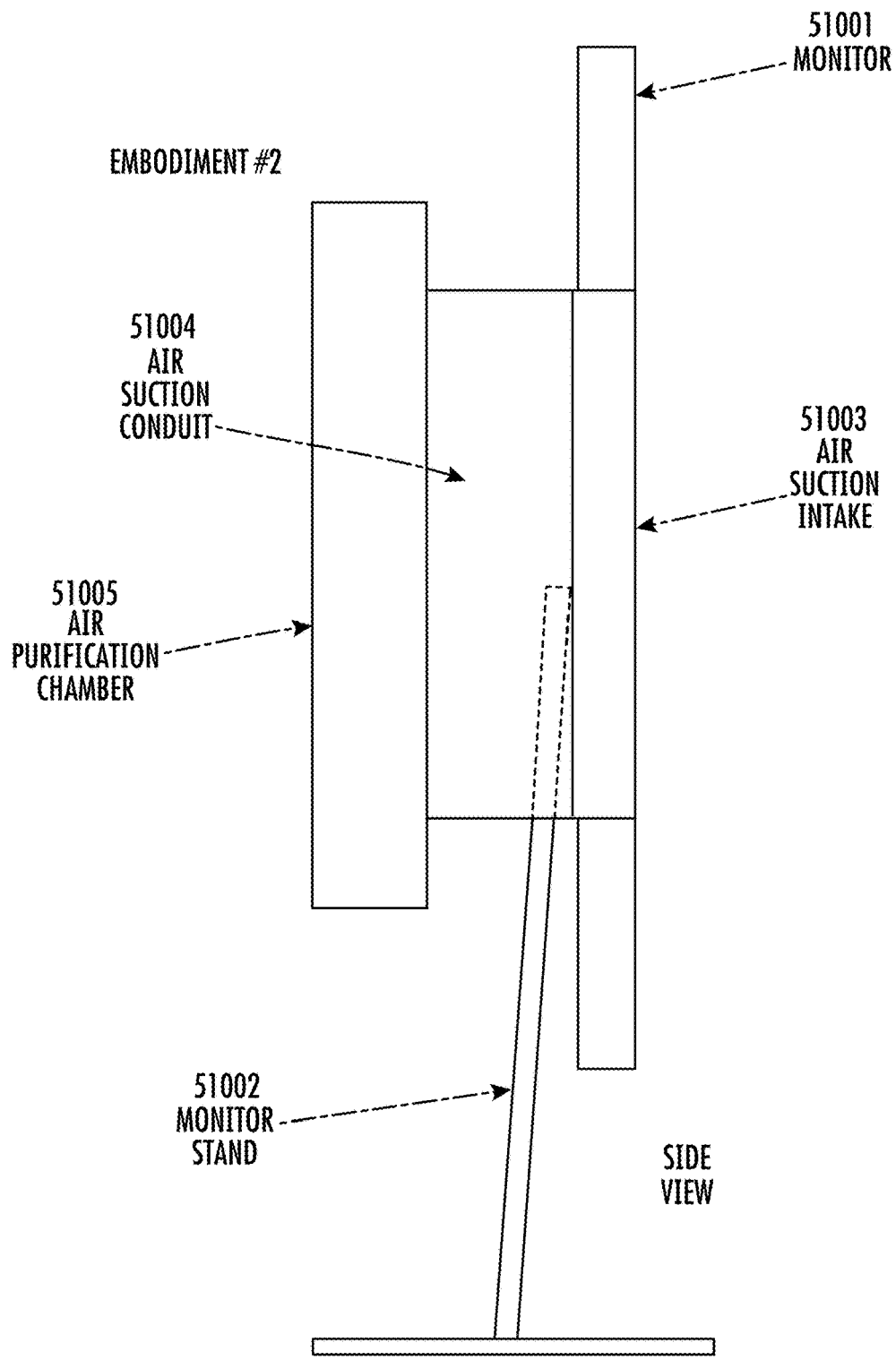
FIG. 51 is an illustration of an embodiment of the current invention as described herein.

FIG. 46 shows an adjustable sized attachable exhaled air collector from a front facing view of a monitor where the air capture and cleaning system is mostly located on a back side of the monitor. In this embodiment, for example, the air suction intakes can be adjusted so that they extend beyond the sides of the monitor to capture exhaled air. The Figure shows air suction intakes 4601 that are adjustable in and out and up and down 4602, and air suction conduits 4604 connecting the exhaled air suction intakes 4601 to the air purification chamber 4603. An air purification chamber having one or more fans and HEPA filters 4603 is also shown. FIG. 47 also shows an adjustable sized attachable exhaled air collector showing air suction intakes 4701 that are adjustable in and out and up and down 4702, and air suction conduits 4704 connecting the exhaled air suction intakes 4701 to the air purification chamber 4703. An air purification chamber having one or more fans and HEPA filters 4703 is also shown. FIG. 47 shows the adjustable air collector of FIG. 46 as detached from the monitor/electronic display screen. FIG. 48 also shows an adjustable sized attachable exhaled air collector showing air suction intakes 4801 that are adjustable in and out and up and down 4802, and air suction conduits 4804 connecting the exhaled air suction intakes 4801 to the air purification chamber 4803. An air purification chamber having one or more fans and HEPA filters 4803 is also shown. In the embodiment of FIG. 48, the air suction conduits slide in and out as needed to fit the requirements of the monitor/computer/display or user. In aspects, the conduits can be made of a rigid or semi-rigid material, like metal or plastic. FIG. 49 also shows an adjustable sized attachable exhaled air collector showing air suction intakes 4901 that are adjustable in and out and up and down 4902, and air suction conduits 4904 connecting the exhaled air suction intakes 4901 to the air purification chamber 4903. An air purification chamber having one or more fans and HEPA filters 4903 is also shown. In the embodiment of FIG. 49, the air suction conduits can be stretched or can shrink as needed to fit the requirements of the monitor/computer/display or user. In aspects, the conduits can be made of a stretchable material like rubber, urethane, or a folded accordion-like expandable plastic. FIG. 50 is a side view of the adjustable size attachable exhaled air collector. This embodiment shows the unit attached to a monitor 50001 and monitor stand 50002. In this embodiment #1, as shown from the side, the air suction intake 50003 has been adjusted to extend outside a perimeter of the monitor 50001, and the air suction conduit 50004 connects the air suction intake to the air purification chamber 50005 so that the air suction intake passes collected/captured exhaled air to the air purification chamber for cleaning. This illustration shows only one of the four air suction intakes and adjustable air suction conduits. Embodiments are also contemplated with more or less than four air suction intakes/conduits. FIG. 51 is a side view of the adjustable size attachable exhaled air collector. This embodiment shows the unit attached to a monitor 51001 and monitor stand 51002. In this embodiment #2, as shown from the side, the air suction intake 51003 has been adjusted to extend outside a perimeter of the monitor 51001, and the air suction conduit 51004 connects the air suction intake to the air purification chamber 51005 so that the air suction intake passes collected/captured exhaled air to the air purification chamber for cleaning. This illustration shows only one of the four air suction intakes and adjustable air suction conduits.

In embodiments a magnet or magnets can be coated or covered with a material (by way of example only, plastic, felt, or cloth) to prevent the scratching of the surface of the monitor, electronic display screen, laptop, tablet, or TV. In embodiments when the attachment is to the bottom or lower front surface of the peripheral frame portion of the monitor, electronic display screen, laptop, tablet, or TV (the frame being that part that surrounds the electronic display screen), the magnet can magnetically pull against the lower front frame surface while a mechanical means can hook over the upper portion of the lower front frame such as to be attached by both a magnetic force and a mechanical hooking means. In embodiments such a hooking member that extends beyond the thickness of the magnet is approximately 2-3 mm front to back in its dimensions (with the back of the hook being closest to the bottom edge of the electronic display screen and the 2-3 mm hooking portion extending over the top exposed edge of the lower frame peripheral portion of the frame that surrounds the electronic display screen). In other embodiments the hook portion being approximately 2-3 mm front to back in terms of its dimension (with the back of the hook being closest to the bottom edge of the electronic display screen and the 2-3 mm hooking portion extending over the top exposed edge of the lower frame peripheral portion of the frame that surrounds the electronic display screen), the hook can support an attached exhaled air catch basin.

Figure 38:
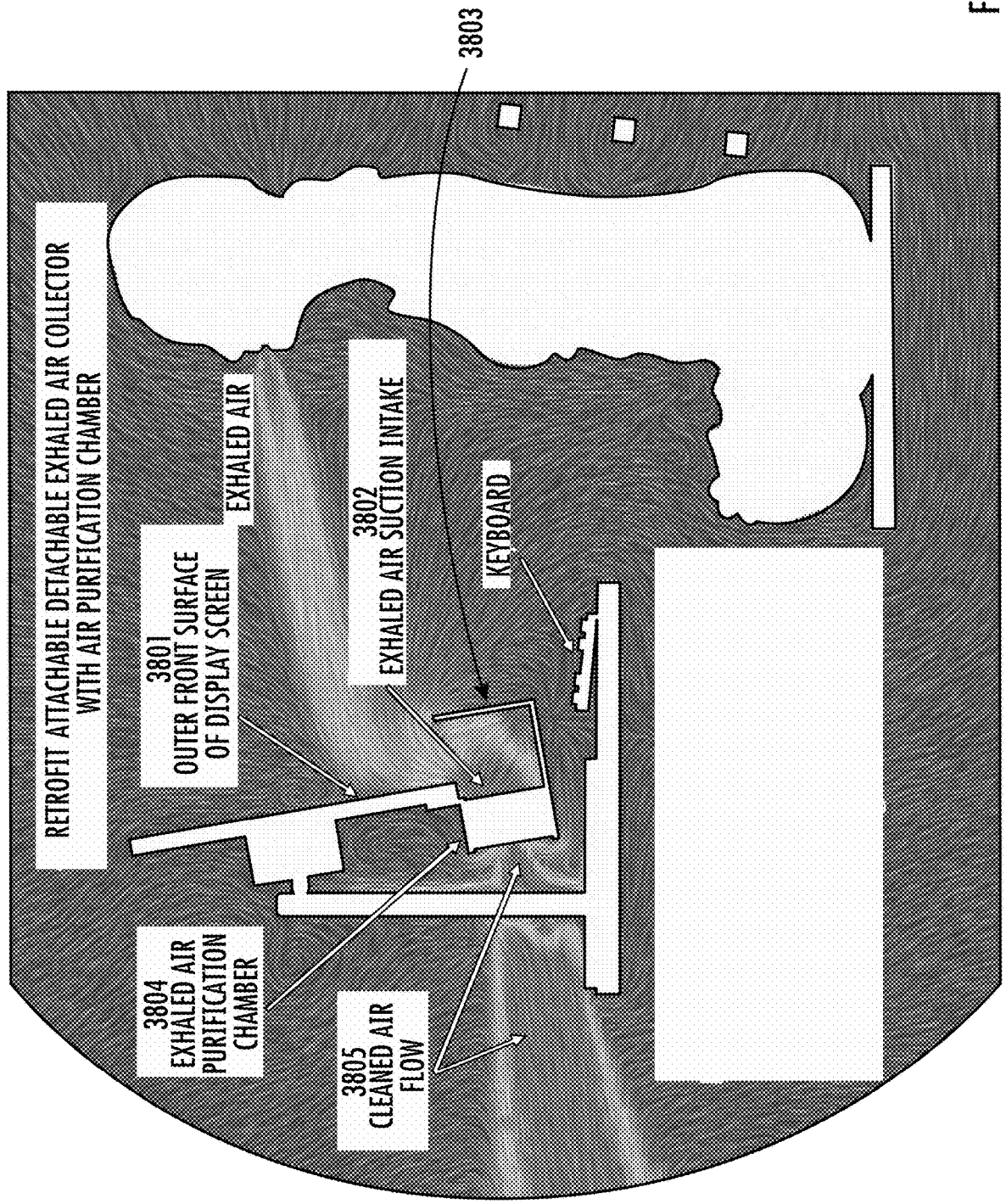
FIG. 38 is an illustration of an embodiment of the current invention as described herein.
Figure 39:
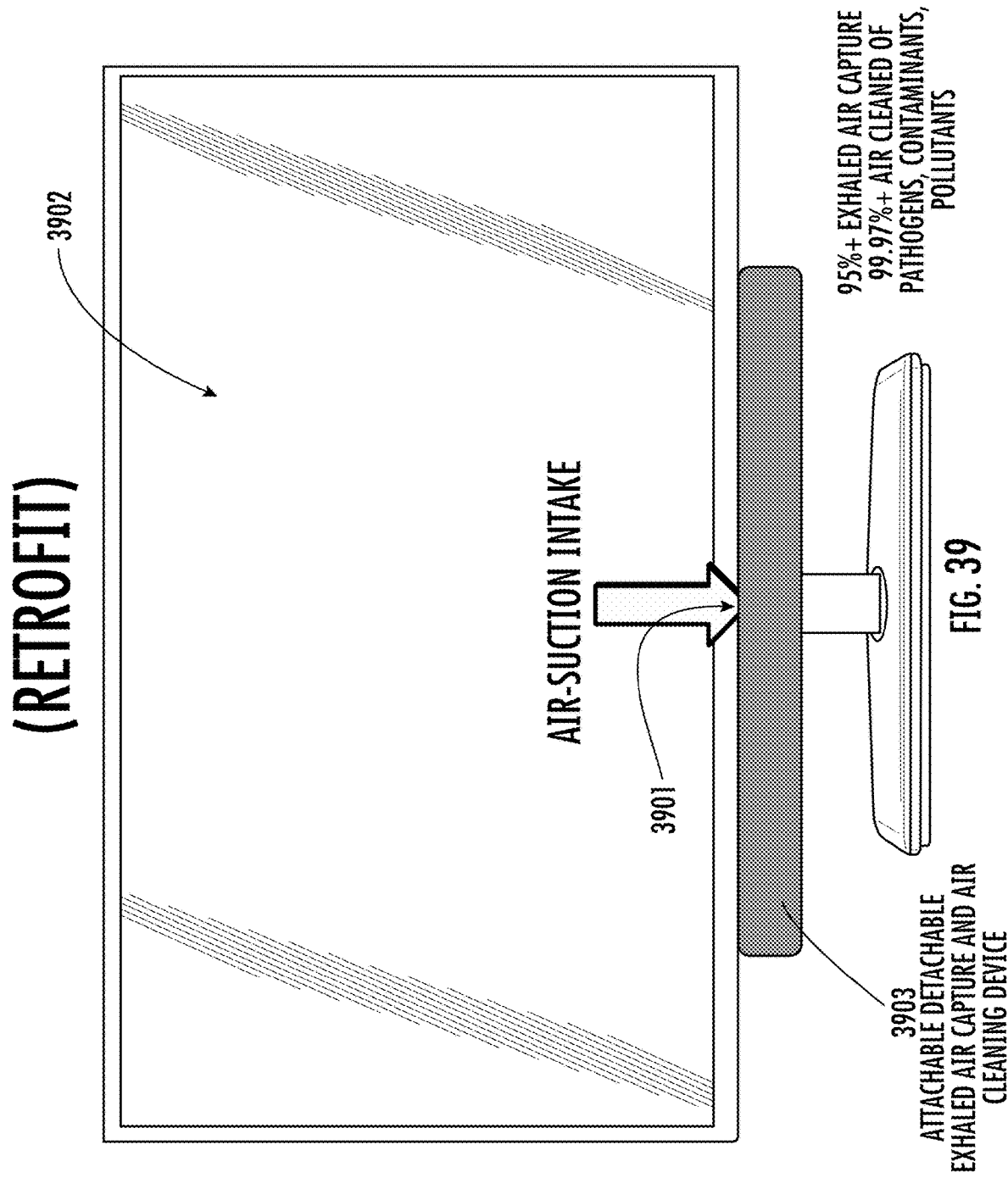
FIG. 39 is an illustration of an embodiment of the current invention as described herein.

In embodiments the exhaled air side walls are hooked over the top right side of the monitor and the top left side of the monitor and then run vertically across the front of the monitor to which the lower portion of the exhaled air side walls provide support for the exhaled air catch basin. The exhaled air catch basin can comprise a fan on the right side and a fan on the left side of the exhaled air catch basin, each blowing air towards the center of the exhaled air catch basin. An air suction intake can be located at the center of the exhaled air catch basin that sucks the captured respiratory particles into an attached or connected exhaled air purification chamber located on or in the bottom, or beneath the bottom of the exhaled air catch basin. The exhaled air purification chamber can utilize any of the methods taught herein for cleaning and/or purifying the exhaled air and then releasing the clean air into the room's environment. In aspects, multiple small fans can be applied to the top of the recessed exhaled air blocking surface for blowing the exhaled air respiratory particles downward into the exhaled air catch basin. This embodiment can be provided as an air handing device that can be retrofitted post-sale for a monitor, laptop, or tablet. This embodiment can also be integrated into the design of a monitor, laptop, or tablet during the original fabrication thereof. FIG. 38 shows an embodiment of a retrofit attachable/detachable exhaled air collector with an air purification chamber. This embodiment shows the outer front surface of an electronic display screen 3801 acting as an exhaled air blocking surface having one or more air suction intakes 3802 beneath the electronic display screen and optionally have an exhaled air catch basin 3803. The air enters an air purification chamber 3804 and cleaned air 3805 is exhausted out the back of the air purification chamber. In other terms, it shows exhaled air flow being deflected by the outer front surface of the electronic display screen 3801 and suctioned into the air suction intake 3802 and then being cleaned by the air purification chamber 3804 with the cleaned air exiting behind 3805 the air purification chamber. FIG. 39 shows a potential retrofit embodiment wherein an air suction intake 3901 is located underneath or at the bottom of the electronic display screen 3902. The retrofit system is an attachable/detachable exhaled air capture and air cleaning device 3903. In this embodiment, exhaled air is deflected and pulled into an air suction intake(s) located at a top of the releasably attachable exhaled air capture and air cleaning device. The air suction intake can be perpendicular or substantially perpendicular to the bottom of the display screen (e.g., exhaled air blocking surface). In embodiments the air suction intake(s) of the air capture and air cleaning device is located beneath and forward to that of the exhaled air blocking surface. In other embodiments the air suction intake(s) is located on the top of the air capture and air cleaning device and/or also its front surface.

Figure 40:
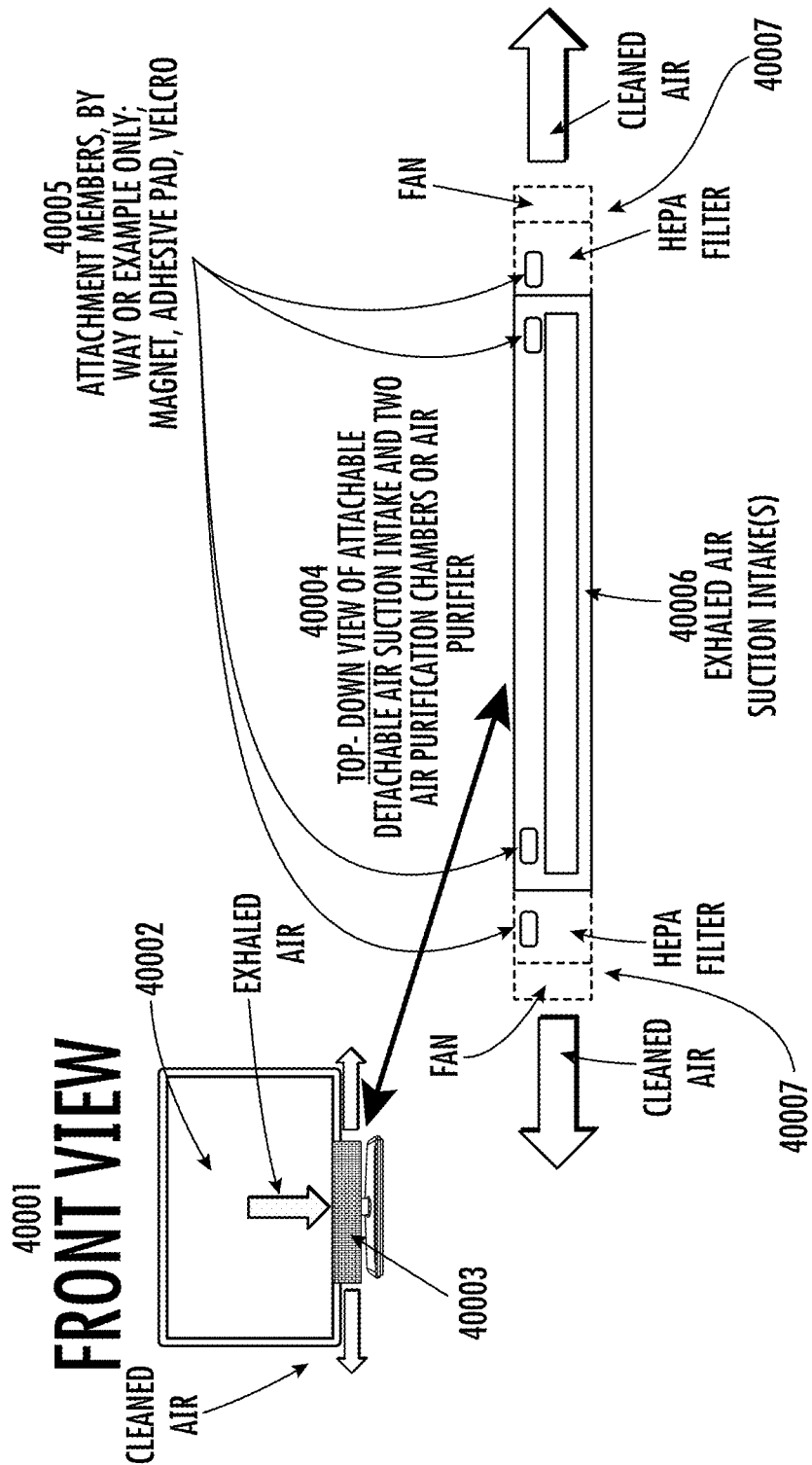
FIG. 40 is an illustration of an embodiment of the current invention as described herein.

FIG. 40 shows a front view 40001 of an electronic display screen or monitor 40002 with an attached exhaled air collector with an exhaled air suction intake and air purification chamber(s) or conventional air purifier 40003. Exhaled air is deflected from electronic display screen or monitor 40002 and into the attached exhaled air collector with an exhaled air suction intake and air purification chamber(s) or conventional air purifier 40003, and cleaned air can exit one or more of: the back, one or both sides, and the bottom of 40003. A close up view of 40003 shows a top-down view 40004 of the releasably attachable system, in embodiments having an air suction intake and two air purification chambers or air purifiers. In the close-up view it is shown to have attachment members, such as magnets, adhesives, or Velcro 40005. It shows the top having one or more air suction intakes 40006, and wherein there is an air purification chamber or air purifier 40007 on each end of the unit looking down, which can comprise one or more fans and one or more filters. The system can be attachable and detachable to fit a plurality of different sized monitors. The exhaled air blocking surface can be the outer front surface of the electronic display screen/monitor which then deflects exhaled air downwards towards an attached exhaled air collector and air suction intake with an air purification chamber or conventional air purifier. The exhaled air capture and cleaning device/system is attachable and detachable (releasably attached). The device/system can have no side walls, in embodiments.

In aspects, an air suction intake that directly or indirectly connects to an air purification chamber can be attached to the bottom of the monitor or electronic display screen, by way of example only, one or more of an adhesive pad, an adhesive strip, an adhesive, a magnet, magnets, mechanical members, and Velcro. Such an air suction intake can be located beneath part or all of the length of the front surface of the monitor, part or all of the length of the bottom of the monitor, part or all of the length of the front surface of the electronic display screen, and/or part or all of the length of the bottom of the electronic display screen. The air suction intake can be 6 inches or longer in length, in aspects. The air suction intake can be 12 inches or longer in length. The air suction intake can be 18 inches or longer in length. The exhaled air purification chamber can comprise any of the means disclosed herein to clean and/or purify exhaled air and room air. In such an embodiment the electronic display screen can act as the exhaled air blocking surface and deflect or direct exhaled air mixed with room air downward towards the air suction intake.

In embodiments, an exhaled air catch basin that comprises an air suction intake that directly or indirectly connects to an air purification chamber can be attached to the bottom of the monitor or electronic display screen, by way of example only, one or more of, an adhesive pad, an adhesive strip, an adhesive, a magnet, magnets, mechanical members, and Velcro. Such an air suction intake can be located beneath part or all of the length of the front surface of the monitor, part or all of the length of the bottom of the monitor, part or all of the length of the front surface of the electronic display screen, and/or part or all of the length of the bottom of the electronic display screen. The air suction intake can be 6 inches or longer in length. The air suction intake can be 12 inches or longer in length. The air suction intake can be 18 inches or longer in length. The exhaled air purification chamber can comprise any of the means disclosed herein to clean and/or purify exhaled air and room air. In such an embodiment the electronic display screen can act as the exhaled air blocking surface and deflect or direct exhaled air mixed with room air downward towards the air suction intake.

In embodiments, an exhaled air purification chamber can be attached to one or more of the bottom portion of the monitor or electronic display screen, a front bottom portion of the monitor or electronic display screen electronic display screen, and a back bottom portion of the monitor or electronic display screen, by way of example only, one or more of an adhesive pad, an adhesive strip, an adhesive, a magnet, magnets, mechanical members, and Velcro. In embodiments, the exhaled air purification chamber can be attached to the bottom of the monitor by way of example only, one or more of an adhesive pad, an adhesive strip, an adhesive, a magnet, magnets, mechanical member(s), and Velcro, and can be connected to the exhaled air walls. When exhaled air walls are utilized they can be attached to the side of the monitor by way of, example only, an adhesive strip, an adhesive pad, an adhesive, a magnet, magnets, Velcro, and mechanical member(s).

In embodiments a magnet or magnets can be coated or covered with a material (by way of example only; plastic, felt, or cloth) to prevent the scratching of the surface of the monitor, electronic display screen, laptop, tablet, or TV. In embodiments when the attachment is to the bottom or lower front surface of the peripheral frame portion of the monitor, electronic display screen, laptop, tablet, or TV (the frame being that part surrounds the electronic display screen), the magnet can magnetically pull against the lower front frame surface while a mechanical means can hook over the upper portion of the lower front frame such as to be attached by both a magnetic force and a mechanical hooking means. In aspects such a hooking member that extends beyond the thickness of the magnet is approximately 2-3 mm front to back in terms of its dimension (with the back of the hook being closest to the bottom edge of the electronic display screen and the 2-3 mm hooking portion extending over the top exposed edge of the lower frame peripheral portion of the frame that surrounds the electronic display screen). In other embodiments the hook portion being approximately 2-3 mm front to back in terms of its dimensions (with the back of the hook being closest to the bottom edge of the electronic display screen and the 2-3 mm hooking portion extending over the top exposed edge of the lower frame peripheral portion of the frame that surrounds the electronic display screen) can support an attached exhaled air purification chamber.

In embodiments the exhaled air side walls are hooked over the top right side of the monitor and the top left side of the monitor and then run vertically across the front of the monitor to which the lower portion of the exhaled air side walls provide support for the exhaled air purification chamber. The exhaled air purification chamber can comprise a fan or fans for pulling air through the exhaled air purification chamber. The exhaled air purification chamber can comprise a fan or fans for pushing air through the exhaled air purification chamber. The exhaled air purification chamber can comprise a fan or fans for pushing and pulling air through the exhaled air purification chamber. An air suction intake can be located at the front of the exhaled air purification chamber that sucks the captured respiratory particles into the exhaled air purification chamber. The exhaled air purification chamber can utilize any of the methods taught herein for cleaning and/or purifying the exhaled air and then releasing the clean air into the room's environment. In aspects, multiple small fans can be applied to the top of the recessed exhaled air blocking surface for blowing the exhaled air respiratory particles downward into the exhaled air purification chamber. This embodiment can be provided as an air handling device that can be retrofitted post-sale for a monitor, laptop, or tablet. This embodiment can also be integrated into the design of a monitor, laptop, or tablet during the original fabrication thereof.

In embodiments, an air suction intake that directly or indirectly connects to an air purification chamber can be attached to the bottom of the monitor or electronic display screen, by way of example only, one or more of an adhesive pad, an adhesive strip, an adhesive, a magnet, magnets, mechanical members, and Velcro. Such an air suction intake can be located beneath part or all of the length of the front surface of the monitor, part or all of the length of the bottom of the monitor, part or all of the length of the front surface of the electronic display screen, part or all of the length of the bottom of the electronic display screen. The air suction intake can be 6 inches or longer in length (left to right). The air suction intake can be 12 inches or longer in length (left to right). The air suction intake can be 18 inches or longer in length (left to right). The exhaled air purification chamber can comprise any of the means disclosed herein to clean and/or purify exhaled air and room air. In such an embodiment the electronic display screen can act as the exhaled air blocking surface and deflect or direct exhaled air mixed with room air downward towards the air suction intake.

In embodiments, the exhaled air purification chamber can comprise a fan or fans for pulling air through the exhaled air purification chamber comprising an air suction intake that directly or indirectly connects to an air purification chamber, wherein the air suction intake and/or the exhaled air purification chamber can be attached to the bottom of the monitor or electronic display screen, by way of example only, one or more of an adhesive pad, an adhesive strip, an adhesive, a magnet, magnets, mechanical members, and Velcro. Such an air suction intake can be located beneath part or all of the length of the front surface of the monitor, part or all of the length of the bottom of the monitor, part or all of the length of the front surface of the electronic display screen, part or all of the length of the bottom of the electronic display screen. The air suction intake can be 6 inches or longer in length (left to right). The air suction intake can be 12 inches or longer in length (left to right). The air suction intake can be 18 inches or longer in length (left to right). The exhaled air purification chamber can comprise any of the means disclosed herein to clean and/or purify exhaled air and room air. In such an embodiment the electronic display screen can act as the exhaled air blocking surface and deflect or direct exhaled air mixed with room air downward towards the air suction intake.

In embodiments, a conventional air purifier can be attached to one or more of the bottom portion of the monitor or electronic display screen, a front bottom portion of the monitor or electronic display screen electronic display screen, and a back bottom portion of the monitor or electronic display screen, by way of example only, one or more of an adhesive pad, an adhesive strip, an adhesive, a magnet, magnets, mechanical members, and Velcro.

In embodiments a magnet or magnets can be coated or covered with a material (by way of example only; plastic, felt, or cloth) to prevent the scratching of the surface of the monitor, electronic display screen, laptop, tablet, or TV. In embodiments when the attachment is to the bottom or lower front surface of the peripheral frame portion of the monitor, electronic display screen, laptop, tablet, or TV (the frame being that part surrounds the electronic display screen), the magnet can magnetically pull against the lower front frame surface while a mechanical means can hook over the upper portion of the lower front frame such as to be attached by both a magnetic force and a mechanical hooking means. In aspects such a hooking member that extends beyond the thickness of the magnet is approximately 1-3 mm front to back in terms of its dimension (with the back of the hook being closest to the bottom edge of the electronic display screen and the 1-3 mm hooking portion extending over the top exposed edge of the lower frame peripheral portion of the frame that surrounds the electronic display screen). In other embodiments the hook portion being approximately 1-3 mm front to back in terms of its dimension (with the back of the hook being closest to the bottom edge of the electronic display screen and the 2-3 mm hooking portion extending over the top exposed edge of the lower frame peripheral portion of the frame that surrounds the electronic display screen) can support the attached conventional air purifier.

Such a conventional air purifier can be located beneath part or all of the length of the front surface of the monitor, part or all of the length of the bottom of the monitor, part or all of the length of the front surface of the electronic display screen, and/or part or all of the length of the bottom of the electronic display screen. When a conventional air purifier is utilized the air suction intake of the conventional air purifier can be is 6 inches or longer in length (left to right) with a height dimension top to bottom of 6 inches or less. When a conventional air purifier is utilized the air suction intake of the conventional air purifier can be 12 inches or longer in length (left to right) with a height dimension top to bottom of 6 inches or less. When a conventional air purifier is utilized the air suction intake of the conventional air purifier can be 16 inches or longer in length (left to right) with a height dimension top to bottom of 6 inches or less. When a conventional air purifier is utilized the air suction intake of the conventional air purifier can be 18 inches or longer in length (left to right) with a height dimension top to bottom of 6 inches or less. In embodiments the air suction intake is located within 45 degrees of being perpendicular to the bottom of the electronic display screen or monitor. In embodiments the air suction intake is located within 45 degrees of being parallel to the front surface of the electronic display screen or monitor. The exhaled air purification chamber can comprise any of the means disclosed herein to clean and/or purify exhaled air and room air. In such an embodiment the electronic display screen can act as the exhaled air blocking surface and deflect or direct exhaled air mixed with room air downward towards the air suction intake of the conventional air purifier. When a conventional air purifier is utilized with an exhaled air blocking surface (e.g., the electronic display screen) that is not that of the conventional air purifier, the combination thereof is referred to, in aspects, as an exhaled air capture and air cleaning system.

In an embodiment a conventional air purifier can be placed beneath, and distance separated from the bottom of a monitor or electronic display screen. In an embodiment a conventional air purifier can be placed beneath, and distance separated from the front bottom of a monitor or electronic display screen. In embodiments, a portion of an air intake of the conventional air purifier is located directly beneath the bottom of the electronic display screen. In embodiments, a portion of an air intake of the conventional air purifier is located directly beneath the bottom and forward of the bottom of the electronic display screen. When placed beneath a portion of the conventional air purifier, it can be forward of the bottom of a monitor or an electronic display screen. Such a conventional air purifier can be located beneath part or all of the length of the front surface of the monitor, part or all of the length of the bottom of the monitor, part or all of the length of the front surface of the electronic display screen, and/or part or all of the length of the bottom of the electronic display screen. When a conventional air purifier is utilized the air suction intake of the conventional air purifier can be 6 inches or longer in length (left to right). When a conventional air purifier is utilized the air suction intake of the conventional air purifier can be 12 inches or longer in length (left to right). When a conventional air purifier is utilized the air suction intake of the conventional air purifier can be 16 inches or longer in length (left to right). When a conventional air purifier is utilized the air suction intake of the conventional air purifier can be 18 inches or longer in length (left to right). In embodiments the air suction intake is located within 45 degrees of being perpendicular to the bottom of the electronic display screen or monitor. In embodiments the air suction intake is located within 45 degrees of being parallel to the front surface of the electronic display screen or monitor. The exhaled air purification chamber can comprise any of the means disclosed herein to clean and/or purify exhaled air and room air. In such an embodiment the electronic display screen can act as the exhaled air blocking surface and deflect or direct exhaled air mixed with room air downward towards the air suction intake of the conventional air purifier. When a conventional air purifier is utilized with an exhaled air blocking surface (e.g., the electronic display screen) that is not that of the conventional air purifier, the combination there of is referred to, in aspects, as an exhaled air capture and air cleaning system.

In an embodiment an exhaled air suction intake and an exhaled air purification chamber can be placed beneath, and distance separated from the bottom of a monitor or electronic display screen. When placed beneath a portion of the exhaled air suction intake, it can be forward of the bottom of a monitor or an electronic display screen. Such an exhaled air suction intake can be part of the exhaled air purification chamber. Such an exhaled air suction intake can be located beneath part or all of the length of the front surface of the monitor, part or all of the length of the bottom of the monitor, part or all of the length of the front surface of the electronic display screen, and/or part or all of the length of the bottom of the electronic display screen. The air suction intake can be 6 inches or longer in length (left to right). When a conventional air purifier is utilized the air suction intake of the conventional air purifier can be 12 inches or longer in length (left to right). The exhaled air suction intake can be 16 inches or longer in length (left to right). The exhaled air suction intake can be 18 inches or longer in length (left to right). The exhaled air suction intake can directly connect or indirectly connect to an exhaled air purification chamber. In embodiments the exhaled air suction intake is located within 45 degrees of being perpendicular to the bottom of the electronic display screen or monitor. In embodiments the exhaled air suction intake is located within 45 degrees of being parallel to the front surface of the electronic display screen or monitor. The exhaled air purification chamber can comprise any of the means disclosed herein to clean and/or purify exhaled air and room air. In such an embodiment the electronic display screen can act as the exhaled air blocking surface and deflect or direct exhaled air mixed with room air downward towards the exhaled air suction intake.

In still another embodiment, the invention can comprise an exhaled air collector that is devoid of an air suction intake. In this embodiment the exhaled air collector comprises an exhaled air blocking surface and an exhaled air gutter that fully or partially surrounds the periphery of the exhaled air blocking surface. As with other embodiments the exhaled air blocking surface can be that of the outer front surface of an electronic display screen. Upon the exhaled air respiratory particles striking the front surface of the exhaled air blocking surface these particles are directed or deflected into the exhaled air collection gutter that partially or fully surrounds the exhaled air blocking surface. The exhaled air gutter connects with an exhaled air microbicidal pathogen catch basin that is located beneath the exhaled air blocking surface. In some cases, particle momentum causes particles to fall into the gutter and then into the exhaled air microbicidal pathogen catch basin. In some cases, particle momentum causes particles to fall directly into the exhaled air microbicidal pathogen catch basin. In aspects, gravity causes the particles to slide down the front surface of the exhaled air blocking surface (e.g., the front surface of the electronic display screen) into the exhaled air microbicidal pathogen catch basin. The exhaled air microbicidal pathogen catch basin can be attached to an exhaled air gutter located beneath the exhaled air blocking surface or can be positioned beneath the exhaled blocking surface without a horizontal gutter being positioned there. In aspects, two vertical gutters, one on the right side of the recessed exhaled air blocking surface and one on the left side, open into the right and left sides of the exhaled air microbicidal pathogen catch basin. This embodiment can be free of an exhaled air suction intake. The exhaled air microbicidal pathogen catch basin can be the air purification chamber. The exhaled air purification chamber can utilize any known microbicidal means of cleaning the captured exhaled air respiratory particles, such as by way of example only, the use of one or more of the following microbicidal means: chemical, mechanical, light, radiation, thermal, ionization, and acoustic. The front surface of the recessed exhaled air blocking surface can be from time to time be cleaned or coated with a hydrophobic coating to enhance the ability of the particles to fall into the exhaled air microbicidal pathogen catch basin. The same or similar effect can be accomplished by utilizing walls (called exhaled air walls) around the right and left sides and optionally the top of the recessed exhaled air blocking surface, as opposed to a gutter, in combination with a exhaled air microbicidal pathogen catch basin (e.g., exhaled air purification chamber) below the recessed exhaled air blocking surface. In aspect this embodiment can be utilized without any energy requirements. In embodiments, by way of example only, a stack of disposable pads or a single replaceable disposable pad comprising a microbicidal agent can be utilized within an exhaled air microbicidal pathogen catch basin (or air purification chamber). Such an agent can be a chemical. Such an agent can be a material. Such an agent can be a combination thereof. In aspects where a battery or other power source is required, one or more sensors can be utilized to advise as to when it is time to replace the disposable pad or replenish the anti-microbial agent. In embodiments, the exhaled air microbicidal pathogen catch basin can provide a 99%+ pathogen kill or elimination effect or rate. In aspects, multiple small fans can be applied to the top of the recessed exhaled air blocking surface for blowing the exhaled air respiratory particles downward into the exhaled air microbicidal pathogen catch basin. These embodiments can be provided as an air handing device that can be retrofitted post-sale for a monitor, laptop, or tablet. This embodiment can also be integrated into the design of a monitor, laptop, or tablet during the original fabrication thereof.

Figure 15:
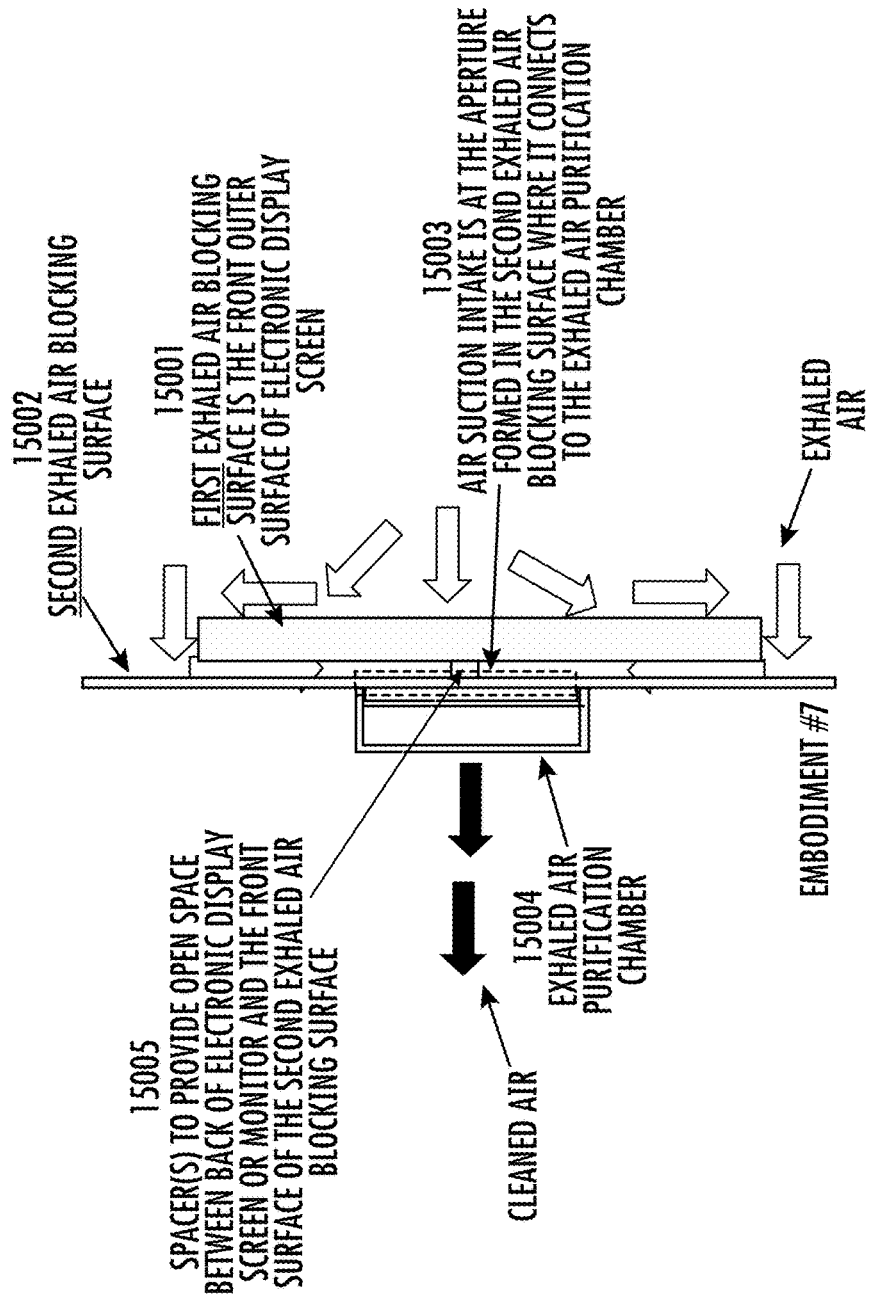
FIG. 15 is an illustration of an embodiment of the current invention as described herein.

In embodiments, the electronic display screen can be the sole exhaled air blocking surface. In other embodiments the electronic display screen and another surface of the exhaled air collector can both be exhaled air blocking surfaces, such as shown in FIG. 15. In embodiments the electronic display screen can be a first exhaled air blocking surface 15001 and a second exhaled air blocking surface 15002 can be distance-spaced behind the electronic display screen. The second exhaled air blocking surface can comprise one or more air suction intakes 15003 that open into an exhaled air purification chamber 15004 or a conduit to and exhaled air purification chamber. Thus, in embodiments, an exhaled air collector can comprise a single exhaled air blocking surface and in other embodiments an exhaled air collector can comprise two or more exhaled air blocking surfaces. This can be the case for stationary monitors, and portable monitors including laptops, tablets and other computer devices comprising an electronic display screen. FIG. 15 further shows a spacer(s) 15005 to provide, in aspects, open space between a back of the electronic display screen/monitor and a front surface of the second exhaled air blocking surface.

In embodiments a monitor support stand can provide both support for the monitor and conduit that connects an air suction intake(s) to that of an exhaled air purification chamber that is distance separated from the monitor. A portion of the monitor stand can be hollow thus providing a conduit for exhaled air to be moved to a distant separated but connected exhaled air purification chamber. The monitor stand can be that of the air purification chamber providing support for the monitor and connecting to an air suction intake within the back or side or bottom of the monitor. The monitor stand can provide support for the monitor and an external conduit that connects a distance separated air purification chamber to an air suction intake within the back or side or bottom of the monitor.

In embodiments of the invention, the exhaled air purification unit (exhaled air collector and exhaled air purification chamber) can comprise a carbon dioxide ("CO2") sensor. The exhaled air collector can comprise a CO2 sensor. The exhaled air purification chamber can comprise a CO2 sensor. The exhaled air purification system can comprise a CO2 sensor. A higher CO2 level can indicate a lack of good or sufficient air circulation within an indoor venue. Depending upon the level of CO2 measured, the CO2 sensor can cause a fan's CFM to increase or decrease in CFM. The exhaled air purification unit, air purification chamber, and/or air purification system can comprise an ozone sensor and cause an alarm, alert, or notification if ozone is present and/or if the level of ozone exceeds a preset threshold.

In embodiments of the invention, the exhaled air purification unit and/or exhaled air purification chamber can comprise an LED signaling the exhaled air purification unit and/or the exhaled air purification chamber is/are on with electrical power. In embodiments of the invention, the exhaled air purification unit and/or the exhaled air purification chamber can comprise an LED signaling that the exhaled air purification unit and/or the exhaled air purification chamber is/are off and without electrical power.

In embodiments, non-cleaned, non-filtered exhaled air from the exhaled air collector can be moved into an exhaled air diagnostic device or analyzer or screener prior to being cleaned by the exhaled air purification chamber. In embodiments, a portion of the non-cleaned, non-filtered exhaled air from the exhaled air collector can be moved into the exhaled air diagnostic device or analyzer or screener prior to being cleaned by the exhaled air purification chamber. The exhaled air diagnostic device or analyzer can be integrated into the exhaled air purification unit or separate from but housed within the air purification unit. The exhaled air diagnostic device or analyzer can be used for screening purposes. The movement can be by way of air suction or fan(s) pushing the exhaled air, or a combination of both. The exhaled air diagnostic device or analyzer or screener can comprise a plurality of sensors. These sensors can be, by way of example only, chemical sensor(s), nano-sensor(s), electrochemical sensor(s), gas sensor(s), and/or thermal sensor(s). The sensors can be used to analyze/screen/test for abnormal chemical concentrations of molecules or compounds found within the collected non-cleaned and/or non-filtered exhaled air of an individual. By way of example only, it is known that one's exhaled breath analysis can indicate the possible presence (or propensity) of the following conditions or health abnormalities: diabetes, multiple sclerosis, Parkinson disease, Alzheimer's, tuberculosis, chronic kidney disease, cancer of (lung, colon, breast, prostrate), asthma, stomach ulcers, COVID, bad breath, liver pathogenesis, and/or alcoholism. The analysis can be limited in scope for the presence, by way of example only, of one or more of nicotine, cigarette smoke, marijuana smoke, alcohol, or an additive drug or pharmaceutical. The exhaled air diagnostic device or analyzer or screener can comprise a communication module. Such a communication module can have the option to provide the individual whose exhaled air has been or is to be analyzed to approve or disapprove of having his or her exhaled air analyzed. Such a communication module can have the option to block any communication of the analysis of the individual's exhaled air. Such a communication module can have the option to approve the communication of the analysis of the individual's exhaled air. The communication module can provide wired or wireless communication to the individual whose exhaled air is being analyzed and/or to a third party. Software can provide for the ability to list those individuals who should be sent the exhaled air analysis. Such software can be shown on a video display screen prompting the individual to answer certain questions and optionally approve or disapprove of having his or her breath analyzed. Such communication can be that of an analysis of the individual's breath or an alert concerning a condition that was potentially identified to which the individual or the individual's doctor should be made aware of. The exhaled air diagnostic device or analyzer or screener can communicate wirelessly to a mobile device of the individual. Such mobile device can be, by way of example only, a cell phone, tablet computer, laptop computer, smart watch, or other electronic device. The exhaled air diagnostic device or analyzer or screener can communicate to a video display screen located on or in the back of a seat, or on a tabletop or a desktop. The exhaled air diagnostic device or analyzer or screener can communicate to a video display screen within or as part of an exhaled air collector. The exhaled air diagnostic device or analyzer or screener can comprise its own video display screen. In embodiments, the exhaled air diagnostic device or analyzer or screener can be independent of the exhaled air purification unit or system. In embodiments, the exhaled air diagnostic device or analyzer or screener can be located on, in, or separated from the exhaled air purification unit. Exhaled air can be that of non-cleaned and/or non-filtered exhaled air. AI (artificial intelligence) and/or Machine Learning can be utilized to improve the analysis of the exhaled air and/or improve the screening and/or diagnosis accuracy. The exhaled air of an individual can be analyzed or screened, for example, while an individual is sitting or standing near an air purification unit or system or an exhaled air collector. The exhaled air of an individual can be analyzed or screened, for example, while an individual is sitting or standing near an air purification unit or system or an exhaled air collector. The exhaled air of an individual can be analyzed or screened, for example, while an individual is sitting or standing near an air purification unit or system or an exhaled air collector such as, by way of example only, one of, while sitting or standing at a desk or table, being transported in a vehicle, sitting in a classroom, sitting in a vehicle, or sitting in a theater, by way of example. In embodiments of the invention the individual's exhaled air can be subjected to microbe screening. In embodiments of the invention, the individual's exhaled air can be subjected to microbe diagnosis and/or its existence. In embodiments of the invention, an individual's exhaled air can be subjected to viral diagnosis and/or its existence. In embodiments of the invention, an individual's exhaled air can be subjected to germ diagnosis and/or its existence. In embodiments of the invention, the individual's exhaled air can be subjected to coronavirus diagnosis and/or its existence. In embodiments of the invention, an individual's exhaled air can be subjected to microbe diagnosis and/or its existence. In embodiments of the invention, an individual's exhaled air can be subjected to viral diagnosis and/or its existence. In embodiments of the invention, an individual's exhaled air can be subjected to germ diagnosis and/or its existence. In an embodiment of the invention the individual's exhaled air can be subjected to an analysis for substance abuse or chemical agents such as, by way of example only, nicotine, valium, Vicodin, marijuana, ecstasy, and alcohol. Or cocaine. In an embodiment of the invention the individual's exhaled air can be subjected to an analysis for substance abuse or chemical agents such as, by way of example only, opioids. The individual's exhaled air can be subjected to a microchip. The individual's exhaled air can be subjected to a gas sensor. The individual's exhaled air can be subjected to an electrochemical sensor. The individual's exhaled air can be subjected to a thermal sensor. The individual's exhaled air can be subjected to a spectrometer. The individual's exhaled air can be subjected to THz spectroscopy. The microchip, after being exposed to the individual's exhaled air, can be subjected to a spectrometer. A spectrometer can be part of the exhaled air purification system or exhaled air purification unit. A THz spectroscopy can be part of the exhaled air purification system or exhaled air purification unit. A computer device can be part of the exhaled air purification system or exhaled air purification unit. A communication device can be part of the air exhaled air purification system or exhaled air purification unit. In embodiments, an exhaled air purification system or exhaled air purification unit using diagnostics can inform an infected individual if they are infected with a virus or germ. In embodiments the exhaled air purification unit or system can inform a captain, driver, or pilot of a vehicle that an infected passenger is traveling on their vehicle. In embodiments the exhaled air purification system or the exhaled air purification unit using diagnostics can inform, by way of example only, the owner of the vehicle that an infected passenger is traveling on their vehicle, or that a worker working at home, by way of example only, is taking a drug that could impair their performance, or that a student, by way of example only is possibly infected with COVID. In embodiments the exhaled air purification system or the exhaled air purification unit using diagnostics can inform an owner, driver, pilot, and/or attendant of the vehicle that an infected passenger is traveling on their vehicle. In embodiments the exhaled air purification system or the exhaled air purification unit using diagnostics can inform an owner, driver, pilot, and/or attendant of the vehicle that an infected passenger is traveling on their vehicle, and in which seat the infected passenger is sitting. The same can occur within a multi-seated theater in which an attendee is sitting, however in this case, by way of example only, theater management or a security guard may be informed. The same can occur within a school or university in which the individual is sitting, however in this case, the school administrator, school nurse, teacher or professor could be informed.

The various embodiments disclosed herein can be attached to or integrated within the monitor, laptop, tablet, or TV. The embodiments disclosed herein can be releasably attached to or integrated within the monitor, laptop, tablet, or TV. The embodiments disclosed herein can be used for retrofitting a monitor, laptop, tablet, or TV that has already been purchased or made. The embodiments disclosed herein can be integrated into the design of a monitor, laptop, tablet, or TV when first fabricated. A monitor, laptop, tablet, or TV can be an exhaled air collector by virtue of having an electronic display screen that can act as an exhaled air blocking surface. This is especially the case if the monitor, laptop, tablet, or TV is associated with an attached, connected, or distance separated exhaled air suction intake. In embodiments an exhaled air collector can be connected to the exhaled air suction intake and an exhaled air purification chamber. In embodiments an exhaled air collector can be attached to an exhaled air suction intake and an exhaled air purification chamber. In embodiments an exhaled air collector can be distance separated from an exhaled air suction intake and an exhaled air purification chamber. In embodiments an exhaled air collector can be attached to a conventional air purifier. In embodiments an exhaled air collector can be distance separated from a conventional air purifier. In embodiments an exhaled air collector can comprise an air suction intake. In embodiments an exhaled air collector can be devoid of an air suction intake. In embodiments an exhaled air collector can partially or fully surround an electronic display screen whereby the outer front surface of the electronic display screen comprises part or all the exhaled air blocking surface. In embodiments a fan or strip of fans can be used to enhance air flow. In embodiments a fan or a plurality of fans can be utilized within an exhaled air purification chamber. In embodiments the exhaled air collector and air purification chamber can be mobile. In embodiments the exhaled air collector and air purification chamber can be portable. In embodiments one of a monitor, laptop, tablet, or TV support stand can support or connect to an air purification chamber. In embodiments one of a monitor, laptop, tablet, or TV support stand can support or connect to an exhaled air suction intake. In embodiments one of a monitor, laptop, tablet, or TV support stand can support or connect to a conventional air purifier. An exhaled air capture, air cleaning monitor, laptop, tablet, or TV can comprise or be connected to an exhaled air diagnostic or exhaled air evaluation module. An exhaled air collector associated with a monitor, laptop, tablet, or TV can comprise or be connected to an exhaled air diagnostic or exhaled air analyzer module. Such an exhaled air diagnostic, evaluation, analysis, or screening module can determine the possible presence of a disease or medical issue, such as, by way of example only, one or more of: COVID, influenza, lung disease, lung abnormality, respiratory abnormality, pneumonia, alcohol, marijuana, and an additive drug.

The invention herein has several Aspects:

Aspect 1: An exhaled air collecting and cleaning system comprising:

an exhaled air collector comprising an electronic display screen, wherein the outer front surface of the electronic display screen acts as an exhaled air blocking surface, wherein the exhaled air blocking surface blocks, deflects, or directs a mixture of exhaled air and room air towards one or more exhaled air suction intakes, and wherein the one or more exhaled air suction intakes are capable of intaking 80% or more of the blocked, deflected, or directed mixture of exhaled air and room air;

an air purification chamber, wherein the one or more exhaled air suction intakes move the mixture of exhaled air and room air towards or into the air purification chamber, and wherein the air purification chamber cleans and exhausts the mixture of exhaled air and room air.

Aspect 2: The exhaled air collecting and cleaning system of Aspect 1, wherein one or more of: the one or more exhaled air suction intakes, the air purification chamber, and the exhaled air collector, are one of: attached to, releasably attached to, integrated with, built into, adjacent to, distance separated and located beneath, distance separated and located behind, and permanently affixed to a monitor, a computer monitor, a laptop computer, a tablet computer, a phone, or a television.

Aspect 3: The exhaled air collecting and cleaning system of Aspect 1, wherein the exhaled air blocking surface comprises all or a portion of a front surface of: a monitor, a computer monitor, a laptop computer, a tablet computer, a phone, or a television.

Aspect 4: The exhaled air collecting and cleaning system of Aspect 1, wherein the exhaled air collector is connected to the air purification chamber by:

an air suction conduit, or an open space between:

a side, a back, or the side and the back, of a connected or integrated monitor, computer monitor, laptop computer, tablet computer, phone, television, or the electronic display screen, and a cover of a portion of the monitor, the computer monitor, the laptop computer, the tablet computer, the phone, the television, or the electronic display screen.

Aspect 5: The exhaled air collecting and cleaning system of Aspect 1, wherein the outer front surface of the electronic display screen is one of: recessed into the exhaled air collector, planar with a front surface of the exhaled air collector, and outwardly extended from the front surface of the exhaled air collector.

Aspect 6: The exhaled air collecting and cleaning system of Aspect 1, wherein the air purification chamber is one of: located behind, located beneath, located beside, and located above, the exhaled air collector, the electronic display screen, or both.

Aspect 7: The exhaled air collecting and cleaning system of Aspect 1, wherein the exhaled air collector further comprises an exhaled air catch basin.

Aspect 8: The exhaled air collecting and cleaning system of Aspect 1, wherein the one or more exhaled air suction intakes are located within an exhaled air catch basin.

Aspect 9: The exhaled air collecting and cleaning system of Aspect 1, wherein the one or more exhaled air suction intakes connect or open to:

an air suction conduit, or an open space between:

a side, a back, or the side and the back, of an attached or integrated monitor, computer monitor, laptop computer, tablet computer, phone, television, or the electronic display screen, and a cover of a portion of the monitor, the computer monitor, the laptop computer, the tablet computer, the phone, the television, or the electronic display screen.

Aspect 10: The exhaled air collecting and cleaning system of Aspect 1, wherein the air purification chamber or a conventional air purifier is at least one of: attached to, connected to, built into, permanently affixed to, and integrated with, a support stand for a monitor, a computer monitor, a laptop computer, a tablet computer, a phone, a television, or the electronic display screen.

Aspect 11: The exhaled air collecting and cleaning system of Aspect 1, wherein the one or more exhaled air suction intakes are one or more of: located around the electronic display screen, to the right of the electronic display screen, to the left of the electronic display screen, above the electronic display screen, and below the electronic display screen.

Aspect 12: The exhaled air collecting and cleaning system of Aspect 1, further comprising a sensor capable of sensing when a person is sitting or standing in front of the electronic display screen.

Aspect 13: The exhaled air collecting and cleaning system of claim 1, wherein the exhaled air collector is directly or indirectly connected to the air purification chamber.

Aspect 14: The exhaled air collecting and cleaning system of Aspect 1, wherein the one or more exhaled air suction intakes, the air purification chamber, or both, are directly or indirectly attached to a portion of the exhaled air collector, and wherein the exhaled air collector supports, is releasably attached to, is attached to, is built into, or is integrated with, a monitor, a computer monitor, a laptop computer, a tablet computer, a phone, a television, or the electronic display screen.

Aspect 15: The exhaled air collecting and cleaning system of Aspect 1, wherein the exhaled air collector is attached or releasably attached to a monitor, a computer monitor, a laptop computer, a tablet computer, a phone, a television, or the electronic display screen, using at least one of: one or more magnets, one or more hooks, one or more fasteners, one or more adhesive pads, an adhesive, one or more mechanical structures, and Velcro.

Aspect 16: The exhaled air collecting and cleaning system of Aspect 1, wherein the exhaled air collector is attached to or integrated with a monitor, a computer monitor, a laptop computer, a tablet computer, a phone, a television, or the electronic display screen, and wherein an open space between:

a side, a back, or the back and the side, of the monitor, the computer monitor, the laptop computer, the tablet computer, the phone, the television, or the electronic display screen, and a cover of a portion of the monitor, the computer monitor, the laptop computer, the tablet computer, the phone, the television, or the electronic display screen, allows for the mixture of exhaled air and room air to flow towards or into the air purification chamber.

Aspect 17: The exhaled air collecting and cleaning system of Aspect 1, wherein the air purification chamber comprises or provides for one or more of: a filter, a high efficiency particulate air (HEPA) filter, a carbon filter, an activated carbon filter, an ultrasonic generator, ionization, a germicidal light, chemical microbicidal purification, light microbicidal purification, a UV light, a UVC light, microbicidal radiation purification, mechanical microbicidal purification, thermal microbicidal purification, one or more microbicidal agents, one or more microbicidal materials, carbon dioxide reduction, and a carbon dioxide reducing agent.

Aspect 18: The exhaled air collecting and cleaning system of Aspect 1, wherein:

an air suction conduit provided between the one or more exhaled air suction intakes and the air purification chamber, or an air suction conduit comprising an open space between:
a side, aback, or the side and the back, of a connected or integrated monitor, computer monitor, laptop computer, tablet computer, phone, television, or the electronic display screen, and
a cover of a portion of the monitor, the computer monitor, the laptop computer, the tablet computer, the phone, the television, or the electronic display screen,
is located around a peripheral portion of the monitor, the computer monitor, the laptop computer, the tablet computer, the phone, the television, or the electronic display screen.

Aspect 19: The exhaled air collecting and cleaning system of Aspect 1, wherein the exhaled air collector comprises an exhaled air catch basin, and wherein the exhaled air catch basin is located at the bottom of, adjacent to the bottom of, under a portion of the bottom of, or distance separated and under a portion of the bottom of, the electronic display screen.

Aspect 20: The exhaled air collecting and cleaning system of Aspect 1, wherein the air purification chamber, the one or more exhaled air suction intakes, or both, whether directly connected, indirectly connected, or distance separated from a bottom of the electronic display screen, are covered, or comprise a grate, screen, mesh, or a member comprising a plurality of small apertures.

Aspect 21: The exhaled air collecting and cleaning system of Aspect 1, wherein at least one of: the exhaled air collector, an exhaled air catch basin, the one or more exhaled air suction intakes, an air suction conduit connecting the exhaled air collector and the air purification chamber, and the air purification chamber, are at least one of: attached to, releasably attached to, built into, and integrated with, a monitor, a computer monitor, a laptop computer, a tablet computer, a phone, a television, or the electronic display screen.

Aspect 22: The exhaled air collecting and cleaning system of Aspect 1, wherein one or more of: the exhaled air collector, an exhaled air catch basin, the one or more exhaled air suction intakes, an air suction conduit connecting the exhaled air collector and the air purification chamber, and the air purification chamber, comprise one or more fans.

Aspect 23: The exhaled air collecting and cleaning system of Aspect 1, wherein the mixture of exhaled air and room air is suctioned into the one or more exhaled air suction intakes, and wherein the one or more exhaled air suction intakes are located below or adjacent to a bottom of the electronic display screen.

Aspect 24: The exhaled air collecting and cleaning system of Aspect 1, wherein at least one of: the electronic display screen and the exhaled air collector, are coated or treated with a microbicidal coating, material, or agent.

Aspect 25: The exhaled air collecting and cleaning system of Aspect 1, wherein all or a portion of at least one of: the air purification chamber, the exhaled air collector, and the electronic display screen, are capable of being removed from the system to allow for changing a filter or a microbicidal element.

Aspect 26: The exhaled air collecting and cleaning system of Aspect 1, further comprising a secondary air purification chamber, wherein the secondary air purification chamber comprises one or more fans and one or more filters.

Aspect 27: The exhaled air collecting and cleaning system of Aspect 1, wherein the air purification chamber is powered by one or more of: alternating current (AC), a battery, a rechargeable battery, and a universal serial bus (USB) cable connected to a USB powered port.

Aspect 28: The exhaled air collecting and cleaning system of Aspect 1, wherein the system is portable or mobile.

Aspect 29: The exhaled air collecting and cleaning system of Aspect 1, wherein the air purification chamber is a conventional air purifier.

Aspect 30: The exhaled air collecting and cleaning system of Aspect 29, wherein the conventional air purifier includes or is attached to the one or more exhaled air suction intakes, wherein all or a portion of the one or more exhaled air suction intakes is in alignment directly beneath the electronic display screen, and wherein the conventional air purifier is one of attached to or distance separated from a bottom of the electronic display screen.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that while certain of the illustrations and figure may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. An exhaled air collecting and cleaning system comprising:
   an electronic display screen, wherein the outer front surface of the electronic display screen acts as an exhaled air blocking surface;
   an exhaled air suction intake wherein at least a portion of the exhaled air suction intake is (a) located below and beneath at least a portion of the electronic display screen, and (b) substantially in alignment with at least a portion of the outer front surface of the electronic display screen, wherein the exhaled air blocking surface blocks, deflects, or directs a mixture of exhaled air and room air towards the exhaled air suction intake, wherein the blocked, deflected, or directed mixture of exhaled air and room air is pulled downwards into and through the exhaled air suction intake, and wherein the exhaled air suction intake is elongated in a horizontal direction such that its length in a horizontal direction is greater than its width and greater than its height; and
   an air purification chamber, wherein the mixture of exhaled air and room air pulled downwards into and through the exhaled air suction intake is directed towards or into the air purification chamber, and wherein the air purification chamber cleans and exhausts the cleaned mixture of exhaled air and room air.

2. The exhaled air collecting and cleaning system of claim 1, wherein the electronic display screen is the electronic display screen of a monitor, a computer monitor, a laptop computer, a tablet computer, a phone, or a television.

3. The exhaled air collecting and cleaning system of claim 1, wherein the outer front surface of the electronic display screen comprises all or a portion of a front surface of: a monitor screen, a computer monitor screen, a laptop computer screen, a tablet computer screen, a phone screen, or a television screen.

4. The exhaled air collecting and cleaning system of claim 1, wherein the exhaled air suction intake is connected to the air purification chamber by an air suction conduit.

5. The exhaled air collecting and cleaning system of claim 1, wherein the outer front surface of the electronic display screen is one of: recessed into a frame for the electronic display screen, planar with a front surface of the frame for the electronic display screen, and outwardly extended from the front surface of the frame for the electronic display screen.

6. The exhaled air collecting and cleaning system of claim 1, wherein the air purification chamber is one of: located behind, located beneath, located beside, and located above, the electronic display screen.

7. The exhaled air collecting and cleaning system of claim 1, further comprising an exhaled air catch basin.

8. The exhaled air collecting and cleaning system of claim 1, wherein the exhaled air suction intake is located within an exhaled air catch basin.

9. The exhaled air collecting and cleaning system of claim 1, wherein the exhaled air suction intake connects or opens to:
   an air suction conduit, or
   an open space between:
      a side, a back, or the side and the back, of an attached or integrated monitor, computer monitor, laptop computer, tablet computer, phone, television, or the electronic display screen, and
      a cover of a portion of the monitor, the computer monitor, the laptop computer, the tablet computer, the phone, the television, or the electronic display screen.

10. The exhaled air collecting and cleaning system of claim 1, further comprising a sensor capable of sensing when a person is sitting or standing in front of the electronic display screen.

11. The exhaled air collecting and cleaning system of claim 1, wherein the exhaled air suction intake is directly or indirectly connected to the air purification chamber.

12. The exhaled air collecting and cleaning system of claim 1, wherein the exhaled air suction intake, the air purification chamber, or both, are directly or indirectly attached to a portion of a monitor, a computer monitor, a laptop computer, a tablet computer, a phone, a television, or the electronic display screen, and wherein the exhaled air suction intake, the air purification chamber, or both, are releasably attached to, attached to, built into, or integrated with, the monitor, the computer monitor, the laptop computer, the tablet computer, the phone, the television, or the electronic display screen.

13. The exhaled air collecting and cleaning system of claim 1, wherein the exhaled air suction intake, the air purification chamber, or both, are attached or releasably attached to a monitor, a computer monitor, a laptop computer, a tablet computer, a phone, a television, or the electronic display screen, using at least one of: one or more magnets, one or more hooks, one or more fasteners, one or more adhesive pads, an adhesive, one or more mechanical structures, and hook and loop fasteners.

14. The exhaled air collecting and cleaning system of claim 1, wherein the air purification chamber comprises or provides for one or more of: a filter, a high efficiency particulate air (HEPA) filter, a carbon filter, an activated carbon filter, an ultrasonic generator, ionization, a germicidal light, chemical microbicidal purification, light microbicidal purification, a UV light, a UVC light, microbicidal radiation purification, mechanical microbicidal purification, thermal microbicidal purification, one or more microbicidal agents, one or more microbicidal materials, carbon dioxide reduction, and a carbon dioxide reducing agent.

15. The exhaled air collecting and cleaning system of claim 1, wherein:
- an air suction conduit provided between the exhaled air suction intake and the air purification chamber, or
- an air suction conduit comprising an open space between:
  - a side, a back, or the side and the back, of a connected or integrated monitor, computer monitor, laptop computer, tablet computer, phone, television, or the electronic display screen, and
  - a cover of a portion of the monitor, the computer monitor, the laptop computer, the tablet computer, the phone, the television, or the electronic display screen, is located around a peripheral portion of the monitor, the computer monitor, the laptop computer, the tablet computer, the phone, the television, or the electronic display screen.

16. The exhaled air collecting and cleaning system of claim 1, further comprising an exhaled air catch basin, wherein the exhaled air catch basin is located at a bottom of, adjacent to the bottom of, under a portion of the bottom of, or distance separated and under a portion of the bottom of, the electronic display screen.

17. The exhaled air collecting and cleaning system of claim 1, wherein the air purification chamber, the exhaled air suction intake, or both, whether directly connected, indirectly connected, or distance separated from a bottom of the electronic display screen, are covered, or comprise a grate, screen, mesh, or a member comprising a plurality of small apertures.

18. The exhaled air collecting and cleaning system of claim 1, wherein at least one of: an exhaled air catch basin, the exhaled air suction intake, an air suction conduit connecting the exhaled air suction intake and the air purification chamber, and the air purification chamber, are at least one of: attached to, releasably attached to, built into, and integrated with, a monitor, a computer monitor, a laptop computer, a tablet computer, a phone, a television, or the electronic display screen.

19. The exhaled air collecting and cleaning system of claim 1, wherein one or more of: an exhaled air catch basin, the exhaled air suction intake, an air suction conduit connecting the exhaled air suction intake and the air purification chamber, and the air purification chamber, comprise one or more fans.

20. The exhaled air collecting and cleaning system of claim 1, wherein the electronic display screen is curved.

21. The exhaled air collecting and cleaning system of claim 1, wherein at least one of: the electronic display screen and the exhaled air suction intake, are coated or treated with a microbicidal coating, material, or agent.

22. The exhaled air collecting and cleaning system of claim 1, wherein all or a portion of at least one of: the air purification chamber, the exhaled air suction intake, and the electronic display screen, are capable of being removed from the system to allow for changing a filter or a microbicidal element.

23. The exhaled air collecting and cleaning system of claim 1, further comprising a secondary air purification chamber, wherein the secondary air purification chamber comprises one or more fans and one or more filters.

24. The exhaled air collecting and cleaning system of claim 1, wherein the air purification chamber is powered by one or more of: alternating current (AC), a battery, a rechargeable battery, and a universal serial bus (USB) cable connected to a USB powered port.

25. The exhaled air collecting and cleaning system of claim 1, wherein the system is portable or mobile.

26. The exhaled air collecting and cleaning system of claim 1, further comprising a carbon dioxide reducing agent located adjacent to or within at least one of the exhaled air suction intake and the air purification chamber.

\* \* \* \* \*